(12) United States Patent
Low et al.

(10) Patent No.: US 9,250,238 B2
(45) Date of Patent: Feb. 2, 2016

(54) PATHOGEN DETECTION

(75) Inventors: Philip S. Low, West Lafayette, IN (US); Alexander Wei, West Lafayette, IN (US); Ronald G. Reifenberger, Lafayette, IN (US); Youngsoon Kim, West Lafayette, IN (US); Avijit Kumar Adak, West Lafayette, IN (US); David Lyvers, Indianapolis, IN (US); Kulbhushan Durugkar, West Lafayette, IN (US); Derek Doorneweerd, Lockport, IL (US); Rajendra P. Bandari, Warangal, IN (US); Rajesh Kumar Pandey, New Haven, CT (US); Alexei Leonov, Lafayette, IN (US); Walter A. Henne, Frankfort, IL (US); Yeong E. Kim, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 422 days.

(21) Appl. No.: 13/805,770

(22) PCT Filed: Jun. 24, 2011

(86) PCT No.: PCT/US2011/041903
§ 371 (c)(1),
(2), (4) Date: Apr. 4, 2013

(87) PCT Pub. No.: WO2012/050645
PCT Pub. Date: Apr. 19, 2012

(65) Prior Publication Data
US 2013/0196872 A1    Aug. 1, 2013

Related U.S. Application Data

(60) Provisional application No. 61/358,735, filed on Jun. 25, 2010.

(51) Int. Cl.
| | |
|---|---|
| *C40B 40/02* | (2006.01) |
| *G01N 33/569* | (2006.01) |
| *G01N 33/543* | (2006.01) |
| *G01N 33/53* | (2006.01) |
| *B03C 5/00* | (2006.01) |

(Continued)

(52) U.S. Cl.
CPC .............. *G01N 33/569* (2013.01); *B03C 5/005* (2013.01); *B03C 5/026* (2013.01); *G01N 33/5302* (2013.01); *G01N 33/5308* (2013.01); *G01N 33/54353* (2013.01); *G01N 33/56905* (2013.01); *G01N 33/56911* (2013.01); *G01N 33/56961* (2013.01); *G01N 33/56983* (2013.01); *B03C 2201/26* (2013.01); *C40B 40/02* (2013.01); *G01N 2035/00158* (2013.01)

(58) Field of Classification Search
None
See application file for complete search history.

(56) References Cited

FOREIGN PATENT DOCUMENTS

| EP | 1 308 520 A2 | 7/2003 | |
|---|---|---|---|
| WO | 2010033847 A1 | 3/2010 | |
| WO | WO 2010/033847 A1 * | 3/2010 | ............. A01N 43/16 |

OTHER PUBLICATIONS

Ghoush et al. (Dec. 1996) Chemistry and Biology vol. 3 pp. 1011 to 1019.*

(Continued)

*Primary Examiner* — Christian Boesen
(74) *Attorney, Agent, or Firm* — Maginot, Moore & Beck, LLP

(57) ABSTRACT

Pathogens are detected through the use of mutation-resistant ligands.

22 Claims, 46 Drawing Sheets

(51) Int. Cl.
*B03C 5/02* (2006.01)
*G01N 35/00* (2006.01)

(56) References Cited

OTHER PUBLICATIONS

Wang, H.F., et al., "Unique Aggregation of Anthrax (Bacillus anthracis) Spores by Sugarcoated Single-Walled Carbon Nanotubes," J. Am. Chem. Soc. 128 (2206), (pp. 13364-13365).
Kale, R.R., et al., "Detection of Intact Influenza Viruses Using Biotinylated Biantennary S-sialosides," J. Am. Chem. Soc. 130 (2008), (pp. 8169-8171).
Disney, M.D. and Seeberger, P.H. "The Use of Carbohydrate Microarrays to Study Carbohydrate-Cell Interaction and to Detect Pathogens," Chem. Biol. 11 (2004) (pp. 1701-1707).
Wu, C.Y., et al., "New Development of Glycan Arrays," Org. Biomol. Chem. 7, (2009) (pp. 2247-2254).
Parks, S., et al., "Carbohydrate Chips for Studying High-Throughput Carbohydrate-Protein Interactions," J. Am. Chem. Soc. 126 (2004), (pp. 4812-4819).
Houseman, B.T., et al., "Maleimide-Functionalized Self-Assembled Monolayers for the Preparation of Peptide and Carbohydrate Biochips," (2003) Langmuir 19 (pp. 1522-1531).
Bryan, M.C., et al., "Covalent Display of Oligosaccharide Arrays in Microtiter Plates," J. Am. Chem. Soc. 126 (2004), (pp. 8640-8641).
Michel, O. and Ravoo, B.J. "Carbohydrate Microarrays by Microcontact "click" Chemistry," (2008) Langmuir 24, (pp. 12116-12118).
Lee, M. R. and Shin, I, "Fabrication of Chemical Microarrays by Efficient Immobilization of Hydrazide-Linked Substances on Epoxide-Coated Glass Surfaces," Angew. Chem. Int. Ed. 44 (2005), (pp. 2881-2884).
Park, S. and Shin, I, "Carbohydrate Microarrays for Assaying Galoclosyltransferase Activity," Org. Lett. 9, (2007), (pp. 1675-1678).
Depaz, J. L., et. al., "Micrarrays of Synthetic Heparin Oligosaccharides," J. Am. Chem. Soc. 128 (2006), (pp. 2766-2767).
Kohn, M., et al., "Staudinger Ligation: A New Immobilization Strategy for the Preparation of Small-Molecule Arrays," Angew. Chem. Int. Ed. 42 (2003), (pp. 5830-5834).
Xia, B.Y., et. al., "Versatile Fluorescent Derivatization of Glycans for Glycomic Analysis," Nat. Methods 2 (2005), (pp. 845-850).
Lee, M.R. and Shin, I., "Facile Preparation of Carbohydrate Microarrays by Site-Specific, Covalent Immobilization of Unmodified Carbohydrates on Hydrazide-Coated Glass Slides," Org. Lett. 7 (2005), (pp. 4269-4272).
Park, S. et al., "Construction of Carbohydrate Microarrays by Using One-Step Direct Immobilizations of Diverse Unmodified Glycans on Solid Surfaces," Bioconjug. Chem. 20, (2009), (pp. 155-162).
Zhi, Z. L., et al., "Fabrication of Carbohydrate Microarrays on Gold Surfaces: Direct Attachment of Nonderivatized Oligosaccharides to Hydrazide Modified Self-Assembled Monolayers," Anal. Chem. 78, (2006), (pp. 4786-4793).
Liu, Y., et al., "Neoglycolipid Probes Prepared Via Oxime Ligation for Microarray Analysis fo Oligosaccharide-Protein Interactions," Chem. Biol. 14, (2007), (pp. 847-859).
Clo, E., et al., "Chemoselective Reagents for Covalent Capture and Display of Glycans in Microarrays," Eur. J. Org. Chem. (2010), (pp. 540-554).
Lohse, A., et al., "Solid-Phase Oligosaccharide Tagging (SPOT): Validation on Glycolipid-Derived Structures," Angew. Chem. Int. Ed. 45 (2006), (pp. 4167-4172).
Dydio, P., et al., "Bishydrazide Derivative of Isoindoline as Simple Anion Receptors," J. Org. Chem. 74, (2009), (pp. 1525-1530).

Bystricky, S., et al., "Determination of the Cross-Linking Effect of Adipic Acid Dihydrazide on Glycoconjugate Preparation," Glycocong. J. 16 (1999), (pp. 691-695).
Ono, T., et al., "Soft-To-Hard Transformation of the Mechanical Properties of Dynamic Covalent Polymers Through Component Incorporation," Chem. Commun. (2007), (pp. 46-48).
Zhao, Y., et al., "Dithiocarbamate Assembly on Gold," J. Am. Chem. Soc. 127 (2005), (pp. 7328-7329).
Zhu, H., et al., "Assembly of Dithiocarbamate-Anchored Monolayers on Gold Surfaces in Aqueous Solutions," Langmuir 24 (2008), (pp. 8660-8666).
Belot, F. and Jacquinet, J.C., "Unexpected Stereochemical Outcome of Activated 4,6-0-Benzylidene Derivatives of the 2-Deoxy-2-Trichloroacetamido-D-Galacto Series in Clycosylation Reactions During the Synthesis of a Chondroitin 6-Sulfate Trisaccharide Methyl Glycoside" Carbohydr. Res. 325 (2000), (pp. 95-106).
Ojala, C.R., et al., "The Saccharide-Hydrazide Linkage: Molecular and Crystal Structures of the Semicarbazide Derivatives of D-Glucose, D-Galactose, and D-Xylose, Including a "forbidden" Conformation of the Galactose Derivative," Carbohydr. Res. 337 (2002), (pp. 21-29).
Flinn, N.S., et al., "A Single-Step Method for the Production of Sugar Hydrazides: Intermediates for the Chemoselective Preparation of Glycoconjugates," Bioconjug. Chem. 16 (2005), (pp. 722-728).
Krivan, H.C., et al., "Many Pulmonary Pathogenic Bacteria Bind Specifically to the Carbohydrate Sequence GalNAcβ1-4Gal Found in Some Glycolilpids," Oroc. Natl. Acad. Sci. USA 85 (1988), (pp. 6157-6161).
Huff, T.B., et al., "Controlling the Cellular Uptake of Gold Nanorods," Langmuir 23 (2007), (pp. 1596-1599).
Huff, T.B., et al., "Hyperthermic Effects of Gold Nanorods on Tumor Cells," Nanomedicine 2, (2007), (pp. 125-132).
Zhao, Y., et al., "Dithiocarbamate-Coated SERS Substrates: Sensitivity Gain by Partial Surface Passivation," Langmuir 25, (2009), (pp. 13288-13829).
Park, M.H., et al., "Robust and Responsive Dendrimer-Gold Nanoparticle Nanocomposites Via Dithiocarbamate Crosslinking," Adv. Matter. 21 (2009), (pp. 2323-2325).
Patel, G., et al., "Potassium Ion Recognition by Facile Dithiocarbamate Assembly of Benzo-15-crown-5-gold nanoparticles," Chem. Commun. (2009), (pp. 1849-1851).
Morf, P., et al., "Dithiocarbamates: Functional and Versatile Linkers for the Formation of Self-Assembled Monolayers," Langmuir 22 (2006), (pp. 658-663).
Lee, A. W. M.,et al., "Ultraviolet Spectrophotometric Determination of Primary and Secondary Aliphatic Amines by Formation of Dithiocarbamates," Anal. Chem. Acta 218, (1989), (pp. 157-160).
Ito, Y., "Photoimmobilization for Microarrays," Biotechnol. Prog. (2006), (pp. 924-932).
Liu, L-H.,et al., "Photoinitial Coupling of Unmodified Monosaccharides to Iron Oxide Nanoparticles for Sensing Proteins and Bacteria," Bioconjug. Chem. 20 (2009), (pp. 1349-1355).
Lewis, R.V., et al., "Photoactivated Heterobifunctional Cross-Linking Reagents Which Demonstrates the Aggregation State of Phospholipase A2," Biochemistry 16 (1977), (pp. 5650-5654).
Marx, K.A. "Quartz Crystal Microbalance: A Usefule Tool for Studying Thin Polymer Films and Complex Biomecolecular Systems at the Solution-Surface Interface," Biomacromolecules 4, (2003), (pp. 1099-1120).
Flynn, N.T., et al., "Long-Term Stability of Self-Assembled Monolayers in Biological Media," Langmuir 19, (2003), (pp. 10909-10915).
Ghosh, Arun, et al., "Iron Transport-Mediated Drug Delivery Using Mixed-Ligand Siderophore-β-Lactam Conjugates," Chemistry & Biology, Dec. 1996, 3, (pp. 1011-1019).

* cited by examiner

- At 0~4 °C (Refrigerator)

- At room temp (20~25 °C)

Viral Plaques
$10^6$ concentration of H1N1 Influenza virus     $10^2$ concentration of H1N1 Influenza virus

Figure 97

Direct Immunostaining against influenza A virus neuraminidase with Tamiflu FITC
(H1N1-infected MDCK cells 20 hrs 20 hrs post infected)

A. Immobilization of TAMIFLU-PEG-mercapto on –COOH slides

B. Immobilization of TAMIFLU –COOH slides

PATHOGEN DETECTION

GOVERNMENT FUNDING

This invention was made with government support under Grant No. 04-C-ACE-PU, awarded by the U.S. Federal Aviation Administration; Grant No. W911SR-08-C-0001, awarded by the Department of Defense; and Grant No. GM-069862, awarded by the National Institutes of Health. The government has certain rights in the invention.

This application is the §371 U.S. National Stage of International Application No. PCT/US2011/041903, filed Jun. 24, 2011, which claims the benefit of U.S. Provisional Application Ser. No. 61/358,735, filed Jun. 25, 2010, each of which is incorporated herein by reference in its entirety.

SUMMARY OF THE INVENTION

The rapid detection and identification of bacterial pathogens is important for medical diagnostics, transportation biosecurity, and the prevention of global pandemics. Microbial pathogens are constantly mutating, producing strains that can evade detection based on recognition of surface antigens by, for example, surface antigen-specific antibodies. While antibody-based detection strategies are often selected because of their speed, mutation of the pathogen can subsequently render such tests ineffective.

In an effort to maintain the simplicity, speed, cost, specificity and miniaturization capabilities of antibody-based detection strategies, yet avoid the pitfalls associated with loss of antibody efficacy due to denaturation or antigen mutation, we have identified other pathogen-specific ligands that are more stable and less affected by the rapid mutability of pathogens. These ligands are referred to herein as "mutation-resistant ligands." A mutation-resistant ligand encompasses a ligand involved functions important for or essential to virulence, such as, for example, capturing essential nutrients (e.g., metal ions such as Fen or infection-related cell surface binding. Thus, while mutations may still occur in these ligands, microbes harboring such mutated ligands typically lose at least a portion of their virulence. The present invention employs "mutation-resistant ligands" to capture the desired microbe on a detection device.

In one aspect, this disclosure describes an article that generally includes a substrate and one or more mutation-resistant ligands affixed to at least a portion of the substrate. In some embodiments, the one or more mutation-resistant ligands may be affixed to the substrate via a linker that can include, for example, bovine serum albumin or polyethylene glycol.

In some embodiments, the mutation-resistant ligand can include a siderophore such as, for example, pyoverdine, pyochelin, a salmochelin (e.g., S1 or S2), aerobactin, mycobactin J, deferoxamine, staphyloferrin A, and/or vibriobactin.

In some embodiments, the mutation-resistant ligand can include a glycan such as, for example, pulmonary trisaccharide, a bishydrazide glycoconjugate (e.g., a $\alpha,\omega$-bishydrazide). In some of these embodiments, the glycan can be, or be derived from, a cell surface molecule involved in a pathogen infecting a host cell.

In some embodiments, the mutation-resistant ligand can include a neuraminidase inhibitor or a derivative thereof such as, for example, oseltamivir or a derivative thereof.

More generally, a mutation-resistant ligand can include a mutation-resistant ligand that can be bound by a pathogen such as, for example, a member of one of the genera *Yersinia, Klebsiella, Providencia, Erwinia, Enterobacter, Salmonella, Serratia, Aerobacter, Escherichia, Pseudomonas, Shigella, Vibrio, Aeromonas, Streptococcus, Staphylococcus, Micrococcus, Moraxella, Bacillus, Clostridium, Corynebacterium, Eberthella, Francisella, Haemophilus, Bacteroides, Listeria, Erysipelothrix, Acinetobacter, Brucella, Pasteurella, Flavobacterium, Fusobacterium, Streptobacillus, Calymmatobacterium, Legionella, Treponema, Borrelia, Leptospira, Actinomyces, Nocardia, Rickettsia, Micrococcus, Mycobacterium, Neisseria,* or *Campylobacter*. A mutation-resistant ligand can include a mutation-resistant ligand that can be bound by a pathogenic virus such as, for example, a member of the Papilloma viruses, Parvoviruses, Adenoviruses, Herpesviruses, Vaccine virus, Arenaviruses, Coronaviruses, Rhinoviruses, Respiratory syncytial viruses, Influenza viruses, Picornaviruses, Paramyxoviruses, Reoviruses, Retroviruses, Rhabdoviruses, or human immunodeficiency virus (HIV). A mutation-resistant ligand can include a mutation-resistant ligand that can be bound by a pathogen such as, for example, a member of one of the genera *Taenia, Hymenolepsis, Diphyllobothrium, Echinococcus, Fasciolopsis, Heterophyes, Metagonimus, Clonorchis, Fasciola, Paragonimus, Schistosoma, Enterobius, Trichuris, Ascaris, Ancylostoma, Necator, Wuchereria, Brugi, Loa, Onchocerca, Dracunculus, Naegleria, Acanthamoeba, Plasmodium, Trypanosoma, Leishmania, Toxoplasma, Entamoeba, Giardia, Isospora, Cryptosporidium, Enterocytozoa, Strongyloides,* or *Trichinella*. A mutation-resistant ligand can a mutation-resistant ligand that can be bound by a fungus that is the causative agent of conditions such as, for example, Ringworm, Histoplasmosis, Blastomycosis, Aspergillosis, Cryptococcosis, Sporotrichosis, Coccidiodomycosis, Paracoccidioidomycosis, Mucomycosis, Candidiasis, Dermatophytosis, Protothecosis, Pityriasis, Mycetoma, Paracoccidiodomycosis, Phaeohphomycosis, Pseudallescheriasis, Trichosporosis, or Pneumocystis.

In some embodiments, the one or more mutation-resistant ligands comprises a first mutation-resistant ligand and a second mutation-resistant ligand. In some of these embodiments, the first mutation-resistant ligand selectively binds to a first pathogen and the second mutation-resistant ligand selectively binds to a second pathogen. In alternative embodiments, the first mutation-resistant ligand and the second mutation-resistant ligand selectively bind to the same pathogen.

In some embodiments, the one or more mutation-resistant ligands further comprise a third mutation-resistant ligand. In some of these embodiments, the third mutation-resistant ligand selectively binds to a third pathogen.

In some embodiments, the one or more mutation-resistant ligands further comprise a fourth mutation-resistant ligand. In some of these embodiments, the fourth mutation-resistant ligand selectively binds to a fourth pathogen.

In some embodiments, the one or more mutation-resistant ligands is affixed to the substrate in a predetermined pattern. In some embodiments, a first mutation-resistant ligand is affixed to the substrate in a first predetermined pattern and a second mutation-resistant ligand is affixed to the substrate in a second predetermined pattern. A third mutation-resistant ligand, if present, may be affixed to the substrate in a third predetermined pattern. A fourth mutation-resistant ligand, if present, may be affixed to the substrate in a fourth predetermined pattern.

The various article embodiments summarized separately above may be combined with any one or more additional embodiments where such combinations are practical.

In another aspect, this disclosure describes a device for detection of a pathogen. Generally, the device can include an analytical chamber, a sample reservoir in fluid communication with the analytical chamber, an article according to any one of the embodiments summarized above, and an image recorder.

In some embodiments, the device can further include a dielectrophoretic concentrator in fluid communication with and positioned between the analytical chamber and the sample reservoir. In some of these embodiments, a pump may be in functional communication with the sample reservoir. In some of these embodiments, the device further comprises a control processing unit in functional communication with the pump.

In some embodiments, the device can include a wash reservoir in fluid communication with the dielectrophoretic concentrator. In some embodiments, a pump may be in functional communication with the wash reservoir. In some of these embodiments, the device further comprises a control processing unit in functional communication with at least one of the pumps.

In some embodiments, the image recorder can include a camera such as, for example, a CCD. In some of these embodiments, the device can include a control processing unit such as, for example, a computer in functional communication with the image recorder. In some of these embodiments, the control processing unit comprises image processing software.

In some embodiments, the device can include a magnifying lens such as, for example, a microscope, functionally positioned between the article and the image recorder.

In some embodiments, the device can include an illumination source situated to illuminate the article.

In some embodiments, the device can include a user interface display functionally connected to the image recorder.

In some embodiments, the image recorder may be positioned for back-side imaging of the article.

The various device embodiments summarized separately above may be combined with any one or more additional embodiments where such combinations are practical.

In another aspect, this disclosure describes a method that generally includes contacting a biological sample that comprises at least one pathogen that is selectively bound by the one or more mutation-resistant ligands with the one or more mutation-resistant ligands for a time sufficient to allow the one or more mutation-resistant ligands to selectively bind the pathogen; and detecting the pathogen bound to the one or more mutation-resistant ligands. The one or more mutation-resistant ligands can be affixed to an article or device according to any embodiment summarized above, and the article or device can be incubated with the biological sample.

In some embodiments, detecting the pathogen bound to the one or more mutation-resistant ligands comprises labeling the bound pathogen and detecting the label. In some of these embodiments, the label can include a fluorescent label, an antibody label, a colorimetric label, a radiolabel, an enzymatic label, or any combination thereof.

In some embodiments, detecting the pathogen bound to the one or more mutation-resistant ligands comprises label-free detection. In some of these embodiments, label-free detection can include optical imaging.

In some embodiments, the one or more mutation-resistant ligands may be affixed to the substrate in a predetermined pattern and detection further can include recognizing the predetermined pattern produced by the pathogen selectively bound to the one or more mutation-resistant ligands. In some of these embodiments, the one or more mutation-resistant ligand can include a first mutation-resistant ligand that selectively binds to a first pathogen and is affixed to the substrate in a first predetermined pattern, and a second mutation-resistant ligand that selectively binds to a second pathogen and is affixed to the substrate in a second predetermined pattern, and detection includes recognizing the first predetermined pattern and the second predetermined pattern.

In some embodiments, recognizing the predetermined pattern can include using a Fourier transform algorithm, such as discrete Fourier transform, fast Fourier transform, or two-dimensional fast Fourier transform.

In some embodiments, the pathogen can include a bacterium, a virus, a parasite, a protozoan, a protist, or a fungus. Thus, in some embodiments, the pathogen can include a member of one the genera *Yersinia, Klebsiella, Providencia, Erwinia, Enterobacter, Salmonella, Serratia, Aerobacter, Escherichia, Pseudomonas, Shigella, Vibrio, Aeromonas, Streptococcus, Staphylococcus, Micrococcus, Moraxella, Bacillus, Clostridium, Corynebacterium, Eberthella, Francisella, Haemophilus, Bacteroides, Listeria, Erysipelothrix, Acinetobacter, Brucella, Pasteurella, Flavobacterium, Fusobacterium, Streptobacillus, Calymmatobacterium, Legionella, Treponema, Borrelia, Leptospira, Actinomyces, Nocardia, Rickettsia, Micrococcus, Mycobacterium, Neisseria,* or *Campylobacter*. In some embodiments, the pathogen may be, for example, a Papilloma virus, a Parvovirus, an Adenovirus, a Herpesviruse, a Vaccine virus, an Arenavirus, a Coronavirus, a Rhinovirus, a Respiratory syncytial virus, an Influenza virus, a Picornavirus, a Paramyxovirus, a Reovirus, a Retrovirus, a Rhabdovirus, or human immunodeficiency virus (HIV). Alternatively, the pathogen may be, for example, a member of one of the genera *Taenia, Hymenolepsis, Diphyllobothrium, Echinococcus, Fasciolopsis, Heterophyes, Metagonimus, Clonorchis, Fasciola, Paragonimus, Schistosoma, Enterobius, Trichuris, Ascaris, Ancylostoma, Necator, Wuchereria, Brugi, Loa, Onchocerca, Dracunculus, Naegleria, Acanthamoeba, Plasmodium, Trypanosoma, Leishmania, Toxoplasma, Entamoeba, Giardia, Isospora, Cryptosporidium, Enterocytozoa, Strongyloides,* or *Trichinella*. In some embodiments, the pathogen may be a fungus that is the causative agent of a condition such as, for example, Ringworm, Histoplasmosis, Blastomycosis, Aspergillosis, Cryptococcosis, Sporotrichosis, Coccidiodomycosis, Paracoccidioidomycosis, Mucomycosis, Candidiasis, Dermatophytosis, Protothecosis, Pityriasis, Mycetoma, Paracoccidiodomycosis, Phaeohphomycosis, Pseudallescheriasis, Trichosporosis, or Pneumocystis.

The various method embodiments summarized separately above may be combined with any one or more additional embodiments where such combinations are practical.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 8a shows a typical optical micrograph of a stamped chip after exposure to a solution containing $10^2$ of *Pseudomonas aeruginosa* per milliliter. FIG. 8b shows the light intensity histogram of part a. FIG. 8c shows the FFT apart a showing the emergence of a well-defined peak, indicating the presence of a periodic $\frac{1}{60}$ μm$^{-1}$ component in the image.

FIG. 9a shows typical darkfield micrograph of a stamped chip after exposure to a solution containing $10^4$ of *P. aeruginosa* per milliliter. FIG. 9b shows the light intensity histogram of part a. FIG. 9c shows the FFT of part a showing the emergence of well-defined peaks at integer multiples of $\frac{1}{60}$ μm$^{-1}$.

FIG. 12A shows affinity and lactose competition assay of peanut lectin binding to micro spheres conjugated with lactose-bishydrazide 6 using flow immunocytometry. FIG. 12B shows ELISA and competition assay of peanut lectin binding to immobilized 6-BSA.

FIG. 25a shows microscopic images of *M. smegmatis* captured onto mycobactin J-BSA immobilized gold chips according to different concentrations ($10^2$ to $10^7$ cfu/mL). FIG. 25b shows the FFT algorithm of images. FIG. 25c shows the data recalculated S/N for linear scale and before capture subtraction.

FIG. 27a shows microscopic images of *S. enterica* captured onto salmochelins-BSA immobilized gold chips according to different concentrations ($10^2$ to $10^8$ cfu/ml). FIG. 27b shows the FFT algorithm of images. FIG. 27c shows the data recalculated S/N for linear scale and before capture subtraction.

FIG. 30a shows microscopic images of *S. flexneri* captured onto aerobactin-BSA immobilized gold chips according to different concentrations ($10^2$ to $10^8$ cfu/ml). FIG. 30b shows the FFT algorithm of images. FIG. 30c shows the data recalculated S/N for linear scale and before capture subtraction.

FIGS. 36a and 4b show *S. aureus* incubation onto functionalized glass slides (CodeLink and Nexterion H, respectively) patterned with microarrays of 21-BSA, with 0.005 wt % Tween 20 in the print buffer. FIG. 36c shows *S. aureus* incubation onto glass slides patterned with 21-BSA microarray, printed without Tween 20. FIGS. 36d and 36e show control slides printed with microarrays of BSA and lactose-BSA respectively, after a 1-hour exposure to *S. aureus* at a concentration of $10^7$ cfu/mL. Scale bar=200 µm.

FIG. 37a shows 21-BSA in PBS only (no surfactant), with average spot size of 85±11 µm; FIG. 37b shows 21-BSA in PBS with 0.01% Tween 20, with average spot size of 58±1.4 µm. Images were acquired after drying but prior to washing.

FIG. 38a is a brightfield image of immobilized bacteria. FIGS. 38b and 38c are fluorescence images after staining with SYTO-9/P1 dyes ($\lambda_{em}$=500 and 635 nm, respectively). Scale bar=5 µm.

FIG. 40a is a bitmap image of a centroid map used to print binary arrays in alternating rows. Array elements are spaced 4 or 6 pixels apart along the x-direction (80 and 120 respectively); rows are spaced 4 pixels apart along the y-direction (80 µm). FIG. 40b is a darkfield image of the binary microarray after 1-hour exposure to *P. aeruginosa* ($10^6$ cfu/mL). FIG. 40c is a 2D-FFT analysis of the interdigitated array after image processing, with two well-defined fundamental harmonic peaks ($k_1$=1/120 µm$^{-1}$; $k_2$=1/80 µm$^{-1}$) and a second-order harmonic peak ($k'_1$=1/60 µm$^{-1}$).

FIG. 68 shows effects of washing on the amount of capture. A) Background image of a patterned substrate using a stamp pressure approximately 6.8 kPa (10× magnification). (B to D) The density of captured *Staphylococcus* (after 1 hour exposure at $10^8$ cfu/mL) as the images get farther from the rinsed edge (B to D) the density increases. The stamp used has periodicity of 20 µm (spacing of 10 µm).

FIG. 2(e-h) show capture of dead bacteria: confocal scanning microscopy image (×20 magnification) of the chip staining with (e) SYTO-9 dye (1) PI dye, confocal image (×60 magnification) of (g) SYTO-9 dyed, (h) merged SYTO-9/PI dyed. Staining of bacteria with intact cell membranes (a,c,e,g) and staining of bacteria with damaged membranes (b,f).

FIG. 95 shows fluorescent micropatterns corresponding to the successful capture of viral particles from an attenuated strain of A/H1N1 (swine flu), at $10^6$ particles/mL.

FIG. 96 shows fluorescent micropatterns corresponding to the successful capture of viral particles from an attenuated strain of A/H1N1 (swine flu), at $10^6$ particles/mL.

FIG. 97 shows plaques formed by influenza viruses on monolayer's of MDCK cells.

DETAILED DESCRIPTION OF ILLUSTRATIVE EMBODIMENTS

Figure 1:
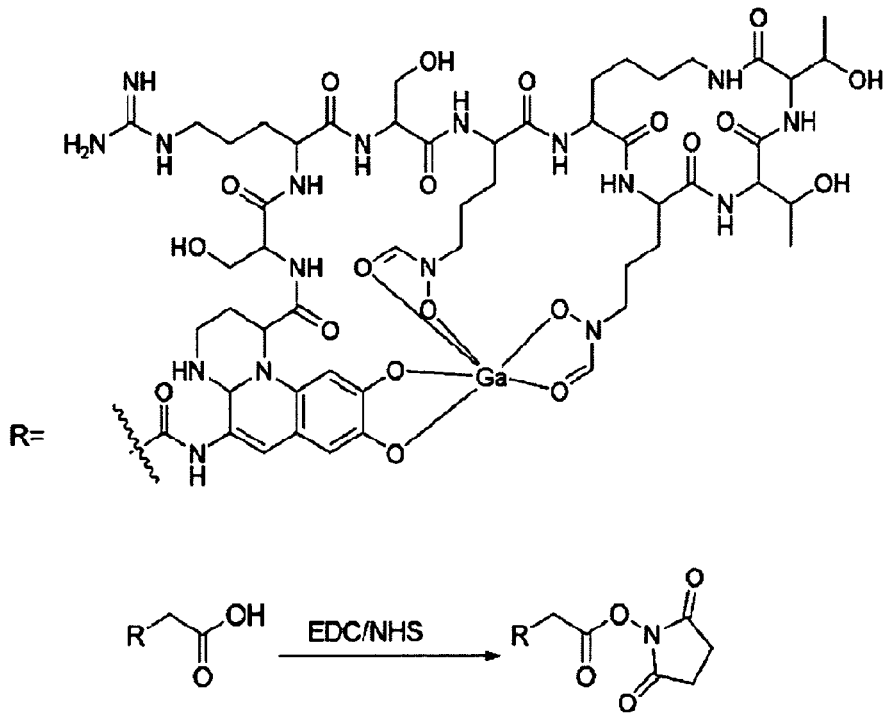
FIG. 1 shows EDC/NHS activation of pyoverdine, chelated with gallium.

In one aspect, the invention provides a mutation-resistant method for pathogen detection. Mutation-resistant ligands, also sometimes referred to as "immutable ligands," are used to detect pathogenic organisms, such viruses, bacteria, fungi, protozoa and the like. Pathogenic organisms can be referred to herein as pathogens. In one embodiment, a mutation-resistant ligand is immobilized onto or within, or affixed to, an article or device for pathogen detection, which article or device is then exposed to an air or liquid sample to allow binding of the pathogen. The detection device can be contacted with the sample for a predetermined time, or the sample can be pumped or otherwise moved across the device. The pathogen may be subsequently and optionally identified and/or quantified using any convenient method. Optionally, the bound pathogen can be labeled prior to detection, for example using an antibody label, a colorimetric label, a radiolabel, an enzymatic label, or any combination thereof.

Nonlimiting examples of mutation-resistant ligands include host cell surface molecules, such as sugars, glycoproteins, and the like, that the pathogen must bind in order to infect its host; nutrient molecules that the microbe must internalize in order to survive, such as a siderophore; and quorum sensing molecules.

Cell surface receptors to which an infectious microbe must bind in order to infect its host cell constitute one class ligands that should be both stable and mutation-resistant. On such exemplary mutation-resistant ligand is illustrated by the pulmonary trisaccharide (Gal($\alpha$1→4)Gal) (Imberty et al., Microb. Infect. 2004, 6:221-28) to which some respiratory pathogens bind prior to entry into alveolar epithelial cells. It is not easily denatured since it has no stable tertiary structure. Moreover, infectious microbes that harbor mutations that limit their ability to be detected by binding to pulmonary trisaccharide necessarily also compromise their ability to invade and infect their host cells. Thus, pathogens that can escape detection using such immobilized capture ligands will likely no longer be virulent and, therefore, less likely to present a public health concern.

Another class of mutation-resistant ligands includes, for example, compounds termed siderophores. Because iron uptake is essential for microbial growth and survival, pathogenic organisms synthesize and secrete low molecular weight iron chelating agents (i.e., siderophores) that bind free iron (III) present in their host and deliver it to siderophore receptors on the pathogen's cell surface for subsequent uptake by the pathogen (Faraldo-Gomez and Sansom, Nat. Rev. Mol. Cell. Biol. 2003, 4:105; Miethke and Marahiel, Microbiol Mol. Biol. Rev. 2007, 71:413; Ratledge and Dover, Ann. Rev. Microbiol. 2000, 54:881; Schaible and Kaufmann, Nat. Rev. Microbiol. 2004, 2:946). Because pathogens that fail to internalize host-derived iron also fail to survive, siderophores can be considered mutation-resistant ligands. While some pathogenic bacteria may recognize the same siderophore and most bacteria bind more than one siderophore, no two species of pathogen have been reported to recognize the same set of siderophores. Thus, determination of the set of siderophores that is recognized by an unknown pathogen should provide sufficient information to identify the pathogen.

In another aspect, the invention provides a device or article for pathogen detection. One exemplary article for pathogen detection is a chip, sometimes referred to as a "pathochip" which can contain an array of immobilized mutation-resistant ligands. The chip or other substrates or substrate surface onto which one or more mutation-resistant ligands have been immobilized or affixed, such as nanobeads or nanoparticles, gels, and the like, can be incorporated into a device for detection of pathogens, sometimes referred to herein as a "Patho-Test" device. An exemplary array and detection method are described in U.S. Pat. No. 7,867,754, issued Jan. 11, 2011. Optionally, a plurality of different mutation-resistant ligands may be employed. The different mutation-resistant ligands may bind the same pathogen, or they may bind different pathogens in order to facilitate a multiplexed analysis of the example. Optionally, the ligand is linked, covalently or non-covalently, to the article or device by means of a linker. Any suitable linker can be used. Exemplary linkers include organic molecules such as a polymer or copolymer (e.g., a substituted or unsubstituted polyalkylene glycol, such as polyethylene glycol), or biological molecules such as bovine serum albumin. Detection can be accomplished in any convenient manner, such as by optical means, electrochemical means, enzymatic means, colorimetric means, chemical means and the like. Optionally, detection can involve the use of a computer algorithm, such as a Fourier Transform.

The devices and methods of the invention can be used for environmental analysis, medical analysis (e.g., in a hospital or doctor's office), counterterrorism applications, and many other applications. An exemplary device for use in medical applications can, for example, be used to detect or screen for multiple sexually transmitted diseases, or multiple respiratory infections, or multiple gastrointestinal infections. An exemplary device for use in countering bioterrorism can be installed, for example, on a battlefield, in a public place such as a stadium, or within a water or air supply. The device is readily scalable for any desired application.

The device can be fabricated so as to be highly sensitive to allow identification and/or quantification of small levels of pathogen, for example in bioterrorism applications. Alternatively, the device can be fabricated such that is it less sensitive, and less expensive, thereby being more useful in general applications such as screening for gastrointestinal or sexually transmitted diseases in large populations.

Examples of various exemplary mutation resistant ligands which are useful to detect various exemplary pathogens, as well as various exemplary methods of detection, are described below. The descriptions and examples are nonlimiting and are intended to be representative of the invention. Other embodiments will be readily apparent to one of skill in the art, and are also encompassed by the invention.

Throughout this disclosure, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

Pathogen Detection Using an Exemplary Siderophore: Pseudomonas aeruginosa Detection Using the Siderophore, Pyoverdine In this example, we immobilize pyoverdine, a siderophore that Pseudomonas aeruginosa must bind to obtain iron, onto gold-plated glass chips and then examine the siderophore's ability to capture P. aeruginosa for its subsequent identification. We demonstrate that exposure of pyoverdine-coated chips to increasing dilutions of P. aeruginosa allows detection of the bacterium down to concentrations as low as $10^2$/mL. We further demonstrate that printing of the siderophore in a periodic pattern on the detection chip enables a sensitive method of detecting the bound pathogen by a Fourier transform analysis of light scattered by the patterned chip. Because unrelated bacteria are not captured on the pyoverdine chip, we conclude that pyoverdine can be exploited for the specific binding and identification of P. aeruginosa. It follows that the utilization of other microbe-specific "mutation-resistant ligands" may allow the specific identification of their cognate pathogens. See also Doorneweerd et al., "Selective Capture and Identification of Pathogenic Bacteria Using an Immobilized Siderophore," 2010 *Langmuir* 26(19):15424-15429.

With the emergence of increasingly virulent strains of many common pathogens, recent interest has been focused on the development of more rapid and reliable methods for detection and identification of the infectious microbes. Unfortunately, current tests for most pathogens require their proliferation in culture before they can be identified, usually by morphological and biochemical assays (Brock, *Milestones in Microbiology:* 1546 to 1940; ASM Press: Washington, D.C., 1999; MacFaddin, *Biochemical Tests for Identification of Medical Bacteria*; Williams & Wilkins: London, 1980; Madigan et al., *Brock Biology of Microorganisms*; Prentice Hall: Upper Saddle River, N J, 1997). Because pathogen proliferation can require hours, it is often not convenient to prevent a person from interacting in public (e.g., boarding a plane, attending school, etc.) to determine whether he or she might be infected with a disease-causing agent. Indeed, such strategies for disease containment will only be possible if rapid methods for pathogen identification are developed.

Whereas antibody-based detection strategies with rapid turnaround times have been described in the literature (Byrne et al., *Sensors* 2009, 9:4407-4445; Petrovick et al., *Lincoln Lab. J* 2007, 17:63-84; Rider et al., *Science* 2003, 301:213-215), such methods often suffer from the disadvantage that they become obsolete when the pathogen mutates its antigenic epitopes (Baigent and McCauley, *BioEssays* 2003, 25:657-671; Drake, *Proc Natl. Acad. Sci. U.S.A.* 1993, 90:4171-4175; Hensley et al., *Science* 2009, 326:734-736). In fact, some pathogens have even been misconstrued for another when they have mutated to express an epitope of the falsely identified species. Instead, we developed a new pathogen detection strategy that is based on a pathogen-specific ligand that the disease-causing organism must bind to remain virulent. We tested this strategy by immobilizing onto a chip a siderophore exploited by Pseudomonas aeruginosa to capture iron (i.e., pyoverdine) and explore whether it could specifically arrest and concentrate P. aeruginosa from dilute suspensions of the bacterium. In this example, we demonstrate that immobilized pyoverdine not only can detect P. aeruginosa but also can distinguish P. aeruginosa from other bacteria.

Because pathogenic organisms have nutritional requirements that must be satisfied to survive, many have evolved specialized mechanisms for acquiring essential nutrients from their hosts. One of the most limiting of the pathogen-required nutrients is $Fe^{3+}$, which because of its complexation by proteins (e.g., transferrin) and sequestration by macrophages (e.g., in response to hepcidin), is maintained at free concentrations of $\leq 10^{-9}$ M (Ratledge and Dover, *Annu. Rev. Microbiol.* 2000, 54:881-941; Raymond et al., *Proc. Natl. Acad. Sci. U.S.A.* 2003, 100:3584-3588). Not surprisingly, to survive under such $Fe^{3+}$-limiting conditions, many pathogens release one or more iron chelating agents, termed siderophores, that scavenge iron at concentrations as low as $10^{-16}$ M and then rebind the siderophores using a cell surface receptor dedicated to siderophore-iron uptake (Ratledge and Dover, *Annu. Rev. Microbiol.* 2000, 54:881-941; del Olmo et al., *J. Inorg. Biochem.* 2003, 97:384-387; Neilands, *J. Biol. Chem.* 1995, 270:26723-26726; Schalk, *J Inorg. Biochem.* 2008, 102:1159-1169). In the case of *Pseudomonas aeruginosa*, the most commonly released siderophores are pyoverdine and pyochelin, and the receptor involved in their retrieval is termed FpvA and FptA, respectively (Schalk, *J Inorg. Biochem.* 2008, 102:1159-1169; Cobessi et al., *J Mol. Biol.* 2005, 347:121-134; Cobessi et al., *J Mol. Biol.* 2005, 352:893-904; Heinrichs et al., *Infect. Immun.* 1991, 59:3680-3684; Poole et al., *J. Bacteriol.* 1993, 175:4597-4604; Schalk et al., *Mol. Microbiol.* 2001, 39:351-360; Shen et al., *J Bacteriol.* 2005, 187:8511-8515).

Use of Pyoverdine-BSA to Capture P. aeruginosa on a Microplate. To determine whether pyoverdine or pyochelin might be exploited to capture P. aeruginosa on a detector surface, pyoverdine was purified from P. aeruginosa culture, chelated with gallium, conjugated to BSA using carbodiimide chemistry, and purified as described in Example 1. The derivatized BSA was then diluted 1:1000 in PBS and examined in a UV-vis spectrophotometer ($\lambda_{max}$=430 nm) to estimate the number of pyoverdine molecules bound per BSA, which was found to be approximately 10 pyoverdine molecules per BSA.

To obtain an initial indication of the ability of pyoverdine-BSA to capture P. aeruginosa, pyoverdine-BSA was coated onto wells of a 96-well plate and incubated with suspensions of either P. aeruginosa or Escherichia coli ($10^7$ bacteria/mL). A relative measure of the quantity of bacteria captured in each well was then obtained by evaluation of the protein content in each well. Although the protein present in *E. coli*-containing wells averaged 3.8±3 mAu (a value that included both bacteria and immobilized pyoverdine-BSA), the protein measured in *P. aeruginosa*-containing wells averaged >27 mAu (i.e., more than 7 times the *E. coli* value). Moreover, in experiments where 1000-fold excess free pyoverdine-BSA was added to the wells prior to incubation with *P. aeruginosa*, the content of retained *P. aeruginosa* was reduced to background levels. These results provided early evidence that pyoverdine conjugated to BSA could dock with the pyoverdine receptor, FpvA, on *P. aeruginosa* cells and that a preparation of immobilized pyoverdine might be exploited to capture *P. aeruginosa* selectively onto a detector surface (Schons et al., *Biochemistry* 2005, 44:14069-14079). As used herein, "selective" and variations thereof refer to having a differential or a non-general (i.e., non-specific) affinity, to any degree, for a particular target as in the case just described in which immobilized pyoverdine selectively retained *P. aeruginosa* compared to *E. coli*.

Figure 2:
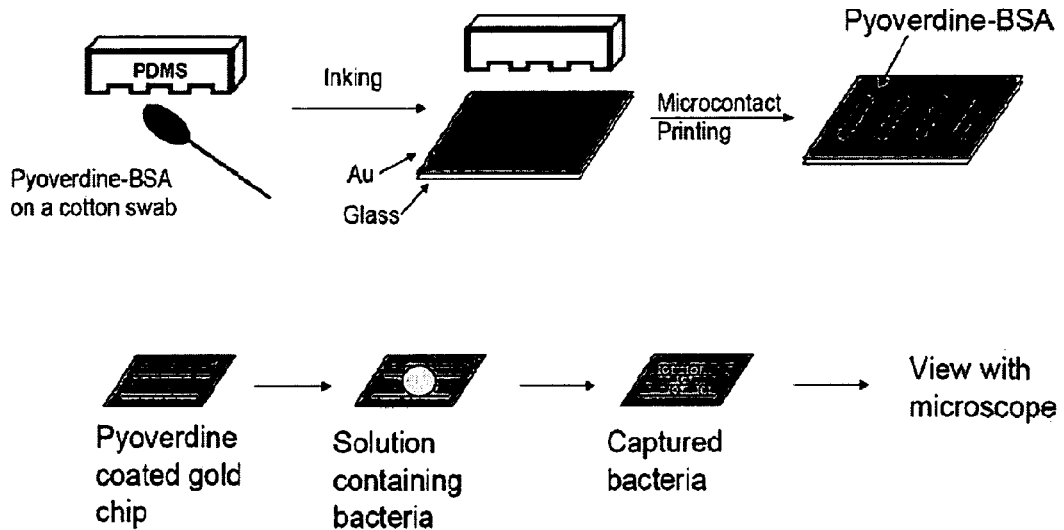
FIG. 2 shows a schematic diagram illustrating the procedure for patterning a sensor and capturing *Pseudomonas aeruginosa*.
Figure 3:
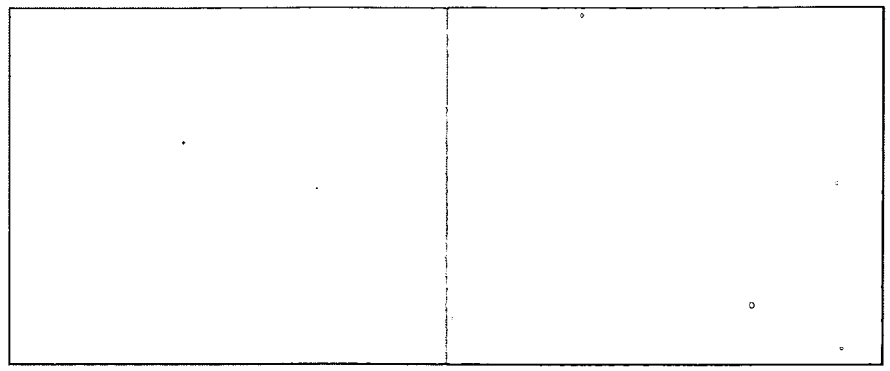
FIG. 3 shows bright field (left) and fluorescent (right) image of pyoverdine-BSA stamped surface.
Figure 4:
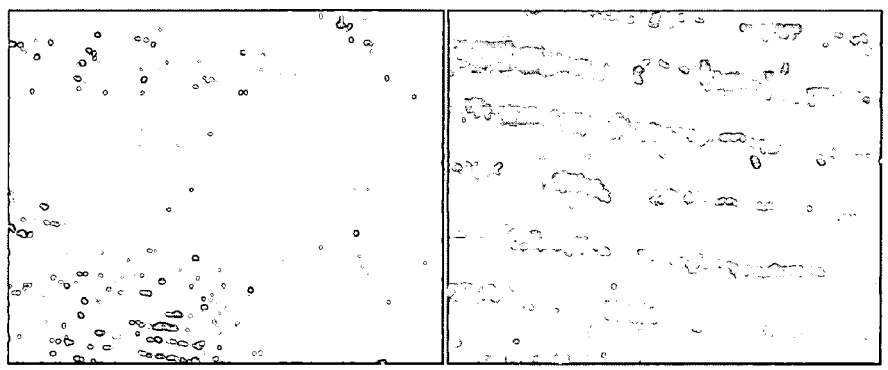
FIG. 4 show images of fluorescently labeled *Pseudomonas aeruginosa* incubated with a pyoverdine-BSA patterned surface. Low (10×) and high (40×) magnification are shown.

Pyoverdine-BSA Immobilized onto a Gold-Plated Glass Chip. After demonstrating that a pyoverdine-BSA conjugate had the capacity to bind *Pseudomonas aeruginosa*, we next examined whether the immobilized siderophore could also be used to arrest the same bacteria from an aqueous suspension onto a pyoverdine-patterned surface. For this purpose, pyoverdine-BSA (or unmodified BSA as a control) was applied onto a PDMS stamp that had been previously contoured with a pattern of repeating parallel ridges separated by 60 μm each (FIG. 2), and after allowing to dry, the stamp was contacted and gently pressed onto a gold-plated glass surface for 5 minutes. The chip was then incubated with a suspension of fluorescently labeled (DiO) *P. aeruginosa* for 45 minutes before washing and evaluation by brightfield and fluorescence microscopy. The stamp was peeled away to leave the banded pyoverdine-BSA replica attached to the gold surface (FIG. 3). To test for pathogen binding, suspensions of *P. aeruginosa* were then labeled with the fluorescent dye, DiO, and the bacteria were incubated with pyoverdine-BSA or nonderivatized BSA patterned chips. After the pyoverdine-BSA was allowed to dry, the stamp was contacted onto a gold-plated chip for 5 minutes. The chip was then incubated with a suspension of fluorescently labeled (DiO) *P. aeruginosa* for 45 minutes before washing and evaluation by fluorescence microscopy at 10× and 40× magnification. Examination of the chip surface by fluorescence microscopy revealed that retention of *P. aeruginosa* conformed to the periodic pattern of the siderophore on the chip, with minimal binding to non-functionalized regions of the surface (FIG. 4).

Figure 5:
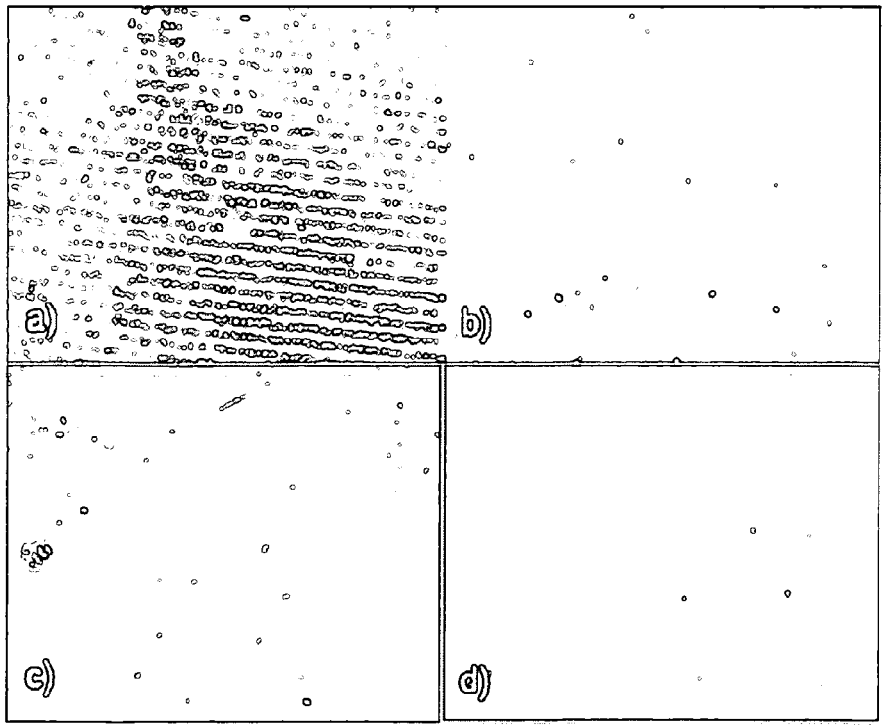
FIG. 5 shows *Pseudomonas aeruginosa* incubated with patterned (FIG. 5a) pyoverdine-BSA or (FIG. 5b) BSA alone, (FIG. 5c) *E. coli* and (FIG. 5d) *Y. enterocolitica* incubated on a pyoverdine-BSA functionalized surface.

Because fluorescence labeling of the bacteria prior to capture on a siderophore-patterned chip constituted a cumbersome, expensive, and time-consuming step, a reagent-free method of pathogen visualization was sought. Culture tubes containing 10 mL minimal media (composed of 6 g $K_2HPO_4$, 3 g $KH_2PO_4$, 1 g $(NH_4)_2SO_4$, 0.2 g $MgSO_4 \cdot 7H_2O$, and 4 g succinic acid per liter, and adjusted to pH 7.0 with 1 M NaOH prior to sterilization) were inoculated with *P. aeruginosa* and incubated for 24 hours at 28° C. with mechanical agitation. Bacteria were washed several times with phosphate buffered saline (PBS) prior to use for experiments. Stamping of the pattern was performed as described in FIG. 4. Images were obtained from light scattered by the captured bacteria using darkfield microscopy without the addition of any labeling reagents. Cells were at a concentration of $10^7$ cells/mL. Repeat experiments using nonfluorescently labeled bacteria surprisingly showed that unlabeled bacteria could be vividly visualized when the light scattered by bacteria on the patterned chip was examined by darkfield microscopy (FIG. 5a,b). Because control experiments using chips coated with BSA alone or pyoverdine-BSA in the presence of excess pyoverdine showed no bacteria binding, we conclude that unlabeled bacteria can be readily detected on thin gold-plated chips by darkfield analysis of light scattered from bacteria.

Finally, to investigate whether the detection methodology might also exhibit pathogen specificity, two FpvA negative bacteria, *Escherichia coli* and *Yersinia enterocolitica*, were also examined for their abilities to concentrate onto the pyoverdine-BSA patterned chips. As shown in the darkfield images of FIG. 5c,d, minimal patterned (siderophore-specific) binding was observed with either *E. coli* or *Y. enterocolitica*, suggesting that pyoverdine-BSA is capable of distinguishing bacteria that express a pyoverdine receptor from those that do not.

Effect of Pathogen Concentration on Pathogen Capture.

Figure 6:
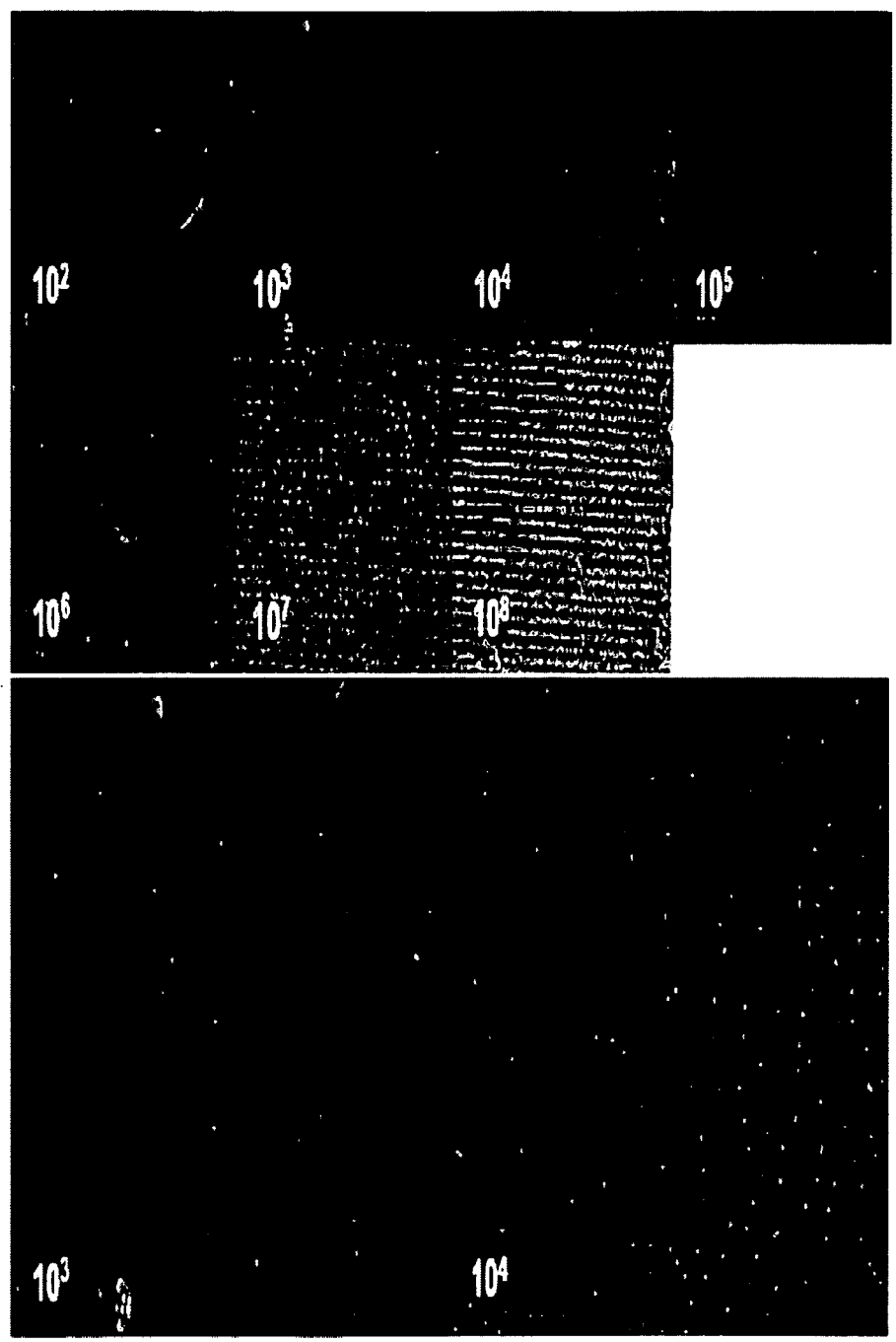
FIG. 6 shows an evaluation of the limit of visual detection of *P. aeruginosa* on pyoverdine-BSA patterned chips. Top two rows: different concentrations ($10^2$ to $10^8$ cells/mL) of *P. aeruginosa* were incubated for 45 minutes with the pyoverdine-BSA patterned chips prior to darkfield imaging. Bottom row: Enlarged view of patterned chips incubated with $10^3$ (left) or $10^4$ (right) cells/mL.

To obtain a preliminary indication of the sensitivity of the detection strategy, pyoverdine-derivatized chips were exposed to unlabeled *P. aeruginosa* suspensions ranging from $1 \times 10^8$ to $1 \times 10^2$ cells/mL and examined by darkfield microscopy for capture of the bacteria. Analysis of the micrographs revealed that a patterned distribution of bacteria could be observed down to concentrations as low as $10^4$ cells/mL, with some chips revealing detectable patterns down to $10^2$ cells/mL. With increasing concentrations of *P. aeruginosa*, an increase in bound bacteria was observed (FIG. 6), suggesting that the banding patterns can also yield quantitative information on the density of pathogens in a suspension.

Effect of Incubation Time on Bacteria Capture.

Figure 7:
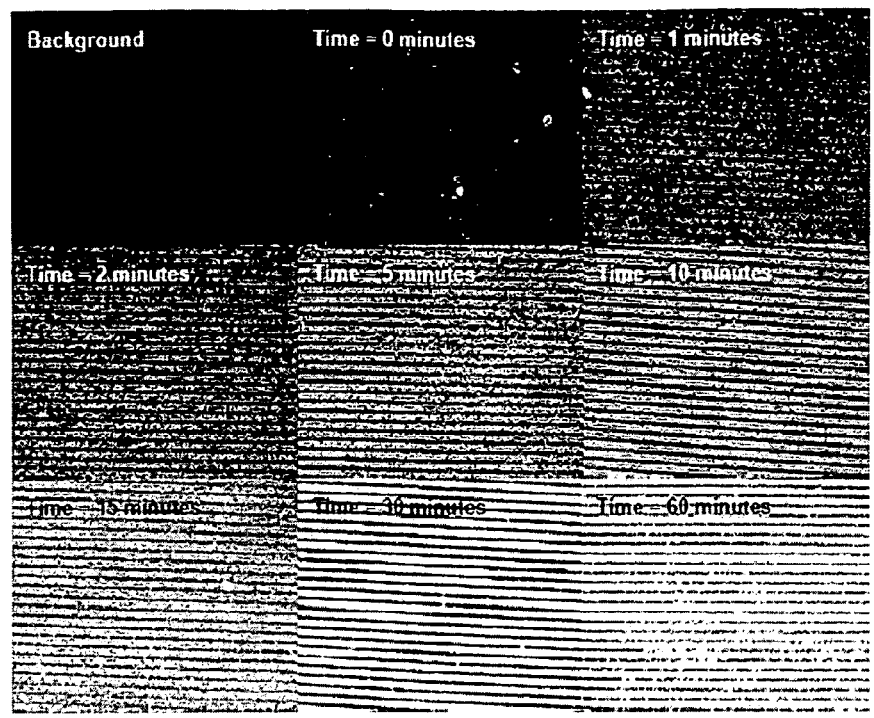
FIG. 7 shows the effect of time on the capture of *P. aeruginosa* of $1\times10^8$ cells/mL on a gold-plated chip patterned with pyoverdine-BSA.

In each of the preceding experiments, incubation of bacteria with a pyoverdine-derivatized surface was performed for 45 minutes. To determine the minimal time necessary for pathogen binding, we varied the incubation time from 0 to 60 minutes using a fixed concentration of unlabeled *P. aeruginosa* of $1 \times 10^8$ cells/mL and examined the chips for bacterial retention. Pattern formation becomes visible almost immediately following exposure to target bacteria (time="0 min") and is fully defined after 1 minute. Although capture of *P. aeruginosa* was found to increase gradually with increasing incubation time, evidence of specific *P. aeruginosa* binding was already observed as early as 1 minute after exposure to the chip. Images were obtained from light scattered by the captured bacteria using darkfield microscopy without the addition of any labeling reagents (FIG. 7). Moreover, binding was found to approach saturation within approximately 15 minutes of incubation. These data support that rapid pathogen analyses are possible using the ligand-patterned chip method, at least at higher pathogen concentrations (Schons et al., *Biochemistry* 2005, 44:14069-14079; Clement et al., *J. Biochemistry* 2004, 43:7954-7965).

Image Analysis.

Figure 8:
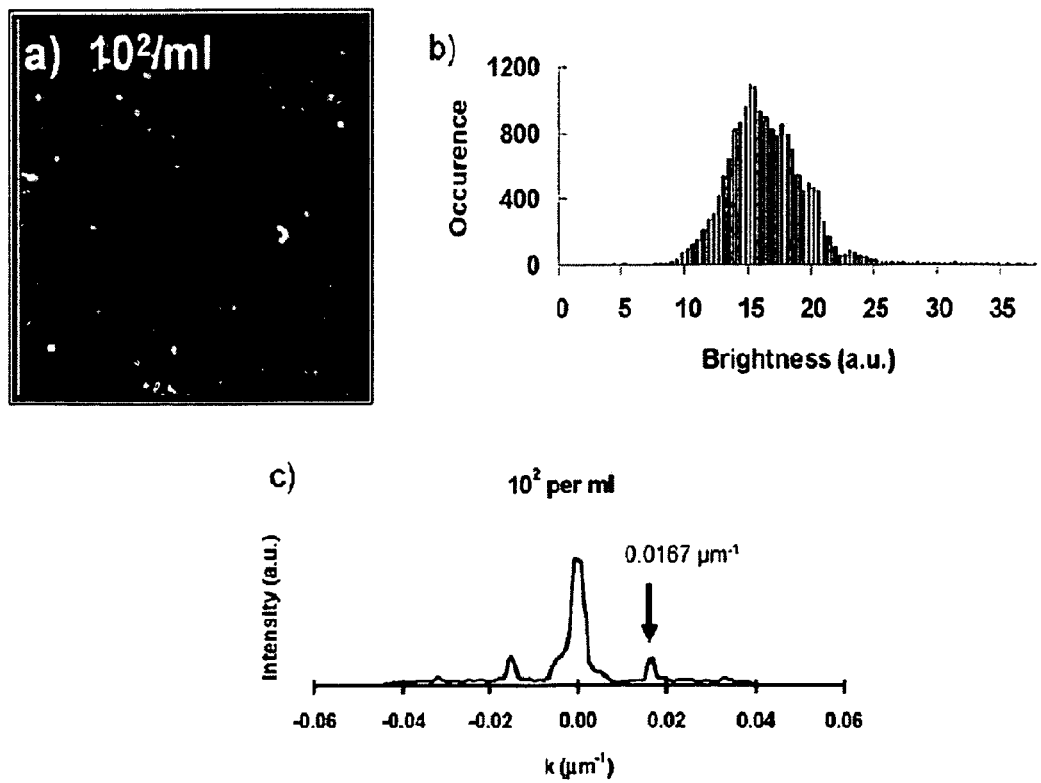
Figure 9:
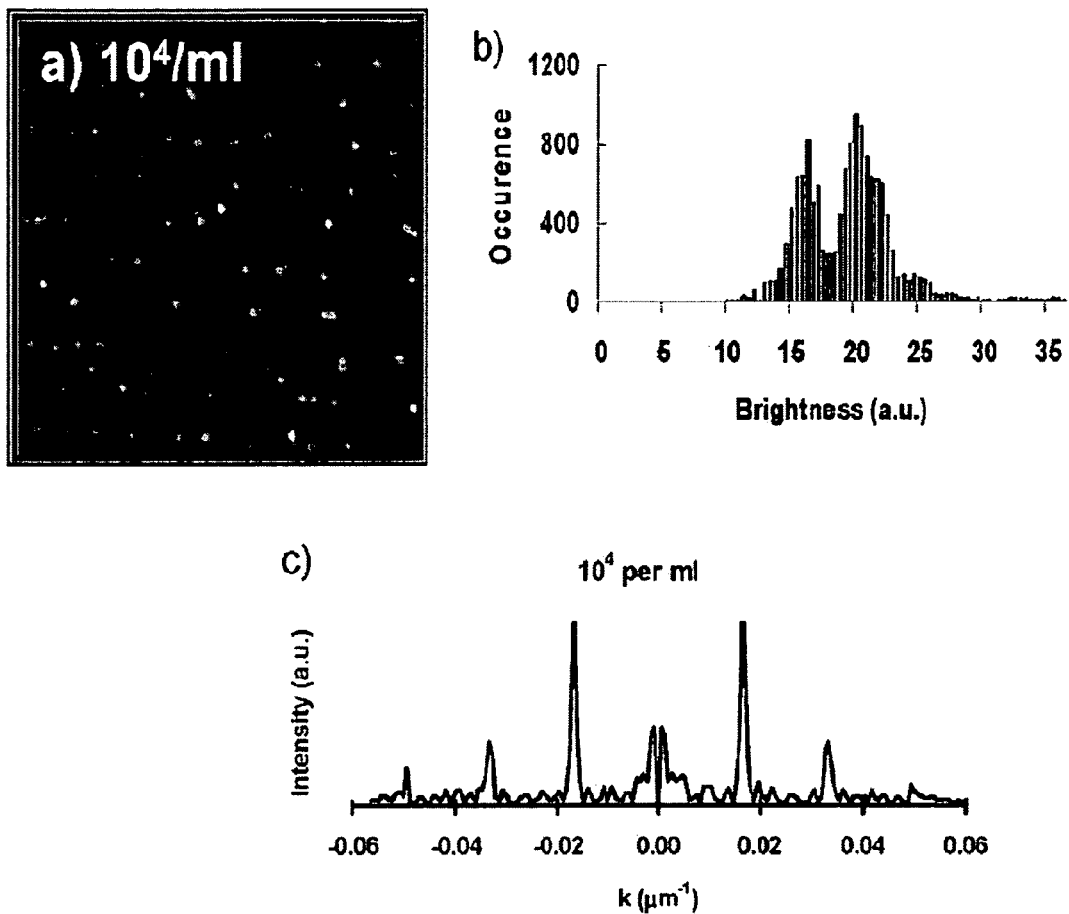

Although visual inspection of the pyoverdine-patterned chips permitted qualitative evaluation of the presence of bacteria, a more quantitative and automated method was desired for maximizing measurement reproducibility and objectivity. After considering a variety of image-processing algorithms for automated assessment of pathogen capture, we selected calculation of a simple intensity histogram for further optimization. Fortunately, with appropriate darkfield optics, the captured pathogen appeared bright against a dark background of pathogen-free surface because of enhanced light scattering by bacterial particles. Moreover, by scanning across an optical micrograph of the same chip, a histogram of light intensity could be constructed that would provide more quantitative information on pathogen capture. Therefore, if an intensity histogram was found to have a regularly repeating bimodal distribution indicating two levels of brightness, then it might be inferred that targeted pathogen binding had occurred. FIGS. 8b and 9b show the results of this histogram analysis. No contrast is observed for the $10^2$ bacteria per mL sample (FIG. 8b; indicating that the extent of *Pseudomonas aeruginosa* binding is sufficiently small that the histogram is unable to resolve the two levels of brightness in the image), whereas the $10^4$ per mL assay (FIG. 9b) clearly shows a bimodal distribution, indicating that the extent of *P. aeruginosa* binding is sufficient to resolve the two levels of brightness in the image and that specific pathogen binding has occurred.

A more sophisticated image processing algorithm, based on fast Fourier transform (FFT) of the same image, was then explored as a means of more quantitatively evaluating pathogen capture. This algorithm takes advantage of the known periodicity that is imposed by the PDMS stamping of the pyoverdine-BSA and subsequent capture of bacterial particles, which in these experiments was 60 µm. If the stamping forms a perfectly symmetric periodic pattern (30 µm bright, 30 µm dark) in one direction, then a 2D FFT should exhibit peaks at odd integer multiples of $\frac{1}{60}$ µm$^{-1}$ that are aligned in a direction determined by the precise orientation of the pattern with respect to the optical camera. If the stamping forms a periodic pattern with a periodicity of 60 µm having bright and dark regions unequal in length, then a 2D FFT should generally exhibit peaks at integer multiples of $\frac{1}{60}$ µm$^{-1}$.

The results of the FFT analysis are plotted in FIGS. 8c and 9c as a function of the reciprocal spacing k. FIG. 8c shows clearly the emergence of Fourier peaks at the expected position of $\frac{1}{60}$ µm$^{-1}$ for the $10^2$ per mL assay. This periodicity matches the periodicity of the stamped ligand for the capture of *Pseudomonas aeruginosa*. When the concentration of *P. aeruginosa* is increased to $10^4$ per mL, the signal-to-noise increases and the FFT reveals evidence of components at integer multiples of $\frac{1}{60}$ µm$^{-1}$ as shown in FIG. 9c, indicating that the PDMS stamping produces, on average, a pattern of bright and dark bands having different lateral dimensions. This periodicity matches the periodicity of the stamped ligand for the capture of *Pseudomonas aeruginosa*, demonstrating that specific pathogen binding has occurred. In principle, the magnitude of the Fourier transform peaks should scale with the concentration of *P. aeruginosa* bound to the chip, allowing a quantitative assessment of bacterial concentration. To implement such a quantitative assay successfully would require the production of identical stamped patterns on a number of Au-coated chips. At this time, such a demonstration is not practical because of variability in the surface of the thin film gold and/or pattern nonuniformity due to stamping.

*Pseudomonas aeruginosa* is a Gram-negative bacterium that causes septicemia in immune-compromised individuals. Although *P. aeruginosa* is considered primarily an opportunistic pathogen, fatalities arising from its infections exceed those of any other Gram-negative bacteria (Grisaru-Soen et al., *Pediatr. Infect. Dis. J.* 2000, 19:959-963; Matsumoto et al., *Clin. Diagn. Lab. Immunol.* 1999, 6:537-541); in fact, as many as 27% of *P. aeruginosa* sepsis cases are fatal (Kuikka and Valtonen, *Eur J. Clin. Microbiol. Infect. Dis.* 1998, 17:701-708). Whereas antibiotic therapy remains the most effective treatment for *P. aeruginosa*, the recent emergence of resistant strains suggests that early diagnosis and containment of the infection might prove to be important for control of the pathogen. Early diagnosis and containment is also likely to benefit the control of most other human pathogens. Thus, more specific and rapid methods of pathogen identification may improve the management of many contagious diseases. We have tested a novel, rapid, and specific method for pathogen detection and identification based on capture of the pathogen by an "mutation-resistant ligand" attached to a gold-plated chip. We immobilized a siderophore that the human pathogen, *P. aeruginosa*, binds to obtain iron from its environment. We demonstrated that pathogen binding is rapid (as rapid as 1 minute), sensitive (detection occurred at *P. aeruginosa* concentrations as low as $10^2$ cells/mL), and specific (*E. coli* and *Y. enterocolitica* were not captured, and underivatized BSA retained no bacteria). Alternative *P. aeruginosa* ligands can include, for example, other siderophores synthesized by *P. aeruginosa* (e.g., pyochelin) or a cell surface carbohydrate to which *P. aeruginosa* must bind to enter cells (e.g., GalNAc(β1→4)Gal or Fuc). Thus, in some embodiments, one may use an array of mutation-resistant ligands for use in the capture and identification of a large variety of human pathogens.

Furthermore, the captured pathogen may be further analyzed using conventional techniques including, for example, analyses with specific antibodies, genomic evaluation by PCR, pathogenicity testing following proliferation in growth media, and so on. In this respect, the "mutation-resistant ligand"-mediated pathogen capture methodology described here could easily be integrated into virtually any existing pathogen identification protocol.

A biochip-based method for pathogen identification has been developed through immobilization of a siderophore onto a gold-plated surface. The sensing device is composed of a functionalized biochip imaged with a standard darkfield microscope fitted with a CCD camera and a computer for Fourier transform analysis of the scattered light. Upon incubation with a suspension of *P. aeruginosa*, identification of the bacteria was possible under optimal conditions within 1 minute. Incorporation of the technology into a single diagnostic device with multiple flow channels, each functionalized with a distinct mutation-resistant ligand specific for its cognate pathogen, could conceivably enable rapid identification of a wide variety of human pathogens.

Pathogen Detection Using an Exemplary Cell Surface Ligand: Bishydrazide Glycoconjugates for Lectin Recognition As discussed in the preceding section, one viable approach to pathogen detection is to develop diagnostic technologies based on recognition of ligands presented on cell surfaces that are in some way associated with at least one of the pathogen's activities associated with virulence, so-called "mutation-resistant ligands" because they are often involved in early steps in the cycle of infection. The previous section demonstrated the usefulness of siderophores as a ligand for detecting and identifying pathogens. Alternative useful ligands include certain recognition elements such as, for example, certain low molecular weight molecules such as glycans, which are exploited by pathogens for gaining entry into their host cells. Pathogens must maintain this ligand affinity in order to remain virulent, as those pathogens that undergo mutations that disable recognition can no longer infect their target cells. Glycan-based strategies have proven to be particularly successful in detecting bacteria that use lectins for adhesion to host cell membranes (Stevens et al., *Nat. Rev. Microbiol.* 2006, 4:857-864; Wang et al., *J. Am. Chem. Soc.* 2006, 128: 13364-13365; El-Boubbou et al., *J. Am. Chem. Soc.* 2007, 129:13392-13393; Kale et al., *J. Am. Chem. Soc.* 2008, 130: 8169-8171; Liu et al., *Bioconjugate Chem.* 2009, 20:1349-1355; Disney and Seeberger, *Chem. Biol.* 2004, 11:1701-1707; Ngundi et al., *Exp. Rev. Proteom.* 2006, 3:511-524; Kulkarni et al., *Med. Res. Rev.* 2010, 30:327-393). Furthermore, the immutability of this functional recognition provides an important advantage over antibody-based detection schemes, which are susceptible to nonfunctional mutations that are often irrelevant to pathogen virulence.

Bishydrazides are versatile linkers for attaching glycans to substrates for lectin binding and pathogen detection schemes. The α,ω-bishydrazides of carboxymethylated hexa(ethylene glycol) 4 can be conjugated at one end to unprotected oligosaccharides, then attached onto carrier proteins, tethered onto activated carboxyl-terminated surfaces, or functionalized with a photoactive cross-linking agent for lithographic patterning. Glycoconjugates of bishydrazide 4 can also be converted into dithiocarbamates (DTCs) by treatment with CS2 under mild conditions, for attachment onto gold substrates. The immobilized glycans serve as recognition elements for cell-surface lectins and enable the detection and capture of bacterial pathogens such as Pseudomonas aeruginosa by their adsorption onto micropatterned substrates. A detection limit of $10^3$ cfu/mL is demonstrated, using a recently introduced method based on optical pattern recognition. See also Adak et al., "Bishydrazide Glycoconjugates for Lectin Recognition and Capture of Bacterial Pathogens," 2010 Bioconj. Chem. 21:2065-2075.

Glycoconjugates are also of considerable importance for high-throughput diagnostics or screening of carbohydrate-binding proteins associated with various biological functions or disease states (Wu et al., Org. Biomol. Chem. 2009, 7:2247-2254; Laurent et al., Chem. Comm. 2008, 4400-4412; Park et al., Chem. Commun. 2008, 37:4389-4399; Horlacher and Seeberger, Chem. Soc. Rev. 2008, 37:1414-1422). Several different covalent chemistries have been successfully implemented for surface functionalization, such as thiol-ene and thiol-maleimide additions (Park et al., J. Am. Chem. Soc. 2004, 126:4812-4819; Park and Shin, Angew. Chem., Int. Ed. 2002, 41:3180-3182; Ratner et al., ChemBioChem 2004, 5:1375-1383; Houseman et al., Langmuir 2003, 19:1522-1531), Diels-Alder or Cu-catalyzed Huisgen cycloadditions (Houseman and Mrksich, Chem. Biol. 2002, 9:443-454; Bryan et al., J. Am. Chem. Soc. 2004, 126:8640-8641; Michel and Ravoo, Langmuir 2008, 24:12116-12118), nucleophilic addition to epoxides and isothiocyanates (Lee and Shin, Angew. Chem., Int. Ed. 2005, 44:2881-2884; Park and Shin, Org. Lett. 2007, 9:1675-1678), amide bond ligation (Blixt et al., Proc. Natl. Acad. Sci. U.S.A. 2004, 101:17033-17038; De Paz et al., J. Am. Chem. Soc. 2006, 128:2766-2767), and Staudinger ligation (Köhn et al., Angew. Chem., Int. Ed. 2003, 42:5830-5834). However, many of these methods require that glycans be in a protected form prior to linker installation and may involve multiple synthetic or purification steps.

Chemoselective coupling of bifunctional linkers to underivatized glycans is an attractive option, particularly if the reducing-end sugar can be retained in its native cyclized form. Traditional methods involve covalent attachment to the free hemiacetal via reductive amination or glycation, but while the conditions are mild, they sacrifice the reducing-end sugar by generating an open-chain structure (Hermanson, Bioconjugate Techniques, 2nd ed., Academic Press: San Diego, Calif.; 2008; Xia et al., Nat. Methods 2005, 2:845-850). However, weakly basic nucleophiles like aminooxy ethers ($H_2NO$—R, MeHNOR) and hydrazides ($H_2NNHCO$—R) have been shown to condense with hemiacetals in aqueous solutions for efficient glycoconjugation (Lee and Shin, Org. Lett. 2005, 7:4269-4272; Park et al., Bioconjugate Chem. 2009, 20:155-162; Zhi et al., Anal. Chem. 2006, 78:4786-4793; Bohorov et al., Glycobiology 2006, 16:21C-27C; Liu et al., Chem. Biol. 2007, 14:847-859; Chen and Pohl, Org. Lett. 2008, 10:785-788; Clo' et al., Eur. J. Org. Chem. 2010, 540-554; Thygesen et al., Chem. Eur. J. 2009, 15:1649-1660; Cervigni et al., Angew. Chem., Int. Ed. 1996, 35:1230-1232; Zhao et al., Proc. Natl. Acad. Sci. U.S.A. 1997, 94:1629-1633; Zhi et al., ChemBioChem 2008, 9:1568-1575; Guillaumie et al., Bioconjugate Chem. 2002, 13:285-294; Lohse et al., Angew. Chem., Int. Ed. 2006, 45:4167-4172). Hydrazides have been widely used for bioconjugation onto aldehyde or carboxyl-presenting surfaces (Hermanson, Bioconjugate Techniques, 2nd ed., Academic Press: San Diego, Calif.; 2008); conversely, hydrazides can also be presented on substrates for the specific generation of carbohydrate microarrays.

Here, we investigate α,ω-bishydrazides as bifunctional linkers for conjugating underivatized glycans onto various substrates and present several surface functionalization methods with application toward the binding of lectins and pathogenic bacteria. Bishydrazides can be useful as chelating agents or as supramolecular recognition motifs (Bacchi et al., Inorg. Chim. Acta 2006, 359:2275-2280; Dydio et al., J. Org. Chem. 2009, 74:1525-1530), but are most often applied as polymer or biopolymer cross-linking agents (Bystrický et al., Glycoconjugate J. 1999, 16:691-695; Urmenyi et al., J. Membr. Sci. 2005, 259:91-102; Ono et al., Chem. Comm. 2007, 46-48). At first glance, bishydrazides appear to be an unlikely choice for heterofunctionalization; however, we find that they can be selectively monofunctionalized and are versatile linkers for glycoconjugate chemistry.

In this work, we use glycan-bishydrazide conjugates to target specific lectins and adhesins found in Pseudomonas aeruginosa, an opportunistic, Gram-negative bacteria often found in hospital settings. Nosocomial Pseudomonas infections have become increasingly drug-resistant and can be especially pernicious in immunocompromised patients or those suffering from cystic fibrosis, so there is a strong need to develop detection platforms against this pathogen. Epidemiological studies suggest that the risk of Pseudomonas infections in healthy individuals increases with environmental pathogen counts above $10^3$ cfu/mL (Price and Ahearn, J. Clin. Microbiol. 1988, 26:1650-1654; Guidelines for safe recreational water environments. Vol 2: Swimming pools and similar environments. pp 43-45, World Health Organization: Geneva, Switzerland; 2006). We address this important public health concern by focusing on glycan recognition as a mechanism for detecting virulent pathogens such as, for example, Pseudomonas at densities as low as $10^3$ cfu/mL, the estimated threshold for nosocomial infection.

The preparation of bishydrazide cross-linkers have been previously reported in the literature, but with little detail regarding their purification (Vercruysse et al., Bioconjugate Chem. 1997, 8:686-694). We found bis(carboxymethyl) esters to be practical intermediates for bishydrazide formation, but hydrazinolysis should be performed under strictly anhydrous conditions to avoid the generation of byproducts during glycoconjugate formation. Bishydrazide linkers 4 and 5 were synthesized from their corresponding α,ω-diols by base-promoted carboxymethylation with ethyl bromoacetate in THF, followed by treatment with excess hydrazine in anhydrous methanol under an inert atmosphere. The bishydrazides prepared in this manner could be collected in nearly quantitative yields simply by removing all volatiles by azeotropic drying with toluene, then used to generate glycoconjugates without further purification.

Scheme 1. Synthesis of Glycan-Bishydrazide Conjugates.

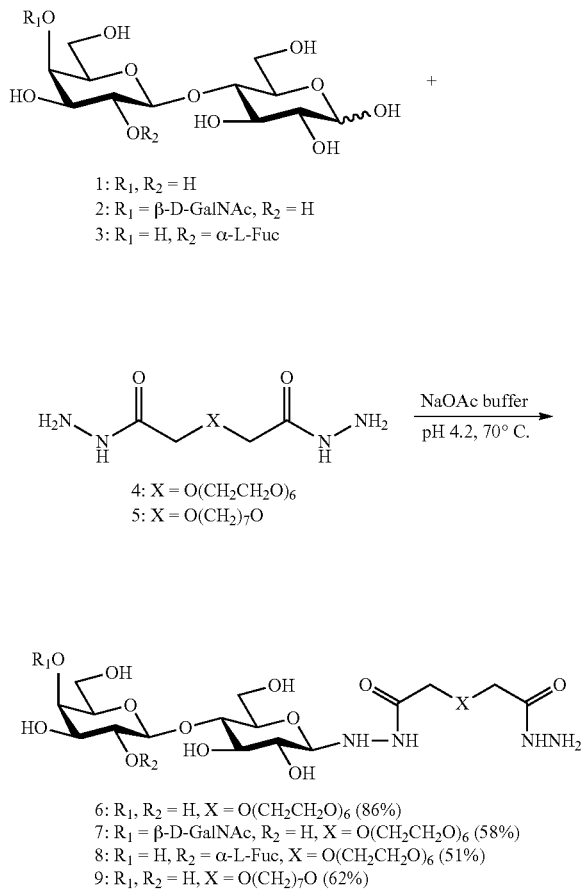

Glycan-bishydrazide conjugates were prepared by adapting the conditions reported by Shin and co-workers (Scheme 1) (Lee and Shin, *Angew. Chem., Int. Ed.* 2005, 44:2881-2884; Park and Shin, *Org. Lett.* 2007, 9:1675-1678). After an extensive evaluation of reaction conditions using hexa(ethylene glycol)-linked bishydrazide 4 and commercial-grade lactose, we determined that the highest yields were obtained by treating 1 equivalent of glycan in AcOH/NaOAc buffer (pH 4.2) with 10 equivalents of bishydrazide linker at 70° C. for 48 hours. The glycoconjugates were readily separated from the excess linker by preparative reverse-phase HPLC using an aqueous $CH_3CN$ gradient. $^{13}C$ NMR analysis of lactose-bishydrazide conjugate 6 indicated the anomeric carbons to have the expected chemical shifts for O,O- and N,O-acetals (δe 105.10 and 91.89 ppm, respectively), confirming the pyranosidic nature of the reducing-end sugar. $^1H$ NMR coupling constant analysis indicated that the bishydrazides form β-glycoside linkages, in accord with earlier reports (Leteux et al., *Glycobiology* 1998, 8:227-236; Shinohara et al., *Anal. Chem.* 1996, 68:2573-2579; Ojala et al., *Carbohydr. Res.* 2002, 337:21-29; Flinn et al., *Bioconjugate Chem.* 2005, 16:722-728). It should be noted that the formation of bishydrazide glycoconjugates 7 and 8 is not always complete after 48 hours under these conditions; on the other hand, the formation of glycan dimers is negligible, circumventing the need for heterobifunctional linkers.

Glycan-bishydrazide conjugates 7 and 8 were prepared using GalNAc(β1→4)-Gal(β1→4)Glc (2) and 2'-fucosyllactose (Fuc-(α1→2)Gal(β1→4)Glc, 3), with the former obtained through multistep organic synthesis (see below). Trisaccharide 2 is a common substructure in the glycans presented on the epithelial lining of the pulmonary tract and is a high-affinity ligand for adhesins presented on the pili of virulent *Pseudomonas* (Krivan et al., *Proc. Natl. Acad. Sci. U.S.A.* 1988, 85:6157-6161; Yu et al., *Infect. Immunol.* 1994, 62:5213-5219). Fucose-presenting glycans such as 3 have been shown to be potent ligands for the lectin PA-IIL, also expressed by *Pseudomonas* (Mitchell et al., *Nat. Struct. Biol.* 2002, 9:918-921; Imberty et al., *Microb. Infect.* 2004, 6:221-228). These glycans presented us an opportunity to evaluate the bishydrazide glycoconjugate chemistry in the context of bacterial pathogen detection.

Briefly, pulmonary trisaccharide 2 was synthesized by the coupling of N-trichloroacetyl-protected GalNAc donor 10 (Bélot and Jacquinet, *Carbohydr. Res.* 2000, 325:95-106) with lactose-derived acceptor 11 (Matsuoka et al., *Carbohydr. Polym.* 2007, 69:326-335) and N-iodosuccinimidetriflic acid activation conditions, yielding the desired glycoside 12 in 86% yield (Scheme 2, see Experimental Procedures section for details). Reductive dechlorination with tributyltin hydride, followed by methanolic deacetylation and global debenzylation, yielded trisaccharide 2 in excellent overall yields.

Scheme 2. Synthesis of Pulmonary Trisaccharide (TCA = trichloroacetyl).

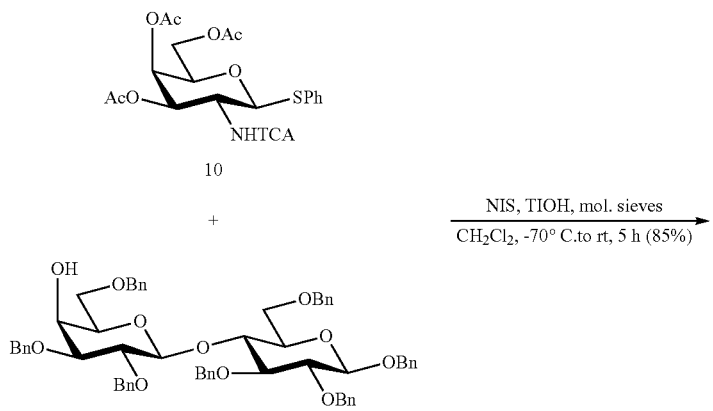

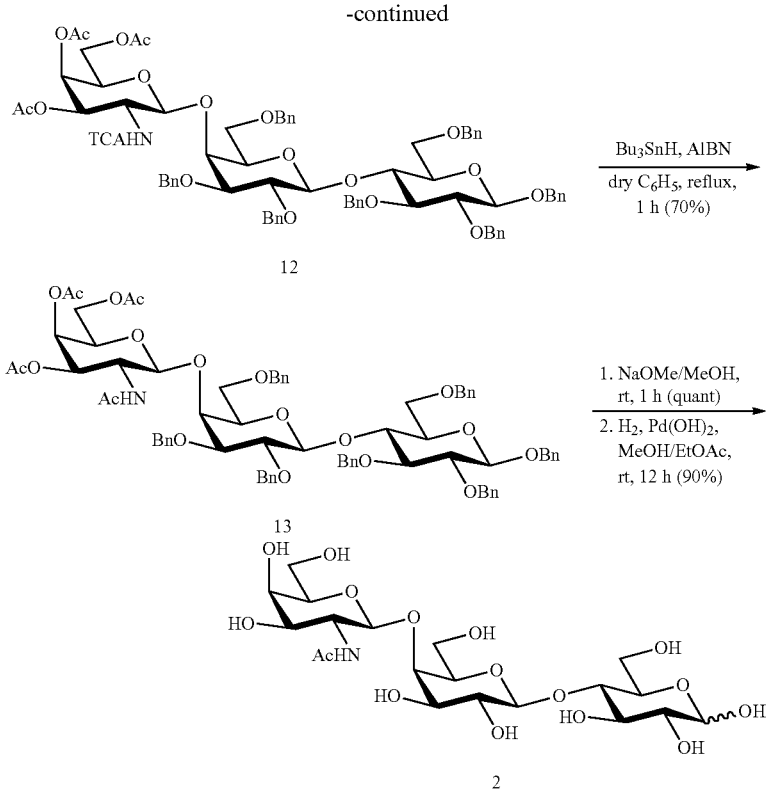

Figure 10:
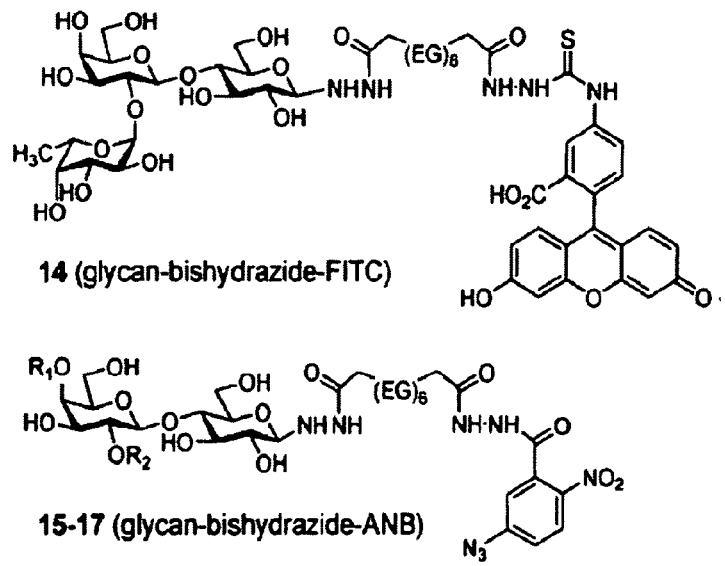
FIG. 10 shows glycan-bishydrazide conjugates labeled with fluorescent or photoreactive chromophores. $(EG)_6$=—O$(CH_2CH_2O)_6$—. 15: R1, R2=H. 16: R1=β-D-GalNAc, R2=H. 17: R1=H, R2=α-L-Fuc.

The glycan-bishydrazide conjugates react readily with standard labeling and bioconjugation reagents. Fluorescent glycoconjugate 14 was generated by treatment of 2'-fucosyl-lactose-bishydrazide 8 with fluorescein isothiocyanate (FITC), whereas photoreactive glycoconjugates 15-17 were produced by coupling bishydrazide-linked glycans 6-8 with N-(5 azido-2-nitrobenzoyloxy)succinimide (ANB-NOS) (FIG. 10). In both of these cases, hydrazide coupling was most efficient in anhydrous polar solvents such as DMF and MeOH, using N,N-diisopropylethylamine as the base (see Experimental Procedures section for details). Neoglycoproteins could also be formed in phosphate-buffered saline (PBS) solutions at physiological pH using typical EDC coupling conditions (Lohse et al., Angew. Chem., Int. Ed. 2006, 45:4167-4172), and stored at 4° C. for several months.

Figure 11:
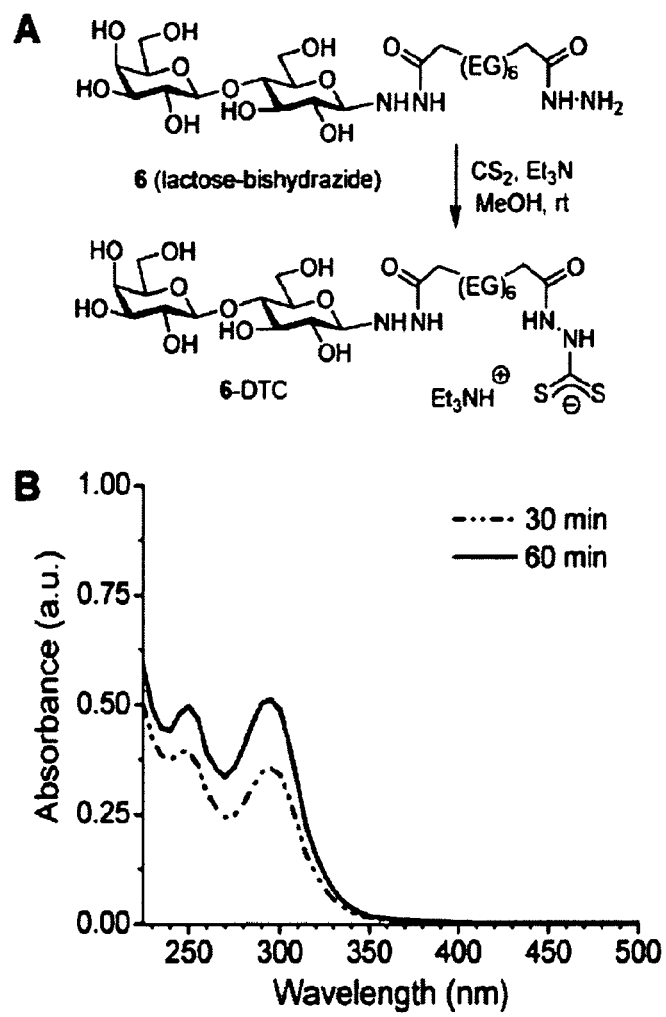
FIG. 11A shows in situ DTC formation starting from lactose-bishydrazide conjugate 6; $(EG)_6$=O$(CH_2CH_2O)_6$.
FIG. 11B shows UV absorption spectra of 6-DTC in dilute aqueous solution, taken during in situ DTC formation. No further increases in peak intensities were observed after 60 minutes.

The hydrazide-terminated glycoconjugates are also amenable to in situ dithiocarbamate (DTC) formation, a recently established method for anchoring amine-terminated ligands onto metal surfaces (Zhao et al., J. Am. Chem. Soc. 2005, 127:7328-7329; Zhu et al., Langmuir 2008, 24:8660-8666; Huff et al., Langmuir 2007, 23:1596-99; Huff et al., Nanomedicine 2007, 2:125-132; Zhao et al., Langmuir 2009, 25:13833-13839; Guerrini et al., Anal. Chem. 2009, 81:953-960; Cao et al., J. Am. Chem. Soc. 2007, 129:6927-6930; Park et al., Adv. Mater. 2009, 21:2323-2325; Patel et al., Chem. Comm. 2009, 1849-1851; Morf et al. Langmuir 2006, 22:658-663). DTCs are conveniently prepared by the addition of nucleophilic amines to $CS_2$ in polar organic or aqueous media and exhibit a strong binding affinity for gold and several types of inorganic oxides. Bishydrazide-DTCs can be prepared in a similar fashion: in this work; an equimolar mixture of lactose-bishydrazide conjugate 6, $CS_2$, and $Et_3N$ in methanol resulted in essentially quantitative formation of DTC triethylammonium salt within 1 hour under ambient conditions (6-DTC, FIG. 11). The reaction time was determined by using UV absorption spectroscopy to monitor hydrazide-DTC formation based on increases in characteristic peak intensities at 250 and 292 nm (Lee et al., Anal. Chim. Acta 1989, 218:157-160).

Figure 12:
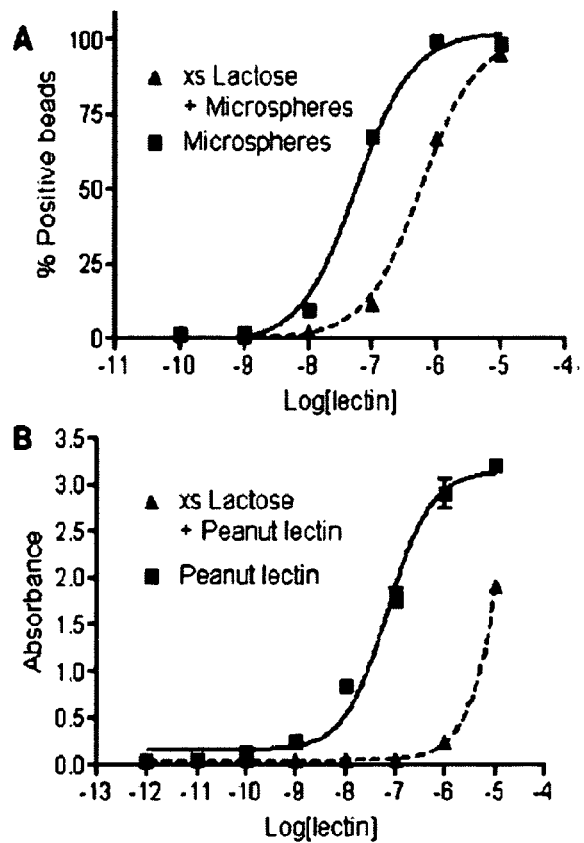
FIG. 12). Positive binding determined by degree of peak overlap between immunolabeled beads and negative control.
Figure 13:
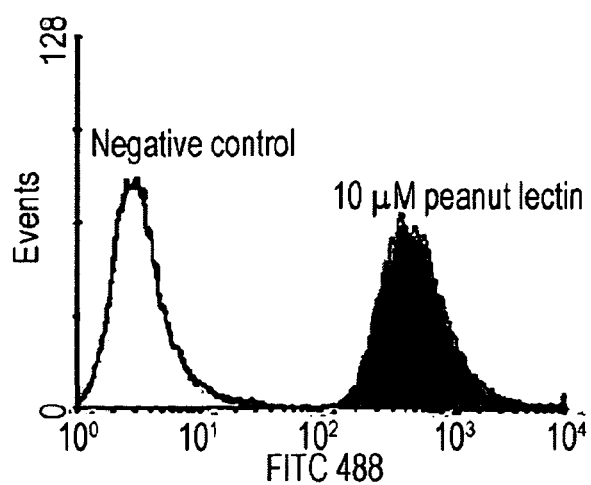
FIG. 13 shows Representative data from flow immunocytometry demonstrating peanut lectin binding to microspheres conjugated with lactose-bishydrazide 6 (cf.

Bishydrazide glycoconjugates can be directly attached onto surface-active substrates for the selective capture of lectins and subsequent binding immunoassays. For example, lactosebishydrazide 6 was attached onto NHS-activated latex microspheres in order to measure the binding affinity of peanut lectin by flow immunocytometry ($K_d$)) 50 nM), using a FITC-labeled secondary antibody for fluorescence detection (FIGS. 12A and 13). Selective binding was established by a competition assay against 1 mM lactose, which increased $K_d$ by 10-fold. However, in some cases the use of carrier proteins such as BSA may be more convenient for surface functionalization by simple physisorption. An ELISA of 6-BSA conjugate indicates its affinity for peanut lectin to be the same as that measured for lactose-conjugated microspheres.

Figure 14:
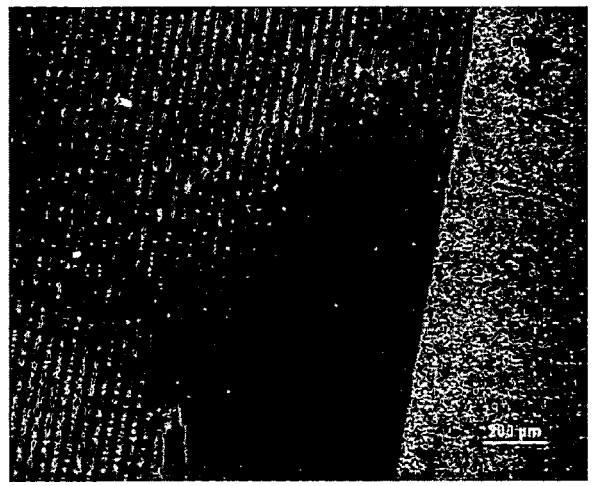
FIG. 14 shows fluorescence immunostaining of peanut lectin bound to lactosebishydrazide-ANB conjugate 15, photopatterned onto a BSA-coated substrate by UV irradiation (λ=254 nm) through a quartz mask.

Glycoconjugates can also be covalently tethered onto protein layers and other organic substrates by photo-cross-linking, which provides opportunities to create glycan microarrays and micropatterns by photolithography (Ito, Biotechnol. Prog. 2006, 924-932; Carroll et al., Glycoconjugate J. 2008, 25:5-10; Carroll et al., Langmuir 2006, 22:2899-2905; Liu et al., Bioconjugate Chem. 2009, 20:1349-1355; Norberg et al., Bioconjugate Chem. 2009, 20:2364-2370). Gold substrates coated with a monolayer of BSA were immersed in a solution of lactosebishydrazide-ANB conjugate 15, then dried in air and exposed to UV irradiation through a photomask. The intermediate nitrenes that are generated upon UV irradiation (Lewis et al., Biochemistry 1977, 16:5650-5654) presumably insert into the amino acid side chains of the immobilized BSA, resulting in a patterned array of glycans after washing away the unexposed ligands. Incubation with peanut lectin followed by fluorescence immunostaining revealed well-defined line patterns, defined by the photomask features (FIG. 14).

Figure 15:
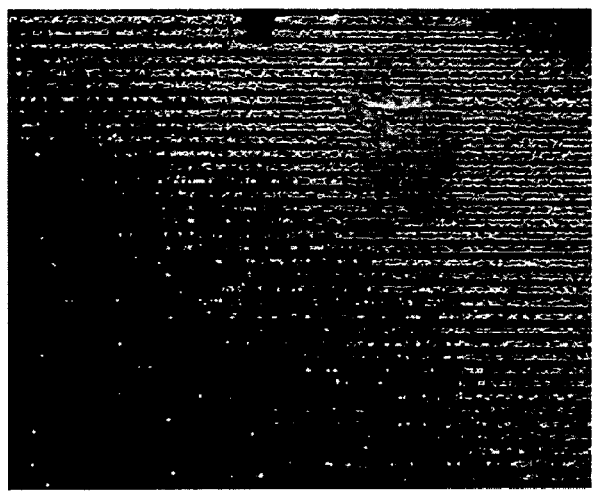
FIG. 15 shows capture of *Pseudomonas* on BSA-coated substrates with photopatterned glycan-bishydrazide-ANB conjugate, imaged by darkfield microscopy. Bacterial capture mediated by 2'-fucosyllactose conjugate 17 at $10^8$ cfu/mL; grating period a=20 μm.
Figure 16:
FIG. 16 shows capture of *Pseudomonas* on BSA-coated substrates with photopatterned glycan-bishydrazide-ANB conjugate, imaged by darkfield microscopy. Bacterial capture at $10^6$ cfu/mL, using pulmonary trisaccharide conjugate 16.
Figure 17:
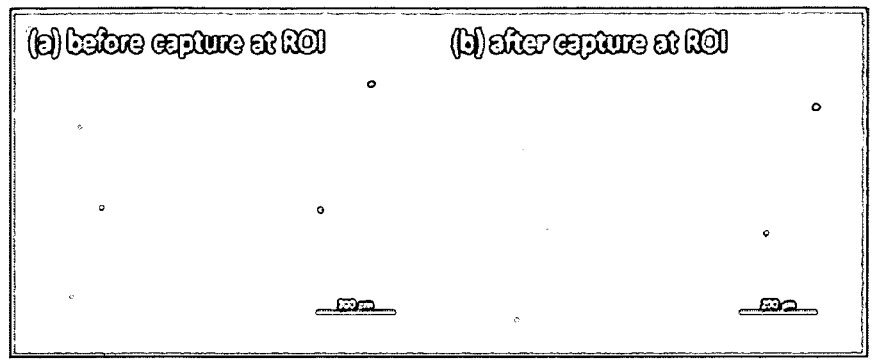
FIG. 17 shows control study showing no *Pseudomonas* capture by substrates patterned with lactose-bishydrazide conjugate. Darkfield images of patterned region of interest (ROI) (a) before and (b) after exposure to *Pseudomonas* for 1 hour at $10^6$ cfu/mL.
Figure 18:
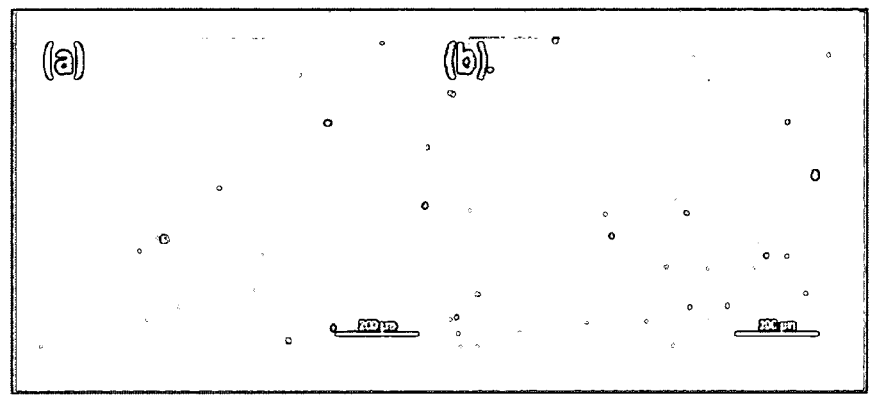
FIG. 18 shows Control study showing no capture of UV-irradiated *Pseudomonas* (2 hours, $\lambda_{max}$=254 nm) by substrate patterned with pulmonary trisaccharide-BSA conjugate (7-BSA). Darkfield images of patterned ROI, (a) before and (b) after exposure to UV-irradiated *Pseudomonas* ($10^6$ cfu/mL).

A similar approach was used to generate photopatterned arrays of the pulmonary trisaccharide and 2'-fucosyllactose on BSA-coated substrates, using glycan-bishydrazide-ANB conjugates 16 and 17, respectively. These micropatterned substrates were exposed to the opportunistic pathogen *Pseudomonas aeruginosa* at $10^6$-$10^8$ cfu/mL, then washed and imaged by optical darkfield microscopy to visualize patterns of glycan-immobilized bacteria in a label-free manner (FIGS. 15-17). Specificity for 16 and 17 was confirmed by introducing *Pseudomonas* to control substrates patterned with lactose-bishydrazide conjugate, which resulted in no apparent binding. Furthermore, only live *Pseudomonas* were captured by the trisaccharide ligands; exposing the bacteria to UV irradiation for 2 hours prior to their introduction resulted again in no observable pattern (FIG. 18). We note that the patterns formed by bacterial adhesion at lower pathogen densities can be well below saturation levels; however, our pathogen detection method only requires a fill factor of a few percent for pattern recognition, as will be discussed below.

Figure 19:
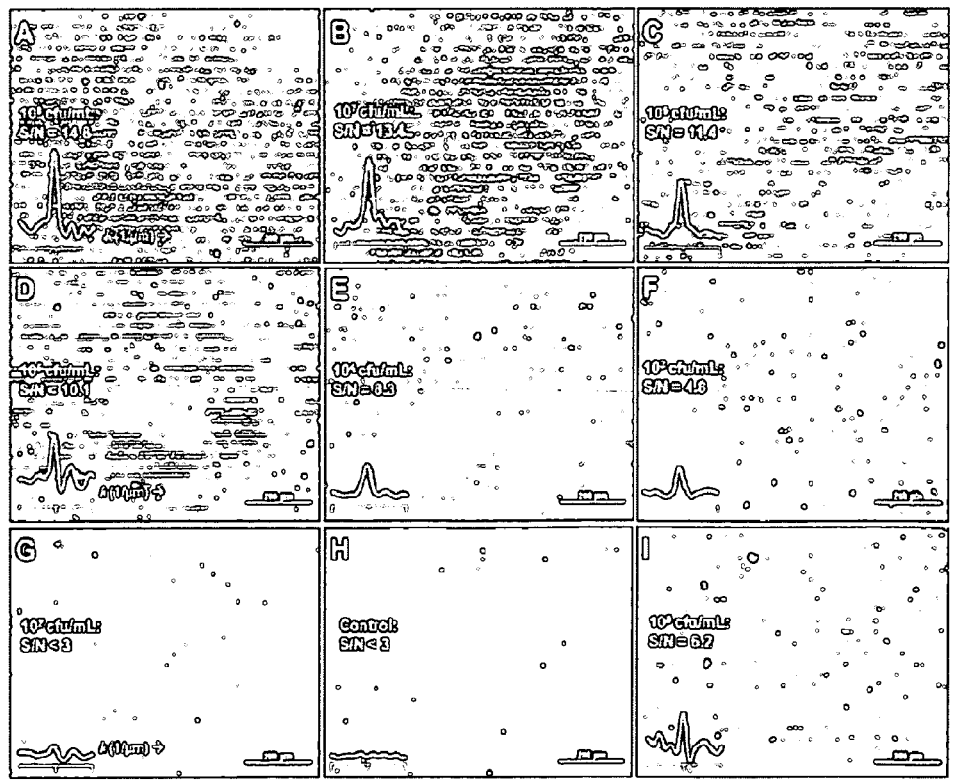
FIG. 19 shows capture of live *Pseudomonas* on glass substrates patterned with BSA-glycan bishydrazide conjugates using μCP, as imaged by darkfield microscopy. Insets A-G show substrates patterned with pulmonary trisaccharide conjugate 7-BSA after a 1 hour exposure to *Pseudomonas*, at concentrations ranging from $10^8$ to $10^2$ cfu/mL. Pattern contrast correlates with signal-to-noise (S/N) ratio defined by reciprocal lattice peak produced by FFT (k=0.05 μm-1). Inset H shows substrate patterned with 7-BSA without exposure to bacteria (control). Inset I shows *Pseudomonas* capture mediated by 2'-fucosyl lactose conjugate 8-BSA, in the presence of choline ($10^8$ cfu/mL).
Figure 19A:
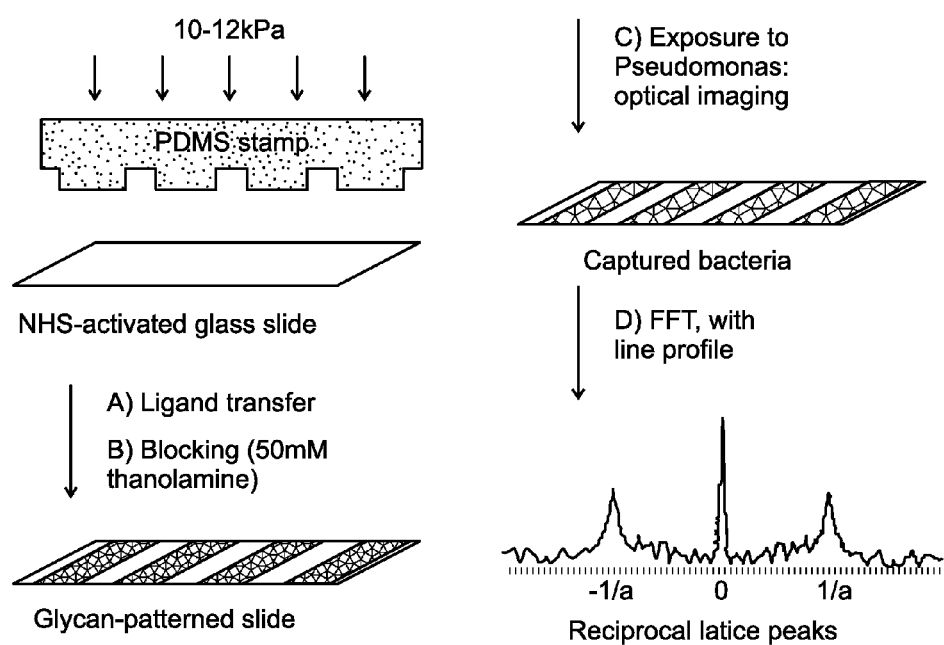
FIG. 19A shows the steps for evaluating the evidence of patterned pathogen capture.

Glycan-bishydrazide conjugates could also be patterned onto substrates by microcontact printing (µCP), a well-established "soft lithography" technique based on microfabricated polydimethylsiloxane (PDMS) stamps for the physical transfer of organic or biomolecular ligands, including glycans (Kumar and Whitesides, *Appl. Phys. Lett.* 1993, 63:2002-2004; Bernard et al., *Adv. Mater.* 2000, 12:1067-1070; Inerowicz et al., *Langmuir* 2002, 18:5263-5268; Godula et al., *Angew. Chem., Int. Ed* 2009, 48:4973-4976; Wendeln et al., *Langmuir* 2010, 26:4933-4940). Stamps imprinted with 20 µm gratings were coated with solutions of 7-BSA or 8-BSA in phosphate buffer, then dried in air and placed in conformal contact with activated glass slides under lightly applied pressure (see Scheme 3 and Experimental Procedures section). The substrates were blocked then exposed for 1 hour to *Pseudomonas* at $10^2$-$10^8$ cfu/mL, then evaluated for evidence of patterned pathogen capture (FIGS. 19, 19A). On average, we find the pattern transfer of 7-BSA by µCP to be more consistent than that produced by photolithography, and remarkably reliable for mediating bacterial adhesion at low pathogen densities.

FIG. 19A illustrates the steps of the evaluation including Steps (A,B) in which Glycan-patterned slides were prepared by micro contact printing of BSA glycoconjugates onto NHS-activated glass substrates, followed by a blocking step; Step (C) in which patterned capture slides were exposed to *Pseudomonas* at variable concentrations, then imaged under darkfield conditions and Step (D) in which image processing by FFT analysis produced reciprocal lattice peaks at $k=\pm 1/a$ in spectral format; central peak ($k=0$) scales with spatially averaged intensity of original image; noise from nonspecific binding is dispersed throughout k-space.

Visual inspection of the patterned glycan slides can indicate *Pseudomonas* capture at a concentration of $10^5$ cfu/mL (Inset D of FIG. 19). However, image processing by fast Fourier transform allows the scattered light to be decomposed into peaks in reciprocal space, enabling much lower limits of detection (Doorneweerd et al., *Langmuir* 2010, 26:15424-15429; Example 1). These Fourier peaks are well localized in reciprocal space and are separated from background noise which tends to be localized near the coordinate origin in 25 reciprocal space, resulting in a much greater signal to noise contrast than the original darkfield images (Insets A-H of FIG. 19).

Figure 20:
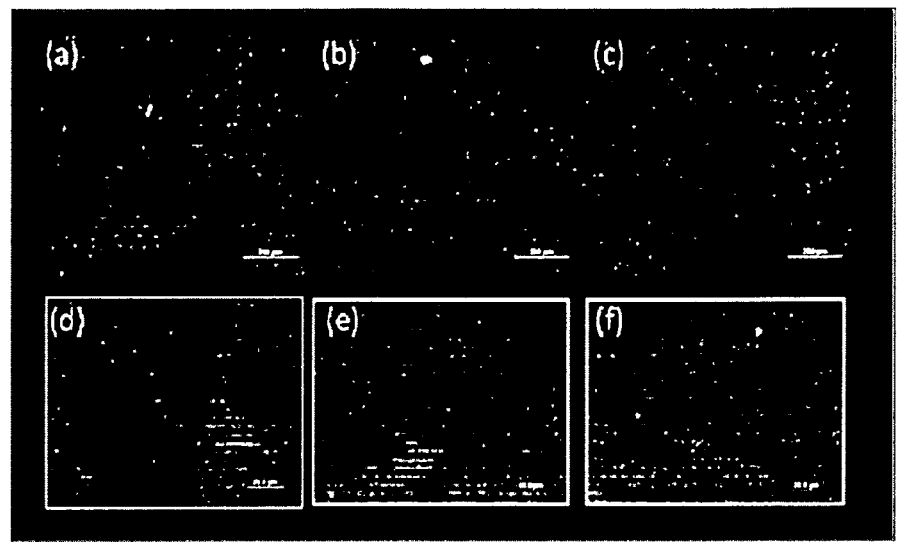
FIG. 20 shows control study showing capture of *Pseudomonas* by substrate patterned with 7-BSA, in the presence of excess lactose (a-c) or GalNAc (d-f). (a) 100 mM lactose; (b) 50 mM lactose; (c) 1 mM lactose; (d) 100 mM GalNAc; (e) 50 mM GalNAc; (f) 1 mM GalNAc.

Interestingly, we observe that our *Pseudomonas* cultures have a much lower avidity for 2'-fucosyllactose 8 than for pulmonary trisaccharide 7, which are recognized by adhesins that are constitutively presented at the tips of bacterial pili (Keizer et al., *J Biol. Chem.* 2001, 276:24186-24193). Whereas affinity for 7-BSA is robust and minimally affected by the presence of competing GalNAc or lactose up to 100 mM (FIG. 20), affinity for 8-BSA is observed only when the bacteria has been cultured in the presence of choline (Gilboa-Garber, "*Pseudomonas aeruginosa* lectins," in *Methods in Enzymology. Vol.* 83: *Complex Carbohydrates*, Part D (Kaplan et al., Eds.) pp. 378-385, Chapter 3. Academic Press: San Diego, Calif.; 1982). It has been shown that the expression of the fucose-binding lectin PA-IIL is regulated by quorum sensing circuitry (las and rhl), which are activated in an environmentally dependent (paracrinal) fashion (Winzer et al., *J. Bacteriol.* 2000, 182:6401-6411; Duan and Surette, *J. Bacteriol.* 2007, 189:4827-4836).

Presentation of glycan-bishydrazides on metal surfaces by in situ dithiolcarbamate formation. Biosensor applications are often performed with gold substrates, like those based on surface plasmon resonance (SPR) and quartz crystal microbalance (QCM) (Homola, *Chem. Rev.* 2008, 108:462-493; Marx, *Biomacromolecules* 2003, 4:1099-1120). For short-term biosensing studies, it is often appropriate to employ chemisorptive ligands such as co-functionalized alkanethiols, which are well-known to form self-assembled monolayers (SAMs) on gold surfaces (Love et al., *Chem. Rev.* 2005, 105:1103-1170). However, alkanethiol-based SAMs can have limited stability when exposed to even mildly oxidizing conditions (Flynn et al., *Langmuir* 2003, 19:10909-10915), so it is worth considering other types of chemisorptive ligands that can support robust surface functionalization under variable environments or in physiological settings.

Figure 21:
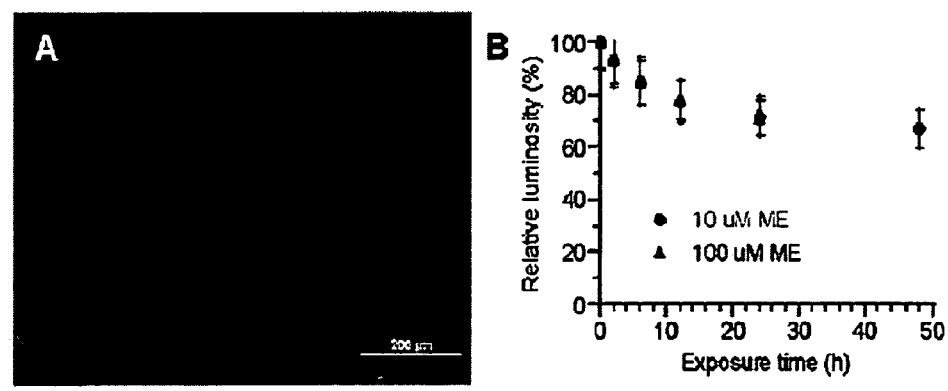
FIG. 21A shows fluorescence immunostaining of peanut lectin bound to lactose conjugate 6-DTC, presented as DAMs on Au substrates by μCP.
FIG. 21B shows a stability profile of hydrazide-DTC patterns on roughened Au in PBS containing ME (10 or 100 μM), based on changes in relative luminosity.

DTC-anchored monolayers (DAMs) are useful alternatives to thiol-based SAMs, as they have been shown to have greater resistance to surface desorption or oxidative degradation (Zhao et al., *J. Am. Chem. Soc.* 2005, 127:7328-7329). Although earlier studies involving in situ DTC and DAM formation have been conducted with alkyl- and dialkylamines (Zhao et al., *J. Am. Chem. Soc.* 2005, 127:7328-7329; Zhu et al., *Langmuir* 2008, 24:8660-8666; Huff et al., *Langmuir* 2007, 23:1596-99; Huff et al., *Nanomedicine* 2007, 2:125-132; Zhao et al., *Langmuir* 2009, 25:13833-13839; Guerrini et al., *Anal. Chem.* 2009, 81:953-960; Cao et al., *J. Am. Chem. Soc.* 2007, 129:6927-6930; Park et al., *Adv. Mater.* 2009, 21:2323-2325; Patel et al., *Chem. Comm.* 2009, 1849-1851; Morf et al. *Langmuir* 2006, 22:658-663), hydrazide-DTCs can be formed just as easily and may also serve as chemisorptive ligands. Lactose-bishydrazide 6 was thus converted into the corresponding DTC (FIG. 11), then diluted in water and deposited onto a PDMS stamp for pattern transfer onto a chemically roughened Au surface by µCP. The patterned substrates were blocked by BSA and incubated with peanut lectin, whose binding to lactose-terminated DAMs was visualized by immunofluorescent staining (FIG. 21). Often, Au substrates may be incompatible with fluorescence imaging due to their propensity to quench emission; however, radiative decay rates can be accelerated on roughened Au substrates by coupling with local plasmon modes and may even produce a net gain in emission (Lakowicz, *Anal. Biochem.* 2001, 298:1-24).

Figure 22:
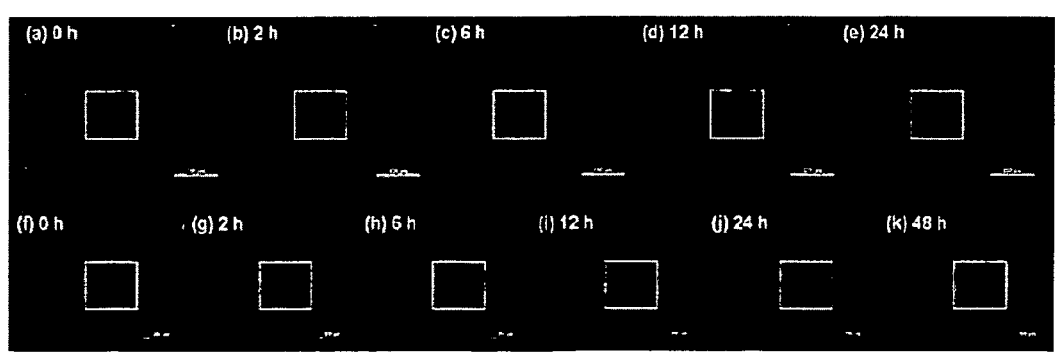
FIG. 22 shows fluorescence microscopy images of the immunocomplexes exposed to different concentration of ME. Top: (a-e) images exposed to 100 μM ME for 2-24 hours. Bottom: (f-k) images exposed to 10 μM ME for 2-48 hours. Square regions (256×256 pixels) in each image were analyzed (by Adobe Photo shop) for changes in luminosities.

The oriented presentation of 6-DTC on Au surfaces is well-suited for the immobilization of multivalent lectins, and patterned substrates can be soaked in PBS for extended periods without concern for degradation. To further establish whether glycan-bishydrazide DAMs are capable of providing robust support as carbohydrate microarrays for protein screening or pathogen binding, we investigated their stability in the presence of 2-mercaptoethanol (ME), a polar thiol that is frequently used to displace alkanethiol-based SAMs from Au surfaces (Castelino et al., *Langmuir* 2005, 21:1956-1961). This displacement assay is important in the context of physiological sensing, as biogenic thiols such as cysteine and glutathione can also be considered as competing adsorbates. The immunofluorescent patterns on roughened Au substrates were thus exposed to 10 μM or 100 μM ME in PBS at room temperature for 2 days, with monitoring of selected regions at different exposure times by fluorescence microscopy (FIG. 22). Both conditions produced very gradual decay profiles, with an estimated half-life of over 80 hours (FIG. 21B). It should be mentioned that displacement assays with millimolar levels of ME could not be performed in this case, as this was sufficient to cause degradation of the roughened Au substrates themselves. Nevertheless, exposure of 6-DTC ligands to ME at these levels has minimal detrimental effect on DAM stability and merits further investigation.

Thus, α,ω-bishydrazides are useful and versatile linkers for attaching glycans onto substrates for bacterial pathogen detection and lectin profiling. Unprotected glycans are conjugated straightforwardly to bishydrazides with retention of the native pyranose conformation at the reducing end, and can be further conjugated to amine-reactive substrates, carrier proteins, and to metal surfaces by in situ DTC formation. With respect to the latter, glycan-bishydrazide-DTCs form robust attachments to roughened gold substrates and are able to withstand displacement by competing thiols under physiologically relevant conditions. Glycan-bishydrazide conjugates can be subsequently employed in microfabrication schemes involving photolithography or PDMS-based microcontact printing for the *facile* detection of glycan-binding proteins and pathogens, as demonstrated by the patterned adsorption of peanut lectin and *Pseudomonas*. This methodology can be used to support real-time biosensing applications involving protein biomarker or pathogen detection.

We have developed, as described above and demonstrated in Example 1, a siderophore-based detection methodology that uses siderophore-immobilized gold plated glass chips to selectively detect pathogenic bacteria (e.g., *Pseudomonas aeruginosa*). Here we demonstrate that the method is also effective for detecting and selectively identifying other microbes by using an appropriate capture ligand for the microbe to be detected and/or identified. Our results show the capture of *Mycobacterium, Salmonella* and *Shigella* onto chips coated with siderophores, mycobactin J, salmochelin S1, and aerobactin, respectively. Our method is a rapid, convenient, and label-free detection of bacteria with an excellent detection limit ($10^3$ cfu/ml), short detection time (~15 min), and high selectivity over other bacteria. We further demonstrate that printing of the siderophore in a periodic pattern on the chip enables a sensitive method of detecting the bound pathogen by a fast Fourier transform (FFT) analysis of light scattered by the patterned chip. This method has potential for rapid pathogen detection by utilization of other micro-specific siderophores.

Pathogen Detection Using an Exemplary Siderophore: *Mycobacterium smegmatis* Detection Using Mycobactin J The increase in mycobacterial infections is a matter of serious public health concern. In particular, *Mycobacterium tuberculosis* (TB) continues to be a major health problem worldwide, affecting millions of people each year. Accurate and rapid diagnosis may help control the spread of this deadly disease, yet the traditional tests for TB produce results that are either inaccurate or take long to be definitive. Current methods for diagnosing TB include a skin test, acid-fast staining, culture of the bacteria, DNA amplification via PCR, and chest radiography (Dinnes et al., *Health Technol. Assess.* 2007, 11; Cho and Brennan, *Tuberculosis* 2007, 87:S14-S17; Kalantri et al., *BMC Infect. Dis.* 2005, 5:59; Perkins and Cunningham, *Infect. Dis.* 2007, 196:S15-27; Sokolove et al., *Acad. Emergency Med.* 2000, 7:1056-1060; Steingart et al., *PLoS Med.* 2007, 4:e202). None of these methods, alone, provides rapid and accurate detection of the microbe; a chest x-ray alone can be inconclusive, tissue culture can takes too long to produce a result, a skin test can lack specificity and/or reliability, and acid-fast staining can require a large number of bacteria in the sputum to give an accurate reading. Serological test using different TB antigens can be rapid but can lack the desired sensitivity. DNA amplification technology can yield false-positive results. Because of these limitations, none of the current tests is suited for rapid screening of large numbers of potential patients. Because of the slow growth of mycobacteria, methods that require growing the microbe in culture can be time-consuming, sometimes taking 4 to 8 weeks to complete. *Mycobacterium smegmatis* is relatively a fast-growing nonpathogenic mycobacteria that is widely used as a model organism to study the biology of other virulent and extremely slow-growing species such as *Mycobacterium tuberculosis*. Therefore, we examined here a rapid detection of *M. smegmatis* by mycobactin J immobilized biochip, bacteria concentration dependent detection, and bacteria selectivity based on binding affinity.

Figure 24:
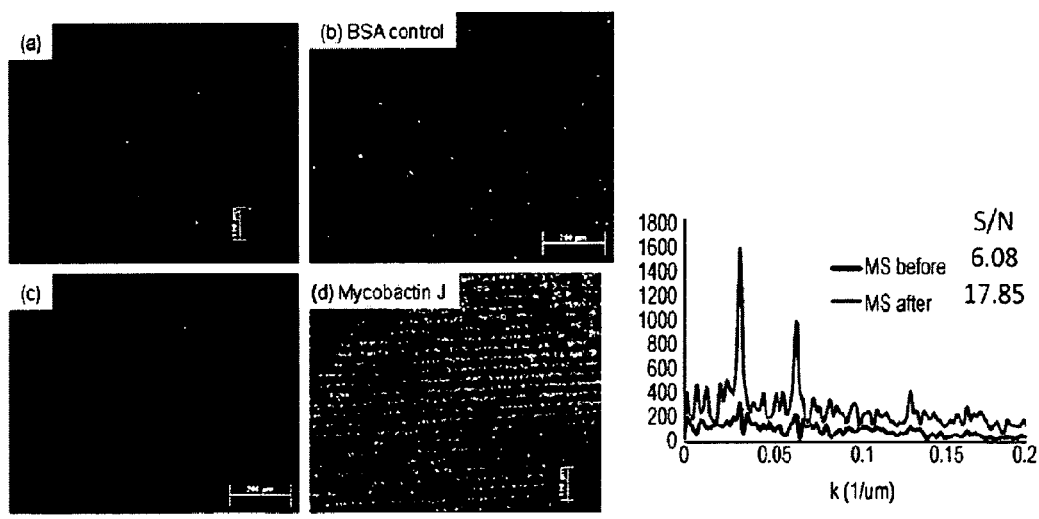
FIG. 24 shows darkfield microscopic images of *M. smegmatis* captured onto mycobactin J-BSA immobilized gold chips: (a, c; background), (b) BSA alone, (c) mycobactin J-BSA conjugate.

To obtain an initial indication of the ability of mycobactin J to capture *M. smegmatis*, mycobactin J, which is a siderophore from mycobacteria, was conjugated to Bovine serum albumin (BSA). We next applied mycobactin J-BSA onto a gold plated glass chip by microcontact printing (μcp) of PDMS stamp as described (Doorneweerd et al., *Langmuir,* 2010, 26:15424; Example 1). The mycobactin J-patterned substrates were then exposed to *M. smegmatis* and examined by darkfield microscopy, which revealed well-defined linear arrays corresponding to the PDMS patterns (FIG. 24). We also performed a control experiment using a chip coated with BSA alone, which showed no bacterial binding. These results demonstrate that siderophores can be used generally to capture their cognate pathogens and, thus, that our detection strategy may be employed universally to detect microbes other than *P. aeruginosa*.

Figure 25:
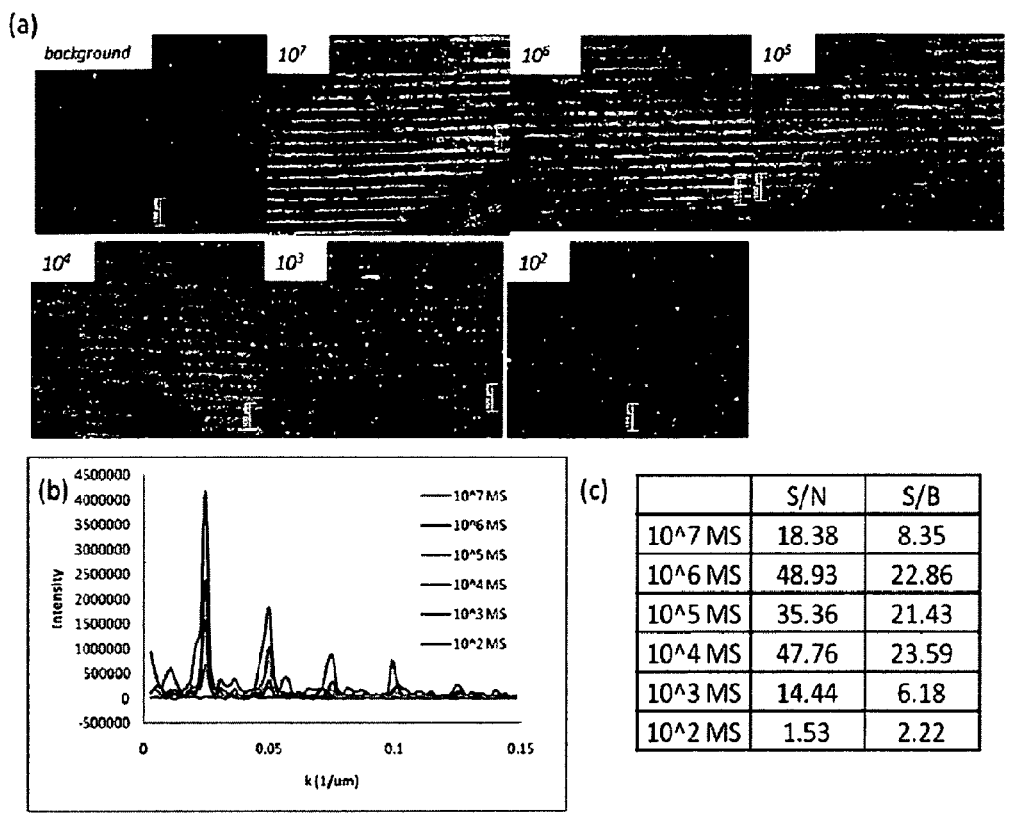
FIG. 25 shows evaluation of limit of detection of *M. smegmatis* on mycobactin J-BSA patterned chips.

To evaluate the sensitivity of our detection strategy, mycobactin J-derivatized chips were exposed to different concentrations of *M. smegmatis* bacteria from $10^7$ to $10^2$ cfu/ml and examined by darkfield microscopy for capture of the bacteria. As shown in FIG. 25, fast Fourier transform (FFT) analysis of microscopic images revealed that our detection methodology is highly sensitive to the concentration of $10^3$ cfu/ml.

Figure 26:
FIG. 26 shows darkfield microscopy of bacteria captured onto linear patterns of mycobactin J-BSA: (a) background, (b) *S. aureus*, (c) *Y. enterocolitica*, (d) *P. aeruginosa*, (e) *V. cholerae*, (f) *M. smegmatis*.

To evaluate the selectivity of our siderophore-based detection method with respect to *Mycobacterium* spp., we also exposed the mycobactin J-BSA μ-contact printed chips to *Yersinia enterocolitica, Pseudomonas aeruginosa, Staphylococcus aureus*, and *Vibrio cholera*, respectively, for up to 2 hours and using $10^8$ cfu/mL of bacteria in each case (FIG. 26); a parallel experiment with *M. smegmatis* was conducted as a positive control. In terms of the images of FIG. 26, *Yersinia, Pseudomonas, Vibrio* and *Staphylococcus* responded to mycobactin J with relatively low affinity compared to *Mycobacterium*, although very faint periodic signal could be detected. Thus, we demonstrated that mycobactin J is a siderophore that may be used to specifically detect a *Mycobacterium* spp. and can distinguish among different bacteria.

Pathogen Detection Using an Exemplary Siderophore: *Salmonella enterica* Detection Using Salmochelin S1/S2

*Salmonella* is a major cause of food-borne illness throughout the world, over 16 million people worldwide are infected with typhoid fever each year, and 500-600 thousands of these cases are fatal. *Salmonella* is facultative, anaerobic gram-negative bacteria belonging to the Enterobacteriaceae family. Suitable detection methods are needed to help control this pathogen. Current detection methods to identify *Salmonella* include the culture test, dot-blot immunoassay, ELISA, DNA-based PCR, and Fluorescent quantitative real-time polymerase chain reaction (FQ-PCR) (Kim et al., *J. Oral Maxillofacial Surgery,* 2002, 60(7):808-815; Lequin, *Clin. Chem.,* 2005, 51(12):2415-2418; Carrique-Mas et al., *J. Appl. Microbiol.* 2009, 6:1976-1983; Patricia and Rosa, *Food Microbiol.* 2008, 5:705-713; Lee et al., *J. Appl. Microbiol.* 2009, 3:805-811; Deng et al., *World I Gastroenterol.* 2007, 48:6568-6574; Tomlinson et al., *Appl. Environ. Microbiol.* 2007, 12:4040-4047). Although the FQ-PCR method can be more rapid, more accurate, and/or more sensitive than the other methods, it also can be laborious, time-consuming, and require expensive equipment. Therefore, a rapid, sensitive, simple, and economical method remains a challenge as a practical application for *Salmonella* detection (Mao et al., *J. Appl. Microbiol.* 2008, 2:389-397).

Here, we demonstrate detecting *Salmonella* using salmochelins, which represent novel carbohydrate-containing catecholate siderophores, including bacteria concentration-dependent detection for sensitivity, exposed to bacteria time-dependent detection for rapidness, and binding affinity to various bacteria for bacteria specificity.

Figure 27:
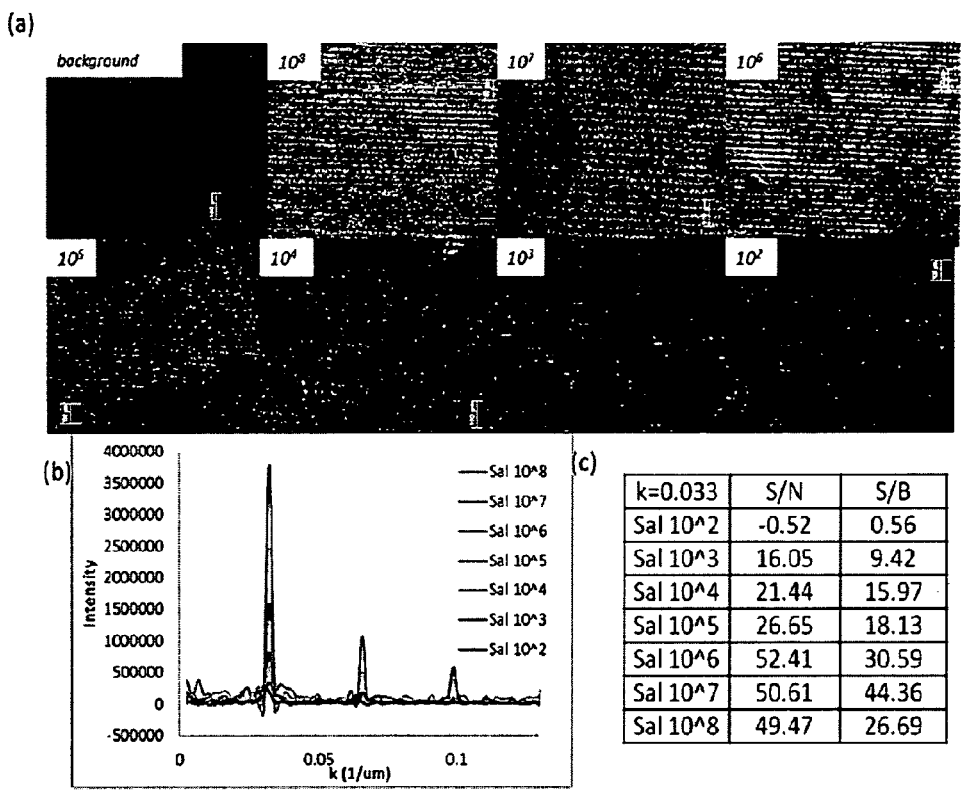
FIG. 27 shows evaluation of limit of detection of *S. enterica* on salmochelins-BSA patterned chips.

To evaluate the sensitivity of salmochelins for *Salmonella enterica*, salmochelin-BSA patterned gold chips were exposed to *S. enterica* at concentrations from $10^2$ to $10^8$ cfu/ml for 1 hour. Darkfield images and FFT analysis revealed that the limit of detection (LOD) for *S. enterica* by salmochelins is $10^3$ cfu/mL (FIG. 27), which is comparable to or better than the detection limit of ELISA assays ($10^4$-$10^5$ cfu/ml), antibody-microarray biochip techniques, biofunctionalized magnetic nanoparticle assays, and gold nanoparticle based assays (Butler, *Nature* 1996, 384:397; Wyatt et al., *Appl. Environ. Micobiol.* 1993, 59:1383-1390; Ravindranath et al., *Anal. Chem.* 2009, 81:2840-2846; Wang et al., *Chemistry,* 2010, 16(19):5600-5606).

Figure 28:
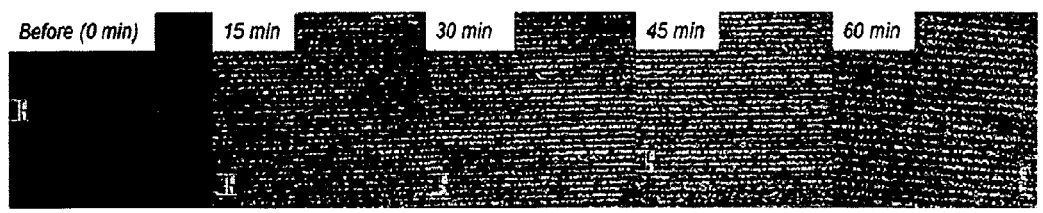
FIG. 28 shows evaluation of detection time on the capture of *S. enterica* of $10^8$ cfu/ml on gold coated chips patterned salmochelins-BSA.

To evaluate the time necessary for pathogen binding, we varied incubation time from 0 to 60 minutes, using a fixed concentration of *S. enterica* of $10^8$ cfu/ml and examined the chips for bacterial retention. Analysis of the darkfield images demonstrated that capture almost approached saturation at 15 minutes of incubation (FIG. 28), similar to that observed for the detection of *P. aeruginosa* (Doorneweerd et al., *Langmuir,* 2010, 26:15424; Example 1). These data demonstrate that rapid pathogen analyses are a general characteristic of our method and are not limited to detection of *P. aeruginosa* (Example 1).

Figure 29:
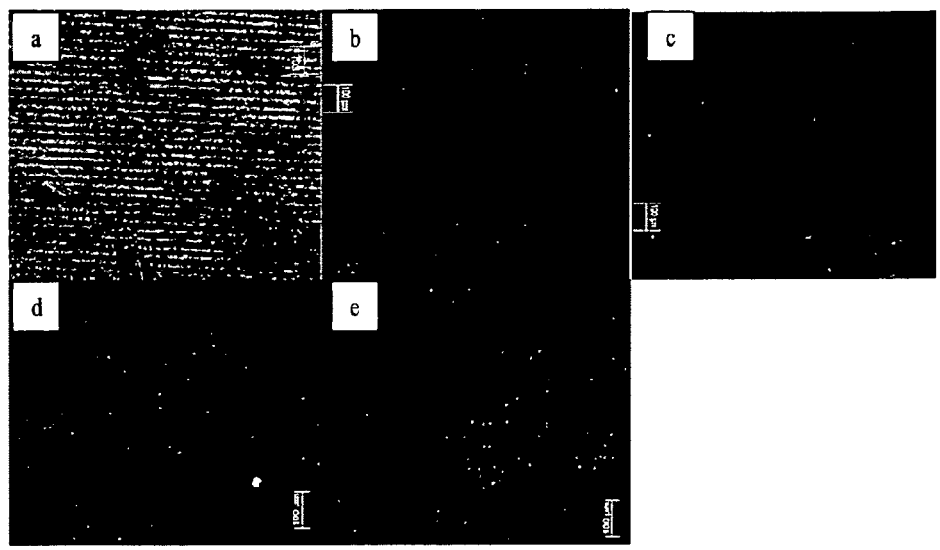
FIG. 29 shows darkfield microscopy of bacteria captured onto linear patterns of salmochelins-BSA: (a) *S. enterica* ($10^6$ cfu/ml), (b) *S. aureus* ($10^6$ cfu/ml), (c) *P. aeruginosa* ($10^6$ cfu/ml), (d) *S. flexneri* ($10^8$ cfu/ml), (e) *Y. enterocolitica* ($10^8$ cfu/ml).

To evaluate the pathogen specificity of salmochelin, salmochelin-BSA patterned chips were exposed to *Staphylococcus aureus, Pseudomonas aeruginosa, Shigella flexneri,* or *Yersinia enterocolitica*. Interestingly, minimal or a little patterned binding of *S. aureus* or *P. aeruginosa* was observed at a microbial concentration of $10^6$ cfu/ml (FIG. 29), comparing to distinct binding patterns of *S. enterica* ($10^6$ cfu/ml). Moreover, minimal patterned binding was observed with either *S. flexneri* or *Y. enterocolitica* at the highest concentration of $10^8$ cfu/ml. We verified that any lack of binding with other bacteria is not caused by stamping problem by re-exposing chips to *S. enterica* and observing binding of *S. enterica* by chips that did not bind the other microbial species. Our results suggest that salmochelin-BSA is capable of distinguishing *Salmonella* over other bacteria.

Pathogen Detection Using an Exemplary Siderophore: *Shigella flexneri* Detection Using Aerobactin

*Shigella* is a gram-negative entero-invasive bacterium, which is one of the major causes of human infectious diseases and is responsible for millions of cases of diarrhea worldwide every year (Li et al., *J. Clin. Microbiol.* 2006, 44:4376-4383). *Shigella* can lead to shigellosis, an acute bloody diarrhea, which accounts for a large number of food poisoning cases throughout the world (Jay, *Modern Food Microbiology,* 5th ed., Chapman & Hall: New York, N.Y.; 1996. pp. 20-24). There are four serogroups of *Shigella; S. dysenteriae, S. flexneri, S. boydii,* and *S. sonnei* (Warren et al., *Crit. Rev. Food Sci. Nutr.* 2006, 46(7):551-567). Among the four serogroups of *Shigella, Shigella flexneri* predominates in areas of endemic infection and shows strong acid resistance and salt tolerance (Zhao et al., *Anal. Biochem.* 2011, 408:53-58). Although *S. dysenteriae* is associated with the most severe form of the disease and high mortality when epidemics occur, most *Shigella*-related deaths are attributable to the endemic form of the disease, which is most often caused by *S. flexneri* (Nato et al., *PLoS One.* 2007, 2(4):e361). While *Shigella* can survive in many types of food, there is not much information about the prevalence of *Shigella*. Therefore, an appropriate conventional detection method of *Shigella* is still needed. Currently, conventional techniques for determination of *Shigella* are culturing methods, PCR, and ELISA. Culturing methods are the best choice for determination, but they can be laborious and time-consuming. PCR can be extremely sensitive, but it also has can be laborious and can require expensive equipment. ELISA can be less sensitive and flexible in terms of design and application. Thus, a convenient, rapid, and cost-effective testing method to detect *Shigella* is needed for, for example, food testing, environmental monitoring, and clinical diagnosis (Li and Mustapha, *Food Microbiol.* 2004, 21:369-375; Chaubey et al., *Anal. Chim. Acta.* 2000, 407:97-103). Here, we demonstrated that biochip-immobilized aerobactin (Iuc), which is a hydroxamate siderophore produced and used in both *S. flexeneri* and *S. boydii* through a distinct siderophore transport system (Jut) (Lawlor et al., *Infect. Immun.* 1987, 55:594-599; Payne, J. Bacteriol. 1980, 143: 1420-1424; Wyckoff et al., *Biometals,* 2009, 22:43-51), can be used for a rapid, robust, and reliable test to identify *Shigella flexneri*.

Figure 30:
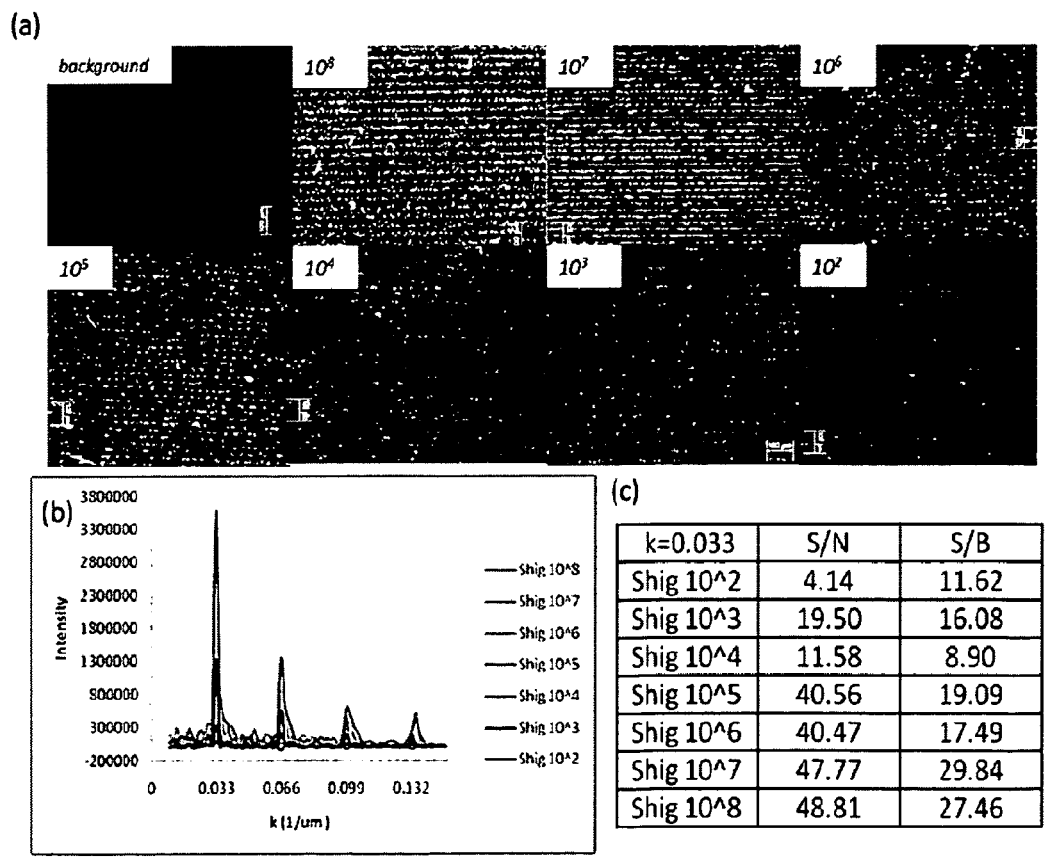
FIG. 30 shows evaluation of limit of detection of *S. flexneri* on aerobactin-BSA patterned chips.

Aerobactin-BSA patterned gold chips were exposed to *S. flexneri* at concentrations from $10^2$ to $10^8$ cfu/ml for 1 hour to obtain the detection sensitivity. Examination of darkfield images for capture of the bacteria and FFT analysis of the micrographs revealed that a patterned distribution of bacteria could be observed down to concentrations a low as $10^3$ cfu/mL (FIG. 30).

Figure 31:
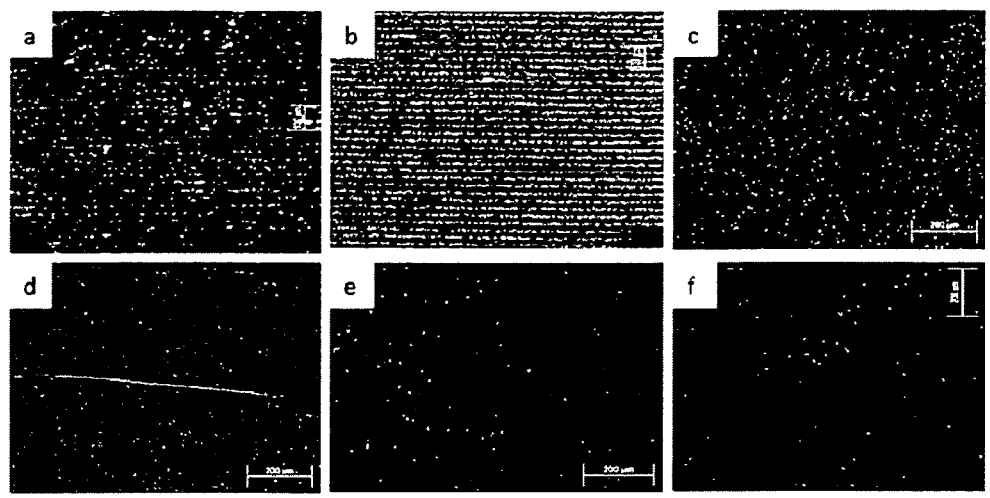
FIG. 31 shows darkfield microscopy of bacteria captured onto linear patterns of aerobactin-BSA: (a) *S. flexneri*, (b) *S. enterica*, (c) *S. aureus*, (d) *Y. enterocolitica*, (e) *M smegmatis*, (f) *P. aeruginosa* of concentration $10^6$ cfu/ml of each bacteria.
Figure 32:
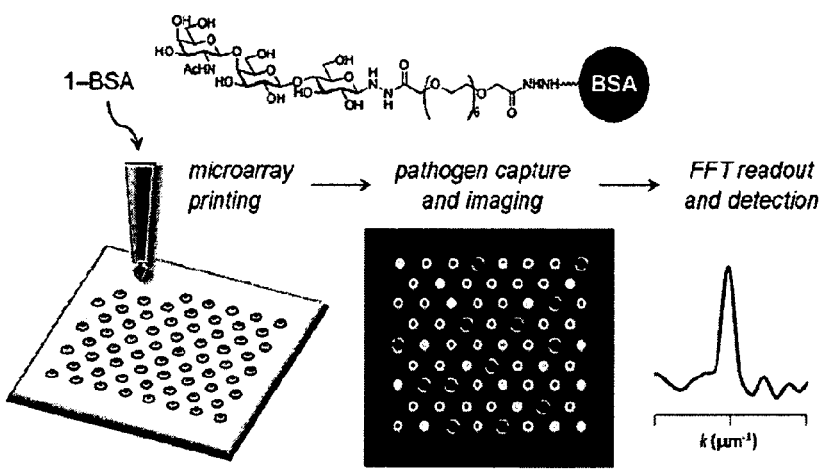
FIG. 32 shows mutation-resistant ligand arrays for bacterial pathogen detection. Left, inkjet printing of microarray onto activated glass substrates (with the option of generating multiple periodicities); middle, capture array exposed to pathogens, with label-free imaging of bacterial capture under darkfield conditions; right, linescan after image processing by 2D-FFT reveals a signature peak in Fourier space, corresponding to the reciprocal lattice of the periodic capture pattern.

To evaluate the pathogen specificity of aerobactin, aerobactin-BSA patterned chips were exposed to *Staphylococcus aureus, Pseudomonas aeruginosa, Shigella flexneri, Mycobacterium smegmatis, Yersinia enterocolitica,* or *Salmonella enterica*. As shown in the darkfield images of FIG. 31, minimal patterned binding of *M. smegmatis* or *P. aeruginosa* was observed using a microbial concentration of $10^6$ cfu/ml for a short incubation time (1 hour). *S. aureus* and *Y. enterocolitica* showed some binding at a microbial concentration of $10^6$ cfu/ml, but the binding was not the well-defined array pattern and included nonspecific-binding between the array patterns. On the other hand, *S. enterica* and *S. flexneri* clearly demonstrated good binding affinity at $10^6$ cfu/ml and showed well-defined linear array patterns to the binding. *Salmonella* and *Shigella* species are close relatives and aerobactin genes are found in certain strains of *Salmonella* (Wyckoff et al., *Biometals*, 2009, 22:43-51; Colonna et al., *J. Bacteriol.* 1985, 162:307-316; Williams, *Infect. Immun.* 1979, 26:925-932). Thus, the use of aerobactin may be useful for detecting *Shigella* spp., *Salmonella* spp., or other microbial species that express aerobactin such as, for example, *E. coli*.

We have expanded our siderophore-based methodology to selectively detect and identify bacteria onto chips that include immobilized siderophores. We have demonstrated the general utility of the method by demonstrating the capture of *Mycobacterium smegmatis*, *Salmonella enterica*, and *Shigella flexneri* onto chips immobilized with siderophores mycobactin J, salmochelins, and aerobactin, respectively. This approach is a label-free, selective detection method for bacteria with an excellent detection limit ($10^3$ cfu/ml) and high selectivity over other bacteria. Moreover, this method is rapid and bacterial binding was found to approach saturation about 15 minutes after exposure to chip. A more sophisticated image processing algorithm, FFT analysis was then explored as a means of more quantitatively evaluating pathogen capture. On the basis of our results reported herein and previously (Doorneweerd et al., *Langmuir*, 2010, 26:15424; Example 1), it is clear that a siderophore-based approach for the rapid detection of bacteria is feasible and can be easily extended for other microorganisms as long as the specific siderophore for its cognate pathogen is available.

Pathogenic bacteria obtain the iron necessary for their survival by releasing an iron chelator, termed a siderophore, and retrieving the iron-siderophore complex via a siderophore receptor. We have exploited the high affinity of *Yersinia enterocolitica* for its siderophore, deferoxamine, to develop a rapid method for detection and identification of *Yersinia*. In this methodology, a deferoxamine-bovine serum albumin conjugate is printed onto a gold-plated chip in a linear banding pattern. After flowing the pathogen across the siderophore-derivatized chip, any pathogen captured onto the chip is detected by recording a dark-field microscope image followed by Fourier transform analysis of that image. Pathogen concentrations as low as $10^3$ cfu/ml are readily detected and peak intensities can be correlated with pathogen concentrations in each sample. Moreover, immobilized deferoxamine can distinguish between *Y. enterocolitica* which binds the siderophore, and *Staphylococcus aureus*, *Mycobacterium smegmatis*, and *Pseudomonas aeruginosa*, which don't. Because human pathogens cannot easily mutate their iron capture systems without loss of viability, few if any escape mutants will evolve that can avoid detection and identification. Together with previous results demonstrating selective capture of *Pseudomonas aeruginosa* by its immobilized siderophore (pyoverdine), of *Salmonella enterica* by its immobilized siderophore salmochelin S1/S2, of by its immobilized siderophore salmochelin S1/S2, of *Mycobacterium smegmatis* by its immobilized siderophore mycobactin J, and of *Shigella* spp. and *Salmonella* spp. by their immobilized siderophore aerobactin, these data suggest that pathogen-specific siderophores as a rule may constitute effective and mutation-resistant capture ligands for rapid detection and identification of their cognate pathogens.

Exemplary Methods and Devices for Pathogen Detection

Binding of a microbe to an immobilized ligand may be detected by any suitable method including, for example, fluorescent labeling, antibody labeling, radiolabeling, colorimetric labeling, enzymatic labeling, or any suitable combination of two or more labeling strategies (e.g., labeling with a fluorescent antibody). In some embodiments, detecting the bound microbe may be accomplished using a label-free detection strategy. One such strategy can involve ligand-specific adhesion, label-free optical imaging, and pattern recognition using two-dimensional fast Fourier transform (2D-FFT) analysis. Adhesion may be mediated by a microbe-specific ligand—e.g., a siderophore or a glycan such as, for example, (GalNAc ($\beta1{\rightarrow}4$)Gal($\beta1{\rightarrow}4$)Glc)—that is conjugated to bovine serum albumin (BSA) and printed into dot-matrix arrays using, for example, a thermal injection method. Inkjet printing provides independent control over periodicity, permitting patterns to be encoded as peak frequencies that are easily monitored in reciprocal k-space upon 2D-FFT analysis. Exposing the ligand-BSA array to a live strain of the pathogen (e.g., *Staphylococcus aureus*) produces periodic patterns that can be detected under darkfield conditions. Image processing of the patterned bacteria by 2D-FFT analysis yields characteristic peaks that are relatively unaffected by nonspecific binding events, enabling the pathogen to be detected at levels below $10^3$ cfu/mL. The FFT readout method produces signature peaks from bacterial capture arrays with remarkably low occupancy, and provides opportunities for designing array patterns for multiplex pathogen detection.

The Fourier transform is an important image processing tool which decomposes a real space image into its sinusoidal components. The output of the transform maps a real space image into the Fourier (reciprocal or wavenumber) space domain. In the Fourier domain, each point represents the amplitude of a particular wavenumber contained in the spatial (i.e. image) domain.

A simple implementation of the Fourier transform algorithm is realized by the Discrete Fourier Transform (DFT) which is based on the analysis of a finite number of pixels and therefore does not contain all wavenumbers forming an image, but only a subset which is sufficiently large to adequately approximate the real-space image. The size of the Fourier Transform corresponds to the number of samples (pixels) in the real-space image. For a square optical image of spatial size L×L (L in μm) containing N×N equally spaced pixels, the two-dimensional DFT $F(k_x, k_y)$ can be calculated from $$F(k_x, k_y) = \frac{1}{N^2} \sum_a \sum_b f(a, b) e^{-2\pi i [k_x a + k_y b]}$$

where the function f(a,b) represents the intensity of the real-space image at the pixel (a,b) with $0 \le a,b \le L$. The exponential term with imaginary argument ($i^2=-1$) specifies the basis function; for a specified $(k_x,k_y)$ the value of the complex function $F(k_x,k_y)$ uniquely determines the amplitude and phase of the specific Fourier component in wavenumber space. The complete set of numbers $F(k_x,k_y)$ in the Fourier domain accurately reflects the original image in a holistic manner, providing global information about any relevant periodicities contained in the real-space image.

When N, the number of pixels, can be specified as $N=2^m$, where m is an integer, the DFT can be efficiently performed using the Fast Fourier Transform (FFT) algorithm. The wavenumbers $(k_x,k_y)$ are restricted to equally spaced values that range from (0,0) to $$\left(\frac{N-1}{L}, \frac{N-1}{L}\right).$$

Typically in our studies, m=8 or 9, so N=256 or 512. In images where m may not be an integer, the real space image can always be padded with zeros until m is equal to an integer, making it possible to still use the FFT technique.

Figure 34:
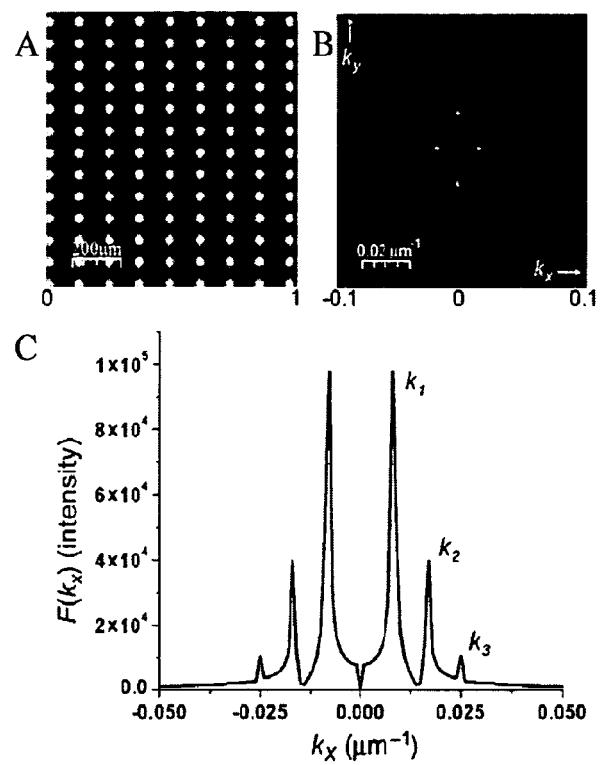
FIG. 34A shows simulation of a dot-matrix array ($L_x$=120 µm, $d_{spot}$=40 µm).
FIG. 34B shows the 2D-FFT image analysis.
FIG. 34C shows the horizontal linescan of FFT readout containing fundamental harmonics ($k_1$=±1/120 µm$^1$) as well as higher-order harmonics ($k_2$=±1/60 µm$^{-1}$; $k_3$=±1/40 µm$^{-1}$).

In FIG. 34(a), a simulated ink-jet pattern is plotted with a spot size ($d_{spot}$) of 40 µm and a spacing between adjacent spots of s=120 µm. The bright spots indicate light reflected from the pathogens that are preferentially bound to the patterned array. FIG. 34(b) gives the corresponding FFT. If we focus attention along the x-axis of the FFT (the $k_x$ axis), the FFT reveals a significant intensity when $k_x = \pm = \pm 0.0083$ with smaller contributions when $k_x = \pm 2/s = \pm 0.0167$ µm$^{-1}$ and $k_x = \pm 3/s = 0.025$ µm$^{-1}$. These signals correspond to the 2$^{nd}$ and 3$^{rd}$ harmonics, respectively, of the fundamental periodicity and are labeled $k_2$ and $k_3$ for convenience in FIG. 34(c). The fundamental harmonic (labeled $k_1$) is the largest contribution and forms the most practical and reliable signature of the periodic pattern since the higher-order harmonics can be influenced by the detailed structure of the array.

The application of 2D-FFT based pattern recognition toward pathogen detection is straightforward, and bestows some important advantages over other readout methods. One is the ability to detect the emergence of non-zero amplitudes at unique ($k_x,k_y$) values that are pre-defined by specific capture patterns, creating opportunities for multiplex detection. This is illustrated below by simulating pathogen adhesion on two interdigitated capture arrays with different periodicities along the x-direction (a=120 µm; b=80 µm). 2D-FFT analysis of the interdigitated arrays produces a function F($k_x,k_y$) that is essentially the sum of the 2D-FFT outputs from the individual arrays. A plot of the Fourier intensities along $k_x$ ($k_y$=0) unambiguously resolves each contribution, with peak $k_1$ values at 1/a and 1/b (0.0083 and 0.0125 µm$^{-1}$ respectively; FIG. 35E).

The multiplexing capacity of interdigitated arrays supporting a unique set of $k_1$ values is ultimately limited by the 2D resolution of the peak signals in the FFT readout, which are influenced by structural factors such as aspect ratio (array period to spot size, or a/$d_{spot}$) or the number of elements in the periodic lattice (FIG. 35F). It is also necessary to avoid overlap between the $k_1$ peak signals and higher-order harmonics: for example, if periodicities are constrained along one dimension, then the range of possible $k_1$ values will be bounded by the fundamental and second harmonic of the array with the largest period ($a_{max}$), such that 1/$a_{max}$<$k_1$<2/$a_{max}$. However, this restriction is artificial to 2D-FFT analysis, and is circumvented by designing array patterns that spread the wavenumber-selected peaks across 2D Fourier space.

Another benefit afforded by the 2D-FFT readout is its capacity to detect pathogens at low binding densities with a high level of fault tolerance (Doorneweerd et al., Langmuir, 2010, 26:15424-15429, Example 1; Adak et al., Bioconj. Chem., 2010, 21:2065-2075, Example 2). In this regard, the emergence of a signature peak at a pre-defined set of ($k_x,k_y$) values represents a global average of affinity capture over the array. This is more dependable than single-point detection strategies for reporting pathogens at trace levels, and greatly reduces the likelihood of false positives. The requirements for producing signature peaks by 2D-FFT analysis are quite robust: wavenumber-selected peaks can be resolved from matrices with low occupancy factors, or have significant levels of background due to nonspecific (random) adsorption.

Various substrate patterning methods can be used to present mutation-resistant ligands as periodic microarrays, such as photolithography and microcontact printing (Doorneweerd et al., Langmuir, 2010, 26:15424-15429; Example 1; Adak et al., Bioconj. Chem., 2010, 21:2065-2075; Example 2; Leonov and Wei, J. Mater. Chem. 2011, 21(12): 4371-4376). However, microscale photopatterning can be difficult to reproduce, and mechanical printing can leave optically detectable marks or residues that are not easily removed by standard washing procedures. We have found that non-contact methods such as inkjet printing offer greater flexibility and control over the choice of printing parameters, and are amenable to producing affinity capture chips on a larger scale. Inkjet technologies can dispense droplets of controlled volumes between 2 pL to 5 nL, and produce spots as small as 15 µm at precisely defined positions (Calvert, Chem. Mater., 2001, 13:3299-3305). Such delivery methods are gentle, scalable, and highly versatile with respect to formulation; examples of solutes deposited by inkjet include inorganic particles (Tekin et al., Soft Matter, 2008, 4:703-713), polymers (de Gans et al., Adv. Mater., 2004, 16:203-213; Schena et al., Trends Biotechnol., 1998, 16:301-306), DNA (Okamoto et al., Nat. Biotechnol., 2000, 18:438-441), and various proteins (Delehanty and Ligler, Anal. Chem., 2002, 74:5681-5687; Weissenstein et al., Proteomics, 2006, 6:1427-1436; Delaney et al., Soft Matter, 2009, 5:4866-4877; Roth et al., Biomaterials, 2004, 25:3707-3715).

Figure 36:
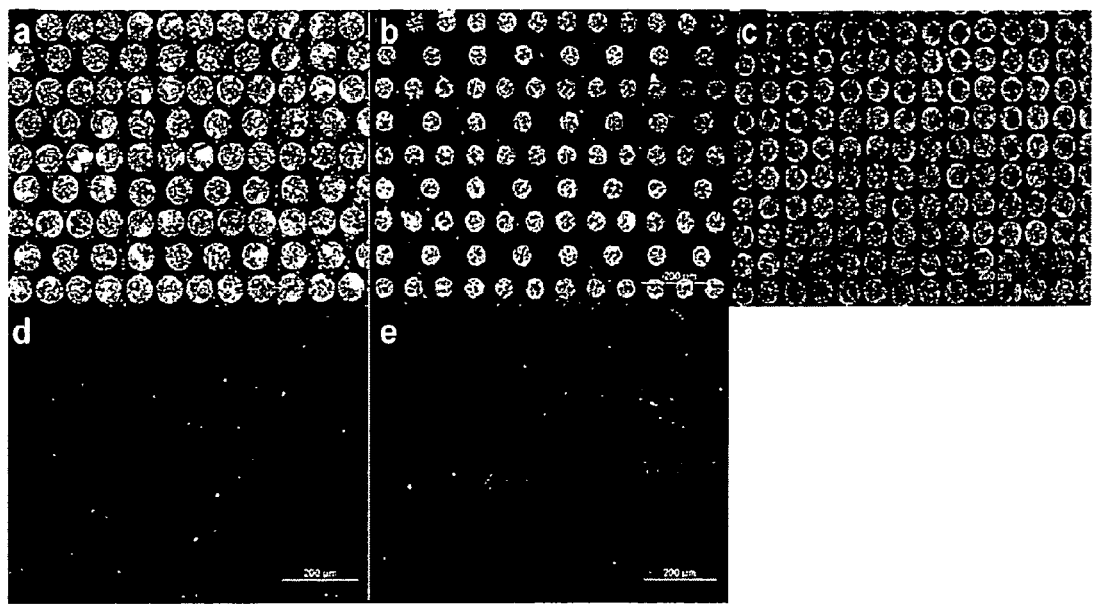
FIG. 36 shows pathogen capture onto neoglycoprotein microarrays, prepared by thermal inkjet printing.
Figure 37:
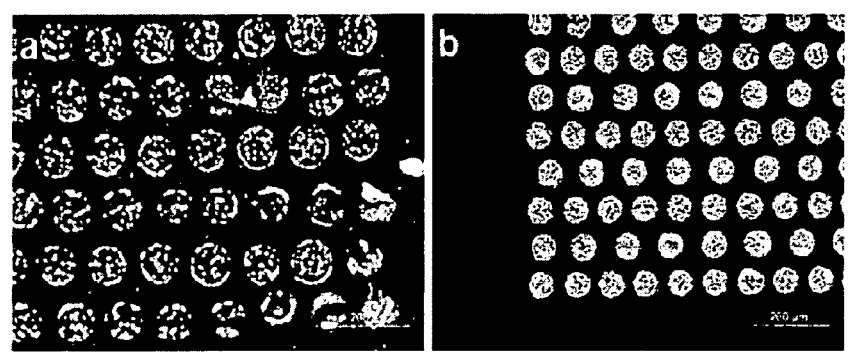
FIG. 37 shows optical darkfield images of dot-matrix arrays of 21-BSA delivered by thermal injection onto functionalized glass slides (CodeLink), using different amounts of surfactant (Tween 20).

A 0.2 wt % solution of 21-BSA in PBS containing nonionic surfactant (0.005 wt % Tween 20) was delivered onto NHS-activated glass slides by thermal droplet ejection, followed by an incubation period at 4° C. prior to blocking. This formulation was able to produce uniform spots with diameters of 50±2.6 µm on CodeLink slides and 40±2.1 µm on Nexterion H glass slides, as indicated from the patterns formed by the capture of S. aureus (FIG. 36a,b). A low concentration of surfactant was found to be helpful in maintaining cohesion of the picoliter droplets during thermal ejection, and also in providing uniform coverage within each spot. The latter is attributed to a lower rate of evaporation after deposition; droplets produced without this additive produced toroidal spots upon drying, compromising the uniformity of the periodic array (FIG. 36c). The amount of Tween 20 must be carefully regulated, as higher concentrations of surfactant increased spreading and yielded larger spot sizes (FIG. 37).

Figure 38:
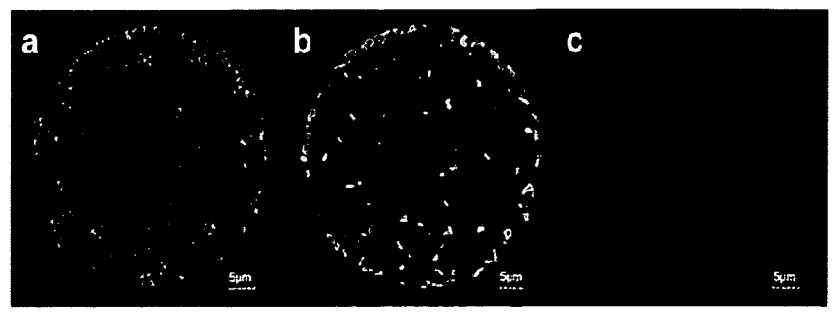
FIG. 38 shows capture of live *S. aureus* by 21-BSA, confirmed by confocal fluorescence microscopy.

Microarrays of 21-BSA were initially exposed for 1 hour to suspensions of S. aureus (10$^7$ cfu/mL), followed by careful rinsing and examination by darkfield microscopy. This imaging method revealed the high quality of the microarrays prepared for bacterial capture, as well as the low levels of non-specific adsorption (FIG. 36a-c). Control experiments established that S. aureus binding affinity is specific for glycan 21: no capture was observed by microarrays printed with either unmodified BSA or lactose-modified BSA (FIG. 36d, e). The latter confirms the importance of the terminal 1,4-β-linked GalNAc residue in bacterial recognition, as previously established for S. aureus and other pathogens (Adak et al., Bioconj. Chem., 2010, 21:2065-2075; Example 2; Krivan et al., Proc. Natl. Acad. Sci. U.S.A., 1988, 85:6157-6161; Thomas et al., J. Med. Microbiol. 2004, 53(9):833-840). Immobilized S. aureus were also treated with a DNA staining kit immediately after capture, using SYTO 9 (a green fluorescent dye that can permeate intact cell membranes) for total cell imaging and PI (a red fluorescent dye that penetrates cells with damaged membranes) to determine the presence of dead bacteria. The immobilized S. aureus were strongly stained by SYTO 9 but only weakly stained by PI, indicating suggesting most if not all bacteria were viable at the time of capture (FIG. 38). Microarrays were also exposed to S. aureus suspensions (10$^7$ cfu/mL) previously irradiated for 4 hours under UV light ($\lambda_{max} \geq 254$ nm), a condition used for sterilization. No bacteria were captured by the microarrays following a 1-hour incubation, and subsequent treatment with SYTO 9/PI yielded no DNA staining. The latter experiment confirmed that the microarrays selectively capture live *S. aureus*, thus permitting detection limits to be defined in terms of colony-forming units.

Figure 39:
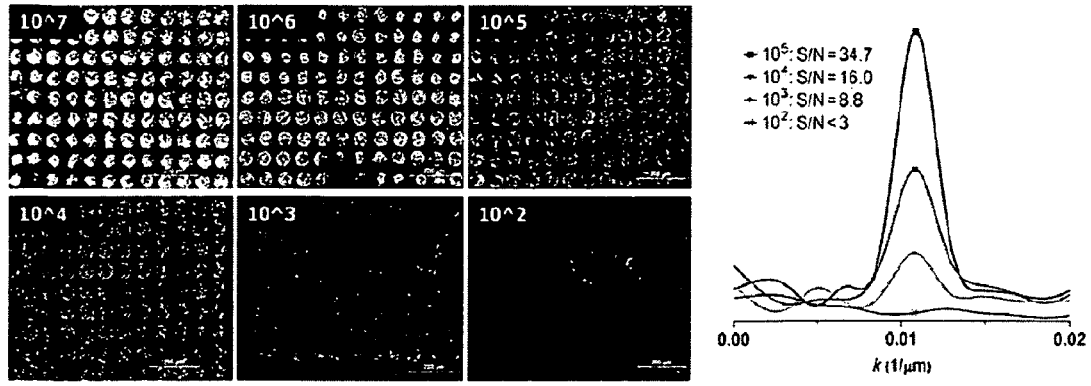
FIG. 39 shows limit of detection for *S. aureus* using 21-BSA microarrays. Left, darkfield microscopy images of microarrays after 1 hour exposure to *S. aureus* as a function of concentration, from $10^7$ to $10^2$ cfu/mL. Right, reciprocal lattice peak intensities (k=1/80 µm$^{-1}$) produced after 2D-FFT analysis of microarray images, with S/N values at different pathogen concentrations (cfu/mL).

The limit of detection (LOD) for bacterial pathogens in solution was evaluated by exposing microarrays of 21-BSA to suspensions of *S. aureus* for 1 hour from $10^7$ to $10^2$ cfu/mL. Visual inspection of darkfield images revealed well-defined arrays of immobilized *S. aureus* at concentrations above $10^5$ cfu/mL, but some loss of array definition at concentrations below this level (FIG. 39). Subjecting these optical images to 2D-FFT analysis enabled us to confirm the emergence of bacterial patterns using reciprocal lattice peaks at k=1/a. Assessing the LOD from the Fourier spectra is straightforward, based on peak signal-to-noise ratios (S/N>3). In this study, the LOD of *S. aureus* by the 21-BSA microarray lies between $10^2$-$10^3$ cfu/mL (FIG. 39, right).

Periodic arrays of 21-BSA were also screened against several Gram-negative bacteria including *P. aeruginosa*, *Y. enterocolitica*, and *V. cholerae* to compare their binding avidities with that of *S. aureus* (Table 1). *P. aeruginosa* is also commonly present in hospitals and a major source of respiratory tract infections (Krivan et al., *Proc. Natl. Acad. Sci. U.S.A.*, 1988, 85:6157-6161), whereas *Y. enterocolitica* and *V. cholerae* are well known for causing enteric diseases (Schmid-Hempel and Frank, PLoS Pathol. 2007, 3(10), 1372-1373). Affinity capture arrays were exposed for 1 hour to target bacteria at $10^6$ cfu/mL, then washed, imaged, and subjected to FFT analysis as previously described. As expected, the opportunistic pathogen *P. aeruginosa* exhibited high affinity to 21-BSA with a conservative LOD at $10^3$ cfu/mL, similar to an earlier study involving linear gratings prepared by microcontact printing (Adak et al., *Bioconj. Chem.*, 2010, 21:2065-2075; Example 2). Conversely, *Y. enterocolitica* and *V. cholerae* had little or no affinity for 21-BSA; the LOD for *Y. enterocolitica* was determined to be $10^6$ cfu/mL, and no LOD could be determined for *V. cholerae*. Although it has been reported that certain strains of *Yersinia* have an affinity for glycan substructures present in asialo-GM1 and lactosylceramide (Thomas et al., *J. Med. Microbiol.* 2004, 53(9):833-840), our results clearly indicate that the affinity of *Y. enterocolitica* to 21-BSA is orders of magnitude lower than that of *S. aureus* and *P. aeruginosa*, in accord with their respective roles in gastrointestinal and respiratory infections.

TABLE 1

Limits of detection (LOD) for bacterial adhesion onto microarrays of 21-BSA.

| Pathogen | LOD[a] (cfu/mL) |
|---|---|
| *Staphylococcus aureus* | $10^3$ |
| *Pseudomonas aeruginosa* | $10^3$ |
| *Yersinia enterocolitica* | $10^6$ |
| *Vibrio cholerae* | n/a |

[a]Estimated to the nearest order of magnitude, using the peak signal quality at k = 1/a in the Fourier spectrum (S/N > 3).

Figure 35:
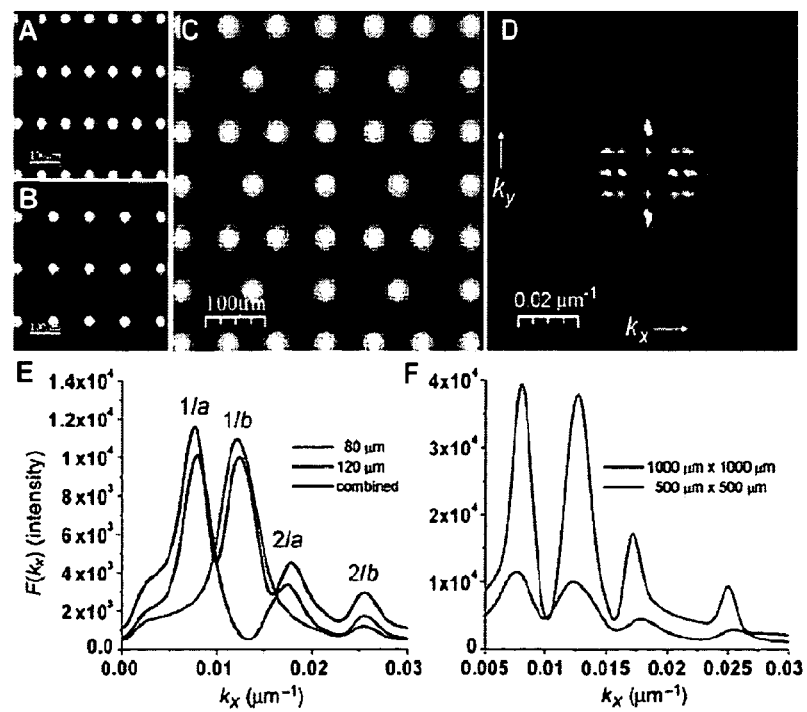
FIG. 35A-C shows simulation of individual and interdigitated arrays with two different periods (a=120 µm, b=80 µm, $d_{spot}$=40 µm, L=500 µm).
FIG. 35D shows the corresponding 2D-FFT analysis of interdigitated arrays.
FIG. 35E shows the 1D plot of FFT readouts along the $k_x$ direction for images A-C, illustrating their additive nature.
FIG. 35F shows the FFT signal quality as a function of array size (L=500 vs. 1000 µm), illustrating its impact on peak resolution.
Figure 40:
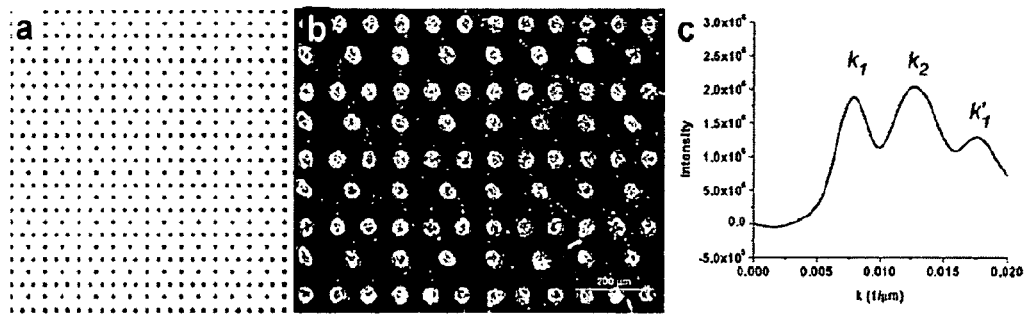
FIG. 40 shows inkjet printing of interdigitated patterns of 21-BSA for pathogen detection at two different reciprocal lattice values.

Inkjet printing is ideally suited for creating ligand arrays with different lattice spacings to support multiplex pathogen capture and detection, as suggested in the simulations discussed earlier (cf. FIG. 35). To validate this notion experimentally, we prepared interdigitated arrays with two different periodicities using 21-BSA ($L_1$=120 μm; $L_2$=80 μm), followed by affinity capture of *Pseudomonas aeruginosa* and 2D-FFT analysis to produce the corresponding 1/a peaks in reciprocal lattice space. Binary microarrays of 21-BSA were printed in alternating rows along the x-direction, programmed according to a 2D input file with a resolution of 20 μm/pixel (FIG. 40*a*). After washing and blocking the substrate as described above, the interdigitated microarrays were exposed for 1 hour to *P. aeruginosa* at a concentration of $10^6$ cfu/mL. Darkfield microscopy indicated an efficient capture with homogeneous spot coverage for both arrays (FIG. 40*b*), and 2D-FFT analysis and readout revealed two distinct peak harmonics $k_1$ and $k_2$ at $1/120$ μm$^{-1}$ and $1/80$ μm$^{-1}$ respectively (FIG. 40*c*), in accord with our earlier simulations. The $k_2$ peak is flanked by the second-order harmonic of the first array ($k'_1$=$1/60$ μm$^{-1}$), which serves as a boundary value for lattice peak positions from the second array. The microarrays in the present study were printed using a single-channel dispenser, which is limited to the delivery of a single capture ligand. However, a multichannel system can produce microarrays with orthogonal recognition ligands, each encoded by a unique period to enable the multiplex detection of specific pathogens.

Periodic arrays of neoglycoproteins can be produced by inkjet printing with rationally defined lattice spacings for application toward sensitive and label-free detection of bacterial pathogens based on the mutation-resistant ligand concept. We demonstrated that pathogens with high affinity to glycan 21 can be immobilized to the microarray pattern with high fidelity; the low level of background noise and nonspecific adhesion enable the bacterial capture patterns to be imaged with high contrast using simple darkfield conditions, with limits of detection at or below $10^3$ cfu/mL. This method of array production can be readily extended to other types of capture ligands such as siderophores and aptamers, as well as biomolecular receptors such as lectins and antibodies. 2D-FFT analysis converts the microarray images into Fourier space, followed by a 1D linescan for convenient readout of their characteristic lattice peaks (k=1/a). FFT analysis can also produce independent signal readouts from multiple arrays on the same substrate using lattice peak values between $k_1$ and $K'_1$, the fundamental and second-order harmonic of the array with the largest lattice spacing. This feature enables mutation-resistant ligand microarrays to be developed for multiplex pathogen detection, encoded by the periodicities of individual lattices.

Figure 74:
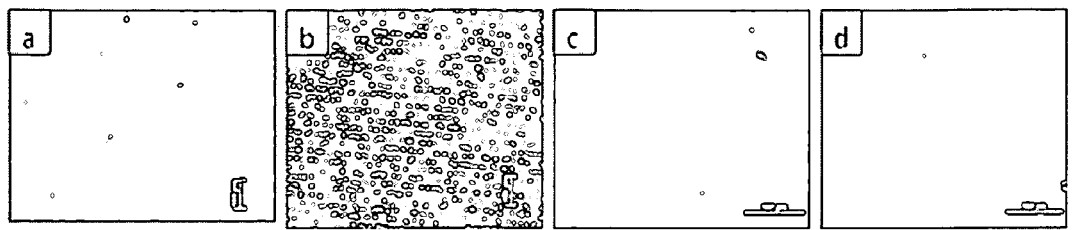
FIG. 74 shows dark field images of the printed FOB-BSA patterns after exposure to *Y. enterocolitica* ($10^8$ cfu/ml) of (a) before capture (ligand only), (b) after capture of *Y enterocolitica*, (c) BSA alone (No DFO ligand), and (d) pre-treated *Y. enterocolitica* with 1 mM DFO before the capture.

Pathogen Detection Using an Exemplary Siderophore: Detection of *Yersinia* Using Deferoxamine A BSA-deferoxamine (DFO)Fe conjugate (FOB) was prepared as described in Scheme 5 shown in Example 6. The FOB conjugate was patterned on the surface with 20 μm periodicity, and then exposed to *Yersinia enterocolitica* to reveal that *Y. enterocolitica* captured to the banding pattern of the siderophore on the chip by darkfield analysis of bacteria light scattering (FIG. 74*a,b*). This result supports siderophore DFO's ability to capture *Y. enterocolitica*. Additionally, to confirm the requirement of DFO ligand for specific binding of *Y. enterocolitica*, onto a gold chip printed BSA (lacking conjugated DFO) was transferred an aliquot of *Y. enterocolitica* ($10^8$ cfu/ml). Optical microscopic examination of the chip revealed that the bacteria did not bind significantly to the underivatized BSA. In addition to that, we conducted competition experiments that a suspension of *Y. enterocolitica* was pre-treated with DFO solution in PBS (1 mM). The DFO-saturated *Y. enterocolitica* were then transferred onto FOB-BSA micropatterns. We observed that *Y. enterocolitica* did not bind in significant numbers to the FOB-BSA micropatterns. These results supported that siderophore DFO plays an important role in bacterial capture (FIG. 74*c, d*).

To evaluate the ability of a siderophore-patterned chip to capture live or dead bacteria, the gold chip μ-contact printed with FOB-BSA conjugate was incubated with *Y. entero-*

Figure 75:
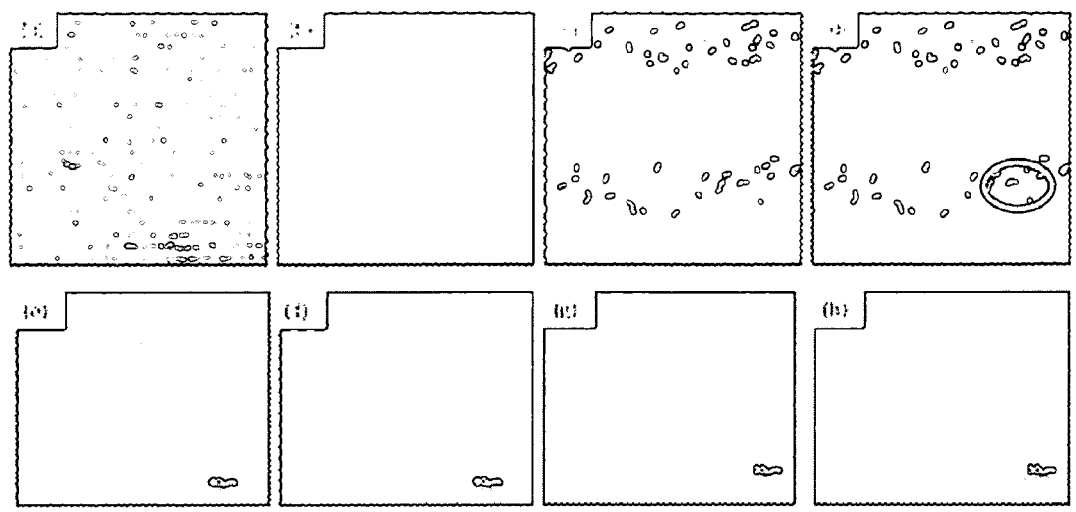
FIG. 75(a-d) shows capture of live bacteria: confocal scanning microscopy image (×20 magnification) of the chip captured *Y. enterocolitica* staining with (a) SYTO-9 dye, (b) PI dye, confocal image (×60 magnification) of (c) SYTO-9 dyed, (d) merged SYTO-9/PI dyed.

*colitica* ($10^8$ cfu/ml) at room temperature for an hour. After washing the chip with PBS and nanopure water without drying under argon, immediately a mixture of fluorescent stains (SYTO-9/PI (propidium iodide); 100 was applied to the chip for staining the captured bacteria for 15 minutes at room temperature. The chip was then washed again with PBS and nanopure water, dried under argon and imaged in confocal scanning-microscopy. Analysis of confocal scanning microscopy images showed that most bacteria were stained with SYTO-9 to confirm that more than 95% of bacteria are alive (FIG. 75). In parallel experiments, dead bacteria were prepared by UV (254 nm) irradiation. The dead *Y. enterocolitica* incubated on the chip for an hour and the chip was treated with same procedure described above. The confocal images exhibited no fluorescent staining to reveal no capturing of dead bacteria (FIG. 75). These explored experiments confirmed that mostly live bacteria *Y. enterocolitica* are detected by siderophore DFO. Therefore, siderophore immobilized chips can distinguish between live and dead cells.

Figure 76:
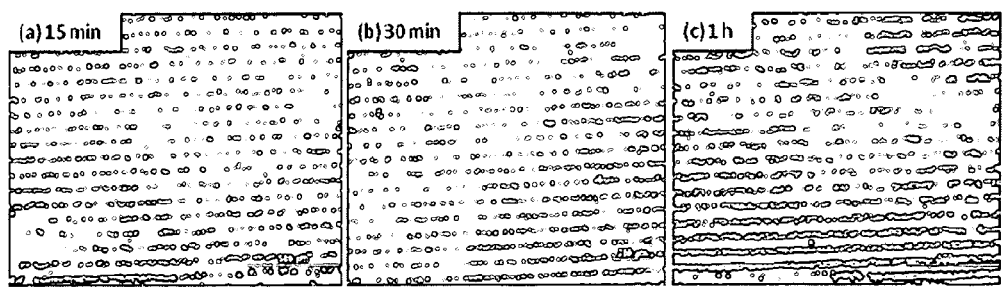
FIG. 76 shows incubation time; (a) 15 minutes, (b) 30 minutes, and (c) 1 hour at *Y. enterocolitica* ($10^8$ cfu/ml) onto gold chips.

The preceding experiments were exposed to bacteria for one hour onto patterned chips. To obtain minimum saturation time, FOB-BSA patterned chips were examined incubation time from 15 to 60 minutes by 15 minute intervals at concentrations of $10^8$ cfu/ml. Bacterial binding was saturated within 15 minutes of incubation, allowing for rapid detection at high concentrations (FIG. 76).

Figure 77:
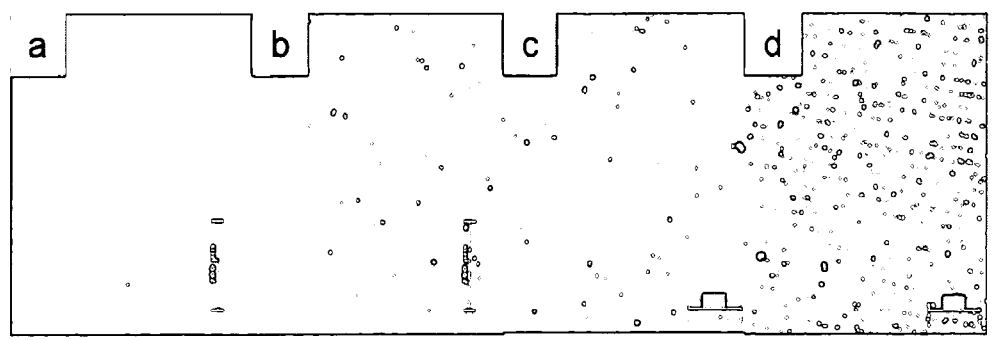
FIG. 77 shows effect of BSA linker; (b) No BSA linker; FOB was directly attached to NHS-codelink slide (a: background), (d) BSA linker; FOB-BSA conjugate was attached to NHS-codelink slide (c: background) at *Y. enterocolitica* ($10^8$ cfu/ml).

Presenting the siderophore attached to BSA can influence the ability of the pathogen to bind the chip. Therefore, FOB in the absence of BSA was directly attached to NHS-activated codelink slide by µ-contact printing method. The remaining unreacted NHS groups were blocked with ethanolamine (50 mM in 0.1 M Tris buffer, pH 9.0), and then exposed to *Y. enterocolitica* at $10^8$ cfu/ml. The darkfield images showed less bacteria binding onto the pattern than in the presence of BSA (FIG. 77). This result indicates that BSA linker provided more steric room for bacteria binding than direct attachment of ligand on the surface.

Figure 78:
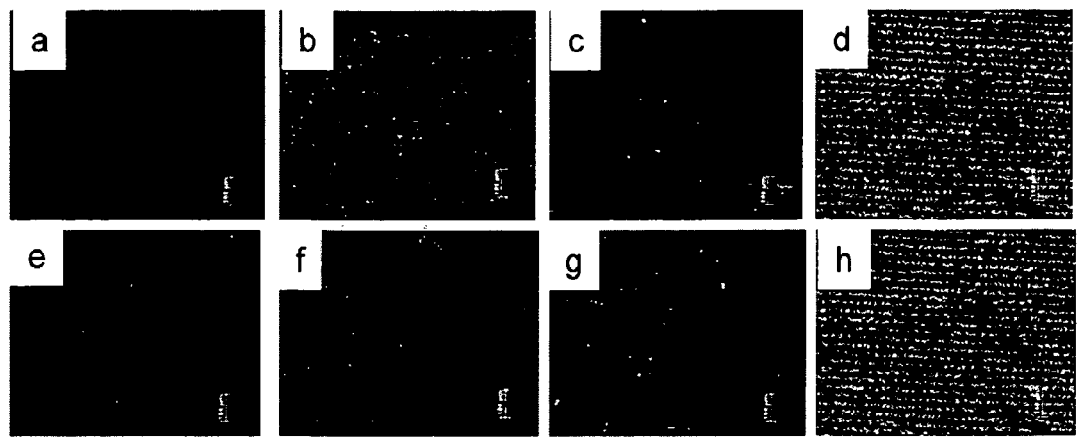
FIG. 78 shows suppression of background by 0.45 µm filtration: 0.45 µm filtration of BSA-FOB (a,e: before capture; b,f: after capture), No filtration of BSA-FOB (c,g: before capture; d,h: after capture) onto gold plated slides (a-d), and NHS activated glass slides (e-h) at *Y. enterocolitica* ($10^8$ cfu/ml).

We tested suppression of background signal by passing through a 0.45 µm membrane filter of FOB-BSA solution before µ-contact printing to minimize residue onto gold surface. Microfiltration was helpful to reduce background signals and improve signal-to-noise ratios, but intensity of bacteria capturing was interestingly lower than non-filtered substrates. It was assumed that the residue, not passing through membrane filter, is aggregated BSA including DFO, so that either DFO was relatively reduced or less BSA resulted in less immobilization onto chips by filtration. This phenomenon was observed in both gold plated glass chips and NHS-code-link slides (FIG. 78).

Figure 79:
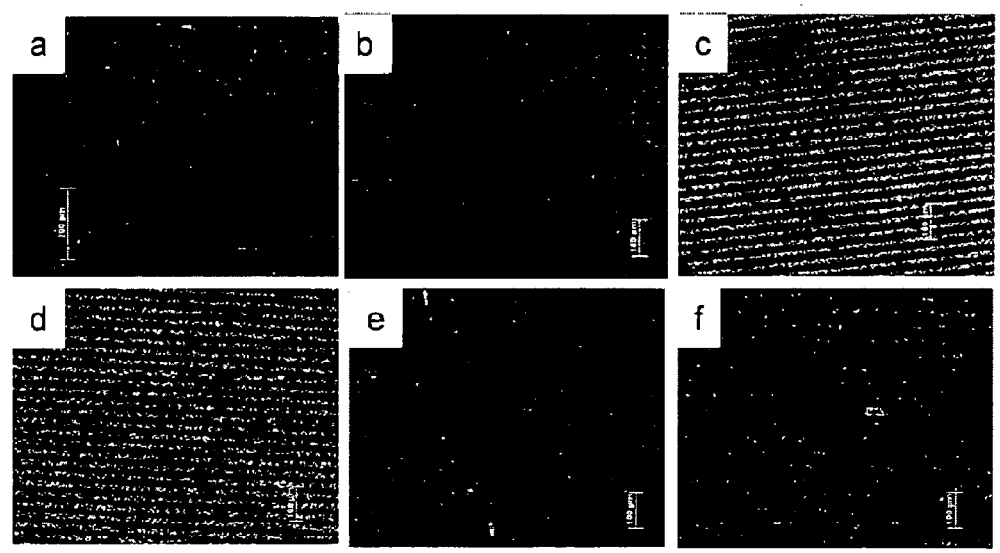
FIG. 79 shows density of DFO: DFO wt % (a) 5 wt %, (b) 10 wt %, (c) 20 wt %, (d) 30 wt %, (e) 40 wt %, (f) 50 wt % relative to BSA at *Y. enterocolitica* ($10^8$ cfu/ml).

The relative amount of DFO to BSA might affect stamping quality and detection sensitivity. Density of DFO to BSA was therefore optimized to provide a good image with a minimal quantity of ligand. DFO weight percentage (wt %) relative to BSA was changed from 5 to 50 wt %. After preparing FOB-BSA patterned chips with various density of DFO, the chips exposed to *Y. enterocolitica* ($10^8$ cfu/ml) for 30 minutes at the same condition. We observed that 20-30 wt % of DFO relative to BSA showed more bacterial adhesion to patterns (FIG. 79).

Figure 80:
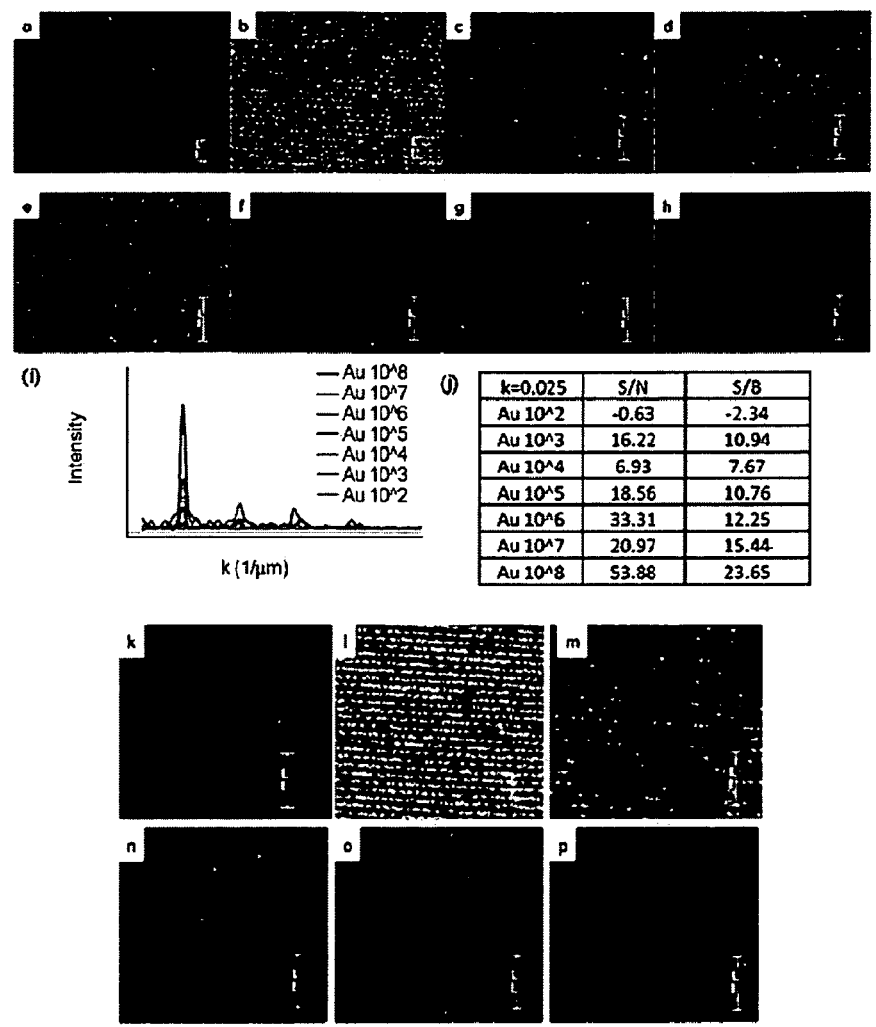
FIG. 80 shows sensitivity of detection of *Y. enterocolitica*. (a,k) control background (0 cfu/ml), (b,l) $10^8$, (c,m) $10^7$, (d,n) $10^6$, (e,o) $10^5$, (f,p) $10^4$, (g) $10^3$, (h) $10^2$ cfu/ml onto gold coated glass slides (a-h), or NHS activated glass slides (k-p). (i) FFT algorithm of images. (j) Data recalculated S/N for linear scale and before capture subtraction.

To test sensitivity of the bacteria detection, FOB-BSA patterned chips onto gold surface were exposed to *Y. enterocolitica* at concentrations of $10^8$ to $10^2$ cfu/mL, and then analysis of dark field microscopy images by fast Fourier transform (FFT) revealed that a patterned distribution of bacteria could be detected down to concentrations of $10^3$ cfu/mL. FFT algorithm is applied for evaluating bacteria capture quantitatively, and prominent signals at the characteristic 1/a position, with good signal-to-noise ratios (>6.0) indicate detection limit of bacteria concentration (FIG. 80). By comparison, inexpensive N-hydroxysuccinimide (NHS) activated glass slides (CodeLink) were examined. Various concentrations of *Y. enterocolitica* ($10^8$ to $10^2$ cfu/ml) were then applied onto the patterned surface. Dark-field images were obtained from a standard optical microscope to investigate the presence of detectable patterns down to concentrations of $10^4$ cfu/mL (FIG. 80).

Figure 81:
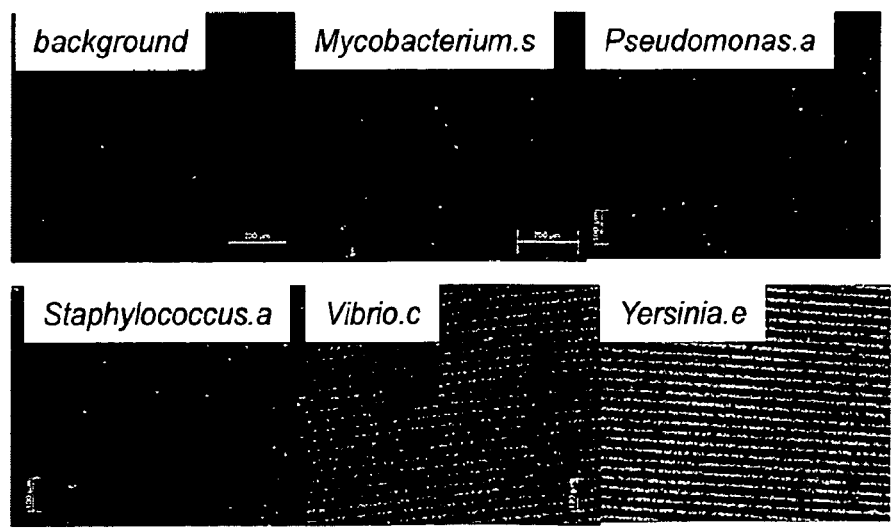
FIG. 81 shows binding specificity of FOB-BSA. (a) background, (b) *Mycobacterium smegmatis*, (c) *Pseudomonas aeruginosa*, (d) *Staphylococcus aureus*, (e) *Vibrio cholera*, and (f) *Yersinia enterocolitica* at $10^8$ cfu/mL.

The pathogen specificity of FOB-BSA printed chips were evaluated by exposing the chip to *Mycobacterium smegmatis*, *Pseudomonas aeruginosa*, *Staphylococcus aureus*, or *Vibrio cholerae* for 30 minutes at $10^8$ cfu/mL and compared to a positive control exposed to *Y. enterocolitica*. As shown in the darkfield images of FIG. 81, minimal or no patterned binding was observed in case of *Mycobacterium*, *Pseudomonas* or *Staphylococcus* for a short incubation time.

Figure 82:
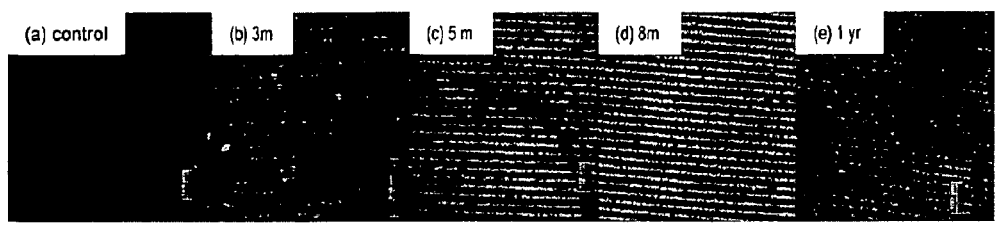
FIG. 82 shows a stability test of FOB-BSA patterned gold plated glass chips; dark field images of *Y. enterocolitica* after storage of chips for (b) 3 months, (c) 5 months, (d) 8 months, and (e) 1 year at 0-4° C. Storage of chips for (f) 3 weeks, (g) 3 months, (h) 6 months, (i) 8 months, and (j) 1 year at room temperature (a: background).
Figure 82:
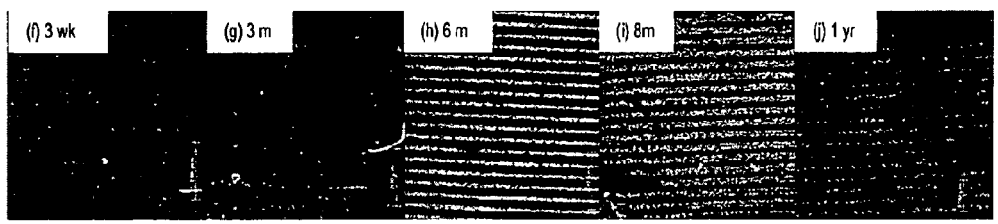
Figure 83:
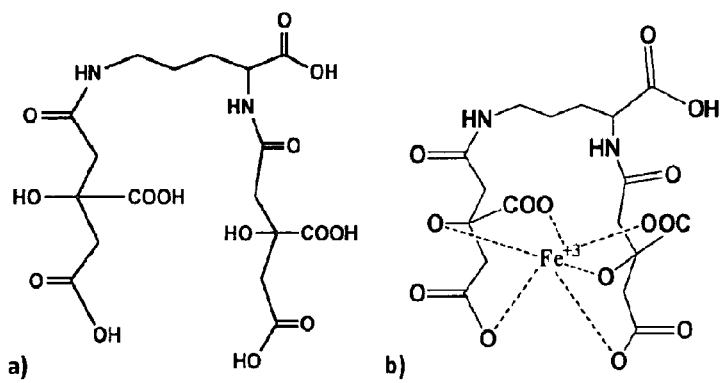
FIG. 83A shows the structure of Staphyloferrin A.
FIG. 83B shows the structure of Staphyloferrin A-Fe conjugate.

Because BSA linker is necessary for better bacterial binding as demonstrated above, we explored stability of FOB-BSA printed chips to test how long the chips are eligible to use for bacterial detection. To examine stability of chips, µ-contact printed gold chips with FOB-BSA conjugate were stored at 4° C. and room temperature under drying agent and aluminum foil. After varying storage time from 3 weeks to one year, the chips were exposed to a fixed concentration of *Y. enterocolitica* ($10^8$ cfu/ml) and then, examined capability of the chips for bacterial detection. Surprisingly, all chips which stored at both 4° C. and room temperature from 3 weeks to one year showed bacterial adhesion onto periodic array (FIG. 82). FOB-BSA chips were stable as much as one year old chip didn't lose ability of bacteria detection.

This study demonstrated that a siderophore DFO immobilized onto a gold-plated or NHS-activated glass substrates captured the bacteria *Y. enterocolitica* beyond an antibody-antigen capture paradigm. The results were found to be a good agreement with pathogen count performed using a dark-field microscope. We optimized conditions such as incubation time of *Y. enterocolitica*, presence of BSA linker, filtration of DFO-BSA, and DFO density relative to BSA. By using optimized method, sensitivity of pathogen binding, specificity of DFO, and stability of the FOB-BSA chips were investigated. Moreover, we confirmed DFO immobilized biochips were detected live bacteria mostly, not dead bacteria. This approach, with simple instrumentation and ease of use, can facilitate the development of a compact device for rapid, label-free and accurate detection. The results can be easily extended for the detection of other microorganisms as long as a specific siderophore for its cognate pathogen is available.
Pathogen Detection Using an Exemplary Siderophore: Capture and Identification of Pathogenic *Staphylococcus aureus* Using the Immobilized Siderophore, Staphyloferrin A An efficient and rapid identification method for the detection of pathogenic *S. aureus* has been achieved. The identification method was achieved by using its own mutation-resistant ligand, staphyloferrin A, a siderophore for the *S. aureus*. We first synthesized Staphyloferrin A in a 4 step synthesis and then conjugated it to bovine serum albumin (BSA) and immobilized the BSA-Staphyloferrin A-Fe conjugate in a specific pattern onto the surface of gold-plated chips by using a polydimethylsiloxane (PDMS) stamp. The patterned stamp is then used for the detection of pathogenic Staphylococcal bacteria using methods similar to those described elsewhere.

Figure 84:
FIG. 84 shows the capture of *S. aureus* to (BSA)-staphyloferrin A-Fe Micropatterns.
Figure 85:
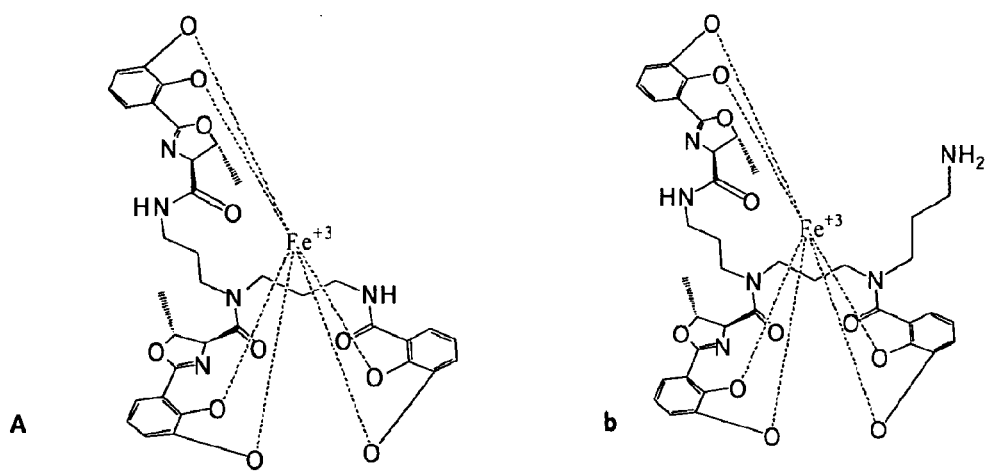
FIG. 85A shows the structure of vibriobactin-Fe conjugate.
FIG. 85B shows vibriobactin-Fe conjugate with spacer.

*S. aureus* was exposed to staphyloferrin ink micropatterned onto gold chip (Reichert #13206060-601) for 1.5 hours at concentration of $10^7$ particles/mL. Results show that a clear pattern formation was observed and this was further confirmed by Fourier transform analysis of the periodicity of light scattered by the pathogens captured on the chip (FIG. 84).

Pathogen Detection Using an Exemplary Siderophore: Selective Capture and Identification of Pathogenic *Vibrio cholerae* Using the Immobilized Siderophore, Vibriobactin An efficient, selective and rapid identification method for the detection of pathogenic cholera bacteria, *V. cholerae* has been achieved. The identification method was accomplished using a mutation-resistant ligand, a siderophore, vibriobactin that is naturally produced by the *Vibrio* genus of bacteria. We first synthesized vibriobactin in a 6 step synthesis and then conjugated it to bovine serum albumin (BSA) via a short spacer, and immobilized the BSA-vibriobactin-Fe conjugate in a specific banded pattern onto the surface of gold-plated chips using a polydimethylsiloxane (PDMS) stamp. The patterned stamp was then used to detect *V. cholerae*.

Figure 86:
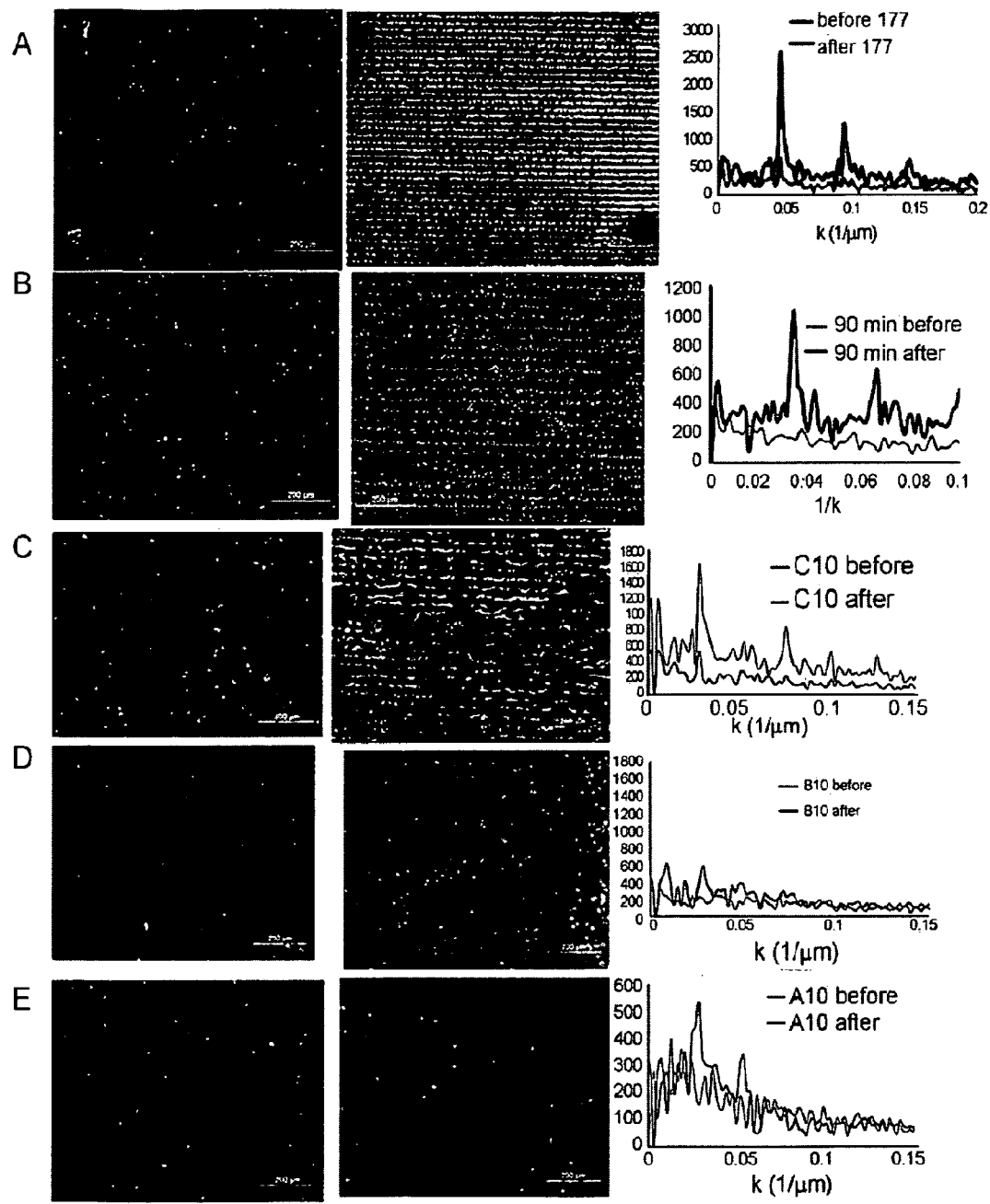
FIG. 86A shows before capture (left) and after capture (right) with filtered ink; concentration of $10^8$ particles/mL.
FIG. 86B shows before capture (left) and after capture (right); concentration of $10^7$ particles/mL.
FIG. 86C shows before capture (left) and after capture (right); concentration of $10^6$ particles/mL.
FIG. 86D shows before capture (left) and after capture (right); concentration of $10^5$ particles/mL.
FIG. 86E shows before capture (left) and after capture (right); concentration of $10^4$ particles/mL.

Capture of *V. cholerae* onto vibriobactin ink micropatterned gold chips (Reichert #13206060-601) was monitored at concentrations of from $10^8$ to $10^4$ particles/mL (FIG. 86) followed by Fourier transform analysis of the repeating pattern (FIGS. 86A and 86B). A characteristic 1/a peak was clearly resolved after 1.5 hours incubation. Results show that at high concentrations of bacteria ($10^8$ to $10^6$ particles/mL), very good pathogen capture was obtained. At lower bacterial titers, weaker but still discernable patterns were observed ($10^5$ to $10^4$ particles/mL).

Figure 87:
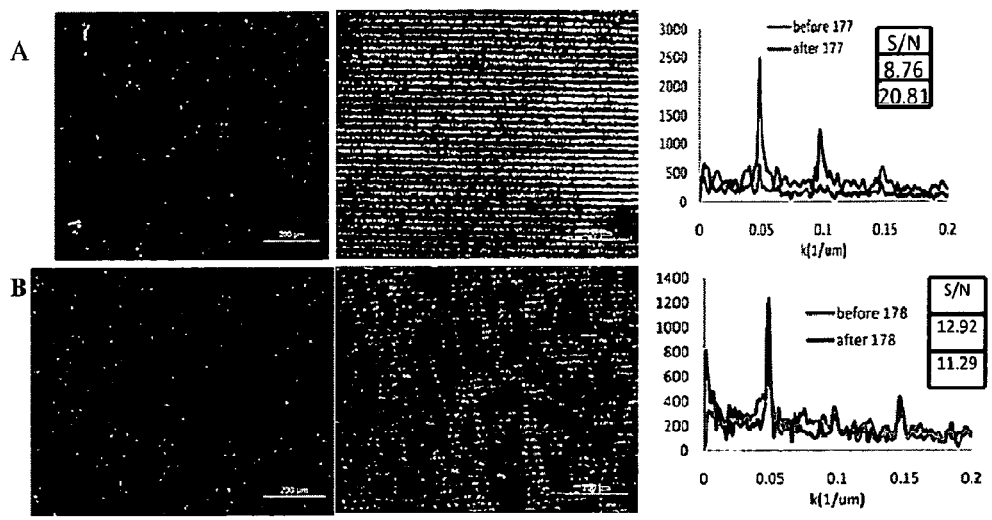
FIG. 87A shows before capture (left) and after capture (right) with filtered ink; concentration of $10^8$ particles/mL.
FIG. 87B shows before capture (left) and after capture (right) without filtered ink; concentration of $10^8$ particles/mL.

When vibriobactin ink was filtered through a 0.45 μm membrane, results showed that the signal-to-noise ratio improved considerably (FIG. 87).

Figure 88:
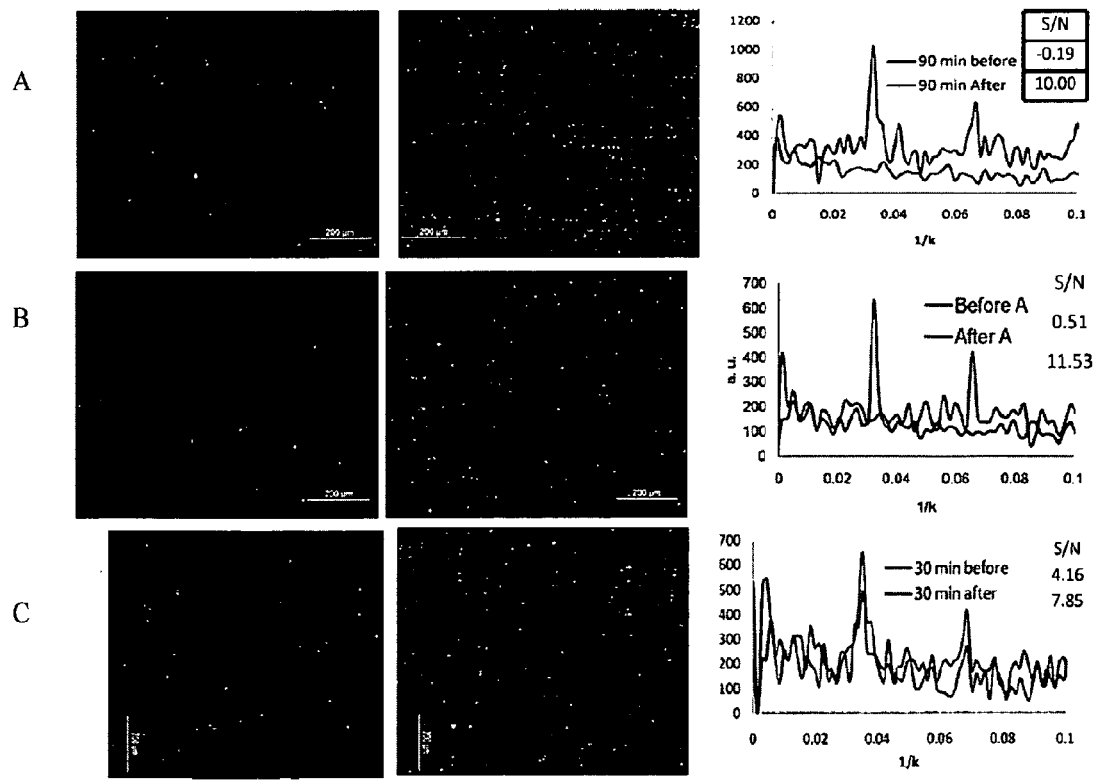
FIG. 88A shows before capture (left) and after capture (right); incubation time 1.5 hours.
FIG. 88B shows before capture (left) and after capture (right); incubation time 45 minutes.
FIG. 88C shows before capture (left) and after capture (right); incubation time 30 minutes.

Gold chips containing vibriobactin ink micropatterns were incubated with *V. cholerae* and examined under an optical microscope at various time intervals from 30 minutes to 1.5 hours and at a concentration of *V. cholerae* of $10^7$ particles/mL. Analysis shows that a 30 minute exposure to *V. cholerae* was enough to capture bacteria for well-defined arrays corresponding to the patterns (FIG. 88).

Figure 89:
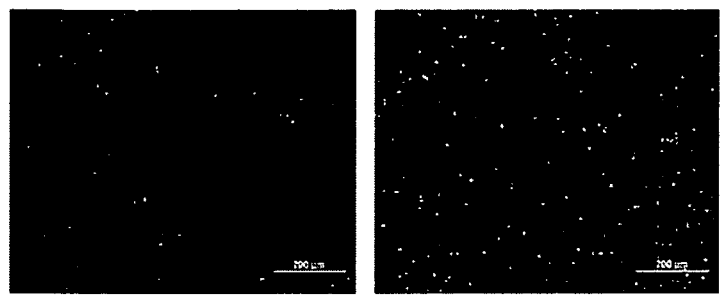
FIG. 89 shows quasi-dark field images of the printed patterns after exposure to *V. cholerae* ($10^8$ particles/mL) for 2 hours (a) BSA only (No vibriobactin ligand) and (b) *V. cholerae* was mixed with 1 mM vibriobactin before exposure onto gold chip.

To demonstrate the requirement of vibriobactin ink for specific binding of *V. cholerae*, we microcontact-printed only BSA in PBS on a gold chip and was exposed to the *V. cholerae* ($10^8$ particles/mL) for 2 hours. Our study shows that the bacteria did not bind to the BSA (FIG. 89A). To further confirm the specific binding of *V. cholerae* to vibriobactin ink, we conducted competition experiments using vibriobactin (1 mM). A suspension of *V. cholerae* ($10^8$ particles/mL) was treated with vibriobactin solution in PBS (1 mM) to saturate vibriobactin ink binding sites and thereby prevent their ability to mediate pathogen capture on the chip. The vibriobactin saturated *Vibrio* were then transferred onto vibriobactin ink micropatterned chips. This pre-blocked preparation of *Vibrio* did not bind to the vibriobactin ink micropatterned chips, confirming the requirement of siderophore receptor with free vibriobactin ink binding sites (FIG. 89B).

Figure 90:
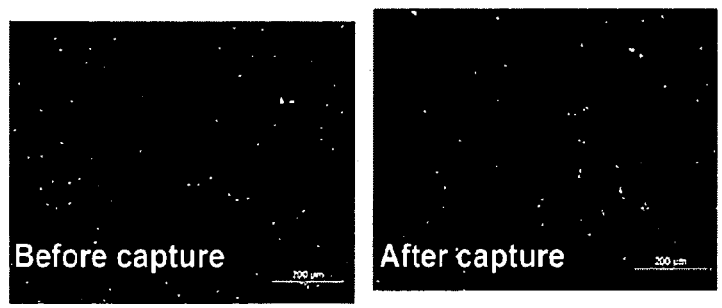
FIG. 90 shows quasi-dark field images of the printed patterns after exposure to dead *V. cholerae* ($10^8$ particles/mL) for 1.5 hours.

We killed *V. cholera* by the UV-irradiation of a suspension of *V. cholerae* ($10^8$ particles/mL) in PBS for 2 hours. The dead *Vibrio* bacteria were transferred onto vibriobactin ink micropatterns on gold chip. Experimental results show that dead *Vibrio* did not bind to the vibriobactin ink micropatterns (FIG. 90).

To evaluate the selectivity of the immobilized vibriobactin, we exposed vibriobactin ink micropatterns on gold chips to *Yersinia enterocolitica, Staphylococcus aureus*, or *Pseudomonas aeruginosa* ($10^8$ particles/mL) for two hours. Experimental results show that only *Vibrio* binds to the vibriobactin ink micropatterns. This result indicates that vibriobactin ink can capture the *V. cholerae* selectively among *Y. enterocolitica, S. aureus*, and *P. aeruginosa*.

Thus, we have developed an efficient, selective, and rapid identification method for the detection of pathogenic cholera bacteria, *V. cholerae* by using mutation-resistant ligands, vibriobactin, a siderophore for the *V. cholerae*.

Pathogen Detection Using an Exemplary Cell Surface Attachment Molecule: Capture and Identification of Pathogenic Influenza Virus (H1N1, H3N1, H5N1) Using Neuraminidase Inhibitors (Oseltamivir-PEG-Amine, Oseltamivir-PEG-Succinyl-Diaminopropionyl-Asp-Cys-Conjugates)

Influenza is caused by RNA viruses of the orthomyxoviridae family. There are three types of these viruses—Type A, Type B, and Type C—and each causes a different type of influenza. Type A influenza viruses infect mammals (e.g., humans, pigs, ferrets, horses) and birds. These viruses are capable of causing worldwide pandemics in humans. Type B influenza viruses (also known simply as influenza B) infect only humans. They occasionally cause local outbreaks of flu. Type C viruses also infect only humans, but rarely cause serious illness.

Current rapid immunodiagnostic tests for influenza antigens can reportedly either detect influenza A or distinguish between influenza A and B. The complexity of the test formats may require special training. In addition, significant amounts of virion particles are commonly required to obtain positive test result, which can limit their effective use to a short window of time when virus shedding is sufficiently high to generate a positive result. Assay sensitivity also can be variable with up to 20% false negative test results in certain assays, and this constitutes a significant current concern (e.g., see "WHO recommendations on the use of rapid testing for influenza diagnosis," July 2005). Reverse-transcriptase PCR-based diagnostics (RT-PCR) have resulted in improved sensitivity, but the test can be laborious and can require highly trained personnel, making on-site or field testing difficult. Because of the relative inefficiency of the reverse transcriptase enzyme, significant amounts of virus (e.g., $10^4$ virion particles) and as many as 20 primers may be required effectively to detect viral RNA. Moreover, RT-PCR is not easily adapted to high throughput screening of subjects in an epidemic setting or to field uses in an agricultural or point-of-care setting.

Annual influenza outbreaks and the threat of development of a pandemic are of great worldwide concern as new strains continue to emerge and mutate. An estimated 36,000 people die from influenza-related illnesses each year in the United States. To date, the most reliable method for identifying influenza virus strains takes 3 to 7 days and can only test a few samples simultaneously. Additionally, the complexity, diversity, and rapid emergence of new (e.g., swine flu) influenza strains has made diagnosis of high risk strains difficult and, therefore, rapid response is at present nearly impossible. Therefore, we have developed a new detection method capable of rapid and accurate identification of influenza A and B subtypes that may ultimately reduce the impact of a potential swine flu and influenza pandemic.

Influenza viruses are classified according to the subtypes of hemagglutinin and neuraminidase proteins expressed on their surfaces. Representative examples of influenza hemagglutinin subtypes include H1, H3, H5, H6, H7, H9 and H10. Representative types of influenza neuraminidase subtypes include N1, N2, N3, N4, N5, N6, N7. Thus, influenza strains can be classified based on the isotopes of hemagglutinin and neuraminidase that they express, and these strains are termed H1N1, H3N1, H5N1, H6N2, H7N3, H7N7, H9N2, H10N4 and H10N5.

The problem with current methods for influenza virus identification and detection is that the current methods involve many variations on either PCR assays or on antibody capture assays. Exemplary limitations of PCR include, for example, cost, time (e.g. isolation of DNA and instrument set-up), and stability and use of reagents. Exemplary limitations of antibody capture assays include, for example, that pathogens often can evade antibody detection through mutation of their outer coats, the outer coat of pathogens also can be bioengineered by trained personnel to have a composition that current antibodies will not recognize, and antibodies are proteins that are easily denatured under harsh conditions (e.g. battlefields, hot environments) and thus may not be compatible with many applications.

An ideal biorecognition methodology is one that is mutation-resistant—i.e., difficult for a pathogen to evade while retaining virulence, pathogen specific, highly reliable, rapid, easy to use (little training required), robust/stable in harsh environments, reagent free, small in size, and inexpensive.

One strategy is to capture pathogens using low molecular weight ligands that the pathogen must bind to remain virulent. One such example is a cell surface attachment molecule. If the receptor for the host cell is mutated, the pathogen becomes avirulent because it can no longer bind and enter the host cell.

Design and Synthesis of Capture Ligands for Human Influenza Virus

Mechanism of Action of Neuraminidase Inhibitors. Viral replication can be blocked by neuraminidase inhibitors, which prevent virions from being released from the surface of infected cell in which they were assembled. This prevents spreading of the virus to distant cells.

The neuraminidase cleaves off sialic acid (SA, also known as N-acetylneuraminic acid or NANA) from the cell receptor for influenza virus, so that the newly formed virus particles can be released from the cells. Neuraminidase inhibitors, such as oseltamivir (TAMIFLU, Genentech USA, Inc., South San Francisco, Calif.), interfere with the release of progeny influenza virions from the surface of infected host cells. In doing so, the neuraminidase inhibitors prevent virus infection of new host cells and thereby halt the spread of infection in the respiratory tract. We have used oseltamivir derivatives to capture influenza viruses onto a detection device, since oseltamivir and its derivatives can bind tightly to all of the known neuraminidase subtypes of influenza virus.

Quasi-dark field images of captured influenza viruses were obtained using a Olympus fluorescence microscope (Olympus BH-2) connected to a CCD camera (Olympus DP70) using phase contrast 100× and a fluorescence exposure time of 1/1.6-2.6 seconds.

Capture of (H1N1, H3N1) Influenza Virus onto Gold-Coated Glass Slide.

We have developed a ligand based on oseltamivir for the detection and capture of influenza virus presenting N1 neuraminidase. Oseltamivir was conjugated onto bovine serum albumin (BSA) via an amine-terminated PEG linker, then patterned into linear arrays using the microcontact printing methodology. An aqueous DMSO solution of the oseltamivir-PEG-NH-BSA conjugate was passed through a 0.45-micron membrane filter, then applied onto the PDMS stamp surface with a cotton swab and left to stand for 2 minutes prior to drying under a gentle stream of argon gas. The stamp was brought into conformal contact with a gold substrate, then removed after 10 minutes; the gold chip was rinsed with PBS and distilled water to remove any unbound ligand. Attenuated strains of H1N1 and H3N1 were introduced, followed by a rinse after 1 hour and treatment with an oseltamivir-PEG-FITC label for fluorescent immunostaining.

Figure 91:
FIG. 91 shows fluorescent micropatterns corresponding to the successful capture of viral particles from an attenuated strain of A/H1N1 (influenza virus), at $10^6$ particles/mL.
Figure 91:
Figure 92:
FIG. 92 shows fluorescent micropatterns corresponding to the successful capture of viral particles from an attenuated strain of A/H3N1 (influenza virus), at $10^6$ particles/mL.
Figure 92:
Figure 93:
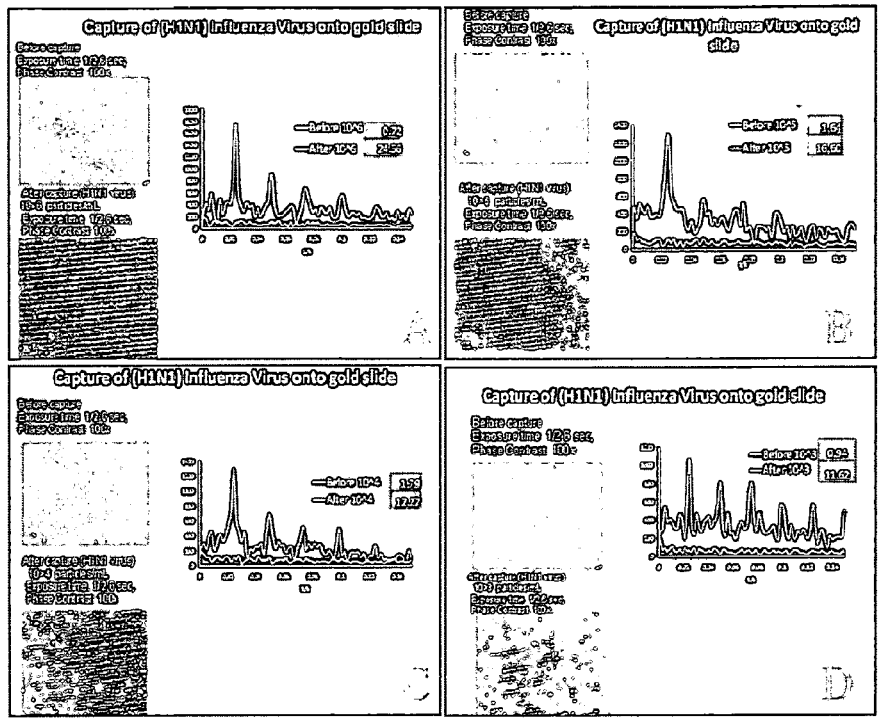
FIG. 93 shows fluorescent micropatterns corresponding to the successful capture of viral particles from an attenuated strain of A/H1N1 (influenza virus), at $10^6$ (A), $10^5$ (B) $10^4$ (C), and $10^3$ (D) particles/mL.

This revealed a well-defined array corresponding to the PDMS-generated line patterns (FIGS. 91 and 92). The substrates were then monitored at concentrations of influenza virus H1N1 from $10^6$ to $10^3$ particles/mL. Detection and capture of attenuated viruses was achieved using an immobilized oseltamivir-PEG-conjugate-linker, followed by fluorescent labeling with oseltamivir-PEG-FITC. The array images were converted into frequency-selective signals using discrete Fourier transform. The signal-to-noise ratio at 1/a is shown in FIG. 93).

Capture of (H1N1, H3N1, H5N1) Influenza Virus onto Gold Coated Glass Slide.

We have developed a ligand based on oseltamivir for the detection and capture of influenza viruses presenting N1 neuraminidase. Oseltamivir was conjugated onto bovine serum albumin (BSA) via an acid-terminated oseltamivir-PEG-Succinyl-Diaminopropionyl-Asp-Cys-conjugate and then patterned into linear arrays using the micro contact printing methodology featured above. An aqueous solution of the oseltamivir-BSA conjugate was passed through a 0.45-micron membrane filter, then applied onto the PDMS stamp surface with a cotton swab and left to stand for 2 minutes, prior to drying under a gentle stream of argon gas. The stamp was brought into conformal contact with a glass coated gold substrate and then removed after 5 minutes; the glass coated gold chip was rinsed with PBS and distilled water to remove any unbound ligand. Attenuated strain of H1N1 was introduced, followed by a rinse after 1 hour and treatment with a oseltamivir-PEG-FITC labeled for fluorescent immunostaining.

Figure 94:
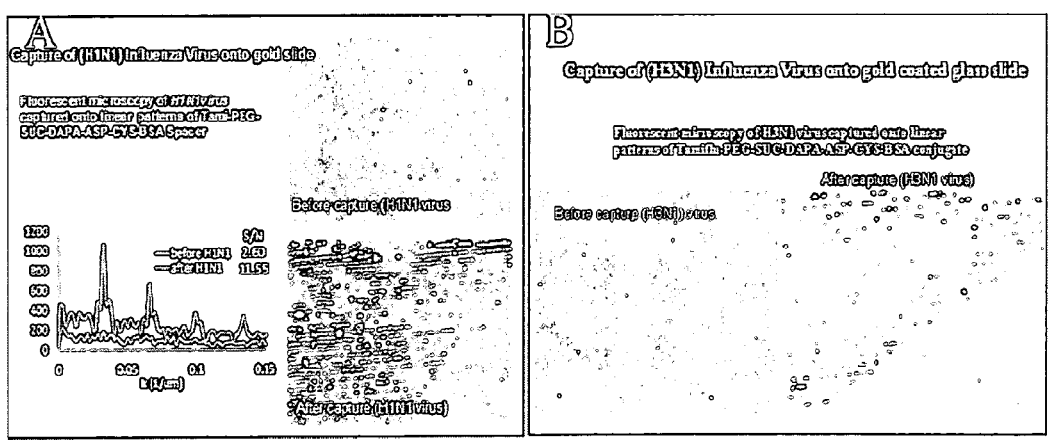
FIG. 94A shows fluorescent micropatterns corresponding to the successful capture of viral particles from an attenuated strain of A/H1N1 (swine flu strain), at $10^6$ particles/mL.
FIG. 94B shows fluorescent micropatterns corresponding to the successful capture of viral particles from an attenuated strain of A/H3N1.
FIG. 94C shows fluorescent micropatterns corresponding to the successful capture of viral particles from an attenuated strain of A/H5N1 (influenza virus) at $10^6$ particles/mL.

This revealed a well-defined array corresponding to the PDMS-generated line patterns (FIG. 94). Detection and capture of attenuated viruses was achieved using an immobilized oseltamivir-PEG-succinyl-diaminopropionyl-Asp-Cys-conjugate, followed by fluorescent labeling with oseltamivir-PEG-FITC. Control images are substrates without exposure to viral particles. The substrates were then monitored at concentration of influenza virus H1N1 $10^6$ particles/mL. The array images were converted into reciprocal space signals using the fast Fourier transform algorithm. The signal-to-noise ratio at 1/a is 11.55 (FIG. 94).

Capture of (H1N1) Influenza Virus onto Gold-Coated Glass Slide.

Oseltamivir-3-pentyloxy-PEG-succinyl-diaminopropionyl-Asp-Cys-conjugate was conjugated onto bovine serum albumin (BSA) via an acid-terminated oseltamivir-3-pentyloxy-amine-PEG-succinyl-diaminopropionyl-Asp-Cys-conjugate and then patterned into linear arrays using the micro contact printing methodology featured above. An aqueous solution of the oseltamivir-3-pentyloxy-amine-PEG-succinyl-diamirtopropionyl-Asp-Cys-conjugate-BSA was passed through a 0.45-micron membrane filter, then applied onto the PDMS stamp surface with a cotton swab and left to stand for 2 minutes, prior to drying under a gentle stream of argon gas. The stamp was brought into conformal contact with a gold coated glass substrate and then removed after 5 minutes; the gold coated glass chip was rinsed with PBS and distilled water to remove any unbound ligand. Attenuated strain of H1N1 was introduced, followed by a rinse after 1 hour and treatment with a oseltamivir-PEG-FITC labeled for fluorescent immunostaining.

This revealed a well-defined array of corresponding to the PDMS-generated line patterns (FIG. 95). Detection and capture of attenuated viruses was achieved using an immobilized oseltamivir-3-pentyloxy-amine-PEG-succinyl-diamimopropionyl-Asp-Cys-conjugate-linker, followed by fluorescent labeling with oseltamivir-PEG-FITC. Control images are substrates without exposure to viral particles. The substrates were then monitored at concentration of influenza virus H1N1 $10^6$ particles/mL.

Capture of (H1N1) Influenza Virus onto Gold Slide.

Oseltamivir-3-pentyloxy-PEG-NH$_2$ was conjugated onto bovine serum albumin (BSA) via an amine-terminated PEG linker, and then patterned into linear arrays using the microcontact printing methodology. An aqueous DMSO solution of the oseltamivir-3-pentyloxy-PEG-NH-BSA conjugate was passed through a 0.45-micron membrane filter, then applied onto the PDMS stamp surface with a cotton swab and left to stand for 2 minutes, prior to drying under a gentle stream of argon gas. The stamp was brought into conformal contact with a gold substrate, and then removed after 10 minutes; the gold chip was rinsed with PBS and distilled water to remove any unbound ligand. An attenuated strain of H1N1 was introduced, followed by a rinse after 1 hour and treatment with a oseltamivir-PEG-FITC label for fluorescent immunostaining.

This revealed a well-defined array of corresponding to the PDMS-generated line patterns (FIG. 96). Detection and capture of attenuated viruses was achieved using an immobilized H$_2$N-PEG-3-pentyloxy-oseltamivir conjugate-linker, followed by fluorescent labeling with oseltamivir-PEG-FITC. Control images are substrates without exposure to viral particles. The substrates were then monitored at concentration of swine flu H1N1 $10^6$ particles/mL.

The Virus Particle Content of Influenza Virus was Determined by Plaque Assay. Confluent monolayers (MDCK cells in 6-well plates) were inoculated with 100 µl of $10^6$ to $10^2$ dilutions of influenza virus stocks in PBS, which was adsorbed for 45 minutes at 37° C. The inoculum was removed; the MDCK cells were washed twice with phosphate-buffered saline (PBS) and were covered with 3 ml of an agar medium consisting of 100 ml of 2× Agarose (0.75%) and 100 ml of 2× Eagle's DMEM which contained 1.95 g of commercial powdered medium (Grand Island Biological Co., F-15), 2.0 mg of chloretetracycline, 100 mg of sodium bicarbonate, and 50 mg of bovine serum albumin (Armour and Co., Chicago, Ill.; fraction V) and grown at 37° C. for 48 hours. Agar-covered monolayers were fixed in 20% methanol. After removal of agar, the cells were stained with 0.5% crystal violet. The plaques were scored by transmitted light. The strains of influenza virus tested produced large sizes of plaques (2 to 3 mm in diameter; FIG. 97).

The Virus Particle Content of Swine Flu Concentration was Determined Flow Cytometry.

MDCK Cell samples were stained with both oseltamivir FITC and FITC-MAbs. Here, cell aggregates were distinguished from single cells via the signal ratio of green fluorescence signal area and signal peak. For the discrimination between infected and uninfected cells (negative control) samples were stained and analyzed. The fluorescence intensity border between infected and uninfected cells was set to a quantile of the cumulative distribution.

Flow cytometric measurements were performed with a Beckman Coulter Epics XL cytometer (Beckman Coulter) equipped with a 488 nm argon laser using the Expo32 software (Beckman Coulter). Two aliquots of each sample were stained and $10^6$ to $10^4$ single MDCK cells analyzed. Cells were distinguished from debris via forward-light scattering (FSC) and side-light scattering (SSC). Single cells were discriminated from cell aggregates using plots of forward light scattering signal area (FSC-A) against forward-light scattering signal height (FSC-H). FITC fluorescence acquisition was performed with logarithmic binning.

Figure 98:
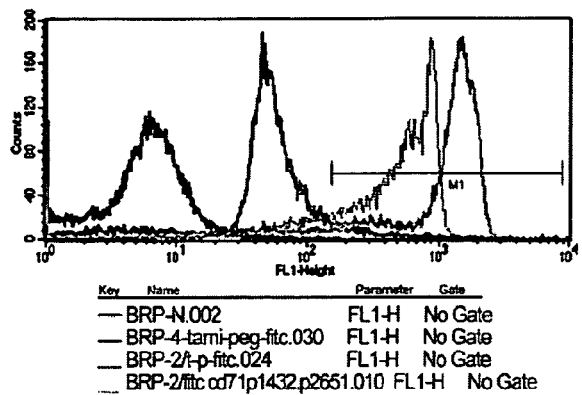
FIG. 98 shows direct immunostaining against influenza A virus neuraminidase with oseltamivir FITC.

Flow cytometric measurement of FITC calibration particles. For each particle population the mean fluorescence intensity was calculated from four samples. M1 gate sample concentration $10^6$ to $10^4$ (middle) and first one is control uninfected MDCK cells and H1N1 infected MDCK cells were direct stained with oseltamivir-FITC (FIG. 98).

Figure 99:
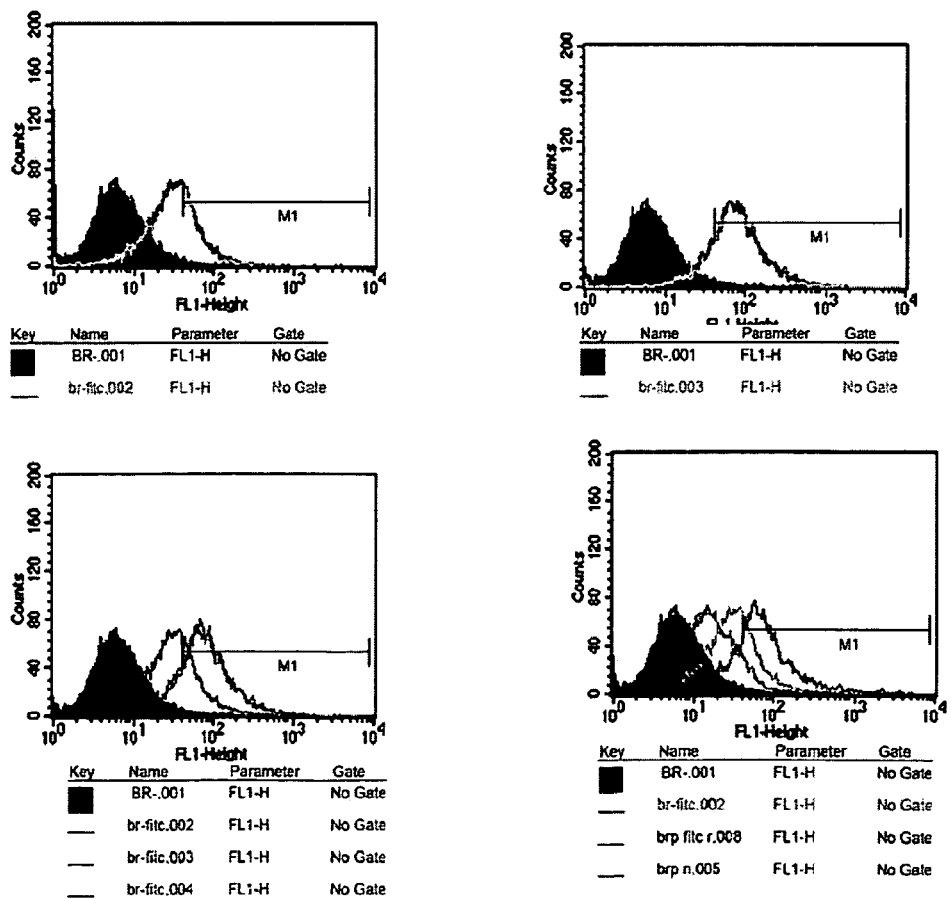
FIG. 99 shows immunostaining against influenza A virus HA.

Flow cytometric measurement of FITC calibration particles. For each particle population the mean fluorescence intensity was calculated from four samples. M1 gate sample concentration $10^6$ to $10^4$ (middle) and first one is control uninfected MDCK cells and H1N1 infected MDCK cells were stained with FITC-MAbs (FIG. 99).

Photolithographic Approach.

Figure 100:
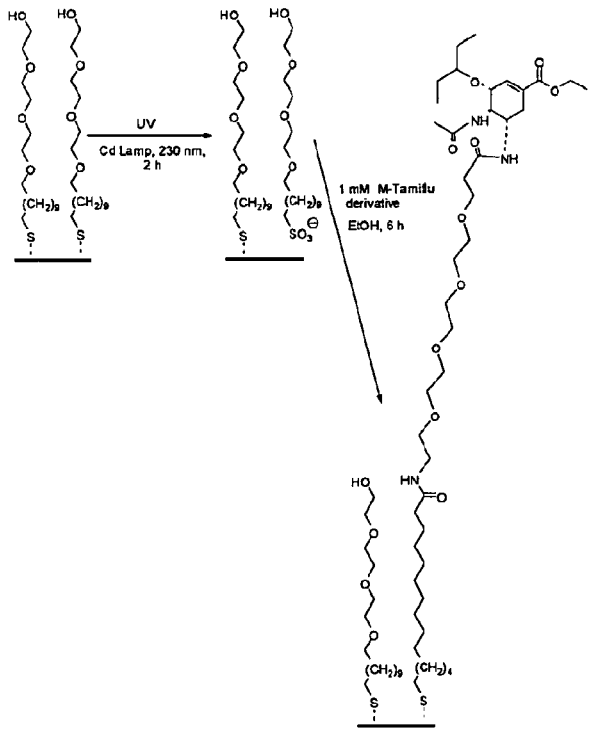
FIG. 100A shows a schematic of the immobilization of oseltamivir-PEG-mercapto on —COOH slides.
FIG. 100B shows a schematic of the immobilization of oseltamivir on —COOH slides.
Figure 100:
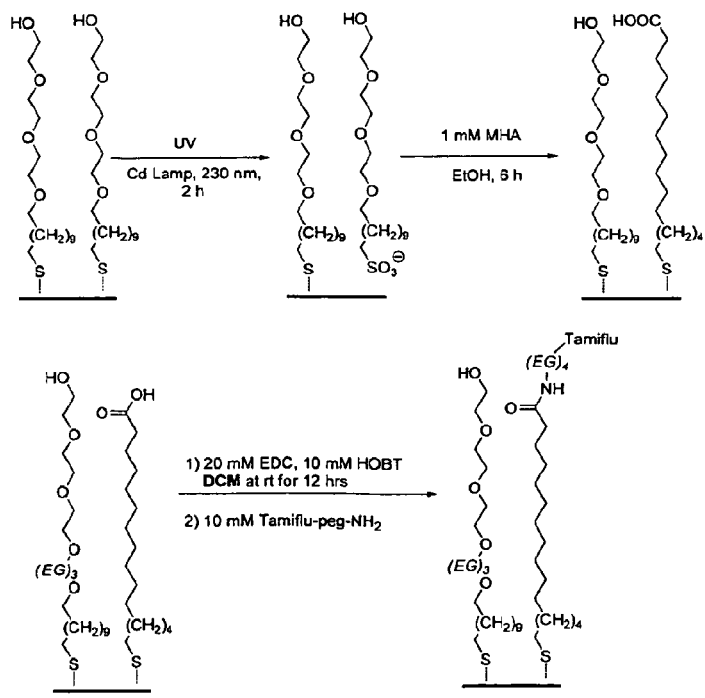

We have alternatively developed a photolithographic approach for creating micropatterns of oseltamivir-PEG-conjugate onto planar substrates coated with thiol substrates. H1N1/A Influenza virus can be detected and identified by a photolithographic method for creating micropatterns of pathogen-specific ligand (oseltamivir-PEG-amine) on to planar gold chip. Mercapto polyethylene glycol was used as self-assembled monolayer (SAMs) on gold surface, mercapto poly(ethylene glycol) chains were commonly used to prevent nonspecific binding interactions. Self-assembled monolayers (SAMs) were prepared by the adsorption of oseltamivir-PEG-mercaptopentadecanoamide onto the surface of gold (FIG. 100).

Figure 101:
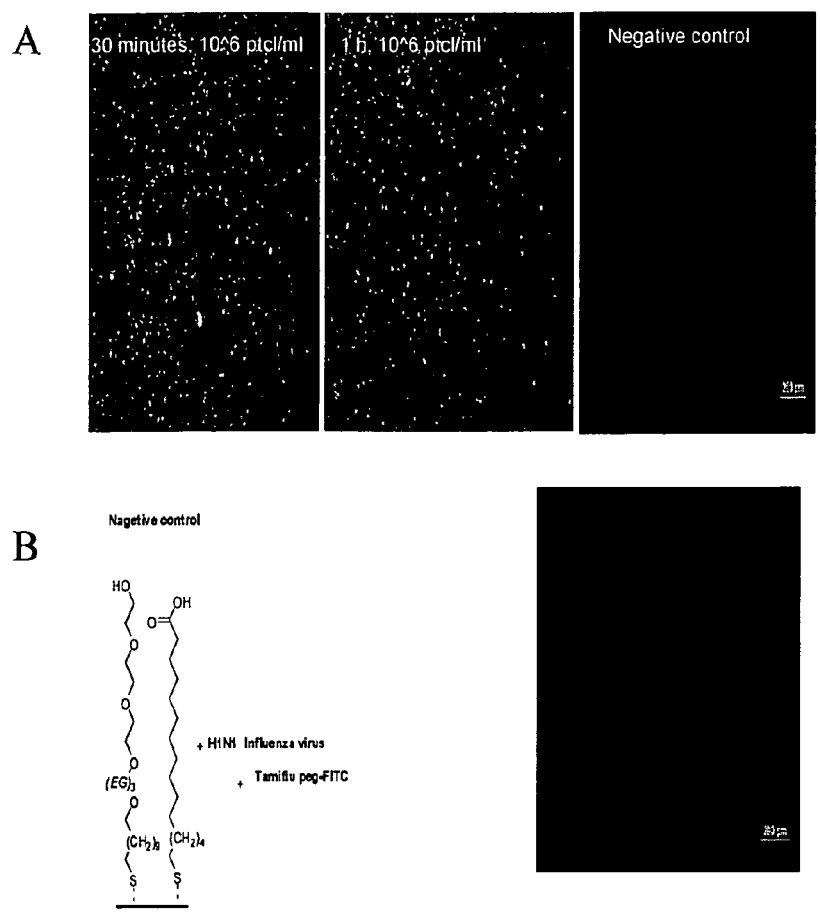
FIG. 101A shows the capture of H1N1 influenza Virus with oseltamivir-PEG-NH$_2$ on to gold chip surface.
FIG. 101B shows the negative control.

Each of the oseltamivir-PEG-ligand and the oseltamivir-PEG-FITC fluorescent analog binds to the neuraminidase on the surface of the H1N1 influenza virus particles. Incubation with H1N1 influenza virus and oseltamivir-PEG-FITC fluorescent immunostaining revealed a well-defined array of corresponding to the mask pattern (see FIG. 101).

Thus, we have developed an efficient, selective, and rapid identification method for the detection of influenza viruses using a ligand based on oseltamivir conjugates for the detection and capture of influenza virus presenting N1 neuraminidase. The oseltamivir conjugates include, for example, oseltamivir-PEG-amine, oseltamivir-PEG-succinyl-diaminopropionyl-Asp-Cys-conjugate, and oseltamivie-3-pentyloxy-PEG-succinyl-diaminopropionyl-Asp-Cys-conjugate).

Thus, we have demonstrated that the use of mutation-resistant ligands can serve as the basis for pathogen detection and identification. The strategies exemplified herein can be applied generally and used to detect and identify any pathogen so long as a ligand associated with the virulence of the pathogen is known. One feature of the strategy, generally, is that the pathogen is less likely to evade detection based on our strategy than through other conventional detection schemes because the pathogen binding to the ligands of our method are necessary for the pathogen to infect a host and replicate. Microbes that evade detection by our system are expected to concomitantly lose at least a portion of their virulence.

Additional suitable exemplary targets for detection and/or identification are summarized in Table 2, below.

TABLE 2

Exemplary Targets for use in Mutation-Resistant Pathogen Identification and Detection.

| Fungal Diseases | Bacterial Pathogens | | Viral Pathogens | Parasitic Pathogens | |
| --- | --- | --- | --- | --- | --- |
| Ringworm | *Yersinia* | *Haemophilus* | Papilloma viruses | *Taenia* | *Plasmodium* |
| Histoplasmosis | *Klebsiella* | *Bacteroides* | Parvoviruses | *Hymenolepsis* | *Trypanosoma* |
| Blastomycosis | *Providencia* | *Listeria* | Adenoviruses | *Diphyllobothrium* | *Leishmania* |
| Aspergillosis | *Erwinia* | *Erysipelothrix* | Herpesviruses | *Echinococcus* | *Toxoplasma* |
| Cryptococcosis | *Enterobacter* | *Acinetobacter* | Vaccine virus | *Fasciolopsis* | *Entamoeba* |
| Sporotrichosis | *Salmonella* | *Brucella* | Arenaviruses | *Heterophyes* | *Giardia* |
| Coccidiodomycosis | *Serratia* | *Pasteurella* | Coronaviruses | *Metagonimus* | *Isospora* |
| Paracoccidioidomycosis | *Aerobacter* | *Flavobacterium* | Rhinoviruses | *Clonorchis* | *Cryptosporidium* |
| Mucomycosis | *Escherichia* | *Fusobacterium* | Respiratory syncytial viruses | *Fasciola* | *Enterocytozoa* |
| Candidiasis | *Pseudomonas* | *Streptobacillus* | Influenza viruses | *Paragonimus* | *Strongyloides* |
| Dermatophytosis | *Shigella* | *Calymmatobacterium* | Picornaviruses | *Schistosoma* | *Trichinella* |
| Protothecosis | *Vibrio* | *Legionella* | Paramyxoviruses | *Enterobius* | *Onchocerca* |
| Pityriasis | *Aeromonas* | *Treponema* | Reoviruses | *Trichuris* | |
| Mycetoma | *Streptococcus* | *Borrelia* | Retroviruses | *Ascaris* | |
| Paracoccidiodomycosis | *Staphylococcus* | *Leptospira* | Rhabdoviruses | *Ancylostoma* | |
| Phaeohphomycosis | *Micrococcus* | *Actinomyces* | HIV | *Necator* | |
| Pseudallescheriasis | *Moraxella* | *Nocardia* | | *Wuchereria* | |
| Trichosporosis | *Bacillus* | *Rickettsia* | | *Brugi* | |
| Pneumocystis | *Clostridium* | *Micrococcus* | | *Loa* | |
| | *Corynebacterium* | *Mycobacterium* | | *Dracunculus* | |
| | *Eberthella* | *Neisseria* | | *Naegleria* | |
| | *Francisella* | *Campylobacter* | | *Acanthamoeba* | |

As mentioned above, in another aspect, the invention provides an instrument, article or device for the detection of pathogens, which may be referred to herein as a PathoTest device. An exemplary device is described in Example 5. The device can detect the presence of pathogens in a solution, in liquid or air, and can be rapid, efficient, portable, robust, cost-effective, and/or user-friendly. Ultimately, the device can be deployed for medical analysis (e.g., in a clinical setting), environmental analysis, and counterterrorism. Clinical applications include the detection and screening of sexually transmitted infections, gastrointestinal infections, or respiratory infections. It might also find applications in battlefield settings for the detection of biological agents in public arenas such as stadiums, shopping malls, or for monitoring water supplies. A quick, reliable, and accurate pathogen detection system can serve as a point of care technology that can greatly reduce the likelihood of a pandemic in the case of highly infectious agents.

The detection system uses "mutation-resistant" ligands to capture pathogens such as bacteria on micropatterned surfaces. The detection system can be rapid (<30 minutes) and it can be employed without the need to label the bound pathogen. This ligand recognition can be pathogen-specific, and is based on the need for the pathogen to, for example, bind to a cell surface for infection or to collect essential nutrients. The advantage of the mutation-resistant ligand approach is pathogens that are virulent will be detected, minimizing the occurrence of false-positive for similar pathogens. Antibody-based approaches also can detect pathogens quickly. However, such strategies could be rendered obsolete by mutations in the bacterial cell surface. Furthermore, the proteinaceous nature of the antibody make them vulnerable to denaturation in harsh environments.

An exemplary device can include an analytical chamber, a sample reservoir in fluid communication with the analytical chamber, a functionalized substrate according to any one of the embodiments of articles described herein, and an image recorder. In some embodiments, the device can include additional components such as, for example, a dielectrophoretic concentrator in fluid communication between the analytical chamber and the sample reservoir, a pump in functional communication with the sample reservoir, a wash reservoir in fluid communication with the dielectrophoretic concentrator, a pump in functional communication with the wash reservoir, an illumination source, a control processing unit in functional communication with at least one of the pumps, a control processing unit in functional communication with the image recorder, and/or a user interface display.

As used herein, the terms "in functional communication" or "functionally connected" refer to direct or indirect communication or connection. That is, the functionally connected components or the components in functional communication need not necessarily be adjacent in series; there may be one or more intervening components between the functionally connected components or the components in functional communication. In some embodiments of the device, the image recorder can include a camera such as, for example a charge-coupled device (CCD camera). In some embodiments, the device can include a magnifying lens functionally between the article and the image recorder.

Figure 41:
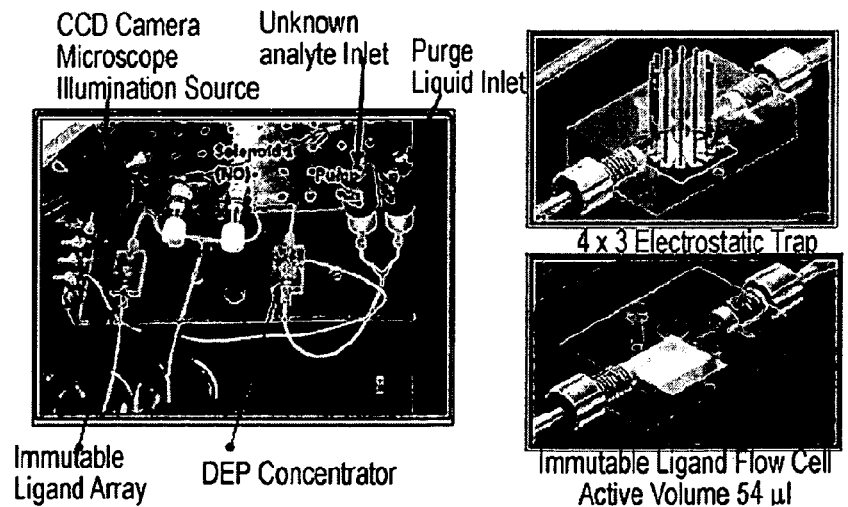
FIG. 41 shows a setup of the PathoTest device (version 1). (Left) Darkfield objective connected to CCD camera on a microscope and illumination source, solenoids 1 and 2 for directing flow, pumps, DEP particle trap, and flow cell with an mutation-resistant ligand array for patterned pathogen capture. (Right) Schematics of DEP trap and flow cell containing the capture chip.

In one embodiment, the device, referred to herein as a "PathoTest" device, can include a magnifying lens such as, for example, a microscope, a CCD camera as the image recorder, a flow cell, pump controls, an illumination source, and a dielectrophoretic (DEP) concentrator (FIG. 41), and is controlled through a control processing unit such as, for example, laptop computer with appropriate programming such as, for example, Labview. Liquid flow to the concentrator may be driven by two pumps: one for analyte solution and functionally connected to the sample reservoir, and one for purge/rinse cycles functionally connected to, for example, a wash reservoir. DEP capture is achieved by flowing analyte solution through the concentrator while the voltage is on, followed by drainage; the trap is then purged and cleansed with water. The voltage is then turned off and the concentrated analyte is passed through an analytical chamber containing a chip presenting an array of mutation-resistant ligands for patterned pathogen capture, which can be recorded under optical dark-field conditions.

In this version of the device, an adjustable ring stand serves as the mount for the microscope and CCD camera, separated from a detection plate that supports the pumps, solenoids, DEP trap, and flow cell with pathogen capture chip. The device is also equipped with a power supply, illumination source, and a laptop user interface that controls both the pump system (duration and frequency) and is equipped with image processing software. Image processing can involves converting digital images into 2D FFT images containing reciprocal lattice information; a linescan of the FFT pattern yields Fourier spectrum with characteristic peaks. The peak intensities in reciprocal space are scaled automatically and presented on a logarithmic scale (20 log S, where S is the norm of the amplitudes of the periodic components of the decomposed raw image.

Figure 42:
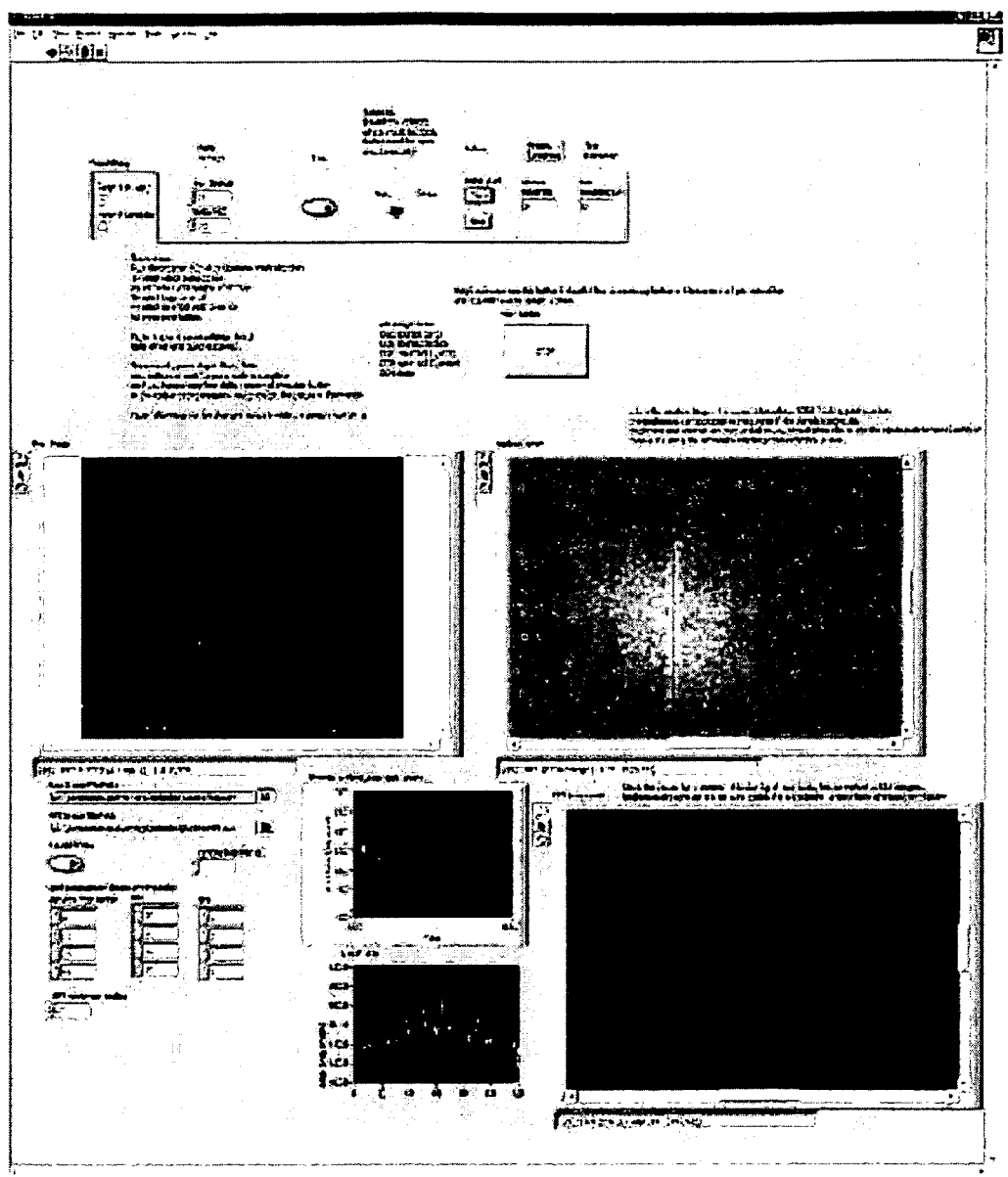
FIG. 42 shows a PathoTest user interface (Labview). Simultaneous imaging and 2D FFT analysis of *Pseudomonas* captured on a pathogen capture chip patterned with BSA-trisaccharide glycoconjugate. The line profile along the y-direction of the 2D FFT image (at right) is re-plotted as a 1D Fourier spectrum (bottom); off-center peaks indicate the harmonics of the periodic capture pattern.

A screen capture of the user interface display is shown in FIG. 42. The linescan performed manually, using a tool that measures the maximum intensity of a specified area and the symmetrical nature of the FFT output. The origin is typically the most intense peak and scales with the overall intensity of the image. The intensities of the fundamental harmonic and higher-order harmonic peaks can be used to identify the correct line profile in the 2D reciprocal space. The FFT linescans can be incorporated into an automated process for later versions of the device so that a user would require a simple key pad interface that would indicate the type of pathogens screened, based on the appearance of its signature lattice peaks.

Cross-Hair Electrodes

Figure 43:
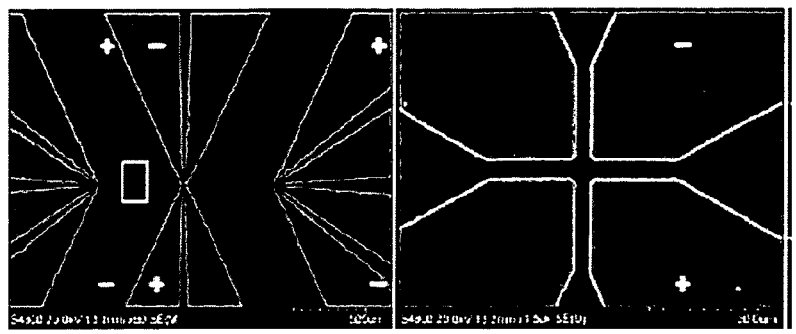
FIG. 43 shows FE-SEM images of gold patterned crosshair electrodes with a 5-µm gap between electrodes (enlarged view of inset at right). The relative polarities of the electrode are indicated by + and − symbols. The size of the substrate is 1.25 1.25 cm$^2$.

Gold crosshair electrodes were fabricated on a Si substrate with a 5-µm gap between electrode tips (FIG. 43). Dielectrophoretic (DEP) capture is typically initiated at the center of the microfabricated crosshairs, which are connected to the power supply electrodes using conducting silver paint. The chip contains three crosshairs along the lining of a flow cell with a contact pin system for the electrodes (see FIG. 41). In this first version, the substrate with crosshair electrodes are sealed inside of a flow cell with vacuum grease, and secured in place by screws and a holder plate. The AC voltage and frequency ranges are 0-20 V and 0-12 MHz, respectively.

Figure 44:
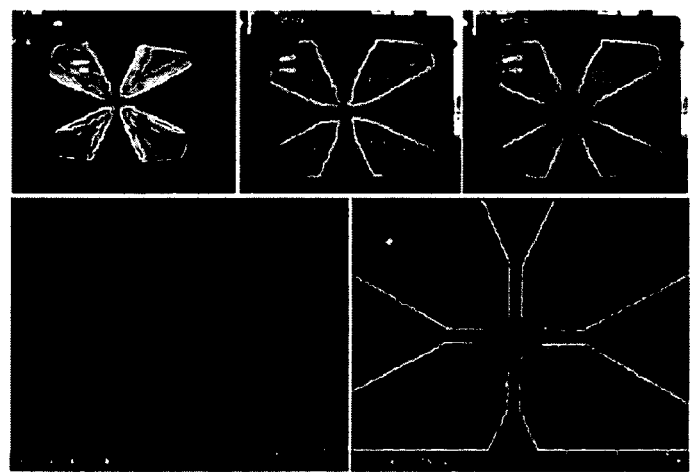
FIG. 44 shows DEP capture of latex particles using crosshair electrodes. (Top) Video images of particles adsorbed onto Au crosshair electrodes (8 V, 1 MHz), 2 seconds after voltage is turned on (left), 1 minute later (middle), then 30 seconds after voltage is turned off (right). Particles can be observed diffusing from the crosshairs. (Bottom) field-emission scanning electron microscopy (FE-SEM) image of latex particles captured by DEP (left) and Au electrodes after the voltage is turned off (right). Shaded area is due to charging effects from microscope.
Figure 45:
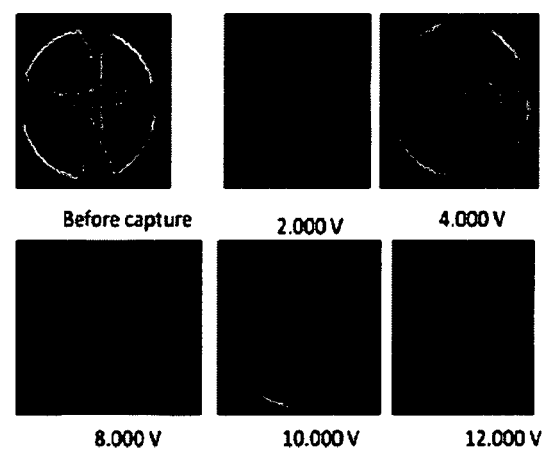
FIG. 45 shows optical images before (upper left) and after capture of *Pseudomonas* at various AC voltages (1 MHz).

The DEP traps were tested by the capture and release of 1-µm latex beads at an initial concentration of $10^9$ particles/mL in deionized water. An applied voltage of 8 V at 1 MHz resulted in rapid and visible capture of the latex beads (FIG. 44). It is worth noting that particle capture at the early stages occurs not only within the cross-hairs, but on the electrodes themselves. Once captured, the particles are easily retained and are not dislodged when flow was initiated in the flow cell with ultra-pure water, until the DEP voltage is turned off (FIG. 44). For each wash following DEP capture, the substrate was dried and examined by FE-SEM. FIG. 45 shows the DEP capture of *Pseudomonas aeruginosa* at a concentration of $1.2 \times 10^9$ CFU/mL in deionized water, using 1 MHz at various voltages. Similar to the case of latex particles, the bacteria were captured first within the crosshairs, then collected on the electrodes themselves. The maximum voltage that could be used in this system at 1 MHz without short-circuiting was 15 V.

Interdigitated Electrodes

Figure 46:
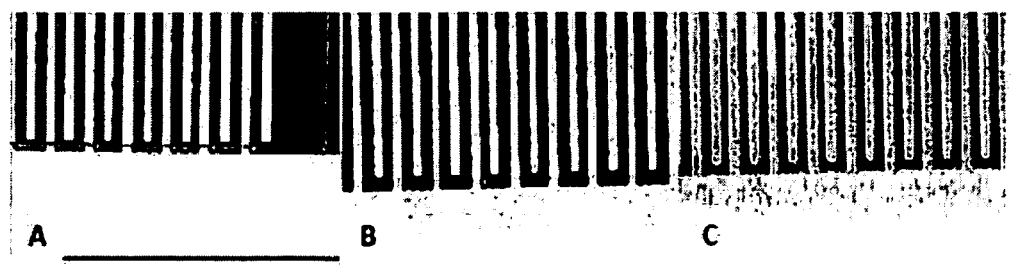
FIG. 46 shows capture of *Pseudomonas aeruginosa* by DEP using interdigitated electrodes (5 µm spacing). (Left) electrodes prior to exposure to bacteria; (Middle) exposure to *Pseudomonas* at $10^9$ cfu/mL without an applied AC voltage; (Right) DEP capture of bacteria with applied voltage (8 V, 1 MHz).

As individual crosshair electrodes may not provide sufficient surface area for pathogen concentration, interdigitated electrodes were also evaluated with the objective of increasing particle concentrations by 3-4 orders of magnitude (i.e. from $10^2$-$10^3$ to $10^6$ cfu/mL). The results using *Pseudomonas* at $10^9$ cfu/mL demonstrate that interdigitated electrodes have excellent potential to the crosshair electrodes for the concentration and release of bacteria (see FIG. 46). As before, release of the capture pathogens occurs after the AC voltage is turned off.

Patterned Substrate

The device of the invention, for example a PathoTest device, facilitates image recognition from a patterned substrate. A periodic pattern of sensing molecules is printed, stamped, or otherwise transferred or affixed to a substrate surface. Exemplary methods include microscale photopatterning, such as photolithography, microcontact printing, and non-contact methods such as inkjet printing. The substrate surface is functionalized, in a patterned array, with at least one sensing molecule, such as a mutation-resistant ligand, that interacts with the pathogen. An array or microarray is typically composed of multiple discrete (noncontiguous) positive array "elements" arranged in a periodic manner. The area within the array that does not contain positive array elements is called the background or the "null" array element. A checkerboard pattern, for example, contains alternating positive and null array elements. Note that when the term "element" or "array element" is used herein without further modification, it refers to a positive array element. The array elements themselves can have a shape (e.g., a line, a square or a circle within which multiple sensing molecules, such as mutation-resistant ligands, are deposited) or they may be so small as to be a digital point element (e.g., only one or a minimal number of mutation-resistant ligands). The overall shape into which the array elements themselves are arranged constitutes the "pattern" of the array. For example, an array of sixteen elements arranged in four columns and four rows such that the elements are equidistant from each other would form a square "pattern." In the device of the invention, mutation-resistant ligands deposited in discrete positions on the substrate constitute the multiple positive "elements" of the array, and the topographical arrangement of these positive elements on the substrate surface forms the pattern. A benefit of patterning analytes in a microarray is the possibility of highly sensitive, rapid detection through pattern recognition algorithms. Advantageously, microarray redundancy (pattern formation) effectively increases the signal to noise ratio and lowers the limit of detection. Images, such as CCD images, can be processed, for example using Fourier transforms or other pattern recognition algorithms to identify the presence of a certain pattern of bound analytes, such as pathogens. The parameters of the transformation can be used to determine various pattern parameters such as the periodicity and, optionally, shape of an observed pattern, which are then are compared to the known pattern of deposition of the sensing molecule. If the two are essentially the same, this confirms the presence of the pathogen in the sample. If desired, the computer can then be given the additional information, such as the actual size of the array elements, and by evaluating the image in view of the additional information can determine the levels of specific and nonspecific pathogen binding. By facilitating the use of pattern recognition algorithms, the use of patterned microarrays increases the limit of detection of the pathogen compared to the use of nonredundant analyte binding methods, particularly in the presence of nonspecific binding, whether in the form of a targeted analyte binding to nonfunctionalized areas or a non-targeted analyte binding to functionalized areas. Specificity can be assessed, for example, by comparing the number of targeted pathogens detected per unit area for the positive array elements to the number of targeted pathogens detected per unit area for the other regions of the microarray (e.g., null array elements and/or other nonfunctionalized regions).

There is no limitation on the size of the array elements or the distance between them, except that the array elements need to be large enough to be detectable, and separated by a sufficient distance to so as to be resolvable, using the detection method selected to detect the interaction event (such as the bound complex of the pathogen and the sensing molecule, i.e., the mutation-resistant ligand). It should be understood that the principles of the invention are not dependent on the detection mechanism or the array size, and will continue to apply as the limits of detection are pushed further. The distance between the elements is typically of the same scale as the size of the elements themselves, but can be smaller or larger as indicated by the particular application. When the pathogen to be detected is a bacterium, for example, the size of the microarray elements can, if desired, be selected such that only one bacterium will bind per array element.

There is no limit to the number of elements in the microarray (the redundancy), and in some applications (for instance, those utilizing long channels) the microarrays can include hundreds, thousands or even millions of elements. A channel can be, for example, 100 µm to 1 mm wide and has array elements with a dimension of about 10 µm distributed within the channel at about 10 µm increments. At a minimum the microarray should include at least 4 elements, more preferably at least 10 elements. There is no limit to the number of microarrays a sensing device can include, nor is there any limit to how many different pathogens can be detected. If multiple pathogen detection is desired, multiple microarrays can be used, each having the elements arranged in a unique pattern and/or such that the different microarrays are located at different positions on the device, so as to allow the different regions binding to the different pathogens to be distinguished. Dozens of different pathogens can be detected on a surface of only a few square millimeters.

There is no limitation to the particular pattern for the microarray of positive array elements. A pattern that lends itself to Fourier transform or other pattern recognition algorithm, for example a repeating symmetric pattern that produces a series of squares (checkerboard), triangles, crosshatches, circles, stripes and the like, is suitable. The more complicated the pattern, the more stringent the test. The positive array elements and the null array elements may be shaped differently (i.e., they do not appear identical to the detector); this is what is referred to herein as a "nonuniform" pattern. For example, a checkerboard is a "uniform" pattern because the positive array elements and the null array elements are both squares of identical size. However, an array consisting of many rows of "plus" marks as positive array elements (with the null "elements" constituting the grid-like surface area between the "pluses") would be a "nonuniform" pattern. The repeating pattern can be linear or two-dimensional. The periodicity of the pattern can be, for example, a linear periodicity or a square or rectangular periodicity. The substrate surface itself is typically planar or in the form of a channel.

There is no limitation on the methods that can be utilized for image analysis of the patterned substrate. Label-free image analysis can be performed, or the bound pathogens can be labeled, e.g., optically, enzymatically, radioactively and the like, for label-assisted image analysis. Image analysis can be performed, for example, through use of an intensity histogram or through use of an image-processing algorithm for automated assessment. Image-processing algorithms can include Fourier transform algorithms such as discrete Fourier Transform (DFT), fast Fourier transform (FFT), and 2D Fourier transform, such as 2D-FFT.

The device can be advantageously fabricated as a miniaturized biosensor, such as microchip, capable of detecting a wide variety of pathogens and other biohazards. The chip or other substrate surface presents an array of mutation-resistant ligands for patterned pathogen capture. Microchips and microarrays are known to the art, and any convenient microchip or microarray can be utilized in the device. The type of microarray and microchip utilized may conveniently be chosen based on the application in which the device is employed.

An exemplary substrate for pathogen capture and detection is described in U.S. Pat. No. 7,867,754, issued Jan. 11, 2011. This exemplary microarray has the advantage of being highly selective, insofar as it utilizes a mathematical algorithm based on the analysis of pattern redundancies. In this exemplary embodiment, the substrate surface can include least one microarray containing multiple positive array elements arranged in a redundant pattern on the substrate surface. The positive array elements contain sensing molecules, such as the mutation-resistant ligands described here, that target the analyte, such as a pathogen to be captured detected. A plurality of microarrays can be employed, which microarrays can be the same or different (different microarrays can contain positive array elements that contain different sensing molecules, or they can have array elements arranged in a different pattern, or both). For example, positive array elements in a first microarray can contain a first sensing molecule targeting a first pathogen, and positive elements in a second microarray can contain a second sensing molecule targeting a second pathogen.

The sample that is contacted with the microarray can be a liquid or an air sample. The sample can be applied in a batch mode to the substrate surface, or it can be flowed over the substrate surface. The substrate surface is preferably planar or, in the case of a sample that is flowed over the surface, contains a channel in which the microarray is disposed. The sample may be introduced into the channel as a point source, via side entry, or in any other way.

The sample is contacted with the microarray for a time and under conditions to cause the pathogen to detectably interact with, e.g., to bind to, the sensing molecules. Detection of a redundant pattern on the substrate surface is indicative of the presence of pathogen in the sample. A periodicity in the pattern can be detected, preferably through the use of a computer algorithm but also in some instances visually or through other means.

Optionally, the microarray also includes multiple null array elements that do not specifically target the pathogen. The shape of the positive array elements on the substrate surface is preferably different from the shape of the null array elements. By assessing the interaction of non-targeted analytes with the positive array elements, and/or the interaction of targeted analytes with the null array elements or other parts of the substrate surface, the specificity of the targeted analyte (i.e., the pathogen) for the positive array elements can be evaluated.

The sensing molecule affixed to the microarray includes at least one mutation-resistant ligand, as described herein. Optionally, one or more other sensing molecules which may or may not be mutation-resistant but which bind the pathogen of interest may be incorporated into the microarray. Such molecules preferably include a biomolecule, such as a protein, glycoprotein, nucleic acid, antibody, or carbohydrate. The targeted analyte is preferably a pathogenic organism such as a bacterium, virus, parasite, fungus, protist or protozoan.

In one embodiment, the pathogen is detected by providing a substrate surface that includes one or more microarrays, preferably within a channel; flowing a sample containing the pathogen over the substrate surface such that the sample sequentially contacts positive array elements in the microarray under conditions to cause the pathogen to interact with the sensing molecules; and detecting the redundant pattern. In addition to the positive array elements, the microarray optionally includes multiple null array elements that do not specifically target the pathogen. Likewise the substrate surface may include alternating regions in which the microarray is present or absent, such that the sample flow sequentially contacts the alternating regions. In any of these embodiments, the sequentially contacted positive array elements can be analyzed to determine concentration of the pathogen in the sample. If desired, the sequentially contacted microarray regions also be analyzed to determine the level of nonspecific binding of sample components to array elements.

In another embodiment, the device includes a channel having a surface that contains a plurality of positive array elements, or a plurality of microarrays, that transect the channel and are disposed sequentially along a length of the channel. The positive array elements or microarrays can be the same or different. A sample that contains an pathogen is flowed through the channel such that the sample flow sequentially contacts the positive array elements under conditions to cause the pathogen to interact with the sensing molecules, and the resulting redundant pattern is detected. The sequentially contacted positive array elements can be analyzed to determine concentration of the pathogen in the sample.

Another embodiment is useful for detecting the presence of multiple pathogens having very different concentration levels in a sample. The sensor device contains a branched channel the includes a first branch having a surface that includes a plurality of microarrays containing positive array elements that target a first pathogen and a second branch having a surface that includes a plurality of microarrays containing positive array elements that target a second pathogen. A sample containing the first and second pathogens is flowed through the branched channel such that a first amount of the sample flow enters the first branch and a second amount of the sample flow enters the second branch. For each branch the redundant pattern is then detected. This method is especially useful to detect pathogens when concentration of the first pathogen in the sample is at least an order of magnitude higher than the concentration of the second pathogen. In that case, a larger amount sample flow is directed second branch, which contains positive array elements that target the pathogen of lower concentration.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Selective Capture and Identification of Pathogenic Bacteria Using an Immobilized Siderophore Materials.

Unless otherwise specified, all chemicals were purchased from Sigma-Aldrich (St. Louis, Mo.). DiO, however, was obtained from Invitrogen (Carlsbad, Calif.), and BCA reagent was purchased from Thermo Scientific (Waltham, Mass.). *Escherichia coli* (ATCC 23503), *P. aeruginosa* (ATCC 15692), and *Yersinia enterocolitica* (ATCC 51871) were purchased from ATCC (Manassas, Va.), and Sylgard 184 polydimethylsiloxane was obtained from Dow-Corning (Midland, Mich.).

Purification of Pyoverdine.

The iron-chelating siderophore synthesized by *P. aeruginosa* PAO1 (ATCC 15692) for uptake of iron (pyoverdine) was purified according to a literature procedure (Albrecht-Gary et al., *Inorg. Chem.* 1994, 33:6391-6402). In brief, 2 L conical flasks containing 1 L of minimal media (composed of 6 g $K_2HPO_4$, 3 g $KH_2PO_4$, 1 g $(NH_4)_2SO_4$, 0.2 g $MgSO_4.7H_2O$, and 4 g succinic acid per liter and adjusted to pH 7.0 with 1 M NaOH prior to sterilization) were inoculated with *P. aeruginosa* and incubated for 48 hours at 28° C. with mechanical agitation. All glassware was rinsed with 3M $HNO_3$, followed by distilled water to remove all traces of iron. After 48 hours, 4 L of culture media was centrifuged at 20 000 g for 30 minutes, decanted from the bacterial pellet, acidified to pH 4.0 by the addition of formic acid, and filtered. The resulting filtrate was applied to an octadecylsilane column (l=15 cm i.d.=2.5 cm) at a flow rate of 2 mL/min, and the column was washed with 500 mL of distilled water (pH 4) to remove inorganic salts. The crude siderophores were eluted from the C18 column using 1:1 acetonitrile/0.05 M pyridine acetate buffer, pH 5.0 (500 mL), followed by removal of solvent using a rotary evaporator. Crude siderophore (250 mg) was dissolved in 5 mL of 0.05 M pyridine acetate buffer (pH 5.0) and applied to a CM-Sephadex C-25 ion-exchange column (l=15 cm, i.d.=2.5 cm) equilibrated with five column volumes of the same buffer. The siderophore was eluted isocratically with 0.05M pyridine-acetic acid buffer pH 5.0 (0.3 L), followed by a linear gradient of the same buffer (0.05 to 2 M; 2×1 L). Fractions (10 mL) were collected, and 200 µL aliquots were removed from each fraction and applied to a 96-well microplate. The microplate was read at 380 nm, and appropriate fractions were combined and evaporated. The identity of pyoverdine was confirmed by MALDI-TOF mass spectrometry and UV-visible spectrophotometry. Pyoverdine gallium chelation was performed essentially as previously described (Folschweiller et al., *J. Biochemistry* 2002, 41:14591-14601).

Preparation of Pyoverdine BSA.

Pyoverdine Ga chelate (3 mg; 1 equiv) (FIG. 1) was activated with 5 equiv of EDC and NHS in 50 µL of PBS in the dark for 15 minutes. Bovine serum albumin (BSA, 10 mg) was dissolved in 100 pL of PBS, and the pyoverdine reaction mixture was added to the BSA solution and gently shaken in the dark for 2 hours. The reaction mixture was purified with PBS using 10 kDa size exclusion filters until the filtrate no longer contained free pyoverdine. Pyoverdine-BSA conjugate was stored in PBS at a concentration of 5 mg/mL in the dark at 4° C.

DiO Labeling of Bacteria.

Bacteria were suspended at $1 \times 10^9$ cells/mL in PBS (1 mL) and then treated with two consecutive 5 µL aliquots of DiO dissolved in DMSO (1 mg/mL). Bacteria were incubated with the dye for 30 minutes at 28° C. with shaking, after which the cells were centrifuged at 5000 rpm for 5 minutes. The supernatant was removed, and bacteria were resuspended in 1 mL of PBS. Washing was performed a total of three times to remove all nonmembrane associated dye. The bacteria were all assumed to be alive for these experiments; we determined concentrations of bacteria by measuring the optical density (OD) at 600 nm.

Microplate Coating and Assessment of Binding.

Pyoverdine-BSA was diluted in PBS (10 µg/mL), and 100 µL of solution was added to the wells of a 96-well ELISA plate and incubated at 4° C. overnight. The plate was washed with PBS and blocked with a solution of 6% BSA(300 µL each well) for 2 hours at 37° C. and again washed with PBS. To each well, 50 µL of bacteria was added and incubated for 1 hour. The wells were gently washed with PBS; then, 200 µL of BCA protein assay reagent was added to each well. After incubation for 30 minutes at 37° C., the absorbance was read at 562 nm.

PDMS Stamping.

The pyoverdine-BSA (5 mg/mL in PBS, pH 7.2) solution was applied onto a PDMS stamp surface using a cotton swab and allowed to stand for 1 minute. We removed excess solution by drying the stamp under a gentle stream of nitrogen gas. The stamp was then brought into contact with a gold chip and gently pressed for 5 minutes to facilitate transfer of the pyoverdine-BSA to the gold surface.

Example 2

Bishydrazide Glycoconjugates for Lectin Recognition and Capture of Bacterial Pathogens General Procedures.

All starting materials and reagents were obtained from commercial sources and used as received unless otherwise noted. Fuc($\alpha$1$\rightarrow$2)Gal($\beta$1$\rightarrow$4)Glc (2'-fucosyllactose 3) was purchased from V-laboratories, Inc., and GalNAc($\beta$1$\rightarrow$4)-Gal($\beta$1$\rightarrow$4)Glc (pulmonary trisaccharide 2) was prepared by multistep synthesis (see below). Bovine serum albumin (BSA), galactose-binding lectin from *Arachis hypogaea* (peanut lectin), anti-lectin rabbit IgG, and FITC-labeled anti-rabbit goat IgG were purchased from Sigma (St. Louis, Mo.) and used as received. *Pseudomonas aeruginosa* (PA01 strain) was obtained from ATCC (Manassas, Va.) and grown overnight on agar plates (15 g/L of Bacto Agar, 8 g/mL of Difco Nutrient Broth) at 37° C. $CS_2$, $CH_2Cl_2$, and $CH_3CN$ were freshly distilled from $CaH_2$ before use; anhydrous and anaerobic MeOH and THF were passed through activated alumina and dispensed from a solvent purification system (MBraun). Reactions were carried out in oven-dried glassware under an inert atmosphere, and solvents were freshly distilled from $CaH_2$ prior to use. $^1H$ and $^{13}C$ NMR spectra were recorded on a Bruker DRX 400 spectrometer operating at 400 and 100 MHz respectively. Chemical shifts ($\delta$) are reported in ppm and referenced to the solvent used ($CDCl_3$, $\delta$ 7.24 and 77.23; $CD_3OD$, $\delta$ 3.31 and 49.15; $D_2O$, $\delta$ 4.80), with coupling constants (0.1) reported in Hz. Deionized water with a resistivity of >18 M$\Omega$·cm was obtained from an ultrafiltration system (Milli-Q, Millipore; Billerica, Mass.) and passed through a 0.22 µm filter to remove particulate matter. Silica gel chromatography was performed using ICN SiliTech 32-63 D; reverse-phase HPLC was performed using a Phenomenex Synergi C-18 column (250×21.2 mm, 4 µM, 80 Å) with UV detection at 214 nm, using an aqueous $CH_3CN$ solvent gradient with a linear flow rate of 10 mL/min.

Neoglycoprotein Formation.

In a typical experiment, a freshly prepared solution of BSA (10 mg) in phosphate buffered solution (PBS, pH 7.4, 200 µL) was treated with 1-ethyl-3-(3-dimethylaminopropyl)carbodiimide hydrochloride (EDC·HCl, 3 mg in 50 µL PBS) and gently stirred at room temperature for 1 hour. The activated protein solution was then treated with pulmonary trisaccharidehydrazide conjugate 7 (5.1 mg) in 200 pL PBS, then stirred for another 2 hours, followed by membrane dialysis and passage through a 0.45 µm filter to remove aggregates and particulate matter. These BSA glycoconjugates could be stored safely at 4° C. for several months.

In Situ Dithiocarbamate (DTC) and Monolayer Formation (Zhao et al., *J. Am. Chem. Soc.* 2005, 127:7328-7329; Zhu et al., *Langmuir* 2008, 24:8660-8666). In a typical experiment, a 10 mM solution of lactose-bishydrazide conjugate 6 in deaerated methanol (1.5 mg in 200 µL) was treated with 10 mM solutions of $CS_2$ (200 µL) and $Et_3N$ (200 µL), then stirred at room temperature for 1 hour in a capped vial prior to use (see below). In situ DTC formation was monitored by diluting aliquots of the reaction mixture in deionized water, then measuring increases in characteristic absorption peak intensities at 250 and 292 nm using a Cary-50 spectrophotometer (cell path length=1 cm).

DTC-anchored monolayers (DAMs) were produced from a freshly prepared solution of 6-DTC, diluted 10-fold with deionized water to a final concentration of 1 mM. A 30 µL aliquot of this stock solution was spread across a lightly oxidized PDMS stamp, then patterned onto Au substrates by microcontact printing (see below). Lactose-terminated DAMs were treated with a solution of peanut lectin (50 µg/mL) and visualized by fluorescence immunostaining. The robustness of the patterned DAMs was evaluated by measuring changes in relative emission intensities over time, with exposure to 2-mercaptoethanol (10 or 100 µM) in PBS. Mean luminosity values and standard deviations were taken from selected regions on the printed substrate using Photoshop v.7.0.1 (Adobe Systems).

UV Photolithography.

Glass substrates coated with a 50 nm Au layer (1.2×1.2 $cm^2$, Reichert) were cleaned with a piranha solution (2 parts 18 M $H_2SO_4$, 1 part 30% $H_2O_2$) for 3 minutes, then thoroughly rinsed with deionized water and dried under a stream of argon. (Caution: Piranha solution is a strong oxidizing agent, and should be handled with extreme care.) Freshly cleaned substrates were coated with BSA by soaking in a 1 wt % solution in PBS for several hours at room temperature, followed by immersion in a solution of photoactive glycoconjugate (20 mM in 2:1 MeOH/CH$_2$Cl$_2$) for 5 minutes. The dried films were covered by a quartz photomask having linewidths of 10 or 15 µm and grating periods of 20 µm (Advanced Reproductions Corp.; North Andover, Mass.), then exposed to a short-wave ultraviolet lamp (Spectroline, ENF-240C) operating at 254 nm for 25 minutes, followed by a rinse with MeOH. Microcontact printing (see below) could also be used for patterning photoactive glycoconjugates onto BSA-coated glass slides.

Microcontact Printing (µCP).

A freshly prepared poly(dimethylsiloxane) (PDMS) stamp (grating period a=20 µm; line width=15 µm) was lightly oxidized by a 15 second exposure in a plasma cleaner, then coated with 30 pL of an aqueous solution of 6-DTC for 2 minutes (see above for preparation of stock solution). The PDMS stamp was dried in air after blotting excess solution, then pressed lightly onto a roughened Au substrate (see below) at an applied pressure of 6 kPa for 3 seconds, as measured by a mechanical stamper developed in our laboratories. A brass plate was placed at the top of the stamp for even distribution of pressure, and the stamp remained in conformal contact with the substrate for an additional 5 minutes.

Similar µCP conditions were used to pattern BSA glycoconjugates onto smooth Au substrates. A 30 µL aliquot of a 1 wt % BSA-lactose hydrazide conjugate (6-BSA) in PBS was cast onto a lightly oxidized PDMS stamp as described above and allowed to sit for 2 minutes prior to blotting. The PDMS stamp was dried in air, pressed lightly onto the substrate at an applied pressure of 6-12 kPa for 3 seconds, and then allowed to remain in conformal contact without added pressure for another 5 minutes. The micropatterned substrate was washed sequentially with PBS, PBS containing 0.05% Tween-20, and then deionized water. The patterned substrate was further incubated with a 5% BSA solution in PBS for 2 hours, then washed as above prior to use.

Glycan-Directed Affinity Binding and Imaging.

Micropatterned glycoconjugates were exposed to either soluble lectins or to live bacterial cultures and visualized by immunofluorescent staining (bound lectin) or darkfield microscopy (bound bacteria) using an upright microscope (Olympus BH2-RFL-T3) equipped with a darkfield condensor, a high-pressure Hg lamp and filter set for FITC emission, and a DP70 camera for image acquisition. Fluorescence imaging was performed either on glass or on roughened Au substrates; the latter were prepared by immersing clean Au substrates into a solution of AgNO$_3$ (3.7 mM) and hydroquinone (120 mM) in 1.3 M citric acid buffer (pH 3.5) for 1.5 minutes, followed by a quick rinse with deionized water and immersion in an aqueous HAuCl$_4$ solution (0.5 mM) for 30 minutes. Roughened Au substrates were dried in air, prior to use.

For affinity patterning with proteins, micropatterned substrates were incubated with a dilute solution of lectin from *Arachis hypogaea* (peanut lectin, 50 µg/mL in PBS) for 2 hours at 4° C. The chip was washed with PBS, then treated with a solution of anti-peanut lectin rabbit IgG (1 µg/mL in PBS) for 2 hours at 4° C., then washed again and treated with a solution of FITC-labeled anti-rabbit goat IgG (1 µg/mL in PBS) for another 2 hours at 4° C. The chip was washed with PBS, deionized water, and then dried under a stream of air prior to fluorescence imaging.

For affinity patterning with bacteria, *Pseudomonas aeruginosa* (PA01 strain, ATCC) was cultured in NB broth containing choline (0.2% w/v), the latter being necessary for the ectopic expression of fucose-binding lectin PA-IIL (Gilboa-Garber, "*Pseudomonas aeruginosa* lectins," in *Methods in Enzymology. Vol. 83: Complex Carbohydrates, Part D* (Kaplan et al., Eds.) pp. 378-385, Chapter 3. Academic Press: San Diego, Calif.; 1982). Micropatterned substrates were incubated with suspensions of live *Pseudomonas* for 1 hour at room temperature, at concentrations ranging from $10^8$ to $10^2$ cfu/mL. After incubation, the chip was washed with PBS and deionized water prior to darkfield imaging. The density of live *Pseudomonas* was estimated by correlating turbidity measurements (ca. $10^9$ cfu/mL at O.D. 1) with colony counts obtained by plating serial dilutions. Fluorescent staining of active cultures (SYTO 9/propidium iodide (PI) stains, Invitrogen; Carlsbad, Calif.) confirmed that >90% of the bacteria were alive prior to their exposure to glycan-patterned substrates.

Darkfield images were subjected to a fast Fourier transform (FFT) for image analysis to reveal characteristic peaks in reciprocal space (k=1/a) indicating pathogen capture, according to a recently established protocol (Doorneweerd et al., *Langmuir* 2010, 26:15424-15429; Example 1). Standard sizes and magnification were established for each micropatterned image, so that the units defining periodicity (in µm) were correctly translated into reciprocal lattice units (in µm$^{-1}$) in the spectra derived from the FFT images. Signal-to-noise (S/N) levels were determined as the ratio of the peak value at 0.05 µm$^{-1}$ (after background subtraction) to the standard deviation of background intensity; signal qualities were considered acceptable above S/N=3.

Glycoconjugate-Lectin Binding Immunoassays.

Each incubation was performed for 2 hours at room temperature, followed by rinsing three times with PBS to remove excess proteins prior to the next step. 96-well microliter plates were coated with 6-BSA conjugate (10 mg/mL), blocked with a 1% BSA solution to minimize nonspecific protein adsorption, and then incubated with increasing concentrations of peanut lectin in the presence or absence of 100-fold excess lactose. Wells were then treated with anti-lectin rabbit IgG (1 µg/mL), followed by anti-rabbit horseradish peroxidase (HRP) IgG (1 µg/mL). The optical absorbances of the wells were analyzed using a microplate reader (VERSAmax, Molecular Devices; Sunnyvale, Calif.) following addition of the HRP substrate (100 µL). Untreated and anti-lectin rabbit IgG treated wells (without primary antibody) in PBS served as negative controls.

For flow cytometry, carboxylic acid functionalized microspheres were conjugated to lactose-bishydrazide 6 via standard EDC coupling for 16 hours at room temperature, followed by multiple washes with PBS. The lactose-conjugated microspheres were dispersed in PBS (1.2 mL) and split into several Eppendorf tubes, which were incubated with increasing concentrations of peanut lectin in the presence or absence of 100-fold excess lactose. After incubating for 2 hours at room temperature, tubes were rinsed and subjected to sequential incubation with anti-lectin rabbit IgG and anti-rabbit FITC IgG as described above. The microspheres were then analyzed for fluorescent immunolabeling using a flow cytometer (Cytomics F500, Beckman Coulter, $10^4$ microspheres/sample). Untreated and anti-lectin rabbit IgG (without primary antibody) treated microspheres in PBS served as negative controls.

Preparation of Glycoconjugates

Hexa(ethylene glycol)-Linked Bishydrazide (4).

A solution of hexa(ethylene glycol) (5.0 g, 17.70 mmol) in dry THF (50 mL) at room temperature was treated portionwise with potassium tert-butoxide (9.92 g, 88.54 mmol) at room temperature, then stirred for 30 minutes. The reaction mixture was treated dropwise with ethyl bromoacetate (20 mL, 170 mmol), then stirred at reflux for 20 hours. The reaction mixture was cooled to room temperature, filtered and concentrated, and then purified by silica gel chromatography (EtOAc/hexanes 1:1) to yield pure diethyl ester as a colorless oil (5.5 g, 68%). $^1$H NMR (400 MHz, CDCl$_3$) δ 4.62 (s, 4H), 4.17 (q, 4H, J=7.2 Hz), 3.71-3.69 (m, 4H), 3.66-3.63 (m, 8H), 3.61-3.59 (m, 12H), 1.23 (t, 6H, J=7.2 Hz). $^{13}$C NMR (100 MHz, CDCl$_3$) δ 170.01, 167.44, 71.01, 70.85, 70.63, 68.88, 68.36, 61.60, 60.79, 14.16. MS (ESI) calculated for $C_{20}H_{38}O_{11}[M]^+$ m/z 454.24. Found: m/z 454.98.

Hexa(ethylene glycol)-linked bishydrazide (4)

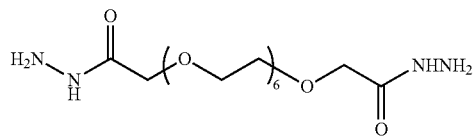

The hexa(ethylene glycol)-linked diester (1.0 g, 2.2 mmol) was dissolved in MeOH (20 mL) passed through an activated alumina column (MBraun) and treated with anhydrous hydrazine (0.34 mL, 11.0 mmol). The reaction mixture was stirred at room temperature for 24 hours, then concentrated followed by the azeotropic removal of hydrazine using toluene (3×10 mL), and finally dried in vacuo to afford a light yellow oil (0.92 g, 98%). The resulting bishydrazide could be used to prepare glycoconjugates without further purification. $^1$H NMR (400 MHz, CDCl$_3$) δ 8.61 (br s, 2H), 4.06 (s, 4H), 3.74-3.58 (m, 28H). $^{13}$C NMR (100 MHz, CD3OD) δ 173.72, 171.15, 73.66, 72.10, 71.51, 71.44, 71.75, 62.12. MS (ESI) calculated for $C_{16}H_{34}N_4O_9Na$ [M+Na]$^-$ m/z 449.44. Found: m/z 449.02.

Heptanediol-Linked Bishydrazide (5).

Heptane-1,7-diol (1.1 g, 7.56 mmol) was treated with ethyl bromoacetate (4.35 mL, 37.82 mmol) as described above, followed by workup and silica gel purification (EtOAc/hexanes 1:2) to yield the pure diester as a colorless oil (0.92 g, 36%). $^1$H NMR (400 MHz, CDCl$_3$) δ 4.15 (t, 4H, J=6.7 Hz), 3.81 (s, 4H), 3.61 (t, 4H, J=6.1 Hz), 1.63 (quint, 4H, J=6.4 Hz), 1.53 (quint, 4H, J=6.7 Hz), 1.34 (3, 6H), 1.26 (m, 2H). $^{13}$C NMR (100 MHz, CDCl$_3$) δ 5167.52, 66.54, 63.04, 32.77, 29.10, 28.48, 26.13, 25.87, 25.76.

Heptanediol-linked bishydrazide (5)

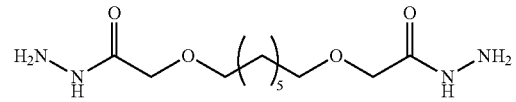

Anhydrous hydrazine (0.185 mL, 5.91 mmol) was treated with heptanediol-linked diester (0.36 g, 1.18 mmol) in methanol (10 mL), according to the reaction conditions described above. After azeotropic removal of the volatiles using toluene, bishydrazide 5 was obtained as an oil (0.32 g, 92%) and could be used to prepare glycoconjugates without further purification. $^1$H NMR (400 MHz, CD$_3$OD) δ 3.40 (t, 4H, J=6.4 Hz), 1.40 (quint, 4H, J=6.6 Hz), 1.25-1.21 (m, 10H). $^{13}$C NMR (100 MHz, CD$_3$OD) δ 173.73, 172.39, 62.94, 33.57, 30.38, 26.90. MS (ESI) calculated for $C_{11}H_{24}H_4O_4$ [M]$^+$ m/z 276.17. Found 276.76.

Hexa(ethylene glycol)-Linked Lactose-Bishydrazide Conjugate (6).

A mixture of lactose (10 mg, 0.029 mmol) and bishydrazide linker 4 (124.6 mg, 0.29 mmol) in NaOAc buffer (1 mL, pH 4.2) was stirred at 70° C. for 2 days. The reaction mixture was evaporated under reduced pressure, then purified by reverse-phase HPLC (1-30% aqueous CH$_3$CN gradient over 60 minutes) to afford 6 as colorless oil (18.9 mg, 86%). $^1$H NMR (400 MHz, CD$_3$OD) δ 4.62 (s, 1H), 4.34 (d, 11-1, J=7.5 Hz), 4.14 (d, 1H, J=8.6 Hz), 4.09-4.03 (m, 3H), 3.98 (dd, 1H, J=4.0, 12.0 Hz), 3.92 (dd, 1H, J=4.0, 8.0 Hz), 3.84-3.79 (m, 2H), 3.78-3.74 (m, 2H), 3.70-3.65 (m, 22H), 3.59-3.52 (m, 6H), 3.49-3.46 (m, 2H). $^{13}$C NMR (100 MHz, CD$_3$OD) δ 172.32, 171.81, 105.10, 91.89, 80.45, 77.76, 77.11, 76.63, 74.81, 73.66, 73.53, 72.51, 72.14, 72.07, 71.54, 71.31, 70.75, 70.29, 62.48, 62.21, 62.12. MS (ESI) calculated for $C_{28}H_{54}N_4O_{19}Na$ [M+Na]$^+$ m/z 773.32. Found: m/z 773.37.

Hexa(ethylene glycol)-linked lactose-bishydrazide conjugate (6)

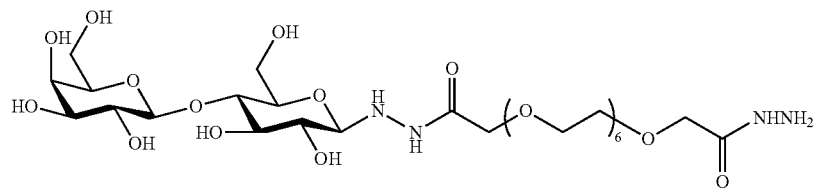

Hexa(ethylene glycol)-Linked Pulmonary Trisaccharide-Bishydrazide Conjugate (7).

This compound was prepared according to the procedure above, starting from pulmonary trisaccharide 2 (32 mg, 0.058 mmol) and bishydrazide linker 4 (60.0 mg, 0.14 mmol). Purification by RP-HPLC (1-30% aqueous CH3CN gradient over 60 minutes) yielded glycoconjugate 7 as a light-yellow oil (32 mg, 58%). $^1$H NMR (400 MHz, CD$_3$OD) δ 4.61 (d, 1H, J=8.3 Hz), 4.32 (d, 1H, J=7.6 Hz), 4.14 (d, 1H, J=5.5 Hz), 4.08-3.97 (m, 10H), 3.89-3.47 (m, 36H), 2.05 (s, 3H). $^{13}$C NMR (100 MHz, CD$_3$OD) δ 180.31, 175.05, 105.05, 104.44, 93.98, 78.18, 76.80, 76.23, 75.98, 74.69, 74.14, 73.57, 73.07, 72.60, 71.44, 69.53, 62.61, 61.72, 55.05, 24.15, 23.18. MS (ESI) calculated for $C_{36}H_{67}N_5O_{24}Na$ [M+Na]$^+$ m/z 976.40. Found: m/z 976.18.

Hexa(ethylene glycol)-linked pulmonary trisaccharide-bishydrazide conjugate (7)

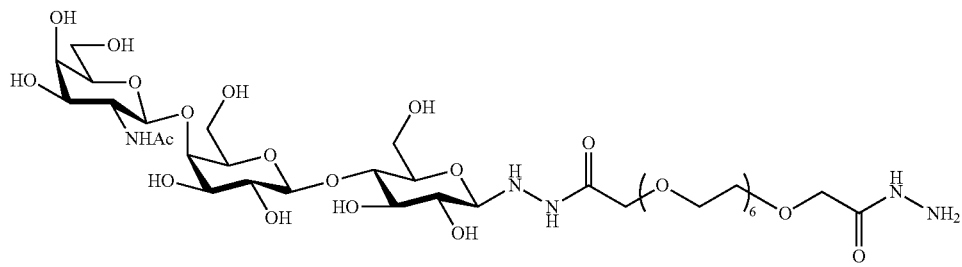

Hexa(ethylene glycol)-Linked 2'-Fucosyllactose-Bishydrazide Conjugate (8).

This compound was prepared according to the procedure above, starting from commercially available 2'-fucosyllactose (2.5 mg, 5.1 μmol) and bishydrazide linker 4 (21.8 mg, 51 μmol). Purification by RP-HPLC (1-40% aqueous CH$_3$CN gradient over 60 minutes) yielded glycoconjugate 8 as a colorless oil (2.9 mg, 51%). NMR (300 MHz, D$_2$O) δ 5.17 (d, 1H, J=3.1 Hz), 4.38 (d, 1H, J=7.7 Hz), 4.10 (m, 1H), 4.02-3.98 (m, 4H), 3.82 (m, 1H), 3.75-3.71 (m, 2H), 3.67-3.43 (m, 41H), 3.29 (m, 1H), 3.23 (m, 1H), 1.09 (d, 1.7H, J=6.6 Hz), 1.03 (d, 1.3H, J=6.6 Hz). MS (ESI) calculated for C$_{34}$H$_{64}$N$_4$O$_{23}$Na [M+Na]$^+$ m/z 919.38. Found: m/z 919.70.

Heptanediol-Linked Lactose-Bishydrazide Conjugate (9).

This compound was similarly prepared as that described above, starting from lactose (50 mg, 0.146 mmol) and 1,7-heptanediol bishydrazide 5 (201 mg, 0.736 mmol). Purification by RP-HPLC (1-50% aqueous CH$_3$CN gradient over 45 minutes) yielded glycoconjugate 9 as a light-yellow oil (54 mg, 62%). $^1$H NMR (400 MHz, CD$_3$OD) δ 4.30 (d, 1H, J=7.6 Hz), (d, 1H, J=8.2 Hz), (d, 1H, J=4.4 Hz), 3.97 (s, 2H), 3.83-3.77 (m, 2H), 3.67-3.59 (m, 4H), 3.54-3.45 (m, 4H), 3.41-3.35 (m, 2H), 3.22-3.19 (m, 1H), 1.92-1.69 (m, 14H). $^{13}$C NMR (100 MHz, CD$_3$OD) δ 181.97, 173.86, 103.51, 89.97, 78.93, 76.39, 75.95, 75.52, 73.09, 71.55, 70.84, 69.18, 61.66, 61.01, 60.84, 23.98, 20.65, 20.44, 20.37. MS (ESI) calculated for C$_{23}$H$_{45}$N$_4$O$_{14}$ [M+H]$^+$ m/z 601.28. Found: m/z 601.09.

Heptanediol-linked lactose-bishydrazide conjugate (9)

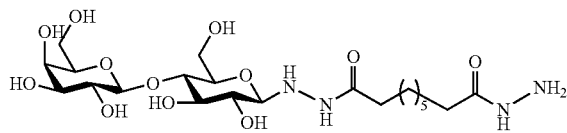

2-Deoxy-3,4,6-tri-O-acetyl-2-trichloroacetamido-β-D-galactopyranosyl-(1→4)-2,4,6-tri-O-benzyl-β-D-galactopyranosyl-(1→4)-1,2,3,6-tetra-O-benzyl-D-glucopyranose (12)

D-Galactosamine thiophenyl glycoside 10 (Bélot and Jacquinet, Carbohydr. Res. 2000, 325:95-106) (36.8 mg, 0.066 mmol) and lactose derivative 11 (Matsuoka et al., Carbohydr. Polym. 2007, 69:326-335) (43.0 mg, 0.044 mmol) were stirred under argon in dry CH$_2$Cl$_2$ (2 mL) for 30 minutes at room temperature in the presence of freshly activated, powdered 4 Å molecular sieves. The reaction mixture was cooled to −70° C., then treated with N-iodosuccinimide (NIS, 17.8 mg, 0.079 mmol) and a catalytic amount of triflic acid (TfOH, 2.0 mg, 0.0132 mmol). The reaction mixture was slowly warmed to 0° C., then stirred for an additional 4 hours at room temperature. The reaction mixture was then neutralized with a few drops of triethylamine and filtered over a pad of Celite with rinsing by CH$_2$Cl$_2$. The mixture was washed with a 10% Na$_2$SO$_3$ solution followed by water, and the aqueous layer was extracted twice with CH$_2$Cl$_2$. The organic phases were collected and dried over anhydrous Na$_2$SO$_4$ and concentrated then purified by silica gel chromatography (EtOAc/hexanes 2:3) to afford trisaccharide 12 as a yellow oil (52.2 mg, 84%). $^1$H NMR (400 MHz, CDCl$_3$) δ 7.44-7.25 (m, 35H, ArH), 6.23 (d, 1H, J=10 Hz, NH), 5.26 (d, 1H, J=2.8 Hz), 4.97 (d, 2H, J=12.0 Hz), 4.94 (d, 2H, J=12.0 Hz), 4.88 (d, 2H, J=8.0 Hz), 4.85 (d, 2H, J=8.0 Hz), 4.81 (d, 2H, J=9.6 Hz), 4.78 (d, 2H, J=8.0 Hz), 4.71 (d, 2H, J=8.0 Hz), 4.66 (d, 2H, J=12.0 Hz), 4.51 (d, 1H, J=8.0 Hz), 4.49 (d, 1H, J=8.0 Hz), 4.44 (d, 2H, J=12.0 Hz), 4.13-3.98 (m, 5H), 3.90 (dd, 2H, J=6.0, 11.2 Hz), 3.74-3.67 (m, 2H), 3.62-3.59 (m, 1H), 3.56 (d, 2H, J=9.2 Hz), 3.49 (t, 1H, J=7.6 Hz), 3.36 (d, 1H, J=9.6 Hz), 2.09 (s, 3H), 2.03 (s, 3H), 1.99 (s, 3H). $^{13}$C NMR (100 MHz, CDCl$_3$) δ 170.49, 170.44, 170.30, 162.00, 139.15, 138.66, 137.84, 137.56, 129.00, 128.88, 128.57, 128.42, 128.30, 128.16, 128.00, 127.94, 127.83, 127.70, 127.59, 102.77, 99.51, 92.53, 82.53, 81.76, 82.53, 81.76, 76.11, 75.43, 75.06, 74.32, 73.88, 71.29, 70.64, 69.95, 68.20, 66.31, 60.87, 53.43, 20.87, 20.78, 20.68. MS (MALDI-TOF) calculated for C$_{75}$H$_{80}$C$_{13}$NO$_{19}$Na [M+Na]$^+$ m/z 1426.4287. Found: m/z 1426.4573.

Pulmonary trisaccharide (β-GalNAc(1→4)β-Gal (1→4)β-Glc), trichloroacetamide (12)

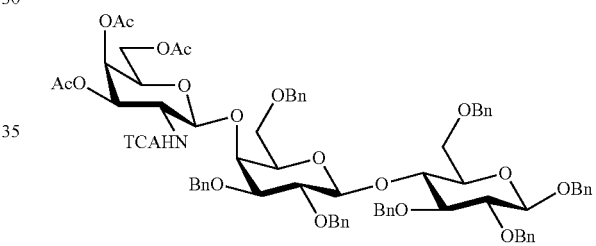

2-Acetamido-2-deoxy-3,4,6-tri-O-acetyl-β-D-galactopyranosyl-(1→4)-2,4,6-tri-O-benzyl-β-D-galactopyranosyl-(1→4)-1,2,3,6-tetra-O-benzyl-D-glucopyranose (13)

A solution of trichloroacetamide 12 (50 mg, 0.036 mmol) in dry benzene (1 mL) was treated with tributyltin hydride (52.4 mg, 0.18 mmol) and 2,2'-azobis(isobutyronitrile) (AIBN, 5.86 mg, 0.036 mmol). The mixture was degassed for 15 minutes with argon, then heated to reflux for 1 hour, cooled to room temperature, and poured into an aqueous solution of NaHCO$_3$, and extracted with CH$_2$Cl$_2$. The combined extracts were washed with brine, dried over anhydrous Na$_2$SO$_4$, and concentrated under reduced pressure. Purification of the residue by silica gel chromatography (EtOAc/hexanes 1:1) afforded acetamide 13 as a yellow oil (32.5 mg, 70%). $^1$H NMR (400 MHz, CDCl$_3$) δ 7.53-7.23 (35H, ArH), 5.47 (d, 1H, J=8.9 Hz, NH), 5.32 (d, 1H, J=2.7 Hz), 4.97 (d, 1H, J=8.0 Hz), 4.91 (d, 2H, J=11.2 Hz), 4.87 (d, 1H, J=8.6 Hz), 4.82 (d, 2H, J=9.3 Hz), 4.78 (d, 2H, J=10.6 Hz), 4.75 (d, 1H, J=11.2 Hz), 4.65 (d, 2H, J=11.2 Hz), 4.61 (d, 2H, J=8.6 Hz), 4.57 (d, 1H, J=4.0 Hz), 4.49 (d, 1H, J=7.8 Hz), 4.42 (d, 1H, J=10.2 Hz), 4.39 (d, 1H, J=6.4 Hz), 4.34 (d, 1H, J=12.0 Hz), 4.24 (d, 2H, J=12.0 Hz), 4.20 (d, 1H, J=10.6 Hz), 4.07 (dd, 1H, J=5.8, 11.2 Hz), 4.00 (d, 1H, J=4.0 Hz), 3.95 (t, 1H, J=12.0 Hz), 3.84 (t, 1H, J=7.4 Hz), 3.77 (dd, 1H, J=4.0, 10.0 Hz), 3.70 (d, 1H, J=9.8 Hz), 3.65-3.62 (m, 1H), 3.55 (t, 1H, J=8.9 Hz), 3.50 (d, 1H, J=7.5 Hz), 3.46 (d, 1H, J=8.0 Hz), 3.42 (dd, 1H, J=2.6, 8.0 Hz), 3.37-3.32 (m, 2H), 2.19 (s, 3H), 2.01 (s, 3H), 1.95 (s, 3H), 1.60 (s, 3H). $^{13}$C NMR (100 MHz, CDCl$_3$) δ 170.72, 170.31, 170.22, 169.91, 138.79, 138.53, 138.40, 138.34, 138.22, 137.44, 137.25, 129.04, 128.94, 128.71, 128.32, 128.19, 127.93, 127.87, 127.73, 127.53, 127.34, 127.07, 103.32, 102.76 (2C), 82.79, 81.95, 80.78, 76.10, 75.58, 75.33, 74.45, 73.51, 73.38, 72.07, 71.19, 70.96, 68.75, 68.31, 66.71, 61.35, 51.01, 23.41, 21.08, 20.87. MS (ESI) 1324.25 [M+Na]$^+$. MS (MALDI-TOF) calculated for C$_{75}$H$_{83}$NO$_{19}$Na [M+Na]$^+$ m/z 1324.5456. Found: m/z 1324.5573.

Pulmonary trisaccharide (β-GalNAc(1→4)β-Gal (1→4)β-Glc), protected derivative (13)

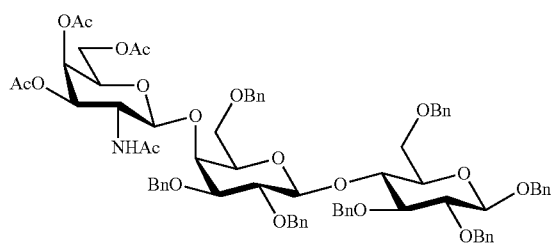

2-Acetamido-2-deoxy-β-D-galactopyranosyl-(1→4) β-D-galactopyranosyl-(1→4)-D-glucopyranose (2)

A solution of triacetate 13 (100 mg, 0.076 mmol) in dry methanol (5.0 mL) was treated at room temperature with a catalytic amount of NaOMe in methanol (1 M, 32 μL). The reaction mixture was stirred for 1 hour at room temperature and then treated with Dowex 50WX8 (H$^+$) resin (500 mg), filtered, and concentrated to dryness. The partially deprotected trisaccharide was dissolved in MeOH (5 mL) and treated with a catalytic amount of Pd(OH)$_2$ on charcoal (80 mg, 20% on active carbon), purged with H$_2$, and stirred under an H$_2$ atmosphere for 12 hours. The catalyst was filtered through a pad of Celite, and the filtrate was concentrated to yield pulmonary trisaccharide 2, as an off-white solid (38 mg, 90% over two steps). $^1$H NMR (400 MHz, CD$_3$OD) δ 4.61 (dd, 1H, J=2.9, 8.4 Hz), 4.48 (d, 1H, J=7.2 Hz), 4.33 (d, 1H, J=7.7 Hz), 4.00 (d, 1H, J=1.7 Hz), 3.90-3.82 (m, 4H), 3.79-3.75 (m, 2H), 3.71-3.64 (m, 2H), 3.62-3.58 (m, 4H), 3.51-3.46 (m, 4H), 3.42-3.39 (m, 1H), 2.02 (s, 3H). $^{13}$C NMR (100 MHz, CD$_3$OD) δ 175.12, 105.12, 104.43, 99.25, 93.69, 80.93, 78.29, 76.82, 76.49, 76.27, 76.00, 74.68, 74.38, 72.59, 69.91, 62.63, 61.95, 61.62, 55.27, 23.15. MS (ESI) calculated for C$_{20}$H$_{35}$NO$_{16}$Na [M+Na]$^+$ m/z 568.47. Found: m/z 568.11.

Pulmonary trisaccharide (β-GalNAc(1→4)β-Gal (1→4)β-Glc) (2)

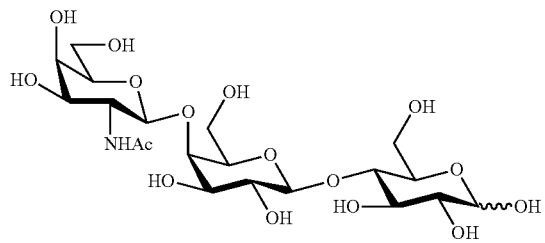

Fluorescein-Labeled 2'-Fucosyllactose Bishydrazide Conjugate (14)

A solution of glycoconjugate 8 (2.2 mg, 2.4 μmol) and fluorescein isothiocyanate (FITC, 1.14 mg, 2.9 μmol) in anhydrous methanol was treated with N,N-diisopropylethylamine (1.2 μL, 9.8 μmol) and stirred for 10 hours at room temperature. The reaction mixture was concentrated and the residue was purified by RP-HPLC (1-30% aqueous CH$_3$CN gradient over 45 minutes) to yield FITC conjugate 14 as a greenish-yellow solid (2.1 mg, 67%). $^1$H NMR (400 MHz, CD$_3$OD) δ 8.18 (d, 1H, J=8.9 Hz), 7.50 (d, 1H, J=2.0 Hz), 7.36 (d, 1H, J=8.8), 4.21 (br s, 2H), 4.14 (d, 1H, J=9.4 Hz), 4.05 (d, 1H, J=9.3 Hz), 3.79-3.78 (m, 4H), 3.74-3.62 (m, 37H), 3.52-3.50 (m, 2H), 3.45-3.42 (m, 1H), 3.24-3.23 (m, 2H), 3.21-3.17 (m, 2H), 3.12-3.09 (m, 1H), 2.00 (3, 3H). MS (MALDI) calculated for C$_{55}$H$_{76}$N$_5$O$_{28}$S [M+H]$^+$ m/z 1290.43. Found: m/z 1290.27.

Photoactive Glycan-Bishydrazide Conjugates (15-17)

In a typical reaction, a solution of pulmonary trisaccharide-bishydrazide conjugate 7 (11 mg, 11.5 μmol) and N-5-azido-2-nitrobenzoyloxy-succinimide (ANB-NOS, 5.3 mg, 17.3 μmol) in anhydrous DMF (1 mL) was treated with N,N-diisopropylethylamine (2.0 μL, 12.7 μmol) and stirred for 12 hours at room temperature, protected from light. The reaction mixture was concentrated, and the residue was purified by RP-HPLC (1-30% aqueous CH$_3$CN gradient over 45 minutes) to afford ANS conjugate 16 as a brown solid (8.4 mg, 63%). $^1$H NMR (400 MHz, CD$_3$OD) δ 8.08 (s, 1H), 7.89 (br s, 1H), 7.69 (d, 1H, J=8.0 Hz), 7.41 (d, 1H, J=7.9 Hz), 7.14 (t, 1H, J=7.9 Hz), 6.53-6.51 (m, 3H), 5.20 (s, 1H), 4.53 (s, 1H), 4.43 (d, 1H, J=8.0 Hz), 4.17-4.13 (m, 2H), 4.06-4.05 (m, 2H), 4.03-4.01 (m, 2H), 3.77-3.57 (m, 35H), 3.53-3.48 (m, 4H), 1.16 (d, 1H, J=6.4 Hz), 1.10 (d, 1H, J=7.4 Hz). MS (ESI) calculated for C$_{43}$H$_{70}$N$_9$O$_{27}$Na [M+H]$^+$ m/z 1144.43. Found: m/z 1144.87.

Example 3

Detection of Mycobacteria, *Salmonella*, and *Shigella* Using Immobilized Siderophores, Mycobactin J, Salmochelin S1 and Aerobactin Materials.

Ferric mycobactin J was purchased from Allied Monitor (Fayette, Mo.). Iron (III) chloride, DEAE cellulose, eerie ammonium nitrate, and Bovine serum albumin (BSA) were obtained from Sigma-Aldrich (St. Louis, Mo.). Octaethylene glycol monododecyl ether ($C_{12}E_8$) was purchased from Affymetrix-Anatrace (Santa Clara, Calif.), *E. coli* Nissle 1917 was kindly donated by Ardeypharm GMbH (Herdecke, Germany) and Biogel P2 was the product from Bio-Rad (Hercules, Calif.). *Mycobacterium smegmatis* (ATCC 7000084), *Salmonella enterica* (ATCC 14028™), *Shigella flexneri* (ATCC 12022™), *Yersinia enterocolitica* (ATCC 51871), *Pseudomonas. aeruginosa* (ATCC 15692), and *Staphylococcus aureus* (ATCC 10537) were purchased from ATCC (Manassas, Va.) and *Vibrio Cholera* strain 0395 was generously donated by Dr. Shelley Payne (U. of Texas, Austin).

Isolation of Salmochelin S1/S2 and Aerobactin.

Figure 23:
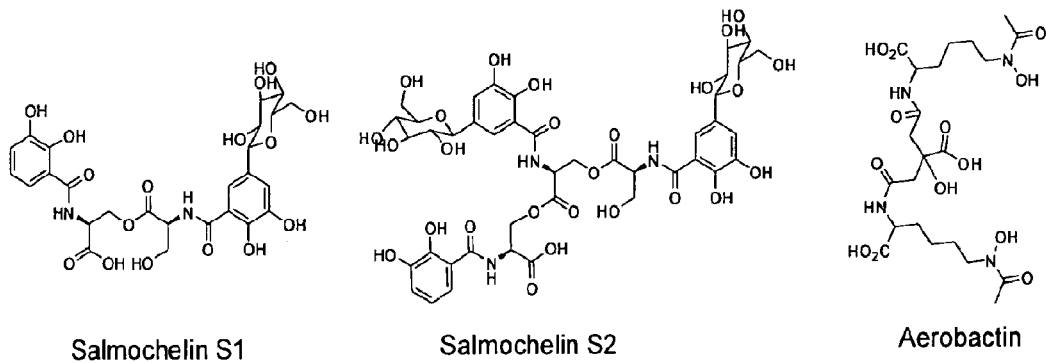
FIG. 23 shows structures of the siderophores, salmochelins (S1 and S2) and aerobactin.

The siderophores, salmochelin S1/S2 and aerobactin were produced and isolated from *E. coli* Nissle 1917 according to literature procedure (Valdebenito et al., *Int. J. Med. Microbiol.* 2006, 296(8):513-520). Briefly, siderophores were produced after 18-19 hours of growth in 1 L iron-poor minimal medium M63 (containing per liter: 5.3 g $KH_2PO_4$, 13.9 g $K_2HPO_4.3H_2O$, and 2.0 g $(NH_4)_2SO_4$; before inoculation, 1 mM $MgSO_4$ and 0.6% glycerol were added), which was inoculated with 1% (v/v) of an overnight culture in TY medium (containing per liter: 5 g yeast extract, 5 g sodium chloride, and 8 g tryptone). The culture was incubated at 37° C. with vigorous shaking for 18-19 hours. After then FeCl3 (2 mM) was added to culture supernatant, which was passed through a DEAF cellulose column to bind all negatively charged siderophores. After washing with two column volume of water, the siderophores were eluted with 2M ammonium chloride. The blue-red fractions containing the siderophores were pooled, concentrated by evaporation, and purified on a Biogel P2 column by using water as an eluent (Hantke et al., *PNAS* 2003, 100(7):3677-3682). The deep red fractions obtained were further purified by HPLC. As a result, aerobactin and salmochelins (S1 and S2) were obtained for the detection of *Salmonella* and *Shigella* (FIG. 23).

Preparation of Ferric Mycobactin J-BSA Conjugate.

To a solution of Ferric mycobactin J (2 mg) and BSA (10 mg) in 1 mL PBS including 2% octaethylene glycol monododecyl ether ($C_{12}E_8$) was added 3 mol % ceric ammonium nitrate (40 μg) and triethylamine (2 μl), followed by stirring for 6 hours at room temperature as shown in scheme 4 (Varala et al., *Syn. Lett,* 2006, 10:1549-1553). The ferric mycobactin J-BSA conjugate was separated from all low molecular weight materials with a 10-kD molecular weight cut off spin filter with multiple washes of PBS and diluted with PBS to a concentration of 2 mg/1 ml.

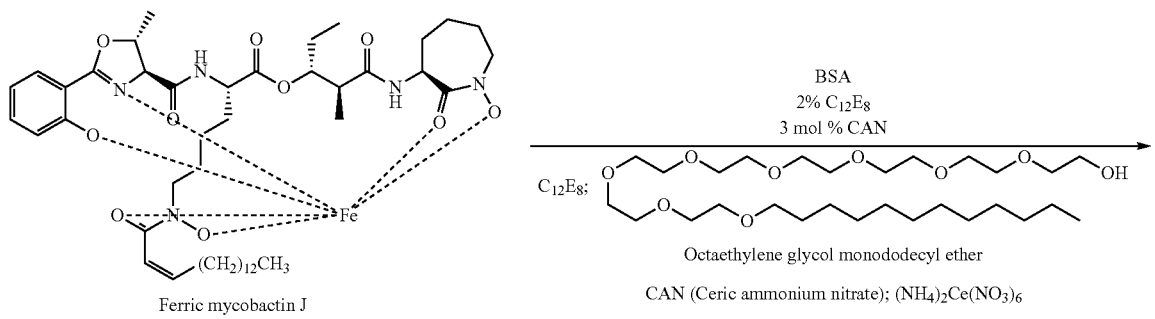

Scheme 4. Reaction scheme of mycobactin J-BSA conjugate.

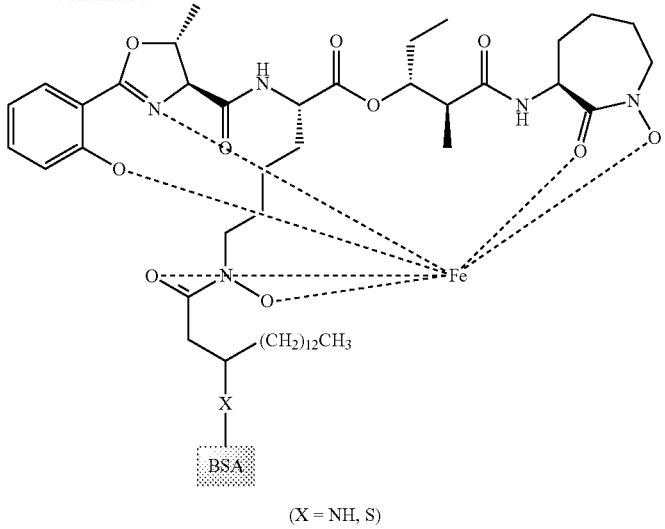

(X = NH, S)

Preparation of BSA-salmochelin S1/S2-Fe.

To a solution of salmochelin S1/S2 (2.5 mg) in 200 μl. H2O was added $FeCl_3$ (0.5 mg in 20 μl $H_2O$). The solution immediately turned to purple ferric salmochelins solution and then 1-ethyl-3-(3-dimethyl-aminopropyl) carbodiimide hydrochloride (EDC.HCl, 3 mg in 50 μl $H_2O$) was added and stirred for the activation for 15 minutes. Bovine serum albumin (BSA, 10 mg) was dissolved in 700 μl PBS (pH 7.4), and added to above salmochelin reaction mixture. Immediately, triethylamine (2 μl in 20 μl DMF) was added and stirred for 3 hours at room temperature. The salmochelins-BSA conjugate was separated from all low molecular weight materials with a 10-kD molecular weight cutoff spin filter with multiple washes of PBS.

Preparation of BSA-aerobactin-Fe.

To a solution of aerobactin (2.5 mg) in 200 μl H2O was added $FeCl_3$ (0.6 mg in 20 μl H2O). The solution immediately turned to dark red ferric aerobactin solution and then 1-ethyl-3-(3-dimethyl-aminopropyl) carbodiimide hydrochloride (EDC.HCl, 3 mg in 50 μl H2O) was added and stirred for the activation for 15 minutes. Bovine serum albumin (BSA, 10 mg) was dissolved in 700 μl PBS (pH 7.4), and added to above aerobactin reaction mixture. Immediately, triethylamine (2 μl in 20 μl DMF) was added and stirred for 3 hours at room temperature. The aerobactin-BSA conjugate was separated from all low molecular weight materials with a 10-kD molecular weight cutoff spin filter with multiple washes of PBS.

Example 4

Label-Free Detection of Bacterial Adhesion by Optical Pattern Recognition

Materials.

GalNAc(β1→4)Gal(β1→4)Glc (21) was prepared by multistep synthesis as recently described (Adak et al., *Bioconj. Chem.*, 2010, 21:2065-2075; Example 2). N-Hydroxysuccinimidate (NHS)-activated glass slides (CodeLink and Nexterion H) were purchased from SurModics, Inc. (Eden Prairie, Minn.) and Schott North America (Elmsford, N.Y.), respectively. Bovine serum albumin (BSA) was purchased in powder form from Sigma (St. Louis, Mo.) and used as received; bacterial culture media (Difco) was obtained from BD Diagnostics (Franklin Lakes, N.J.). Lyophilized strains of *Staphylococcus aureus* (ATCC 10537), *Yersinia enterocolitica* (ATCC 51871), and *Pseudomonas aeruginosa* (PA01 strain) were purchased from ATCC (Manassas, Va.). *Vibrio cholerae* (0395) culture was graciously provided by Prof. Shelley Payne (University of Texas, Austin). Deionized water with a resistivity of ≥18 MΩ·cm was obtained from an ultrafiltration system (Milli-Q, Millipore; Billerica, Mass.) and passed through a 0.22-μm filter to remove particulate matter.

Figure 33:
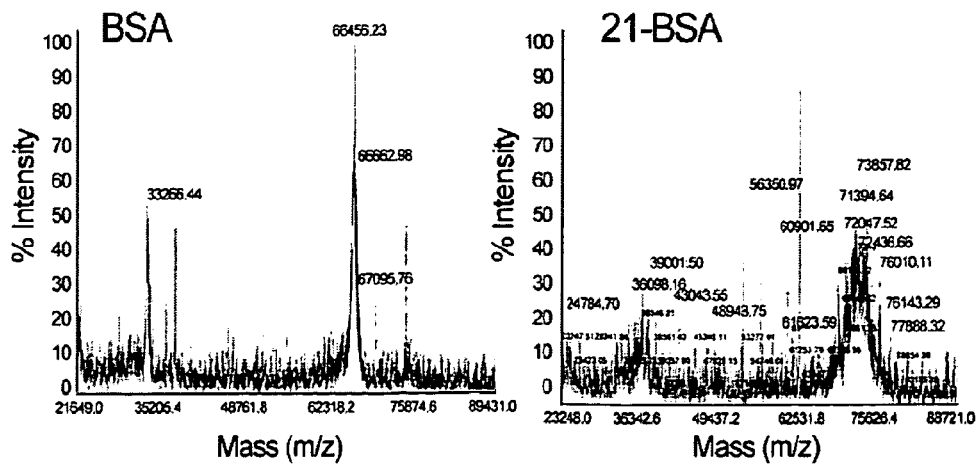
FIG. 33 shows MALDI-TOF mass spectra of underivatized BSA (left) and 21-BSA (right). The shift in mass distribution indicates a median of 5-6 glycoconjugates (mw 976) per BSA.

Neoglycoproteins 21-BSA and lactose-BSA were prepared using a hexaethyleneglycol-bishydrazide linker, as previously described (Adak et al., *Bioconj. Chem.*, 2010, 21:2065-2075; Example 2). Typically, a freshly prepared solution of BSA (10 mg) in phosphate buffered solution (PBS, pH 7.4, 200 μL) was treated with 1-ethyl-3-(3-dimethylaminopropyl) carbodiimide hydrochloride (EDC.HCl, 3 mg in 50 μl, PBS) and gently stirred at room temperature for 1 hour. The activated protein solution was then treated for another 2 hours with a glycan-bishydrazide conjugate (5 mg) in 200 pL PBS. The mixture was passed through a 0.45-μm filter to remove aggregates and particulate matter, followed by membrane dialysis (MWCO=10 kDa). The resulting neoglycoproteins could be stored for several months at 4° C. Mass spectral analysis of 21-BSA indicated a median of 5-6 glycans per protein (FIG. 33).

Bacterial Growth Conditions.

All microbiological manipulations were performed under biosafety level 2 (BSL-2) conditions, using sterile materials in a microbiological safety cabinet (NU-425-300, Nuaire Inc.; Plymouth, Minn.). Bacteria strains were grown at 37° C. on a rotary shaker with vigorous agitation in a low $CO_2$ atmosphere (2.6%), using different growth media: *P. aeruginosa*, *S. aureus*, and *Y. enterocolitica* were cultivated in Difco Nutrient Broth, and *V. cholerae* in low-iron T-medium (Tris-buffered minimal medium). The bacteria samples could be centrifuged and stored at −70° C. in glycerol/broth medium (10% v/v), and reactivated by incubating the bacteria in 5 mL of sterile broth medium at 37° C. for 24 hours. Bacterial cells were harvested by centrifugation (8050 g for 5 min) and washed thrice with phosphate buffer (PBS, pH 7.4); the pellets were then resuspended in PBS to a final density of $10^8$ cfu/mL (cfu=colony-forming unit). Bacterial counts were established using standard plating methods, and correlated with turbidity measurements of culture suspensions. All pathogen detection assays were performed promptly after serial dilution of the bacterial suspensions.

Inkjet Printing.

Microarrays were produced by a stationary HP TIPS thermal droplet ejection system, coupled with a motorized XY stage (Anorad WKY-150), a laser registration system for repositioning the substrate, and an optical imaging camera. The thermal ejection system can produce individual drops with volumes in the range of 1-220 pL, with a drop displacement uncertainty of less than 9 µm at 95 percent confidence. The motorized XY stage has an encoder resolution of 0.5 µm with a maximum linear speed of 400 mm/s in each direction, and a substrate positioning error of 2-5 µm when subjected to a maximum acceleration of 1.6 m/s$^2$. The registration system consists of a laser with a beam diameter of 23 µm, reflected into a photodiode connected to a trigger circuit. The imaging system consists of a CCD camera (Sony/XC-ST50, 640×480 pixels) with an optical zoom lens for viewing printing results in real time, using a field of view less than 5 mm. Visual C-based printing software was written in-house for automated printing protocols.

A 0.2 wt % solution of 21-BSA in PBS containing 0.005% Tween 20 was dispensed in microarray format onto NHS-activated glass slides, using the custom-built inkjet printing system described above. A single-channel thermal nozzle with an orifice diameter of 8 µm positioned 0.5 mm above the substrate, with a scan velocity of 1 mm·s$^{-1}$. An input waveform was applied for droplet generation with an amplitude of 25 volts and a pulse width of 1.4 µs. Typical print runs produced arrays of 25×25 spots with periodicities of 80 or 120 µm in the scanning direction, with an average spot diameter below 50 µm. The glycan-BSA arrays were allowed to sit overnight at 4° C., then washed sequentially with PBS, PBS containing 0.05% Tween 20, and deionized water. The printed slides were then immersed for 1 hour in a buffered solution of ethanolamine (50 mM), using either sodium borate (50 mM, pH 9.2) for Nexterion H slides or Tris-buffered saline (TBS; 100 mM, pH 9.0) for CodeLink slides. The functionalized slides were washed with PBS buffer and deionized water as described above, dried under a stream of nitrogen, then stored at 4° C. until use.

Pathogen Affinity Capture and Image Acquisition.

In a typical experiment, glycan microarrays were incubated with suspensions of live *S. aureus* for 1 hour at room temperature and concentrations ranging from $10^7$ to $10^2$ cfu/mL. The density of live *S. aureus* was estimated by correlating turbidity measurements with colony counts obtained by plating serial dilutions (ca. $10^8$ cfu/mL at O.D. 1, λ=600 nm). After incubation, the chip was washed with PBS and deionized water prior to imaging. All darkfield images (before and after exposure to bacteria) were acquired at 10× magnification using an upright microscope (Olympus BH2-RFL-T3) equipped with a darkfield condensor and a DP70 camera (1360×1024 pixels). Images for FFT analysis were acquired at a resolution of 1 pixel/µm2.

Viability Assay.

Immobilized bacteria were stained using a commercial viability kit based on the DNA-staining dyes SYTO 9 and propidium iodide (PI), according to a manufacturer's protocol (LIVE/DEAD BacLight, Invitrogen; Carlsbad, Calif.). In brief, SYTO 9 (1.0 pL, 3.34 mM) and PI (1.0 µL, 20 mM) were combined and diluted with 1 mL of sterile, deionized water. The chip was incubated with the above staining solution for 15 minutes in the dark, then washed and viewed using a confocal laser-scanning microscope (FV1000, Olympus; Center Valley, Pa.). The green fluorescence signal of SYTO 9 and red fluorescence signal of PI were detected using excitation/emission wavelengths at 488/500 nm and 520/635 nm, respectively.

FFT Analysis.

Darkfield images were cropped to 1024×1024 pixels using a commercial program (Adobe Photoshop). Standard sizes and magnifications were established for each image with pixels scaled in microns, for proper conversion of the reciprocal lattice units (into µm$^{-1}$) in the FFT-derived spectra. A standardized protocol was also applied for optimizing brightness and contrast of each image, prior to saving in TIFF format without compression. Processed images were subjected to 2D-FFT analysis using commercial software (WSXM 4.0 Develop 12.3) (Horcas et al., *Rev. Sci. Instrum.*, 2007, 78:013705). Linescans in the x-direction were used to evaluate reciprocal lattice peaks (k=1/a) characteristic of pathogen capture, as described in the simulations below. Reference images prior to pathogen capture were also obtained and processed for background subtraction. The signal quality in the Fourier spectrum was then quantified as the peak signal-to-noise ratio (S/N), which was calculated as the ratio of the peak harmonic intensity to the standard deviation of the residual spectral data between 0 and 0.15 µm$^{-1}$.

Example 5

Pathological Microbe Detection Device

The PathoTest Device

The PathoTest device comprises a microscope, camera, flow cell, pump controls, illumination source, and a dielectrophoretic (DEP) concentrator (FIG. 41), and is controlled through a laptop computer with appropriate programming such as, for example, Labview. Liquid flow to the concentrator may be driven by two pumps, one for analyte solution and one for purge/rinse cycles.

Figure 47:
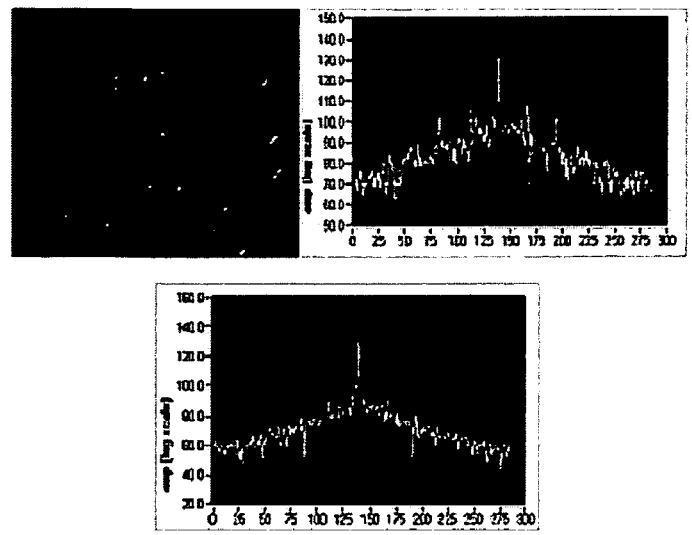
FIG. 47 shows optical image of *Yersinia enterocolitica* immobilized on a patterned Au substrate (Upper Left) (dried in air, n=1.0). (Upper Right) 1D FFT spectrum with x-axis representing reciprocal lattice units (a.u.) and the y-axis represents amplitude on a logarithmic scale. (Lower) FFT spectrum of the same capture chip, in an aqueous medium (n=1.33). The ±1/a peaks (x=110, 160) are still visible, despite the reduced S/N ratio.
Figure 48:
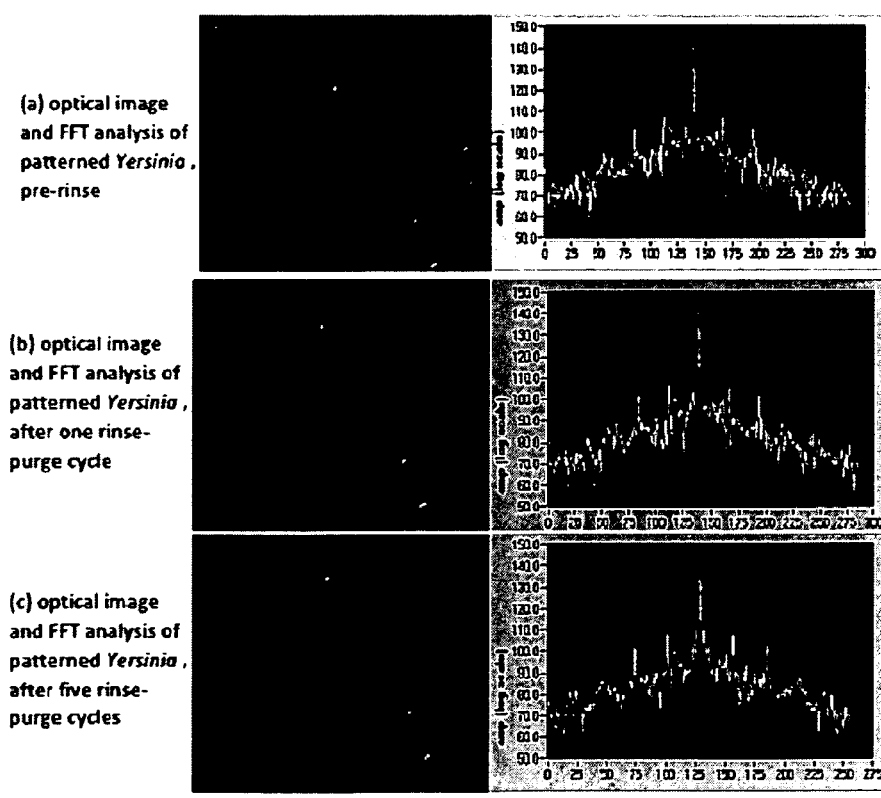
FIG. 48 shows Optical darkfield images (Left) of capture pattern on Au substrate and the corresponding FFT spectra (Right). (a) Patterned *Yersinia*, prior to purge-rinse cycles; (b) capture pattern after first cycle; (c) capture pattern after fifth cycle. The slight shift in the x-axis of the FFT spectrum in (c) is due to a shift in the imaged area.
Figure 49:
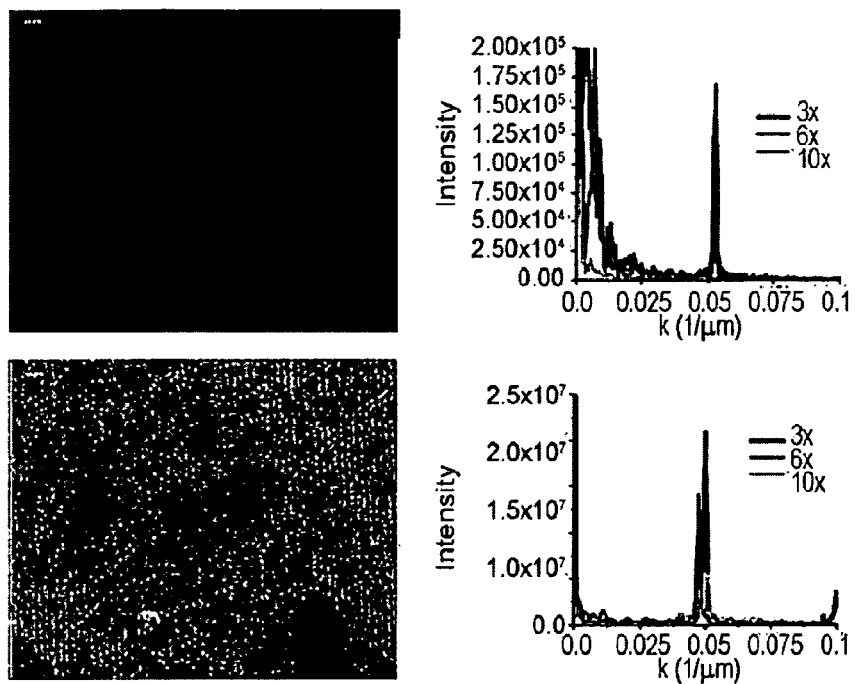
FIG. 49 shows a comparison of glass substrate (Top) and a gold-coated substrate (Bottom). The grating stamped onto each substrate is made of 10 µm lines with a periodicity of 20 µm at a pressure ~6.8 kPa using the BSA-trisaccharide conjugate, followed by capture of *Staphylococcus aureus* (~10$^8$ cfu/mL, 75 min exposure). The position of the 1/a peak appears shifted from 0.05 µm$^{-1}$ due to changes in magnification.
Figure 50:
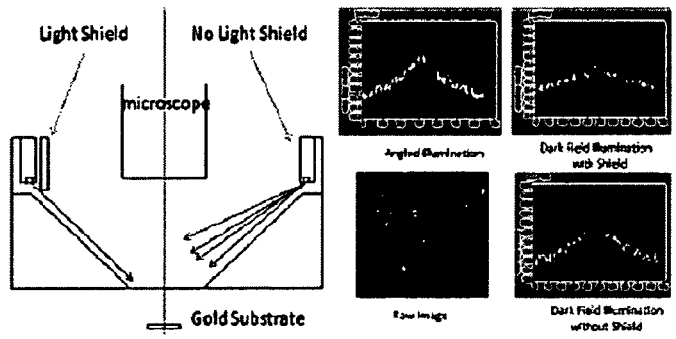
FIG. 50 shows schematic of the dark light setup with and without the light shield (Left). The dark field apparatus is a ring light. The vertical line is to show two different setups of the dark field apparatus. (Right) FFT of the pectin lectin patterned substrate with angled illumination (non-ring) and dark field illumination with and without the shield, and a raw image of the peanut lectin patterned substrate.
Figure 51:
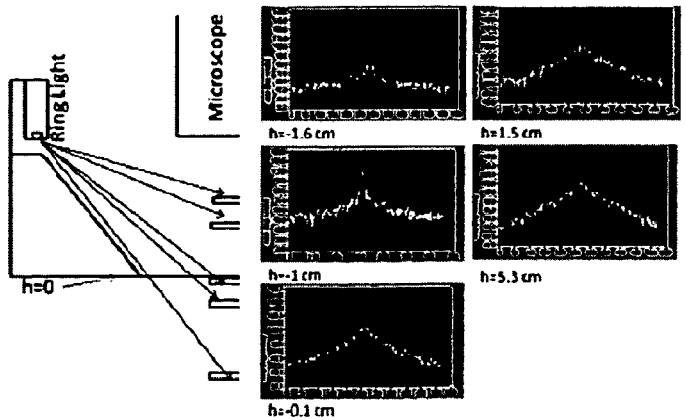
FIG. 51 shows optimizing the height of the gold substrate. Negative heights indicate the gold substrate is within the dark field apparatus (above h=0 in the diagram) and positive when the substrate is out of the apparatus (below h=0 in the diagram).
Figure 52:
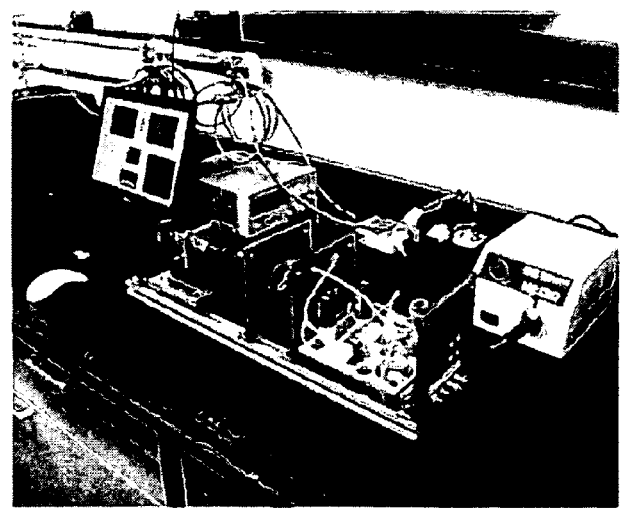
FIG. 52 shows the PathoTest Device version 2. The complete PathoTest Device setup as a bench top model. From left to right, the laptop user interface, power supply for pumps, the 2nd generation of the PathoTest Device, and the fiberoptic light source.
Figure 53:
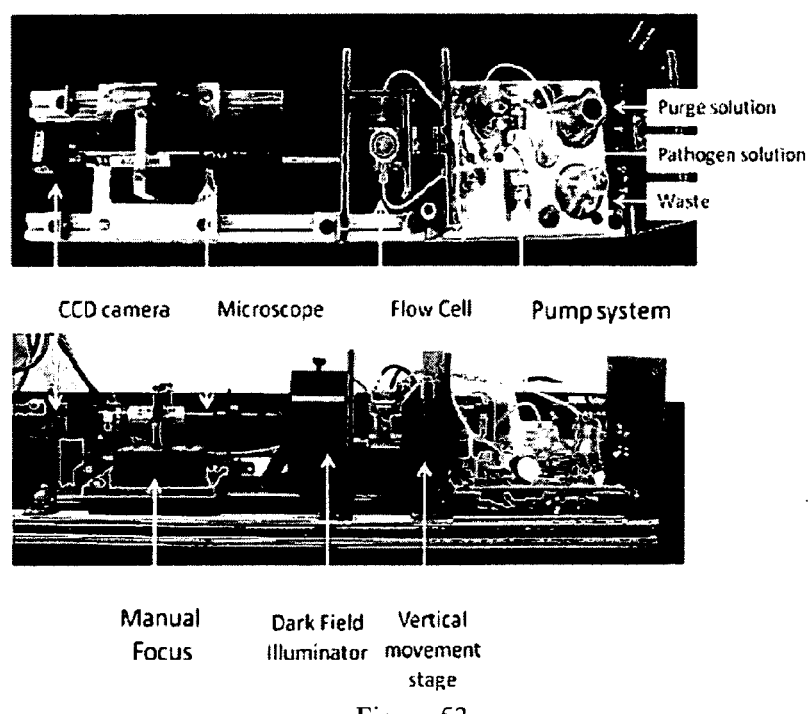
FIG. 53 shows a top view (Upper) and side view (Lower) of the 2nd generation PathoTest Device. The improvements include a new flow cell, stage controls for image focus and vertical positioning of the flow cell, and mechanical stability to image a region of interest without a shift in registration.
Figure 54:
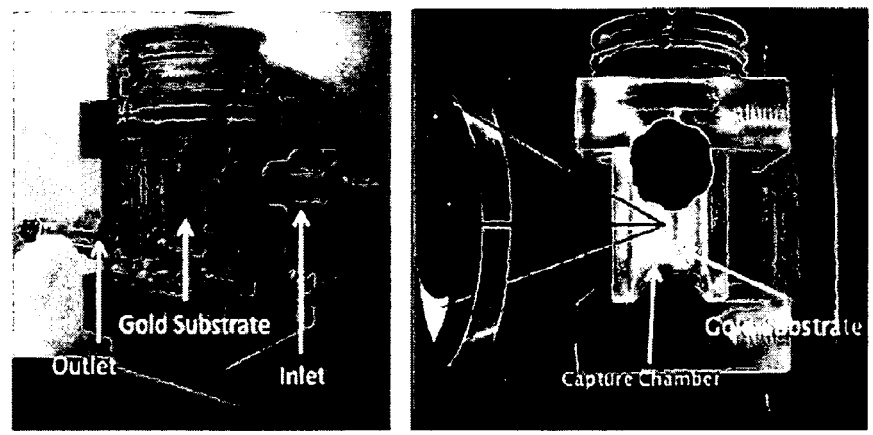
FIG. 54 shows flow cell and position of the substrate for front-side imaging. (Left) The flow cell with inlet on top and an outlet on bottom to facilitate the purging of liquid. The substrate is attached with double-sided tape to a removable cap that also serves sample holder. The volume of the capture chamber is approximately 1.5 mL. (Right) The illuminated flow cell within the PathoTest device during front-side imaging, showing the changes in media along the optical path.
Figure 55:
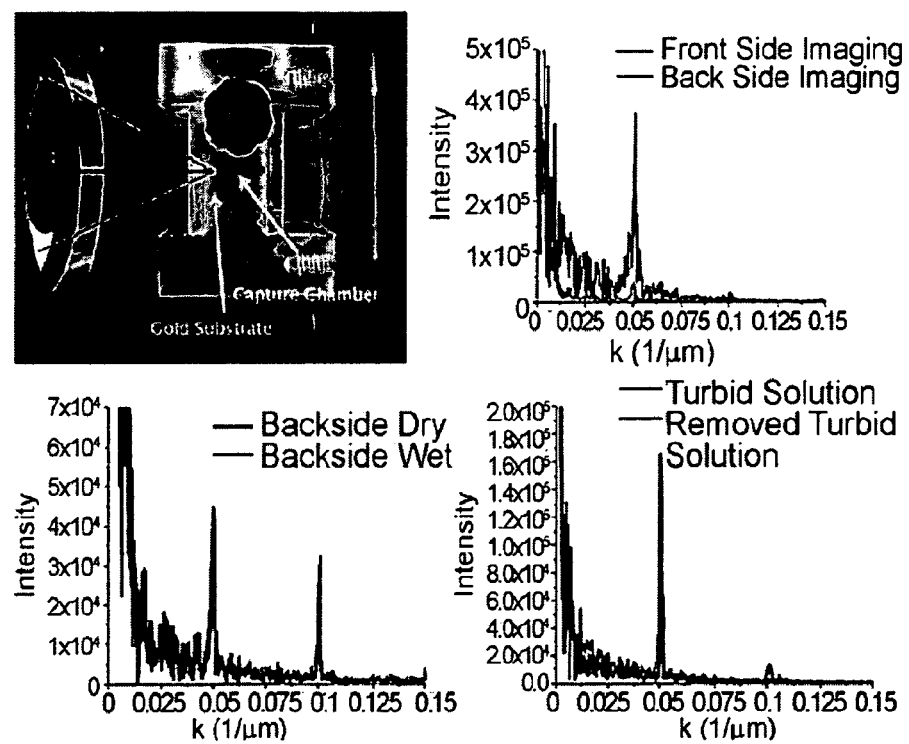
FIG. 55 shows back-side imaging. (Upper Left) Picture of the flow cell with the gold-coated substrate affixed (double-sided tape) to the imaging wall of the capture chamber. The capture pattern (BSA-trisaccharide conjugate has a 20-µm periodicity (kβ0.05 µm$^{-1}$) and printed with a stamp pressure of 6.7 kPa, and then exposed to *Staphylococcus aureus* for 1 hour. (Upper Right) FFT spectra (linear scale) comparing front-side and back-side imaging. (Lower Left) comparison of back-side imaging under dry or wet (aqueous) conditions; results are nearly identical. (Lower Right) Back-side imaging with a turbid solution (~10$^7$ cfu of *Staphylococcus aureus*) and after the removal of the turbid solution without assisted drying. Note the change in intensity scales for each FFT plot.

A gold-coated capture chip patterned with BSA-Desferrioxamine conjugate was placed within the flow cell, then exposed to a suspension *Yersinia enterocolitica* at a concentration of $10^8$ cfu/mL for 60 minutes (FIG. 47). The flow cell was sealed with vacuum grease along the edges and fastened by screws to prevent leakage between plates. A drop of immersion oil (index-matching fluid) was placed on the back side of the substrate, and the pattern was illuminated with a ring light mounted around the objective lens (Dolan-Jenner MI-150 Fiber Optic Illuminator) and imaged using the PathoTest device. The optimal position of the gold substrate relative to the ring lamp was determined to be 1.5 cm. FFT analysis of the optical images in either air or water (n=1.0 and 1.33, respectively) revealed the harmonic peaks corresponding to patterned *Yersinia* in both air and water; validating the ability to detect pathogens in situ.

Although imaging in a liquid medium is possible and enables the monitoring of pathogens in real time, change in the optical illumination setup may be desired to optimize detection at lower concentrations. Alternatively, the flow cell can be temporarily purged and dried for optical analysis of the capture chip. To test this embodiment, a sample in the flow cell was immersed in deionized water, then rinsed in situ with absolute ethanol and purged with a commercial air duster (1,1,1,2-tetrafluoroethane) until the imaged area appeared dry. The water/ethanol/purge sequence was repeated every 15 minutes for 5 cycles, with pattern monitoring and FFT analysis after each purge. The S/N ratios in the corresponding FFT spectra did not appear to decrease, even after the fifth purge cycle (FIG. 48). The same flow-purge cycle was repeated on a glass substrate with patterned *Pseudomonas* captured by a BSA-trisaccharide conjugate, which yielded similar results.

NHS-activated glass slides (CodeLink) and Au-coated glass substrates (Reichart SPR chips) were compared for background levels while imaging capture patterns in aqueous media at different magnifications (FIG. 49). The S/N ratio decreases with increasing magnification, accompanied by peak broadening. Au-coated substrates supported lower backgrounds at high magnification and were capable of producing multiple harmonic signals, and used as the substrate of choice in subsequent experiments.

Optical imaging was performed under the quasi-darkfield imaging conditions, using a concentric ring light for illumination at a high angle of incidence. FIG. 50 shows the image quality using the ring light setup with and without a light shield; the latter blocks illumination of a certain angle of incidence using the light shield at the lowest setting reducing the overall intensity, but does not improve the peak S/N in the FFT spectra. The FFT are best resolved without the shield; higher harmonics can be seen with maximum illumination whereas for the other cases, the fundamental harmonic can barely be resolved.

Next the height of the substrate in and out of the dark field apparatus was varied. The distance between the substrate and the illumination plane was optimized. The maximum peak S/N in the FFT spectra was obtained when the substrate was position 1.5 cm from the place of the ring light, and 3.5 cm from the objective lens (FIG. 51).

Improvements to the PathoTest Devise

PathoTest Device Version 2

The PathoTest device is intended to be portable, reliable, and cost-effective for rapid detection of bacteria or viruses, particularly in resource limited environments. The device may be supported by interchangeable capture chips patterned with multiple ligands for multiplex pathogen detection with each substrate being specific to a certain subset of pathogens.

For these reasons, we developed another version of the PathoTest device with increased reliability and superior collection optics for dark-field imaging. Improvements to the device include the mechanical stability of the system, stage control focus, and vertical movement of the flow cell. This version also integrates the microscope, CCD camera, redesigned flow cell, and pump system onto a single physical platform. Other components supporting the PathoTest device include a laptop user interface, power source for the pumps and valves, and fiber-optic light source. The software has been modified to allow for multiple linescan profiles in Cartesian or polar coordinates at fixed radii, which can be exported as data files. The calibration of the device has been improved and can calibrated with a standard or pattern of know periodicity. The device can be seen in FIGS. 52 and 53.

Imaging of the bacterial capture patterns within our flow cell can be limited by the turbidity of the solution, particularly if derived from unfiltered specimens. FIG. 54 shows the flow cell and the initial positioning of the capture chip, which is attached to a removable sample holder with double-sided tape. The cell is sealed by an o-ring above the fluid level. The flow cell is made of optically clear plexiglass, with an inlet and outlet positioned at different heights to facilitate efficient solution exchange.

Front-side imaging will be defined as follows. The path of the light must first go through the wall of the flow cell chamber then the sample medium (air or liquid) before reaching the surface of the patterned substrate. This setup suffers from the composition of the medium in the flow cell chamber which can introduce high levels of background scatters. A turbid solution with OD=0.1 at $\lambda$=600 nm can make darkfield imaging of the capture chip difficult. Removal of the solution is possible, but the focus must then be readjusted when switching between a gaseous medium and liquid medium in the capture chamber.

FIG. 54 shows the real-time capture of *Staphylococcus aureus* onto a gold-coated capture chip patterned with the BSA-trisaccharide ligand. The concentration of the bacteria can be adjusted to decrease the turbidity of the solution to enable real-time imaging. However, it may not always be advantageous to lower the concentration of a highly turbid solution (e.g., blood or urine) if the concentration of the pathogens of interest is already near the limit of detection.

To circumvent these possible limitations, we investigated imaging of bacteria capture through the back-side of the gold-coated substrate, mounted so the optically path did not pass through the flow cell chamber (see FIG. 55). This is possible because the thin (50 nm) gold coating is semi-transparent at wavelengths above 550 nm. Back-side imaging can be performed in the presence of any medium (wet or dry), and was not affected by solution turbidity, and did not require changes in the focal adjustment between changes in experimental parameters (FIG. 55). The intensity of the fundamental harmonic is lower in an aqueous medium and the higher harmonics are obscured due to the higher refractive index (n=1 vs n~1.33). Also, simply removing a solution in the capture chamber without assisted air drying was sufficient to produce a reliable FFT spectrum. This can allow for a time-dependent analysis of bacterial capture without additional pumps or air compressors.

A comparison of back-side and front-side imaging, with and without flow, was performed at the limit of detection of $10^4$ cfu/mL of *Staphylococcus aureus* (FIG. 56). The S/N ratios for front side imaging without flow (chamber filled with bacteria for the duration of the experiment), front-side imaging with flow, back-side imaging without flow, and back-side imaging with flow (rate of 8 μL every 10 seconds) are below zero, 3.46, 11.56, and 5.66, respectively. Backside imaging without flow provides the best signal for *Staphylococcus* detection, and also suggests that bacterial adhesion may be reduced under fluid flow.

Figure 56:
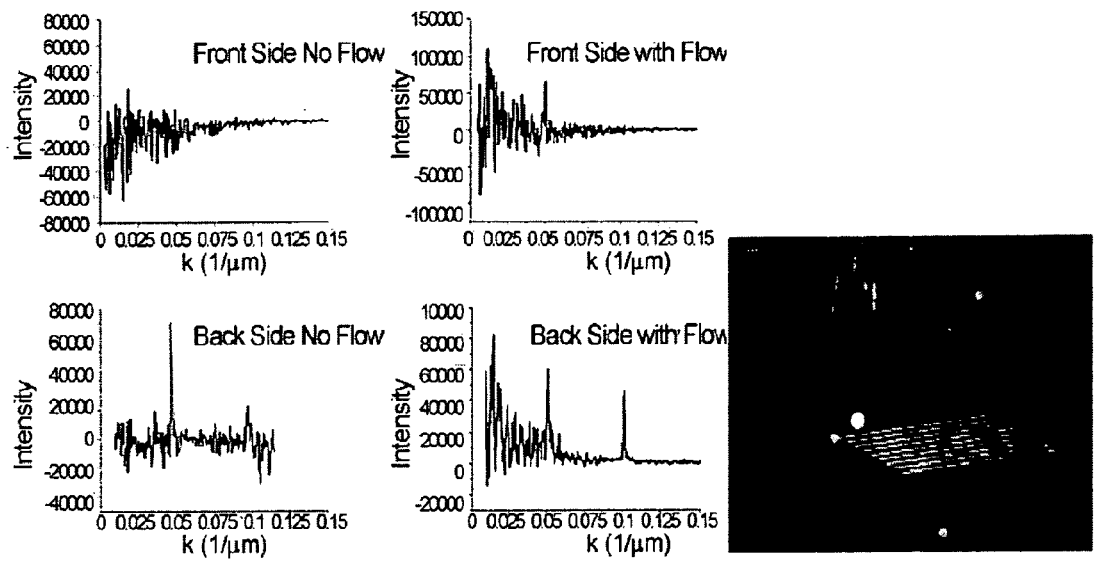
FIG. 56 shows imaging method for *Staphylococcus aureus* (10$^4$ cfu/mL for 30 minutes), under different flow conditions, captured with the BSA-trisaccharide ligand. Bacteria were patterned onto a gold substrate (20 µm periodicity). For each sample with flow, 8 µL of solution was injected into the flow every 10 seconds. FFT spectra (with before capture subtraction) for front-side imaging without flow (Upper Left) and with flow (Upper Right) and backside imaging without flow (Middle Left) and with flow (Middle Right). The S/N ratios for left to right and top to bottom are <0, 3.46, 11.56, and 5.66, respectively. The raw image of the backside imaging without flow with capture pattern superimposed for clarity (Lower).
Figure 57:
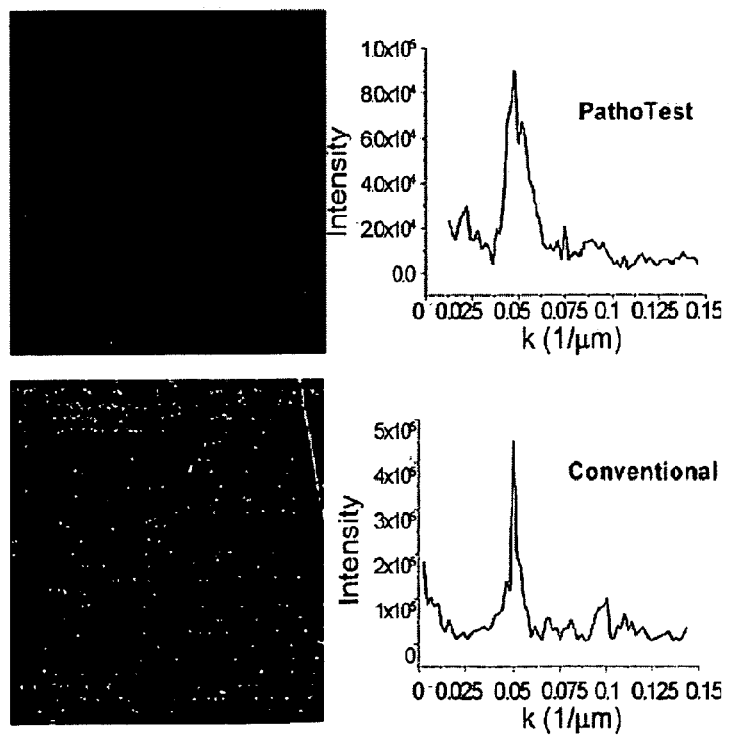
FIG. 57 shows a comparison of the PathoTest Device (Upper) and a conventional microscope (Lower) for the same ROI for the capture of *Yersinia enterocolitica*. The FFT was performed manually for each image. The noise of the PathoTest device is greater, causing the S/N and SB to be smaller than that of the conventional microscope, 12.27 and 6.36 vs 20.99 and 15.36, respectively. Note that dry front-side imaging was used for the PathoTest Device and is the only mode of imaging for a conventional microscope.
Figure 58:
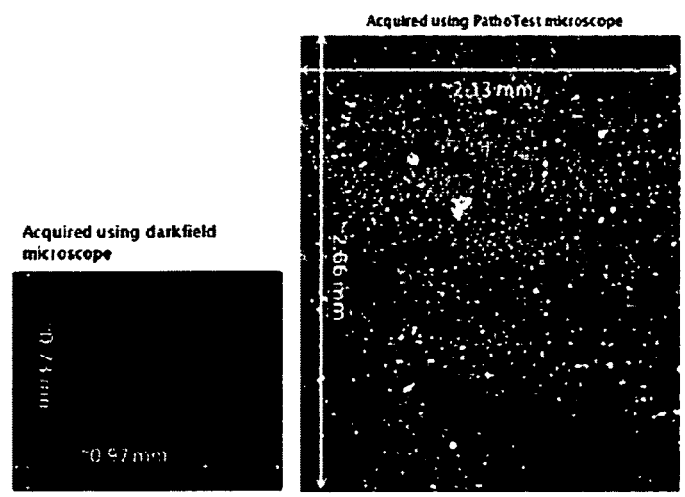
FIG. 58 shows a comparison of images acquired on different instruments. (Left) Size of the image obtained from a conventional microscope, with a resolution of 0.71 µm$^2$/pixel. (Right) Size of image obtained by the PathoTest device, with a resolution of 2.1 µm$^2$/pixel.

A comparison of the imaging capabilities of the PathoTest device and a conventional microscope shows that the S/N for the same ROI is better on a conventional microscope (21) than the PathoTest device (12.3). This is not surprising because illumination/collection optics of the microscope are superior to that of the PathoTest device (FIG. 56). In addition, the resolution of the conventional microscope is 0.71 $\mu m^2$/pixel compared with 2.1 $\mu m^2$/pixel for the latter image (FIG. 57). On the other hand, the larger image area using the PathoTest device provides a several fold increase in the periodic signal (FIG. 58). This corresponds to a higher intensity in the FFT signal, which increases with the square root of the number of periods.

Figure 59:
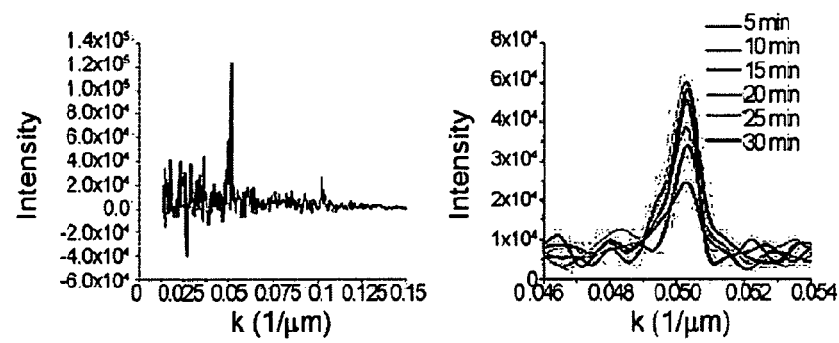
FIG. 59 shows real-time detection of *Staphylococcus aureus* (10$^6$ cfu/mL for 30 minutes) captured with BSA-trisaccharide ligand printed on a gold-coated substrate (front-side imaging). (Left) FFT spectra for the capture of *Staphylococcus aureus* after drying with before capture subtraction. The S/N and S/N for the fundamental harmonic (k=0.05 µm$^{-1}$) are 15 and 20, respectively. (Right) FFT spectra acquired line profiles during capture of *staphylococcus aureus*. The signal to background of the fundamental harmonic goes from 5 to 19 indicating capture.

FIG. 59 shows the patterned capture of *Staphylococcus aureus* on a gold-coated substrate in real time, utilizing front-side imaging. FFT spectra before and after capture of *Staphylococcus aureus* provide an endpoints for comparison with earlier studies. For real time capture (under aqueous conditions), imaging the intensity of the fundamental harmonic ($k=0.05 \mu m^{-1}$) is observed to increase gradually over a period of 30 minutes. It is worth noting that up to this point, all quantification of capture had been done strictly before and after capture, not during capture.

Figure 60:
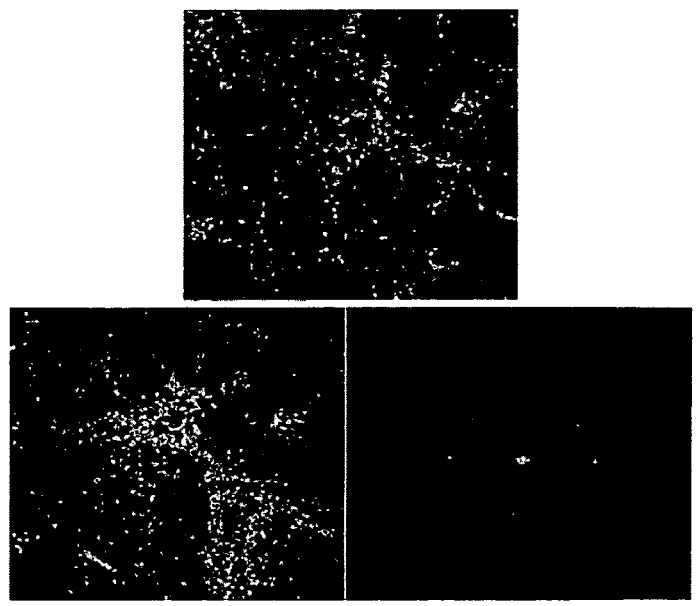
FIG. 60 shows multiple pattern detection. (Upper) Simulation of the FFT pattern where the orientation (0°, 45°, 90°, and 135°) such that fundamental harmonics are oriented at different angles in k-space but maintain the same distance from the origin. (Middle) Before capture image of the quad stamped BSA-trisaccharide ligand on gold-coated substrate (3.4 to 7.3 kPa). (Lower) After capture of *Staphylococcus aureus* (10$^7$ cfu/mL) and the corresponding FFT image. Each pattern orientation can be identified by its fundamental harmonic; in some cases, the second harmonic is also visible. Note the FFT image is not square so padding the image is required for angular line profile.

To evaluate multiplex detection using up to four distinct capture patterns, we simulated linear gratings oriented along different directions arranged into to quadrants (FIG. 60). This readout strategy used the 2D aspect of the FFT spectra. This allows for the detection of multiple patterns without a concern of overlap along the 1D line profile and will allow for the multiplexing with more than 4 patterns. FIG. 60 shows the FTT simulation of a quad pattern consisting of linear gratings with the same periodicity but oriented at different angles (0°, 45°, 90°, and 135°). This arrangement takes better advantage of the two-dimensional aspect of FFT image processing rather than reducing the 2D FFT into a 1D line profile. The simultaneous detection of all four reciprocal lattice peaks is readily achieved and can be plotted as a function of angle rather than inverse distance (FIG. 60). The angle-dependent readout was then addressed experimentally by manually printing linear gratings along different directions in quad format, as simulated in FIG. 60. Each pattern was printed with 10-$\mu m$ lines and 20 $\mu m$ periodicity using the BSA-trisaccharide ligand, with stamp pressures ranging from 3.4 to 7.3 kPa. The quad pattern was then exposed to *Staphylococcus aureus* for 1 hour at $10^7$ cfu/mL. The reciprocal lattice peaks from all four quadrants could be obtained at once upon FFT analysis, confirming the results obtained by simulation. Thus, it is possible to perform multiplex detection using mutation-resistant ligands for select pathogen recognition.

The detection of a single pathogen using different periodic patterns established the possibility of detection multiple pathogens each assigned to specific patterns. The first demonstration of this was performed using *Staphylococcus aureus* and *Vibrio cholerae*. A gold-coated substrate was divided into quadrants, each with a different patterned ligand in lines with a periodicity of 20 $\mu m$, at different orientations (0°, 45°, 90°, and 135°). For *Staphylococcus aureus* capture, the patterns correspond to trisaccharide BSA-conjugate printed along the axes (0° and 90°), whereas *Vibrio cholerae* had patterns of BSA-vibriobactin printed in an orientation of 45° or 135° (similar to FIG. 60). The pathogens were mixed in the same solution at concentration of $10^7$ cfu/mL for each microbe, and the exposure time to the patterned substrate was 60 minutes. In order to confirm multiplex detection, only two sets of patterns were imaged simultaneously rather than all four at the center. FFT S/N calculations confirm simultaneous capture of both pathogens in the same imaged area.

Figure 61:
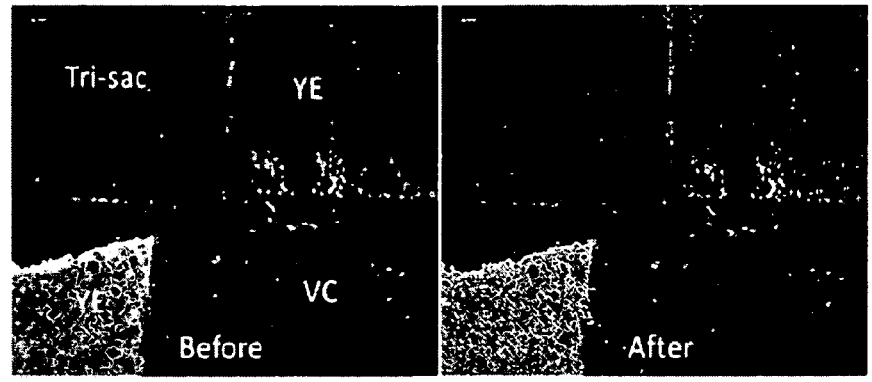
FIG. 61 shows multiplexed pathogen detection with 3 different ligands. (Left) Each quadrant contains a ligand, with the first and third quadrants presenting BSA-DFO for *Yersinia enterocolitica* capture (YE, 90° and 135° orientation, respectively), the second quadrant presenting BSA-trisaccharide for *Staphylococcus aureus* capture (Tri, 0° orientation), and fourth quadrant presenting BSA-vibriobactin for *Vibrio cholerae* capture (VC, 45° orientation). (Left) After capture of *Staphylococcus*, *Yersinia*, and *Vibrio* after 30-minutes exposure at concentrations of 10$^6$ cfu/mL for each bacteria.

To increase the multiplexing capabilities of our substrate, an additional ligand, BSA-Desferrioxamine, was patterned onto the substrate for capture of *Yersinia enterocolitica* in addition to the BSA-trisaccharide for capture of *Staphylococcus aureus*, and *Vibrio cholerae*. The quad-patterned substrate was exposed to all three pathogens at concentrations of $10^6$ cfu/mL for each microbe for 30 minutes. The printing of the ligands on the substrate can be seen in FIG. 61.

Figure 62:
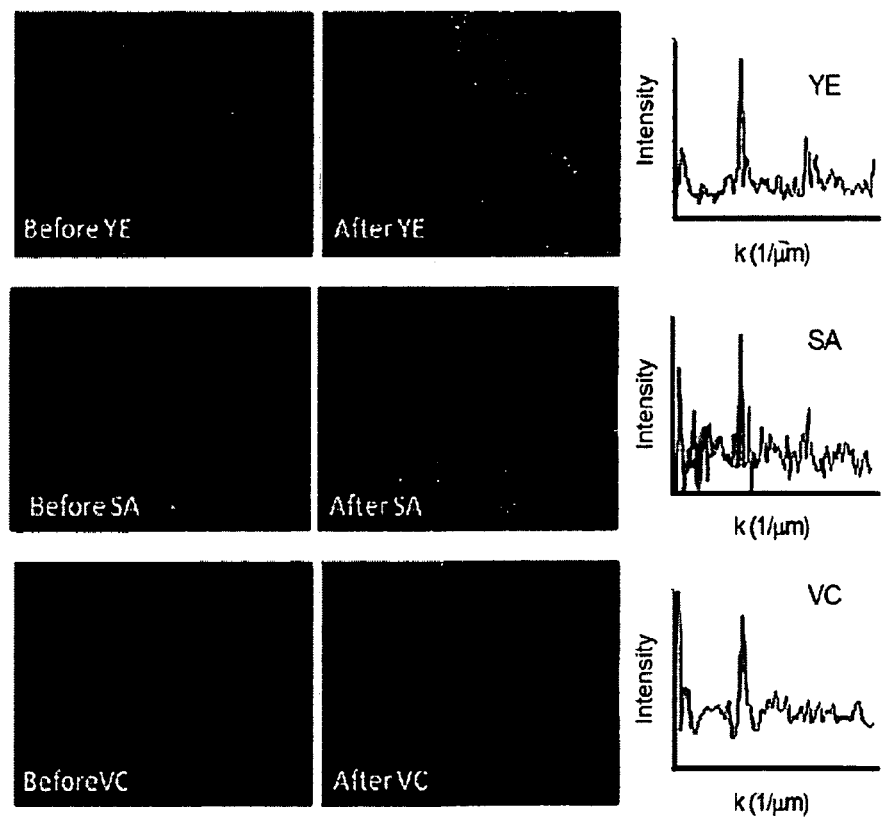
FIG. 62 shows simultaneous capture of *Staphylococcus aureus*, *Vibrio cholerae*, and *Yersinia enterocolitica* on the same chip but different ROI's. The spectra on the left are the FFT line profiles with before capture subtraction, and indicates capture of *Yersinia*, *Staphylococcus*, and *Vibrio* with S/N ratios of 12.2, 7.0, and 9.3, respectively (k=0.05 µm$^{-1}$).

The same substrate was imaged with a conventional microscope before and after pathogen exposure in regions of interest (ROD away from the center (FIG. 62). In all cases, pathogen capture could be detected. This indicates the difficulty of using manual micro-contact printing to deliver ligand patterns of adequate quality to the same ROI.

Figure 63:
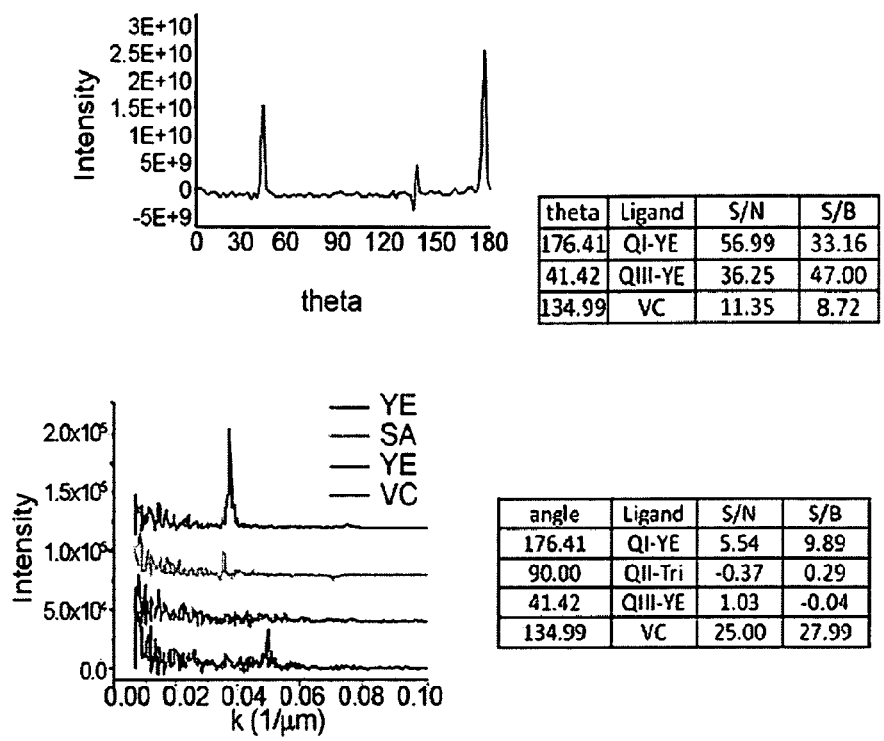
FIG. 63 shows a comparison of polar versus linear line profiles. The polar FFT output at a fixed distance from the center of the fundamental harmonic with S/N and SB for a gold-coated substrate after capture of *Staphylococcus aureus*, *Vibrio cholerae*, and *Yersinia enterocolitica* (Upper). The stacked FFT line profile spectra with S/N and SB (Lower).

Due to the exponential behavior of the FFT linear line profile and the easy of combining the FFT information into a single spectrum, an angular dependent line profile was explored in FIG. 63. When using an angular FFT spectrum, the S/N and SB ratios are higher due to the linear background behavior; the noise along the line profile is reduced.

Figure 64:
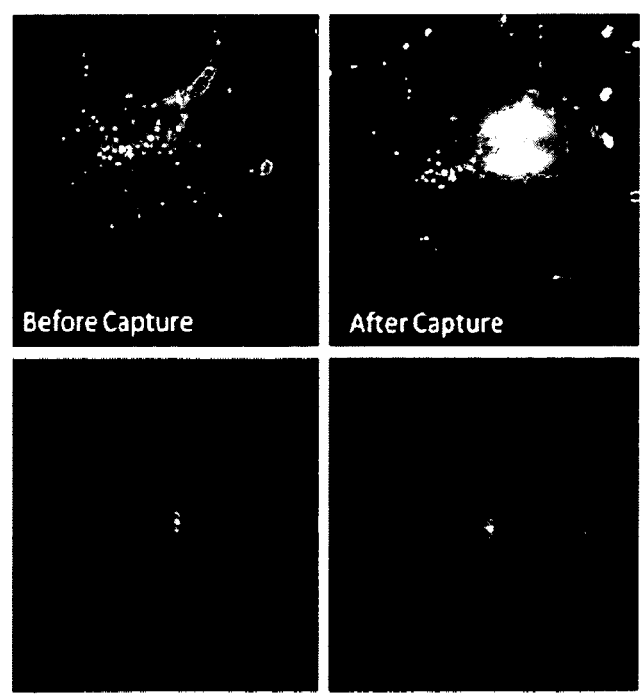
FIG. 64 shows multiplex detection of three pathogens simultaneously. The substrate is patterned with four different ligand/siderophores: salmochelin (Quadrant I), pulmonary trisaccharide (Quadrant II), aerobactin (Quadrant III), and BSA-desferrioxamine (Quadrant IV). The pattern chip was exposed to *Salmonella*, *Yersinia enterocolitica*, *Pseudomonas aeruginosa*, and *Mycobacterium smegmatis* (10$^6$ cfu/mL for each pathogen, for 30 minutes). The orientation for each ligand/siderophore is 0°, 45°, 90°, and 135° for pulmonary trisaccharide-BSA conjugate, salmochelin, aerobactin, and DFO-BSA conjugate, respectively. Raw images of before and after capture with the corresponding FFT images.
Figure 65:
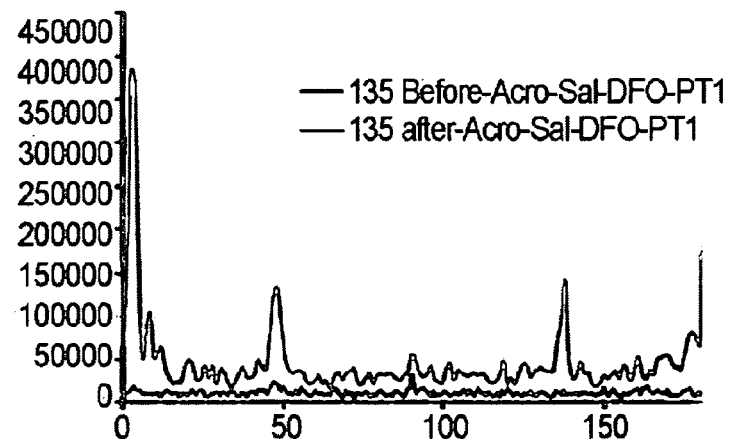
FIG. 65 shows the polar FFT spectrum of the fundamental harmonics. *Pseudomonas*, *Salmonella*, and *Yersinia* were captured but not *Mycobacterium*.

The first multiplex detection for three individual pathogens simultaneously was achieved using a quad stamp. The gold-coated substrate was patterned with four distinct ligands with imaging done at the same ROI, the center of the quad stamp containing all four patterns. FIG. 64 shows the images of a patterned substrate printed with salmochelin (Quadrant I), BSA-desferrioxamine (Quadrant IV), BSA-pulmonary trisaccharide conjugate (Quadrant II), aerobactin (Quadrant III), and BSA-desferrioxamine conjugate (Quadrant IV) before and after capture of *Salmonella, Yersinia enterocolitica, Pseudomonas aeruginosa*, and *Mycobacterium smegmatis*, respectively. The polar FFT spectrum in FIG. 65 demonstrates multiplex detection of *Pseudomonas, Salmonella*, and *Yersinia* (0°, 45°, and 135° orientations, respectively).

The lower limit of illumination intensity for dark-field scattering was established using for the PathoTest device, measured in units of kilo-foot candles (kfc), lux, and lumens with a digital light meter (Mannix DLM-1337). These values were obtained for a patterned substrate with back-side imaging (through the substrate rather than the chamber medium) under both aqueous and dry conditions, and evaluated by the peak S/N produced in the FFT spectra at the fundamental harmonic (k=0.05 Linear patterns were printed at different orientation angles (7° and 52°), and Fourier spectra were plotted as a function of angle (Table 3). For each peak, the minimum detectable S/N ratio is at 5.40 and 3.1 lumens for dry and wet samples, respectively. The noise produced under aqueous conditions is significantly higher than under dry conditions, reducing the S/N ratio. Imaging studies were also conducted in front-side imaging (dry state) and yielded peak S/N values on the order of 200, higher than that for back-side imaging under comparable lighting conditions (S/N=60 and 30 for dry and wet samples, respectively). We note that the quality of the back-side imaging mode has become compromised by the abrasions to the inner wall of the flow cell, and will require a modification in substrate holder or polishing the chamber walls. The abrasions were caused by handling the flow cell and the use of ethanol and as disinfectant. In the front-side imaging mode, we find that ambient room lighting may provide sufficient illumination for pattern detection. Lighting measurements under daylight (18 lumens in midday shade, 23.4 lumens on a cloudy late afternoon) suggests that with the proper engineering, an electrically powered light source may not be necessary.

TABLE 3

Amount of light measured by a light meter mounted on the PathoTest device in the same location as flow cell in terms of kilo-foot candles, lux, and lumens.

| | kfc | lux | lumens |
| --- | --- | --- | --- |
| No power* | 0.01 | 96.88 | 0.15 |
| Min | 0.04 | 400 | 0.65 |
| 0 | 0.04 | 400 | 0.7 |
| 1 | 0.06 | 600 | 1 |
| 2 | 0.11 | 1200 | 1.8 |
| 3 | 0.19 | 2000 | 3.1 |
| 4 | 0.33 | 3600 | 5.4 |
| 5 | 0.49 | 5300 | 8.0 |
| 6 | 0.88 | 9500 | 14 |
| 7 | 1.32 | 14200 | 21.6 |
| 8 | 2.12 | 22800 | 34.7 |
| 9 | 2.66 | 28600 | 43.5 |
| 10 | 3.58 | 38500 | 58.6 |
| 11 | 4.78 | 51500 | 78.2 |
| 12 | 5.67 | 61000 | 92.8 |
| max | 5.89 | 63400 | 96.4 |

*"No power" indicates that the light source was turned off with the number corresponding to the tick mark on the light source with min and max before or beyond any tick marks.

Figure 66:
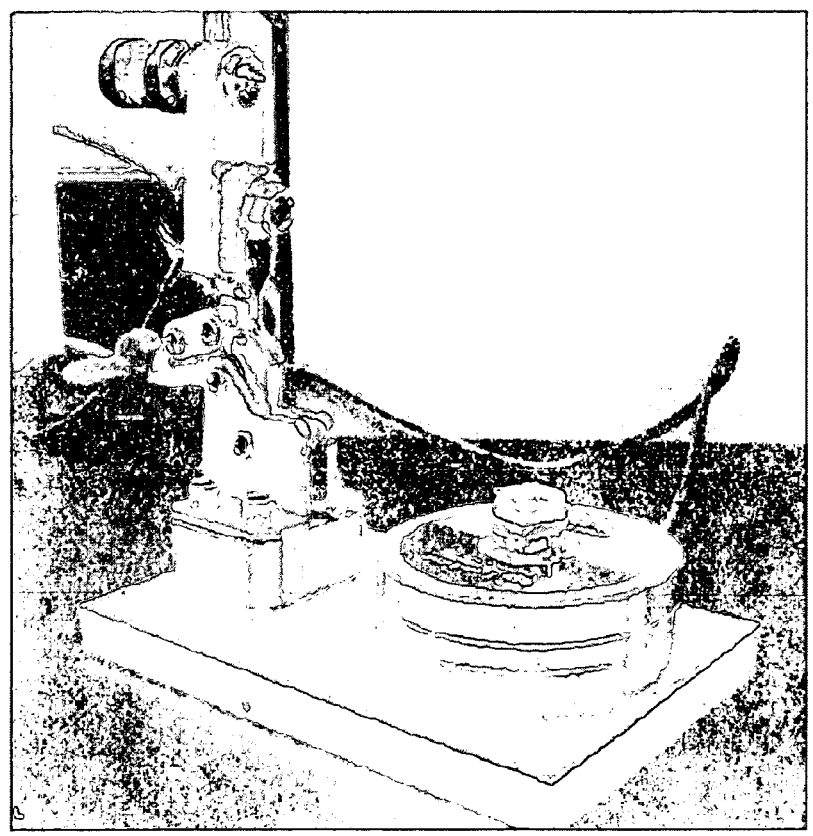
FIG. 66 shows a mechanical stamping device (PathoStamper) in the open position to allow for the loading of the substrate.
Figure 67:
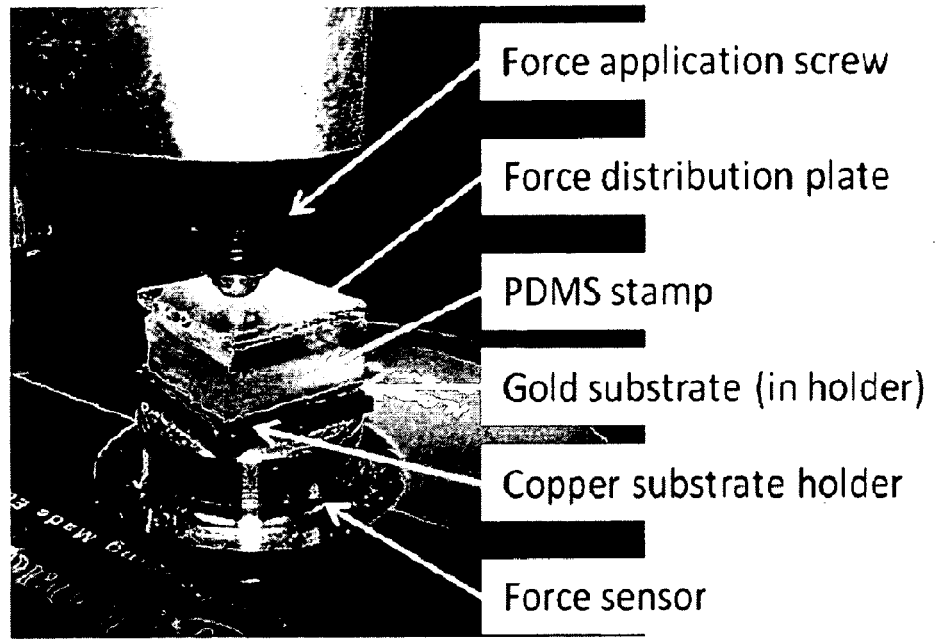
FIG. 67 shows a closeup view of a mechanical stamping device (PathoStamper) in the closed position with the force distribution plate, PDMS stamp, and the gold substrate in the substrate holder.

We have implemented a manual stamping device (PathoStamper) that can be used to measure the force applied during micro-contact printing and to distribute force evenly for reproducible patterning on a centimeter scale (FIG. 66). A top-loading sensor (LoadStar) is connected to a computer with appropriate software for recording pressure (LoadVUE). Typically, the pressure feedback is continuous and can be recorded during the entire stamping procedure. The substrate is positioned onto the sensor, followed by careful placement of the pre-inked, patterned PDMS stamp in conformal contact with the substrate, and a plate (brass or glass) for even distribution of force. The stamp head is then manually lowered and put in close proximity of the brass plate, but without applying any measurable force. Contact is made between the brass plate and a ball bearing on the stamper by turning the coarse and fine adjustment knobs clockwise (black rings in FIG. 67). The desired pressure can then be set by further tuning of these knobs. After a defined interval (typically 15-60 seconds), the PathoStamper is released to the open position and the PDMS stamp is allowed to remain in contact with substrate to ensure the transfer of capture ligand from the PDMS stamp to the substrate.

The PathoStamper enables us to record the maximum pressure applied (in kPa), and provides more reproducible results for micro-contact printing than other manual methods of applying pressure, which are nonquantitative and uneven in force distribution. These manual methods often result in overstamping, leaving a strong before capture pattern that interferes with the detection of pathogen capture. This interference is illustrated by examples of line patterns generated using manual methods (e.g., by thumb or by rolling a wooden "Q-tip" handle). Overstamping and uneven pressure causes the transfer of excess organic material (mostly BSA-ligand conjugate) that cannot be removed by simple washing methods, resulting in a high residual background pattern. In contrast, the PathoStamper minimizes the transfer of excess material, leaving a barely noticeable residue that is within acceptable S/N limits (<3).

Figure 68:
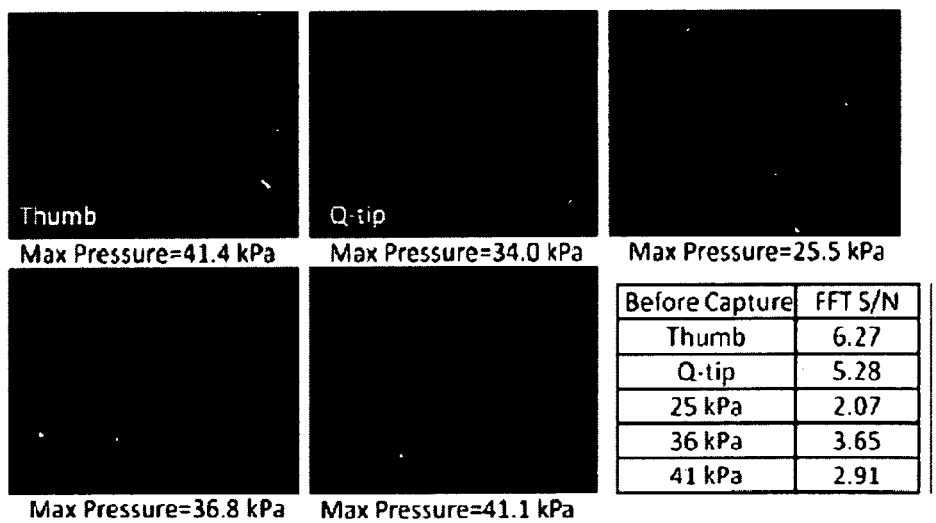
FIG. 68 shows visually and numerically (FFT Signal-to-Noise (S/N) calculations in the table), the amount of residual material does decrease as the pressure decreases. The region examined by manual FFT was 256 µm by 256 µm, at the fundamental harmonic (1/a) at 0.05 µm$^{-1}$. The first two images were produced with uncalibrated manual force (Thumb and Q-tip) with all other images, the pressure was applied with the PathoStamper. Each image had microscope settings with a phase contrast of 100, exposure time of 0.10 seconds, and a magnification of 10× with FFT S/N on a square root scale.
Figure 69:
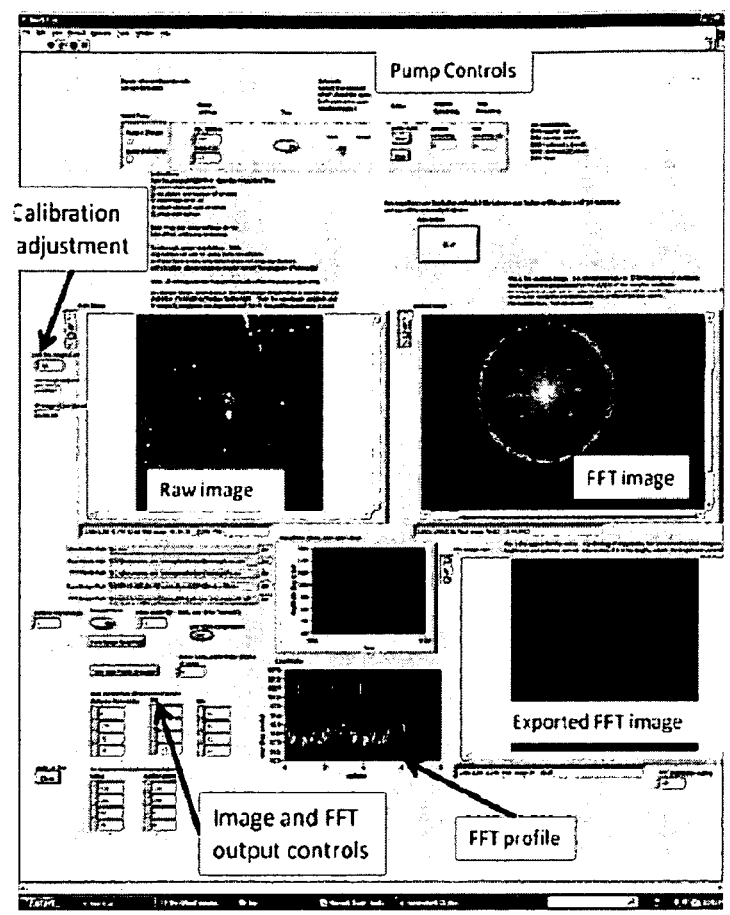
FIG. 69 shows a screen shot of the Labview user interface for the PathoTest device (version 2). The raw image now has a calibration adjustment that is calibrated against a standard of known periodicity. The FFT image can be analyzed by multiple line profiles simultaneously (lines) and/or by multiple angular profiles (circle).
Figure 70:
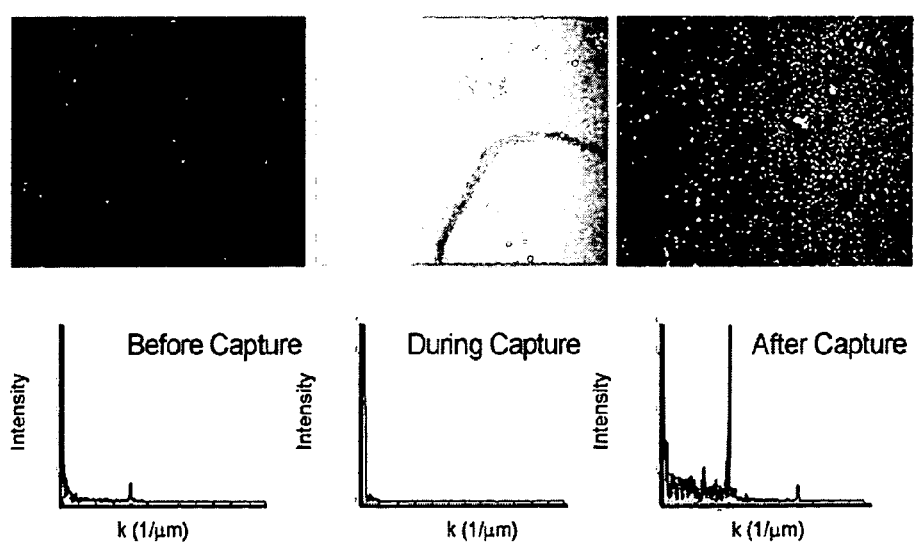
FIG. 70 shows capture of *Staphylococcus aureus* within the PathoTest Device on a gold-coated substrate patterned with the BSA-trisaccharide capture ligand (periodicity 20 µm, k=0.05 µm-1). (Left) Before capture dry, (Middle) after 30 minutes of exposure in a bacterial aqueous medium, and (Right) after capture dry images and FFT (~$10^6$ cfu/mL), 60 minutes exposure, 6.7 kPa PDMS stamp pressure) on a linear scale.
Figure 71:
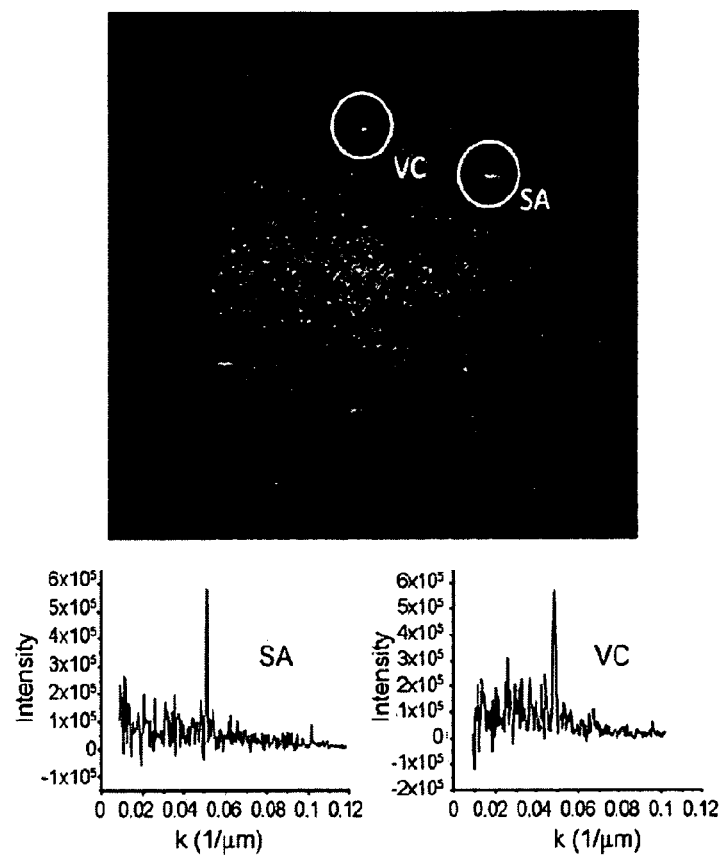
FIG. 71 shows multiplex detection *Staphylococcus aureus* and *Vibrio cholerae*. Patterns were printed manually with exposure to *Staphylococcus* and *Vibrio* simultaneously for 1 hour ($10^7$ cfu/mL per bacteria) using front-side imaging within the PathoTest Device. (Upper) FFT image after capture. (Lower) FFT spectra corresponding to *Staphylococcus* (S/N=8.5 at k=0.05 µm$^{-1}$, 45°) and *Vibrio* (S/N=12.4 at k=0.05 µm$^{-1}$, 90°).
Figure 72:
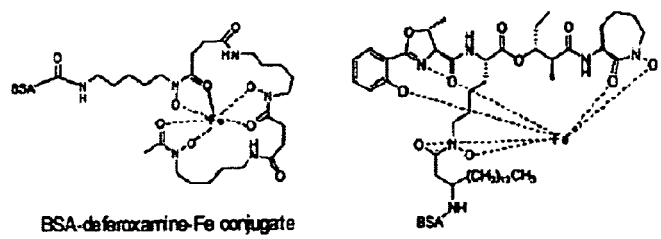
FIG. 72 shows capture ligand for our detection. (Upper Left) BSA-DFO (Upper Right) Ferric Mycobactin J and BSA.
Figure 73:
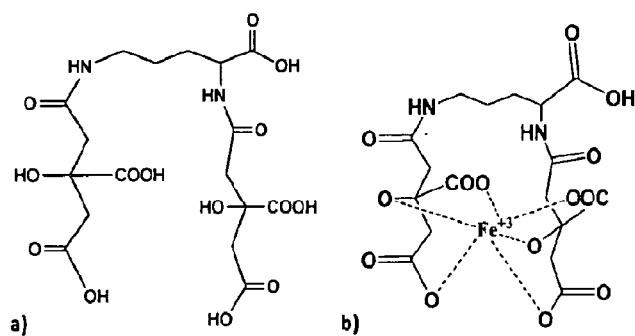
FIG. 73 shows staphyloferrin. Structure of staphyloferrin (Left) and staphyloferrin A-Fe conjugate (Right).

Patterned capture of *Staphylococcus aureus* (S.A.) may be sensitive to the washing step after capture. If washing is done too vigorously there is a good possibility that the bacteria can be washed away when using the BSA-trisaccharide ligand. When an aqueous stream is applied directly to the edge of the substrate on the patterned side, a gradient in the population of absorbed bacteria can be seen from the microscope images in FIG. 68. If the stream of water is used to rinse the entire substrate, this will result in the removal of the bacteria. To solve this problem, the water stream is exposed to the back-side of an upside down substrate so that the captured side is rinsed gently by capillary forces and gravity.

Of the three types of printing methods discussed in this chapter, ink-jet patterning may be preferred for multiplex detections. Ink-jet printing allows for the integration of spots that have different periodicities throughout the entire substrate rather than a particular quadrant. The concentration of bacterial solution (cfu/mL) is determined by plating bacteria. Counting bacteria by plating various dilution of a maximal growth solution to calculate the concentration and calibrated it to an UV absorbance measurement. This concentration is based on the assumption that for a viable bacterium in a solution, it will form a single colony on a growth plate and will result in knowing the number of colony forming units for a known volume. For *Pseudomonas*, the bacteria are grown from a source (ATCC) in a LB growth medium and stock solutions of bacteria are frozen at −80° C. ($2^{nd}$ growth) in volumes of 1 mL. The 2nd growth solutions are thawed, spread across an agar plate (15 g/L of Bacto Agar and 8 g/mL of Difco Nutrient Broth) such that there are 3 regions with differing concentrations, and allowed to incubate overnight at 37° C. The plate, full of bacteria colonies (3rd growth), is keep in a refrigerator. Whenever *Pseudomonas* is needed for capture, a LB growth solution (~4 mL clear yellow solution) is inoculated with one or two colonies from the 3rd growth plate. The inoculated growth solution is allowed to incubate overnight in a mechanical stirrer (220 rpm) until a cloudy green fluorescence solution is seen. Next the 4th growth is washed in 1× phosphate buffer saline (PBS) solution by 3 centrifugations (1 mL, 5 minutes at 6-12 thousand rpm) and re-disperse in between each centrifugation. The absorbance of the 4th growth solution is measured at λ=600 nm and typically has a maximum of 1.3. It was assumed an absorbance of 1 at λ=600 nm corresponds to a concentration of $1 \times 10^8$ cells/mL. To confirm this assumption, serially dilutions of the washed bacterial solution by factors of 10 up to an 8th dilution were grown on agar plates. Next for the each dilution (5th-8th) 25 or 50 μL of solution is spread onto the agar plate. The known volume is spread across the plate in a line from edge of the plate (not the very edge) to the center. An "L" shaped spreader (a glass stirring rod) such that the length of spreading arm is less than the diameter of the plate is dipped in ethanol (to eliminate any contamination) and flashed with a Bunsen burner. The spreader is placed on a region of the agar plate that does not contain the solution to insure that it cools before coming into contact with bacterial solution. While the spreader remains fixed, the agar plate is rotated such that the solution is spread across the entire plate. The finished plates are allowed to incubate until the formation of colonies is visible. The concentration of the undiluted solution is on the order of $10^9$ cfu/mL at an absorbance of 1 at X=600 nm and agrees with similar literature values for *Pseudomonas*. The concentration of *Staphylococcus* is on the order of $10^8$ cfu/mL.

Example 6

Label-Free Detection of a Bacterial Pathogen Using an Immobilized Siderophore, Deferoxamine Materials.

Deferoxamine (DFO) mesylate, iron (III) chloride, and bovine serum albumin (BSA) were purchased from Sigma-Aldrich (St. Louis, Mo.). PBS (pH 7.4, 1×, GIBCO), SYTO-9 and PI (propidium iodide) were obtained from Invitrogen (Carlsbad, Calif.). Gold plated glass slides were provided by Reichert Inc. (#13206060-601; Depew, N.Y.), NHS-activated glass slides were purchased from Surmodics (DN01-0025; Eden Prairie, Minn.) and Sylgard 184 polydimethylsiloxane was obtained from Ellsworth (Germantown, Wis.). Unless otherwise specified, all other chemicals were purchased from Sigma-Aldrich (St. Louis, Mo.). *Yersinia enterocolitica* (ATCC 51871), *P. aeruginosa* (ATCC 15692), *M smegmatis* (ATCC 7000084), and *Staphylococcus aureus* (ATCC 10537) were purchased from ATCC (Manassas, Va.) and *Vibrio cholerae* strain 0395 was generously donated by Dr. Shelley Payne (U. of Texas, Austin).

Preparation of BSA-Deferoxamine (DFO)-Fe Conjugate.

To a solution of deferoxamine mesylate (2.5 mg) in 200 µl $H_2O$ was added triethylamine (2 µl in 20 µl DMF) and $FeCl_3$ (0.6 mg in 20 µl $H_2O$). The solution immediately turned dark red, indicating it had formed the iron chelate termed, ferrioxamine (FOB). BSA (10 mg) was dissolved in 700 µl PBS (pH 7.4) and added to above ferrioxamine (FOB) solution. Immediately, 1-ethyl-3-(3-dimethyl-aminopropyl) carbodiimide hydrochloride (EDC.HCl, 3 mg in 50 µl $H_2O$) was added and the solution was stirred for 3 hours at room temperature. The FOB-BSA conjugates were separated from all low molecular weight material using a 10-kD molecular weight cutoff spin filter with multiple washes of PBS (Scheme 5).

Scheme 5. Preparation of BSA-Deferoxamine(DFO)-Fe conjugate (FOB-BSA)

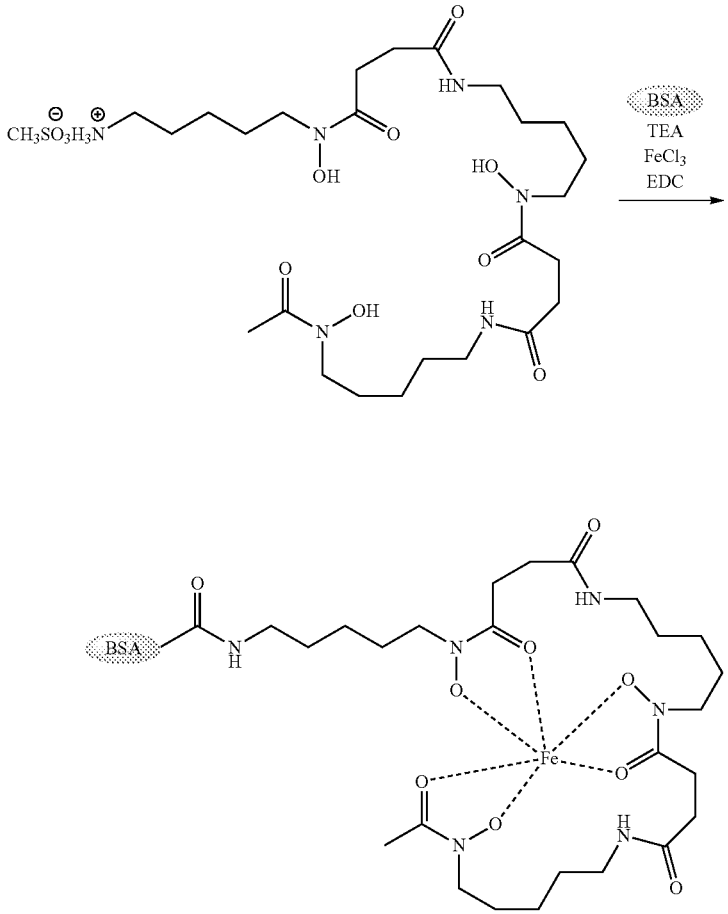

Microcontact Printing of FOB-BSA onto Gold-Plated Chips.

FOB-BSA (2.5 mg/mL in PBS, pH 7.4) solution was applied with a Q-tip cotton swab onto a PDMS stamp pad characterized by parallel 20 µm wide bands separated by 20 µm wide gaps. After allowing the FOB-BSA solution to adsorb for 2 minutes, excess solution was removed by drying the stamp under a gentle stream of nitrogen gas. The stamp was brought into contact with a gold-plated glass chip (cleaned first with ethanol and then nanopure water, followed by argon drying) and gently pressed to assure good contact. After 10 minutes, the stamp was removed and the printed gold chip was placed in a refrigerator to facilitate maximal bonding. After 2 hours, the chip was removed, rinsed with PBS and nanopure water, allowed to dry, and stored in a sterile chamber until use.

Growth of *Y. enterocolitica*.

*Y. enterocolitica* was grown in 10 ml of iron-poor LB media (Tryptone 10 g, yeast extract 5 g/L, and NaCl 5 g/L, pH 7.5, supplemented with 40 µl of 20 mM 2,2'-bipyridyl) for 24 hours at 35° C. with shaking.

Quantification of *Y. enterocolitica*.

The concentration of *Y. enterocolitica* (cfu/ml) was determined by plating various dilutions of the bacteria and counting viable colonies. Briefly, the bacteria were grown as described above and then washed in phosphate buffered saline (PBS, 1 ml) up to 4 times by centrifugation followed each time by resuspension in buffer. Serial ten-fold dilutions of the washed bacteria were prepared and 25-100 µL of each suspension was spread on an agar plate (15 g of Difco Agar and 8 g of Difco Nutrient Broth per 1 L of water). Plates were allowed to incubate until colonies could be readily observed and counted.

Exposure of *Y. enterocolitica* to Micro Patterned Chips.

Micro-patterned gold chips were immersed in various concentrations of bacteria ($10^8$-$10^2$ cfu/ml) for one hour and then rinsed with PBS and nanopure water. The chips were then dried with nitrogen and examined by diffractometry, as described previously.

Example 7

Capture and Identification of Pathogenic *Staphylococcus aureus* Using the Immobilized Siderophore, Staphyloferrin A Preparation of T-Medium.

T-medium was prepared by mixing the NaCl (5.8 g), KCl (3.7 g), $CaCl_2$ (0.113 g or 0.15 g of $CaCl_2.2H_2O$), $NH_4Cl$ (1.1 g), $KH_2PO_4$ (0.272 g), $Na_2SO_4$ (0.142 g) and tris base (12.1 g) in a final volume of 1000 ml in nanopure water. pH of the solution was adjusted to within 1 pH unit of 7.4 with concentrated HCl (because salts were not going into the solution until the pH is close to physiological pH) under stirring condition. Once all the salts were in solution, final pH was adjusted to 7.4. This solution was autoclaved and dispensed in 200 ml aliquots and medium was stored at room temperature Culture of *S. aureus* in Low Iron Medium.

*S. aureus* was grown in low iron medium by culturing the bacteria in a mixture of T-medium and LB medium. This culturing in low iron induces upregulation of the pathogen's iron uptake system, similar to its upregulation in human hosts. Ratio of T-medium: LB medium was in the range of 4:1 to 3:1 and incubation time was 20 to 24 hours at 35° C. with shaking.

Preparation of Bovine Serum Albumin (BSA)-Staphyloferrin A-Fe Conjugate.

To a solution of staphyloferrin A (1.5 mg; synthesized in a 4 step synthesis) dissolved in 50 µL $H_2O$ was added $FeCl_3$ (1.25 mg in 50 µL $H_2O$) and the solution was stirred for 1 hour. Then stirring solution was treated with EDC (1.5 mg in 50 µL PBS) and stirred again for 1 hour at room temperature. To this stirring solution BSA solution (5 mg in 1004 PBS) was added and mixture was stirred at room temperature. After 4 hours the mixture was passed through the 0.45 µm filter. Filtrate was used as ink for PDMS stamp for the detection of *S. aureus*.

Microcontact Printing of BSA-Staphyloferrin A-Fe Conjugate.

The above prepared BSA-staphyloferrin A-Fe conjugate solution (hereafter referred to as staphyloferrin ink) was applied onto the PDMS stamp surface (~20 mm patterns) and left to stand for 2 minutes. Excess solution was removed by drying the stamp under a gentle stream of nitrogen. The stamp was brought into contact with a gold chip (prior to use it was washed with piranha solution, nanopure water, ethanol, followed by nitrogen drying) and gently pressed to make good contact between both surfaces. The stamp was removed after ~8 minutes, and then stored in refrigerator under a sterile petri-dish for overnight. Then gold chip was removed from the refrigerator and blocked with BSA solution (5 wt % BSA in PBS) for 5 to 10 minutes, followed by washing with PBS and nanopure water to remove any unbound ligands.

Exposure of *S. aureus* to (BSA)-Staphyloferrin A-Fe Micropatterns.

The bacterial culture (1 mL) was washed twice with PBS solution (pH 7.4; 1 mL) and *S. aureus* solution was diluted to concentration of $10^7$ particles/mL. Then this bacterial solution was transferred onto the gold chip containing staphyloferrin ink micropatterns. After 1.5 hours exposure to the gold chip, the chip was washed with PBS and nanopure water and dried with nitrogen.

Detection of Bacteria by Microscope.

Quasi-dark field images for bacteria detection were obtained using a Olympus transmitted light microscope (Olympus BH-2) connected to a CCD camera (Olympus DP70) using magnification of 10×, phase contrast (100), light exposure time 0.2 seconds and light intensity (6) in the presence of yellow filter.

Example 8

Selective Capture and Identification of Pathogenic *Vibrio cholerae* Using the Immobilized Siderophore, Vibriobactin Culture of *V. Cholerae* in Low Iron Medium.

*V. Cholera* was grown in a low iron medium by using a mixture of and LB medium. Ratio of T-medium & LB medium was in the range of 3:1 to 2:1 respectively and incubation time was 20 to 24 hours at 35° C. with shaking. [T-medium was prepared by mixing the NaCl (5.8 g), KCl (3.7 g), $CaCl_2$ (0.113 g or 0.15 g of $CaCl_2.2H_2O$), $NH_4Cl$ (1.1 g), KH$_2$PO$_4$ (0.272 g), Na$_2$SO$_4$ (0.142 g) and tris base (12.1 g) in a final volume of 1000 ml in nanopure water. pH of the solution was adjusted to within 1 pH unit of 7.4 with concentrated HCl (because salts were not going into the solution until the pH is close to physiological pH) under stirring conditions. Once all the salts were in solution, final pH was adjusted to 7.4. This solution was autoclaved and dispensed in 200 ml aliquots and medium was stored at room temperature].

Preparation of Bovine Serum Albumin (BSA)-Vibriobactin-Fe Conjugate.

BSA-Vibriobactin-Fe conjugate (hereafter referred to as vibriobactin ink) was prepared by the activation of BSA (5 mg) in PBS (100 µL) with EDC solution (1.5 mg) in PBS (50 µL) for 1 hour at room temperature. To this stirring solution was added the solution of vibriobactin-Fe conjugate (1.5 mg) in PBS (100 µL) and the mixture was stirred at room temperature. After 4 hours, the mixture was passed through the 0.45 µm filter. Filtrate was used as ink for PDMS stamp for the detection of V. cholerae.

Microcontact printing of Vibriobactin Ink.

The above prepared vibriobactin ink was applied onto the PDMS stamp surface (patterned with ~10-20 µm parallel bands separated by ~10-20 µm empty spaces) and left to stand for 2 minutes. Excess solution was removed by drying the stamp under a gentle stream of nitrogen. Then stamp was carefully and gently pressed onto a gold chip using approximately 100-150 gram pressure. Prior to use, the gold chip was washed with Piranha solution first and then nanopure water and ethanol followed by nitrogen drying. The stamp was removed after ~0.8 minutes, and then stored in a refrigerator under sterile conditions overnight. After that, gold chip was blocked with BSA solution (5 wt % in PBS) for 5 minutes followed by washing with PBS and nanopure water to remove any unbound ligands or BSA.

Exposure of V. Cholerae to Vibriobactin ink Micropatterns.

The bacterial culture (1.0 mL) was washed twice with PBS solution (pH 7.4). V. cholerae in fresh PBS was diluted to various concentrations ($10^8$-$10^4$ particles/mL), each bacterial solution was transferred onto the gold chip containing vibriobactin ink micropatterns, and incubated for 30 minutes to 2 hours. Finally, the chip containing the captured V. cholerae was washed with PBS solution and nanopure water and dried under a gentle stream of nitrogen.

Detection of Bacteria by Microscope.

Quasi-dark field images for bacteria detection were obtained using a Olympus transmitted light microscope (Olympus BH-2) connected to a CCD camera (Olympus DP70) using magnification of 10×, phase contrast (100), light exposure time (0.2 to 1 second) and light intensity (6) in the presence of yellow filter.

Example 9

Capture and Identification of Pathogenic Influenza Virus (H1N1, H3N1, H5N1) Using Neuraminidase Inhibitors (Oseltamivir-PEG-Amine, Oseltamivir-PEG-Succinyl-Diaminopropionyl-Asp-Cys-Conjugates)

Synthesis of Oseltamivir-16 Atoms PEG-Spacer (Scheme 6).

A stirred solution of oseltamivir phosphonate 100 mg, in 50 mL DCM was treated with 50 mL water, Na$_2$CO$_3$ (60 mg). The white solution was stirred over a period of 45 minutes at room temperature. The combined aqueous and organic layers were extracted with dichloro methane (100 mL) and the organic phase was dried over Na$_2$SO$_4$ and the combined organic phase was evaporated in a rotary evaporator to yield the product oseltamivir as a liquid. This oseltamivir was used without further purification in the next step. Oseltamivir amine was coupled with Fmoc-PEG-acid (16 atoms) in the presence of EDC, HOBt and DIPEA in DCM. The solution was stirred over a period of 16 h at room temperature. The crude product was purified by silica column chromatography using a 8:2 mixture of DCM and hexane. The combined fractions were evaporated and dried on a rotary evaporator to obtain the product as a yellow oil. A solution of 20% piperidine in dichloromethane was added to the above a yellow oil and stirred for 30 min. The crude product was purified by preparative RP-HPLC using aqueous CH$_3$CN, then freeze-dried to yield the desired compound as a pale yellow resin.

Scheme 6. Synthesis of oseltamivir-16 atoms PEG-Spacer.

-continued
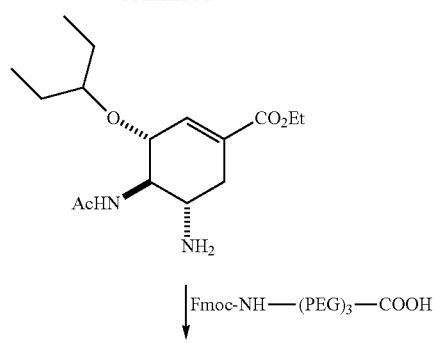
Fmoc-NH—(PEG)₃—COOH
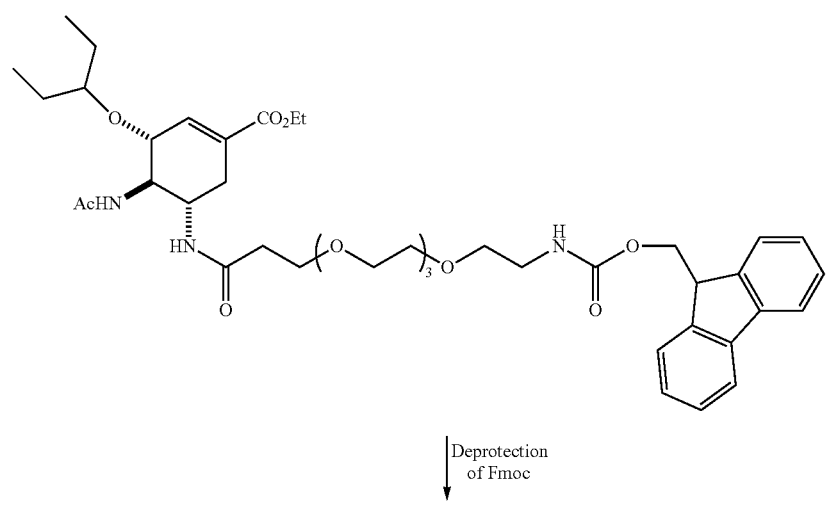
Deprotection of Fmoc
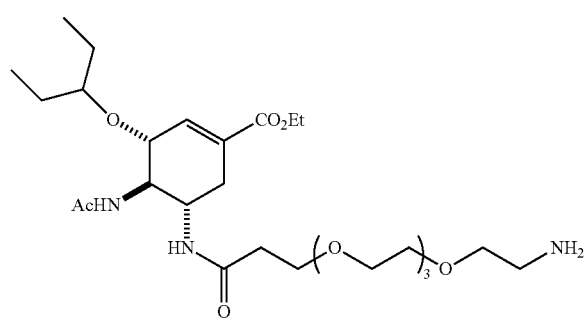

Synthesis of Oseltamivir-PEG-Conjugates with Different PEG Spacer Lengths (Scheme 7).

PEG conjugates of oseltamivir were also synthesized as described above with PEG spacers of 6, 20, and 88 atom spacers. These constructs were also characterized and shown to have the predicted structures.

Synthesis of Oseltamivir-16 Atoms PEG-FITC Conjugate (Scheme 8).

A stirred solution of oseltamivir phosphonate (100 mg) in 50 mL DCM was treated with 50 ml aqueous $Na_2CO_3$ (60 mg). The white solution was stirred over a period of 45 minutes at room temperature. The combined aqueous and organic layers were extracted with dichloromethane (100 mL) and the organic phase was dried over $Na_2SO_4$. The combined organic phases were evaporated in a rotary evaporator to yield the product oseltamivir as a liquid, which was used without further purification in the next step. Oseltamivir amine was Scheme 7. Synthesis of oseltamivir-PEG-conjugates with different PEG spacer lengths.

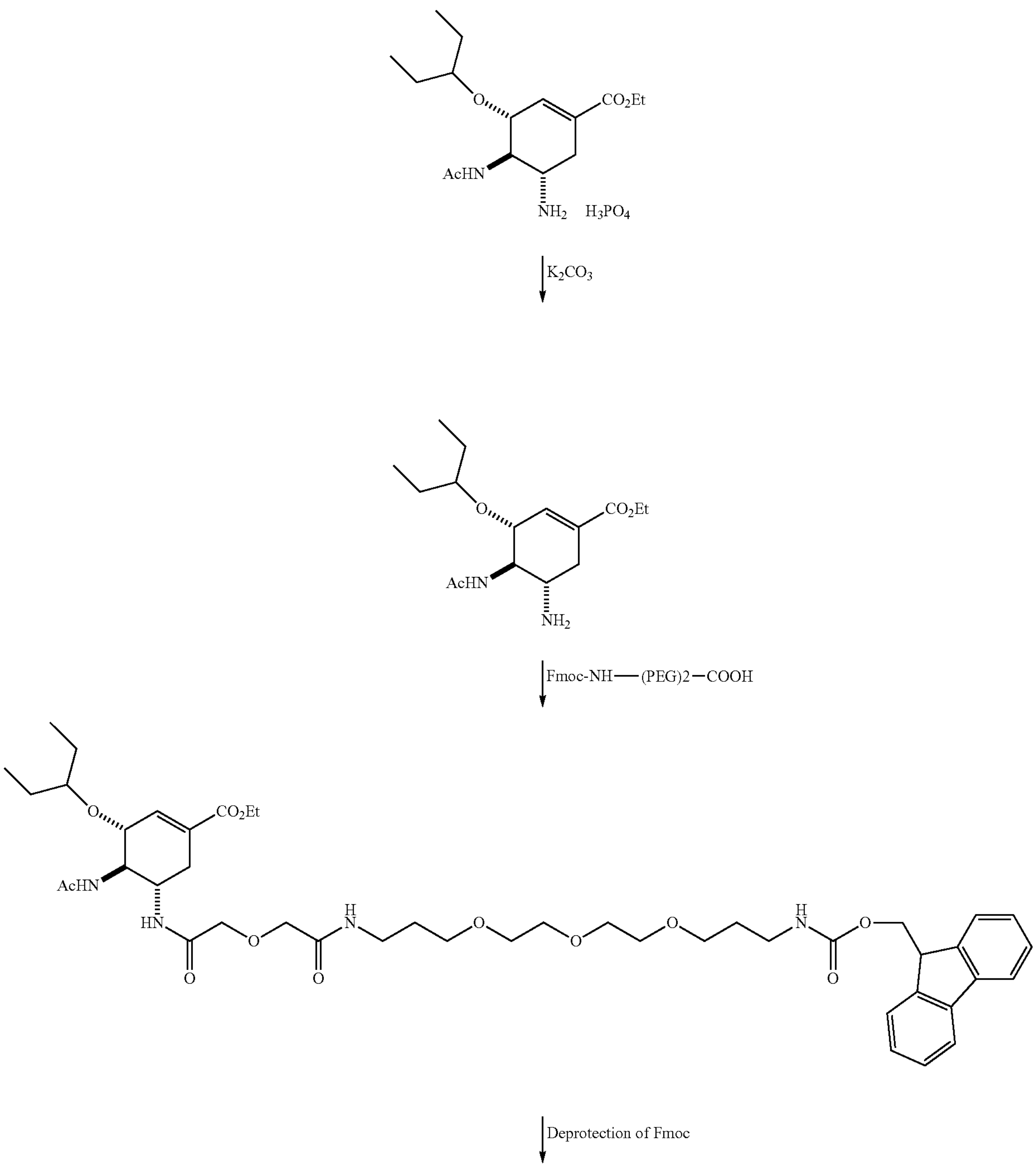

-continued
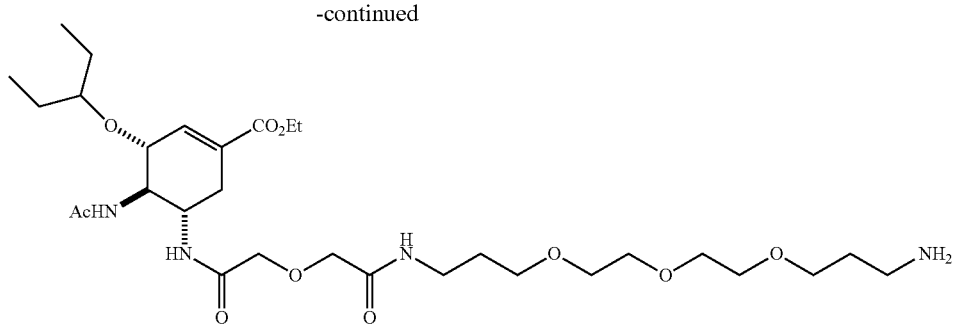
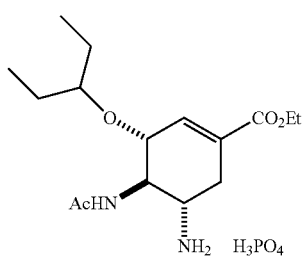
↓ K₂CO₃
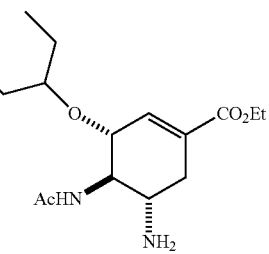
↓ Fmoc-NH—(PEG)₂₇—COOH
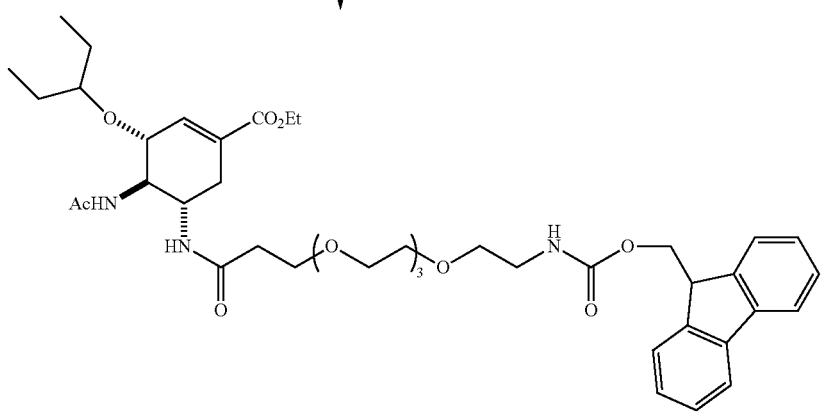
↓ Deprotection of Fmoc

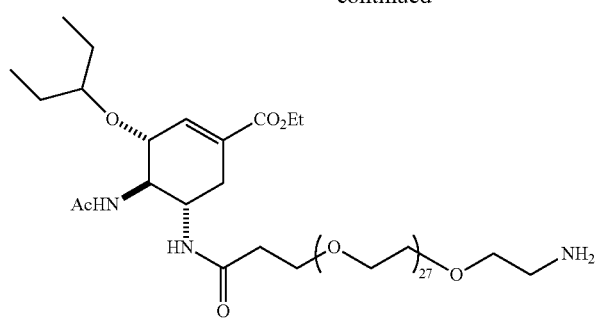
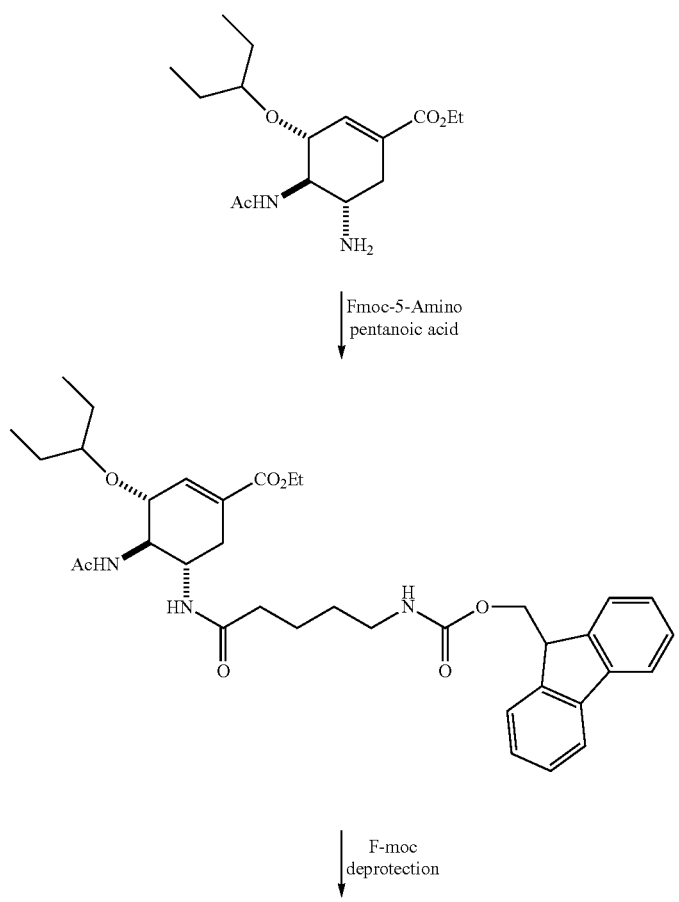
Fmoc-5-Amino pentanoic acid
F-moc deprotection
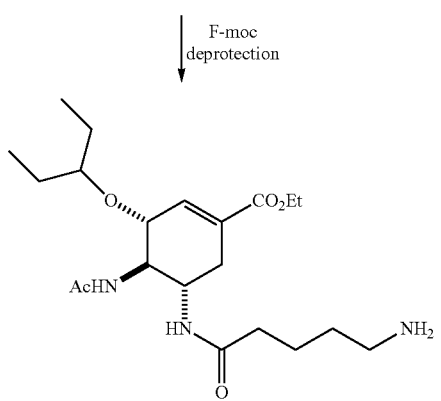

coupled with Fmoc-PEG-acid (16 PEG atoms) using EDC, HOBt and DIPEA in DCM. The solution was stirred over a period of 16 hours at room temperature. The crude product was purified by silica column chromatography using a 8:2 mixture of DCM and hexane. The combined fractions were evaporated and dried on a rotary evaporator to obtain the product as a yellow oil. A solution of 20% piperidine in dichloromethane was added to the above yellow oil and stirred for 30 minutes. The crude product was purified by preparative RP-HPLC using aqueous $CH_3CN$, then freeze-dried to yield the desired compound as a pale yellow liquid. oseltamivir-PEG (16)-amine was reacted with fluorescein-5-isothiocyanate and DIPEA in DMF. The solution was stirred over a period of 24 hours at room temperature and concentrated under vacuum. The crude product was purified by preparative RP-HPLC using aqueous $CH_3CN$. Acetonitrile was removed under vacuum, and pure fractions were freeze-dried to yield oseltamivir-16 atoms PEG-FITC as a brownish-orange solid.

Synthesis of Other Oseltamivir-PEG-FITC Conjugates (Scheme 9).

oseltamivir-PEG-FITC conjugates with PEG spacers of other lengths (0 and 20 atoms) were similarly synthesized and characterized.

Scheme 8. Synthesis of oseltamivir-16 atom PEG-FITC conjugate.

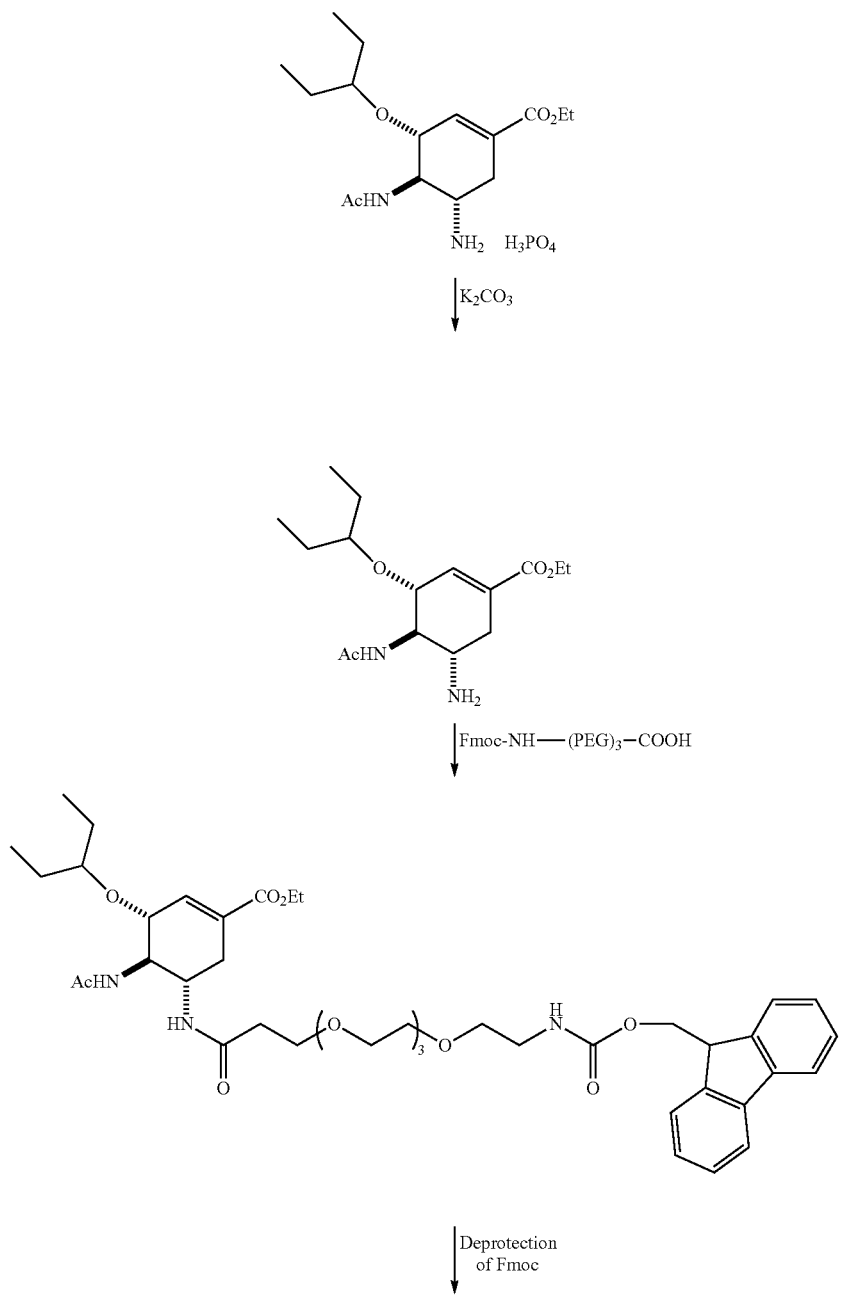

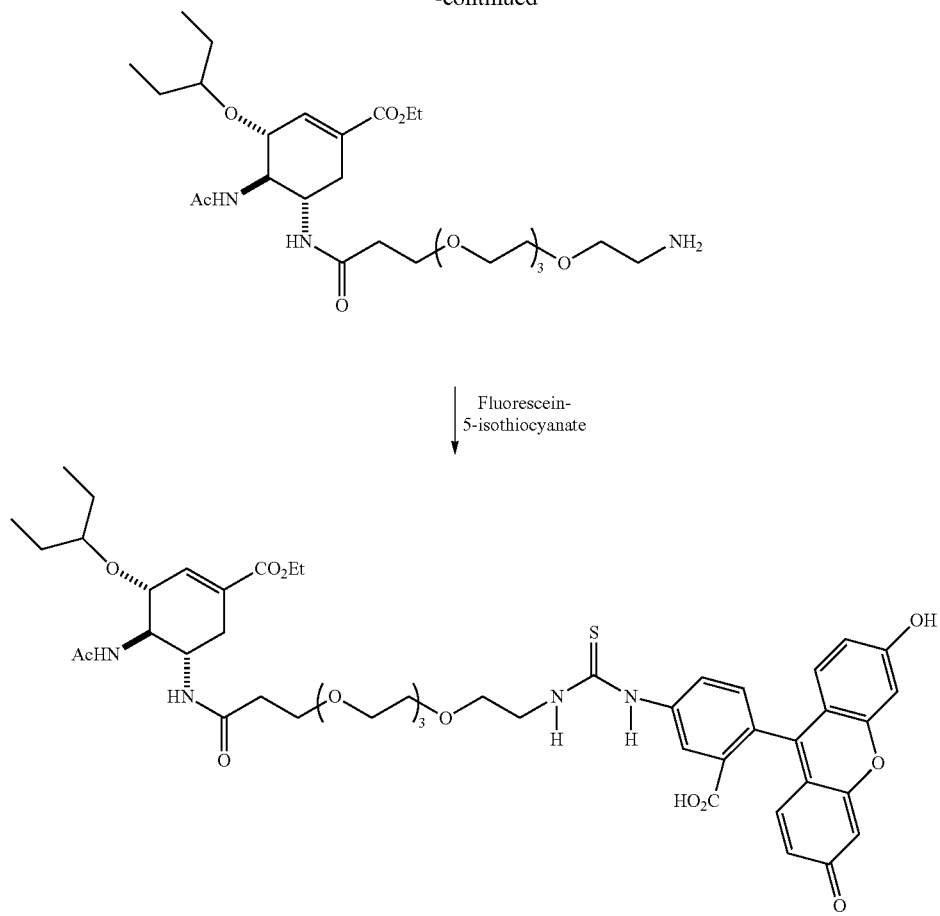
Scheme 9. Synthesis of other oseltamivir-PEG-FITC conjugates.
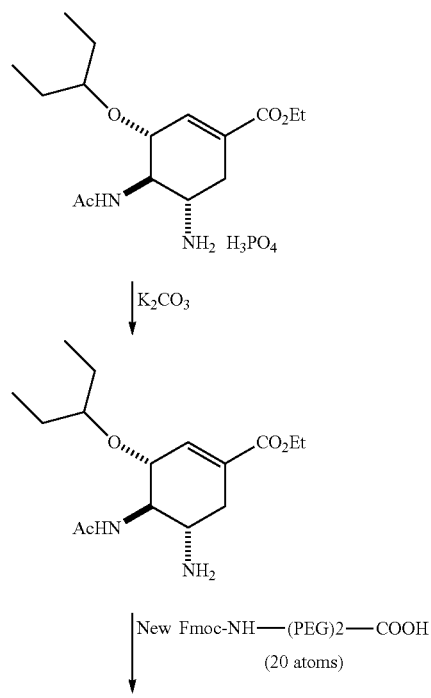

-continued
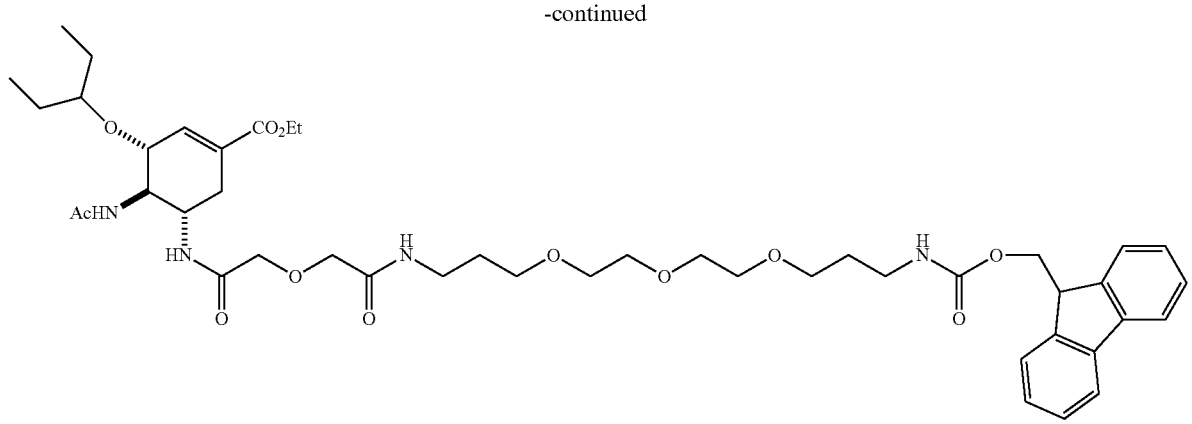
Deprotection of Fmoc
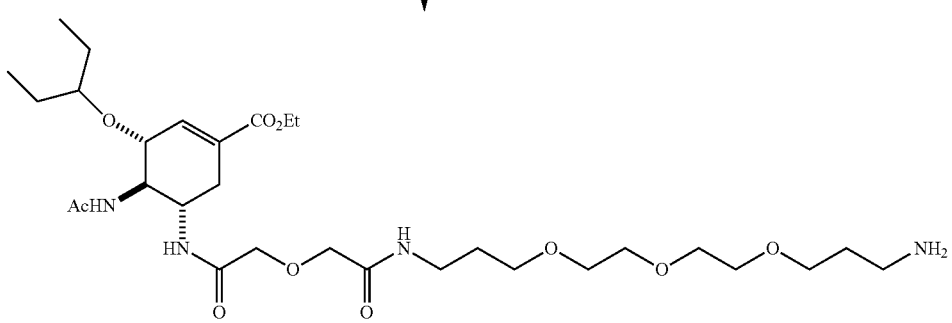
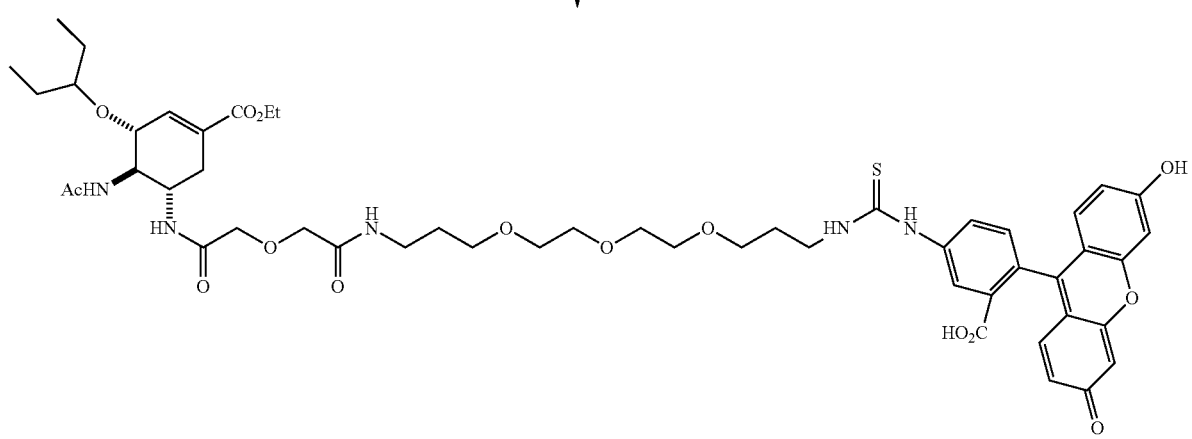
K₂CO₃

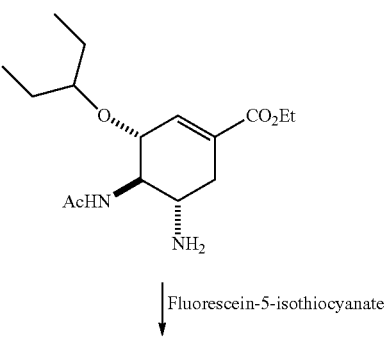

Fluorescein-5-isothiocyanate

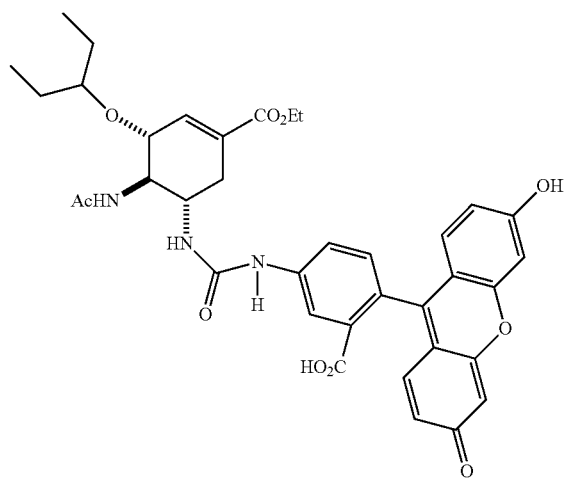

Synthesis of Oseltamivir-Fluorescein-5-Maleimide (Scheme 10).

A stirred solution of oseltamivir phosphonate 100 mg, in 50 mL DCM was treated with 50 mL aqueous $Na_2CO_3$ (50 mg). The white solution was stirred over a period of 45 minutes at room temperature. The combined aqueous and organic layers were extracted with dichloromethane (100 mL) and the organic phase was dried over $Na_2SO_4$. The combined organic phases were evaporated in a rotary evaporator to yield the product oseltamivir as a liquid, which was used without further purification in the next step. Oseltamivir was reacted with ethylene sulphide in dichloromethane in a sealed tube and heated at 65 degrees centigrade for 6 hours. The reaction was then cooled to room temperature and evaporated in a rotary evaporator to yield the product, which was purified by silica column chromatography (hexane/dichloro methane 20:80 ratio). Ethylene sulphide derivative of oseltamivir and fluorescein-5-maleimide was added to 5 mL of DMF. The reaction mixture was stirred for 24 hours at room temperature and concentrated under vacuum. The crude product was purified by preparative RP-HPLC using aqueous $CH_3CN$. Acetonitrile was removed under vacuum, and pure fractions were freeze-dried to yield oseltamivir-alkyl-fluorescein-5-maleimide as an orange solid.

Scheme 10. Synthesis of Oseltamivir-Fluorescein-5-maleimide.

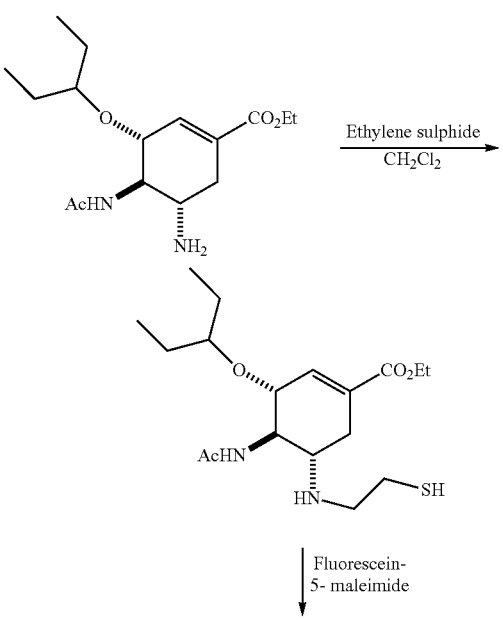

Synthesis of an Oseltamivir-PEG-Succinyl-Diaminopropionyl-Asp-Cys-Conjugate (Scheme 11).

An oseltamivir-PEG-Succinyl-Diaminopropionyl-Asp-Cys-conjugate (a novel water soluble neuraminidase inhibitor for the detection of influenza viruses) has been synthesized for direct attachment to inorganic surfaces. This conjugate was prepared from Fmoc-Cys(4-methoxytrityl)-Wang resin, swollen with $CH_2Cl_2$ followed by DMF. A solution of 20% piperidine in DMF was added to the resin, and argon was bubbled for 5 minutes. The resin was washed with DMF and isopropyl alcohol. Formation of free amine was assessed by the Kaiser test. After swelling the resin in DMF, a solution of Fmoc-Asp-(OtBu)-OH, DAPA-OH, succinic anhydride, oseltamivir-PEG-amine, and HBTU, HOBt plus DIPEA in DMF was added. Argon was bubbled for 2 hours, and resin was washed with DMF and i-PrOH. The coupling efficiency was assessed by the Kaiser Test. The above sequence was repeated for the 4 required sequential coupling steps. The final compound was cleaved from the resin using a TFA/$H_2$O/iPr3SiH/ethanedithiol cocktail (37:1:1:1) and concentrated under vacuum. The concentrated product was precipitated in diethyl ether and dried under vacuum. The crude product was purified by preparative RP-HPLC using aqueous $CH_3CN$ and then freeze-dried to yield the desired compound as a white solid.

Scheme 11. Synthesis of a oseltamivir-PEG-Succinyl-Diaminopropionyl-Asp-Cys-conjugate.

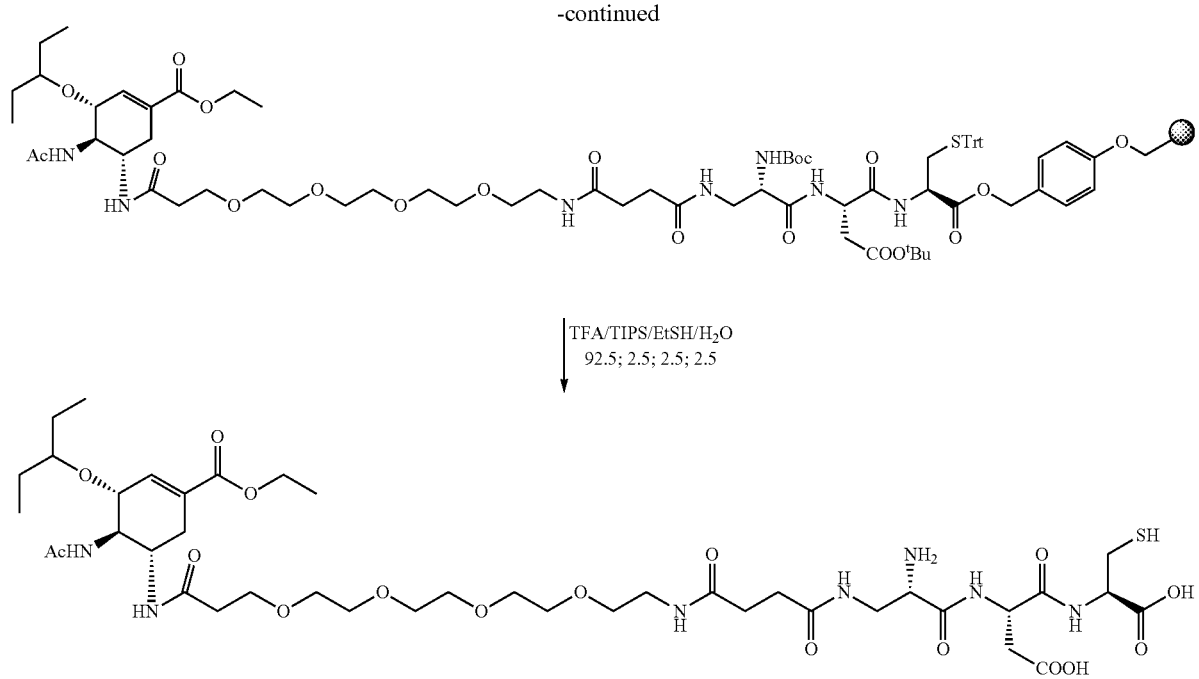

Preparation of Oseltamivir-PEG-NH-Bovine Serum Albumin (BSA) (Scheme 12).

To a solution of oseltamivir-PEG-NH$_2$ conjugate (2.5 mg) in 30 microliters DMSO was added BSA (10 mg) dissolved in 350 microliters PBS (pH 7.4) containing EDC (3 mg) and the solution was stirred for 3 hours at room temperature. The oseltamivir-PEG-NH-BSA conjugate was separated from all low molecular weight materials with a 10-kD molecular weight cutoff spin filter with multiple washes of PBS per the manufacture's instructions.

Scheme 12. Preparation of oseltamivir-PEG-NH-Bovine serum albumin (BSA).

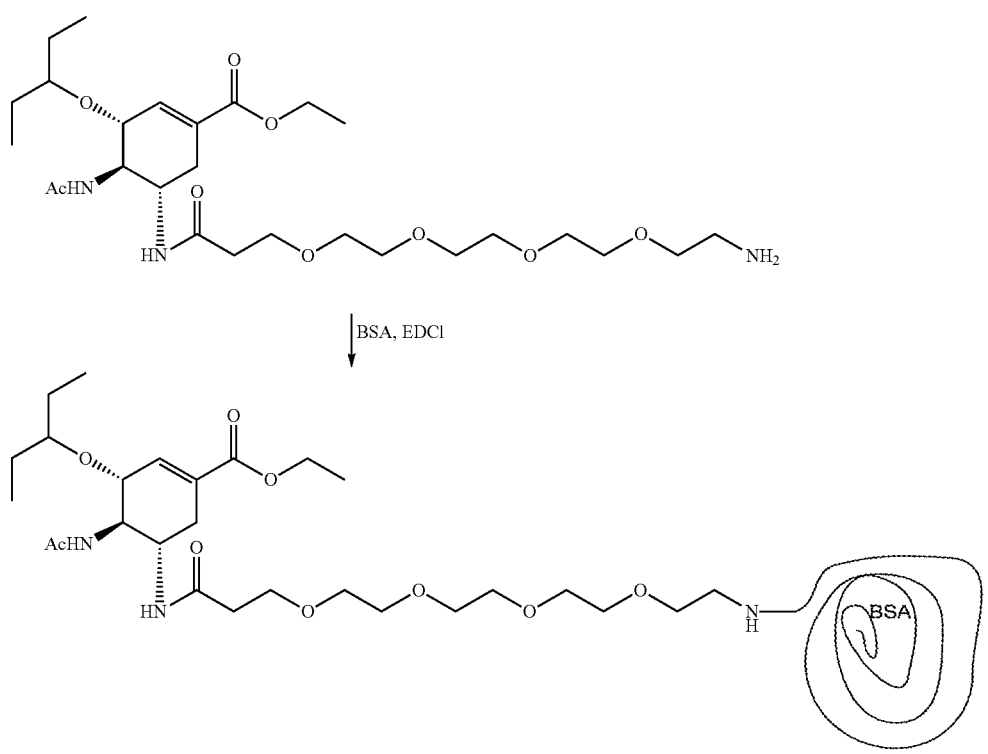

Microcontact Printing of Oseltamivir-PEG-NH-BSA.

The oseltamivir-PEG-NH-BSA (2.5 mg in PBS, pH 7.4) solution was applied onto the PDMS stamp surface (15~20 mm banded pattern) with a Q-tip cotton swab and left to stand for 2 minutes. Excess solution was removed by drying the stamp under a gentle stream of nitrogen gas. The stamp was brought into contact with a gold coated glass chip (washed with ethanol and nanopure water, followed by nitrogen drying) and gently pressed to make a good contact between both surfaces. The stamp was removed after 5-10 minutes, and then stored in a refrigerator in a sterile petri-dish overnight.

Preparation of Oseltamivir-PEG-Succinyl-Diaminopropionyl-Asp-Cys-Bovine Serum Albumin (BSA) Conjugate (Scheme 13).

To a solution of oseltamivir-PEG-Succinyl-Diaminopropionyl-Asp-Cys-conjugate (2.5 mg), BSA (10 mg) dissolved in 350 microliters PBS (pH 7.4) containing EDC (3 mg) was added and the solution was stirred for 3 hours at room temperature. The oseltamivir-PEG-Succinyl-Diaminopropionyl-Asp-Cys-Bovine serum albumin (BSA) conjugate was separated from all low molecular weight materials with a 10-kD molecular weight cutoff spin filter with multiple washes of PBS per the manufacturer's instructions.

Scheme 13. Synthesis of oseltamivir-PEG-Succinyl-Diaminopropionyl-Asp-Cys-BSA conjugate.

The gold coated glass chip was then protected against non-specific binding by blocking empty sites with BSA (1 wt % in PBS) for 2 minutes, followed by rinsing with PBS and nanopure water to remove any unbound ligands.

Exposure of Influenza Virus to Oseltamivir-NH-BSA Micropatterns.

The desired viral culture (1 mL) was washed in phosphate buffered saline (PBS, pH 7.4) by up to 4 centrifugation (each 1 mL) and resuspended in between each centrifugation in fresh PBS diluted to various concentrations ($10^6$-$10^3$ particles/ml). Each viral solution was then transferred onto the gold-coated glass chip containing oseltamivir-PEG-amine-BSA micropatterns, and incubated for 15 minutes-1 hour. At the end of this period, the chip was rinsed with PBS and nanopure water and dried with nitrogen.

Synthesis of 1-Azido-3-Pentanol (31) (Scheme 14)

A solution of methyl-3-oxo-pentanoate (31) (20 g) noyori hydrogenation with $RuCl_2$ [(S)-BINAP] (60 mg), in methanol was added. The flask was charged with hydrogen gas (5 atm) at 100° C. The resulting suspension was vigorously stirred for 48 hours. The reaction mixture was diluted with methanol and the combined organic layers were filtered through a Celite pad. The combined organic phases were evaporated in a rotary evaporator to yield the product (S) isomer of methyl-3-hydroxy-pentanoate (32). The methyl-3-hydroxy-pentanoate (secondary alcohol-32) was protected with TBDM-SCl in the presence of imidazole in dichloro methane. The reaction mixture was stirred for 24 hours at room temperature. This reaction was quenched with aqueous saturated sodium bicarbonate and extracted with dichloro methane.

The combined organic phases were dried over $Na_2SO_4$ and the combined organic phases were evaporated in a rotary evaporator to yield the TBS protected product (33). A stirred solution of ester was reduced with di-isobutyl aluminum hydride in dichloro methane at −78° C. for 5 hours. This reaction mixture was quenched with saturated aqueous sodium potassium tartarate. The combined organic and aqueous layers were filtered and organic layer was separated by separating funnel. The aqueous layer was extracted with dichloro methane. The combined organic phases were dried over $Na_2SO_4$ and the combined organic phases were evaporated in a rotary evaporator to yield the product primary alcohol (34) as a pale yellow liquid. The primary alcohol was protected with methane sulfonyl chloride in the presence of TEA in dichloromethane. The reaction mixture was stirred for 4 hours at 0° C. This reaction was quenched with aqueous saturated sodium bicarbonate and extracted with dichloro methane. The combined organic phases were dried over $Na_2SO_4$ and the combined organic phases were evaporated in a rotary evaporator to yield the methane sulfonyl protected product (35). The methane sulfonyl protected primary alcohol was stirred at 70° C. with $NaN_3$ in DMF for 16 hours. A stirred solution of TBS protected secondary alcohol. This reaction was quenched with pre cooled ice water and extracted with diethyl ether. The combined organic phases were dried over $Na_2SO_4$. The combined organic phases were evaporated in a rotary evaporator to yield the azido product as a colorless liquid (36). This was deprotected with TBAF in tetrahydrofuran at room temperature. This reaction was quenched with saturated ammonium chloride solution and extracted with diethyl ether; the combined organic phases were dried over $Na_2SO_4$ and evaporated on rotary evaporator to yield the product 1-azido-3-pentanol (36A) as a colorless liquid.

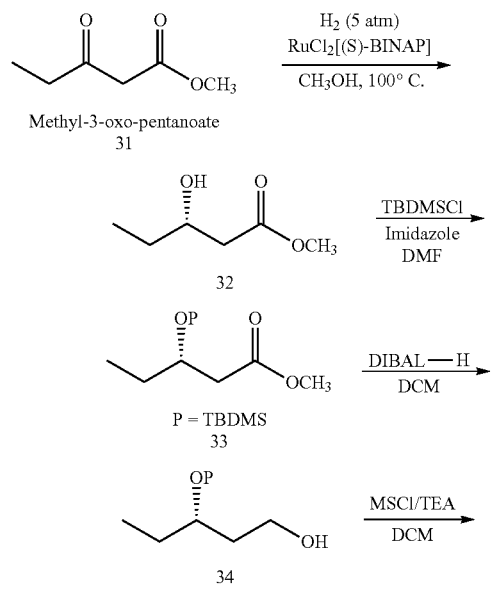

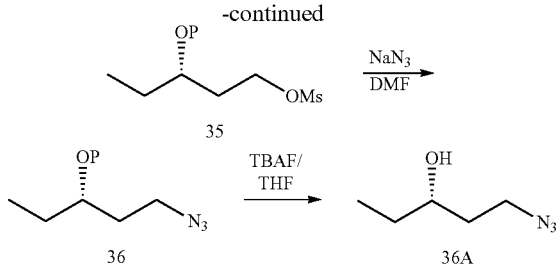

Synthetic Procedure of (3R,4S,5S)-4-Acetylamino-5-boc-amide-3-({1-(2{amine-Peg-amide}-ethyl}-propoxy)-cyclohex-1-enecarboxylic acid ethyl ester (Scheme 15)

3R,4S,5R)-3,4,5-Tris-methanesulfonyloxy-cyclohex-1-enecarboxylic acid ethyl ester (43)

A stirred solution of (3R,4S,5R)-3, 4, 5,-trihydroxy-cyclohex-1-enecarboxylic acid ethyl ester, compound 42 prepared according to Federspiel et al., (*Org. Process Res. Dev.* July 1999, 3(4):266-274) in EtOAc was treated with $CH_3SO_2Cl$. The dark brown solution was cooled to 0° C. and treated with stirring with $NEt_3$ over a period of 45 minutes at temperature in the range of 0-5° C. The brown suspension was stirred for 30 minutes at 0-5° C., filtered over a porous glass filter (pre-cooled to 0-5° C.) and the filter cake was washed with EtOAc. The combined filtrates were extracted with aqueous $H_2SO_4$ and the organic phase was dried over $Na_2SO_4$, filtered and the filter cake was washed with EtOAc and the combined filtrates were evaporated in a rotary evaporator to yield the product (3R,4S,5R)-3,4,5-trismethanesulfonyloxy-cyclohex-1-enecarboxylic acid ethyl ester 43, as a brown liquid which was used without further purification in the next step.

(3R,4S,5R)-3-Azido-4,5-bis-methanesulfonyloxy-cyclohex-1-enecarboxylic acid ethyl ester (44)

(3R,4S,5R)-3,4,5-tris-methanesulfonyloxy-cyclohex-1-enecarboxylic acid ethyl ester 43, product of the preceding experiment) was dissolved in DMSO. To the clear light yellow solution $NaN_3$ was added at room temperature and the suspension was stirred for 3 hours. The orange solution was diluted with EtOAc and toluene and extracted 3 times with aqueous $NaHCO_3$. The organic phase was separated, dried over $Na_2SO_4$, filtered and the combined filtrates evaporated in a rotary evaporator at 20° C./70-10 mbar. The remaining yellow oil was dissolved twice in toluene and evaporated in a rotary evaporator at 20° C./70-10 mbar to obtain the crude dry product (3R,4S,5R)-3-azido-4,5-bis-methanesulfonyloxy-cyclohex-1-enecarboxylic acid ethyl ester (44), as yellow oil which was used in purification. A sample of 4 was obtained from crude 44 via a silica column chromatography using a 1:2 mixture of EtOAc and n-hexane. The combined fractions were evaporated and dried on a rotary evaporator to obtain 44 as a pale yellow oil.

(1S,5R,6S)-7-(Diethoxy-phosphoryl)-5-methanesulfonyloxy-7-azabicyclo[4.1.0]hept-2-ene-3-carboxylic acid ethyl ester (45)

(3R,4S,5R)-3-azido-4,5-bis-methanesulfonyloxy-cyclohex-1-enecarboxylic acid ethyl ester (44) was dissolved under argon with stirring in toluene. The clear solution was treated at room temperature with triethyl phosphite and stirred at room temperature for 30 minutes whereby after about 5 minutes gas evolution started. The light yellow reaction mixture was heated to reflux for 6 hours, evaporated at 40° C./60-10 mbar to yield of the crude product (1S,5R,6S)-7-(diethoxy-phosphoryl)-5-methanesulfonyloxy-7-aza-bicyclo[4.1.0]hept-2-ene-3-carboxylic acid ethyl ester (45) as a yellow oil, which was used in the next step without further purification. An analytical sample of (1S,5R,6S)-7-(diethoxy-phosphoryl)-5-methanesulfonyloxy-7-aza-bicyclo[4.1.0]hept-2-ene-3-carboxylic acid ethyl ester was obtained via a silica column chromatography using a 2:1 mixture of toluene and acetone. The combined fractions were evaporated and dried on a rotary evaporator at 40° C./250-10 mbar to obtain 45 as a yellow oil (45).

(3R,4S,5R)-4-(Diethoxy-phosphorylamino)-3-({1-(2-azido-ethyl}-propoxy)-5-methanesulfonyloxy-cyclohex-1-enecarboxylic acid ethyl ester (46)

(1S,5R,6S)-7-(diethoxy-phosphoryl)-5-methanesulfonyloxy-7-azabicycle [4.1.0]hept-2-ene-3-carboxylic acid ethyl ester (45), was dissolved under argon with stirring in 1-azido-3-pentanol and dichloromethane. The clear light yellow solution was treated with copper triflate at temperature in the range of 0-5° C. The reaction mixture was stirred for 18 hours at room temperature then diluted with EtOAc and extracted twice with water. The organic phase was separated, dried over Na$_2$SO$_4$ filtered and the filtrate evaporated in a rotary evaporator to yield a yellow oil which was dissolved in methyl tertiary butyl ether. Crystallization overnight and filtration led to (3R,4S,5R)-4-(diethoxy-phosphorylamino)-3-({1-(2-azido-ethyl}-propoxy)-5-methanesulfonyloxy-cyclohex-1-enecarboxylic acid ethyl ester (46) as white crystals.

(3R,4S,5R)-4-(Diethoxy-phosphorylamino)--3-({1-(2-Fmoc-Peg-amide-ethyl}-propoxy)-5-methane-sulfonyloxy-cyclohex-1-enecarboxylic acid ethyl ester (47)

(3R,4S,5R)-4-(diethoxy-phosphorylamino)-3-({1-(2-azido-ethyl}-propoxy)-5-methanesulfonyloxy-cyclohex-1-enecarboxylic acid ethyl ester (46) and Lindlar catalyst in ethanol was added. The flask was charged with hydrogen gas (1 atm) at room temperature. The resulting suspension was vigorously stirred for 24 hours. The reaction mixture was diluted with dichloro methane and the combined organic layers were filtered through a Celite pad. The combined organic phases were dried over Na$_2$SO$_4$ and the combined organic phases were evaporated in a rotary evaporator to yield the (3R,4S,5R)-4-(diethoxy-phosphorylamino)-3-({1-(2-amino-ethyl}-propoxy)-5-methanesulfonyloxy-cyclohex-1-enecarboxylic acid ethyl ester as a pale yellow liquid, which was used without further purification in the next step. (3R,4S,5R)-4-(diethoxy-phosphorylamino)-3-({1-(2-amino-ethyl}-propoxy)-5-methanesulfonyloxy-cyclohex-1-enecarboxylic acid ethyl ester was coupled with Fmoc-PEG-acid (16 atoms) in the presence of EDC, HOBT plus DIPEA in dichloro methane. The solution was stirred over a period of 18 hours the room temperature. The crude product was purified by a silica column chromatography using a 8:2 mixture of dichloro methane and hexane. The combined fractions were evaporated and dried over Na$_2$SO$_4$ and the combined organic phases were evaporated on a rotary evaporator to obtain as (3R,4S,5R)-4-(diethoxy-phosphorylamino)-3-({1-(2-Fmoc-Peg-amide-ethyl}-propoxy)-5-methanesulfonyloxy-cyclohex-1-enecarboxylic acid ethyl ester (47).

(3R,4S,5R)-4-Acetylamino-3-({1-(2-Fmoc-Peg-amide-ethyl}-propoxy)-5-methanesulfonyloxy-cyclohex-1-enecarboxylic acid ethyl ester (48)

(3R,4S,5R)-4--(diethoxy-phosphorylamino)-3-({1-(2-Fmoc-Peg-amide-ethyl}-propoxy)-5-methanesulfonyloxy-cyclohex-1-enecarboxylic acid ethyl ester 47, was dissolved in EtOH, treated with 8 equivalents of sulphuric acid and the reaction mixture was heated and stirred for 16 hours at 70° C. The brown-yellow reaction mixture was cooled to room temperature, diluted with EtOAc and water and the mixture was treated with aqueous NaOH and with acetic anhydride After 1 hour stirring at room temperature an additional portion of acetic anhydride was added and the two phase system was stirred for 3.5 hours at room temperature. The organic phase was separated and the aqueous phase was extracted with ethyl acetate. The combined organic layers were dried over Na$_2$SO$_4$, filtered and the filtrate was evaporated at 40° C./200-6 mbar to obtain crude 47 as a white solid, which was digested with methyl tertiary butyl ether. The suspension was heated to reflux for 5 minutes, cooled in the course of 30 minutes to room temperature and stirred for 2 hours. After cooling the suspension to 0-5° C. for 17 hours filtration through a pre-cooled (0-5° C.) glass filter funnel provided off-white crystals which were dried at 40° C./10 mbar for 1 hour to obtain the product (3R,4S,5R)-4-Acetylamino-3-({1-(2-Fmoc-Peg-amide-ethyl}-propoxy)-5-methanesulfonyloxy-cyclohex-1-enecarboxylic acid ethyl ester (48).

(3R,4S,5S)-4-Acetylamino-5-Boc-amide-3-({1-(2{amine-Peg-amide}-ethyl}-propoxy)-cyclohex-1-enecarboxylic acid ethyl ester (50)

(3R,4S,5R)-4-Acetylamino-3-({1-(2-Fmoc-Peg-amide-ethyl}-propoxy)-5-methanesulfonyloxy-cyclohex-1-enecarboxylic acid ethyl ester (48) was dissolved in EtOH and DMSO and the mixture was treated with NaN$_3$. The colorless suspension was heated with stirring to 85° C. for 24 hours. The resulting red brown suspension was treated with aqueous saturated sodium bicarbonate and the mixture was extracted with methyl tertiary butyl ether (MTBE). The organic phases were extracted with brine, dried over Na$_2$SO$_4$ and evaporated in a rotary evaporator to yield crude product as a yellow oil. This yellow oil was treated with tri-N-butylphosphine, in ethanol by heating to reflux for 4 hours. The organic phase was evaporated in a rotary evaporator to yield crude product. The crude product was dissolved in dichloro methane and boc-anhydride, triethyl amine was added. The pale yellow suspension was stirred at room temperature for 16 hours. The resulting pale yellow suspension was treated with water and the reaction mixture was extracted with dichloro methane, dried over Na$_2$SO$_4$ and evaporated in a rotary evaporator to yield crude product (49). A solution of 20% piperidine in dichloromethane was added to the above a yellow oil and stirred was 30 minutes. The resulting yellow suspension was treated with water and the reaction mixture was extracted with dichloro methane, dried over $Na_2SO_4$ and evaporated in a rotary evaporator to yield crude product. The crude product was purified by preparative RP-HPLC using aqueous $CH_3CN$, then freeze-dried to yield the desired compound (3R,4S,5S)-4-acetylamino-5-boc-amide-3-({1-(2{amine-Peg-amide}-ethyl}-propoxy)-cyclohex-1-enecarboxylic acid ethyl ester (50) as a pale yellow liquid.

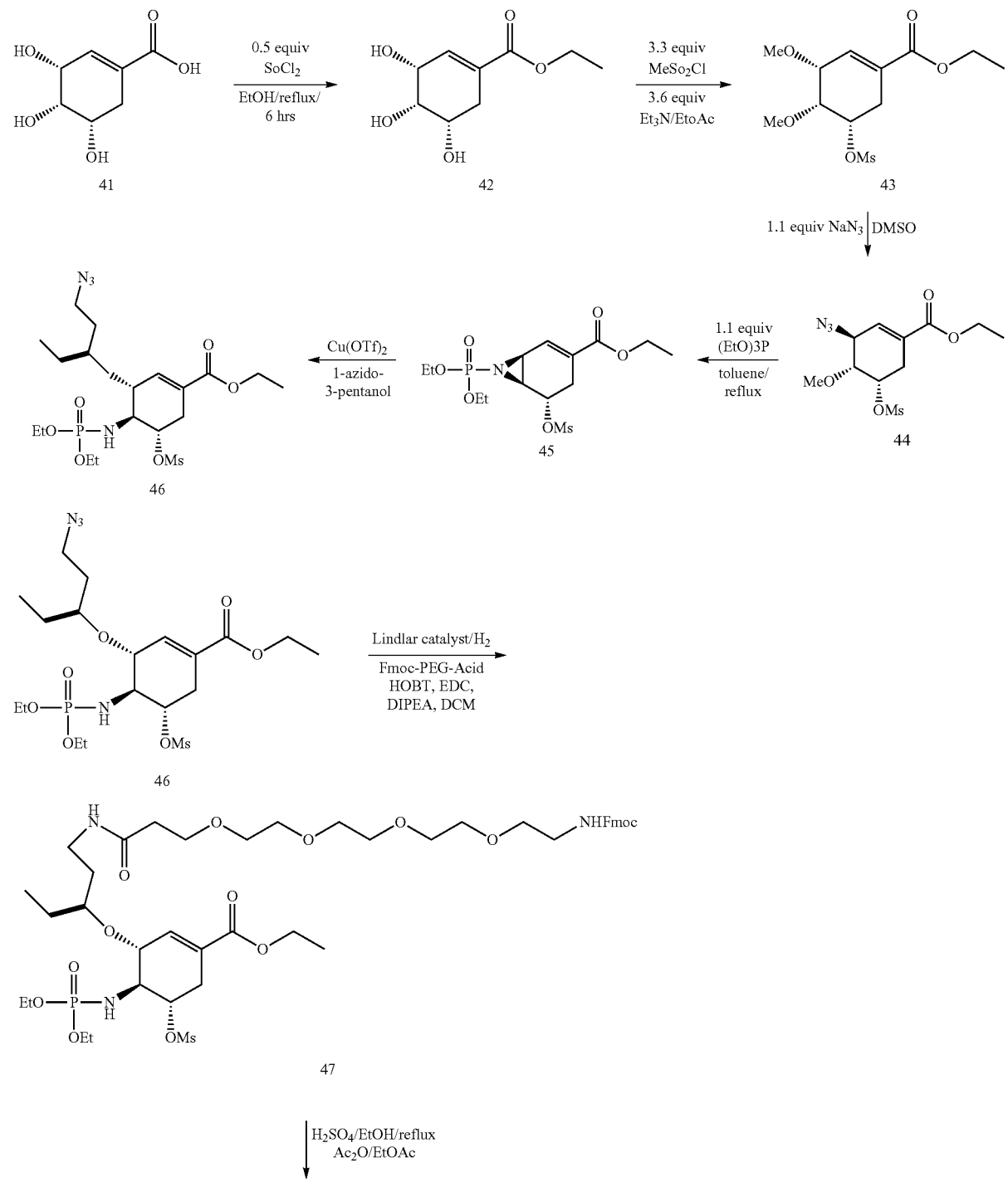

Scheme 15. Synthesis of (3R,4S,5S)-4-Aetylamino-boc-amide-3-({1-(2{amine-peg-amide}-ethyl}-propoxy)-cyclohex-1-enecarboxylic acid ethyl ester.

-continued

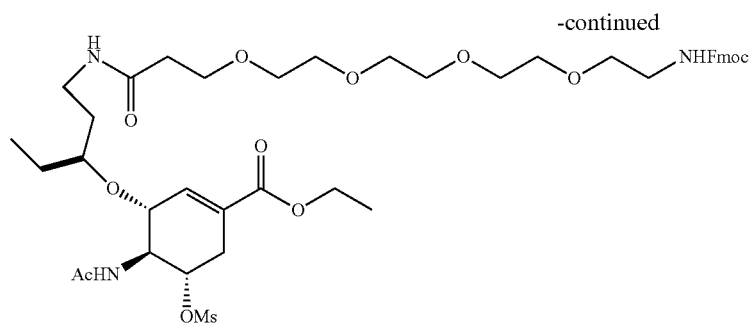
48

(1) 2.0 equiv $NaN_3$
DMSO/EtOH
(2) $PnBu_3$/EtOH
(3) Boc Anhydride
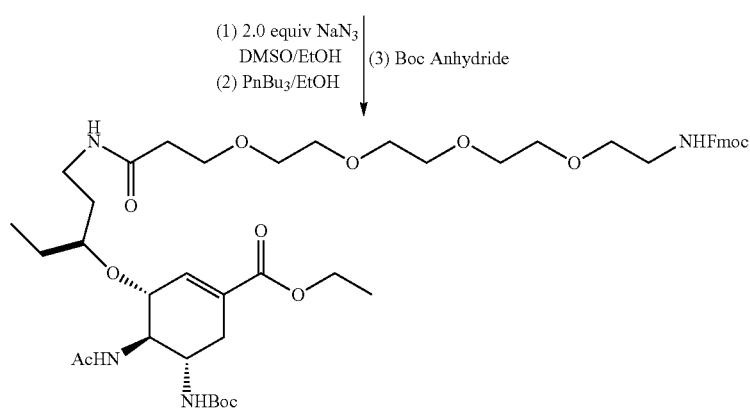
49
Piperdine/DMF
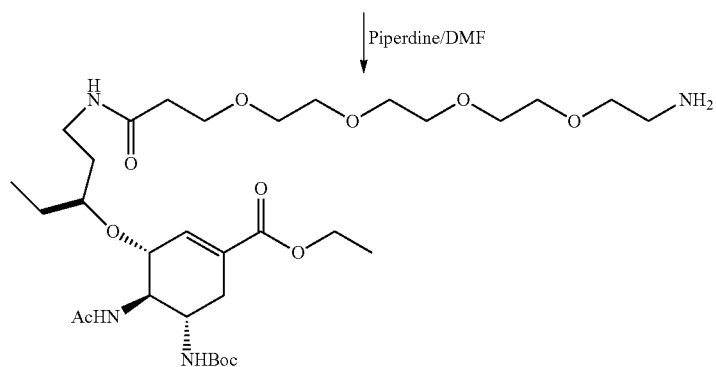
50

Synthesis of oseltamivir-3-pentyloxy-Peg-Succinyl-Diaminopropionyl-Asp-Cys-conjugates (Scheme 16)

A oseltamivir-3-pentyloxy-PEG-Succinyl-Diaminopropionyl-Asp-Cys-conjugate (a novel water soluble neuraminidase inhibitor for the detection of influenza viruses) has been synthesized for direct attachment to inorganic surfaces. This conjugate was prepared from Fmoc-Cys(4-methoxytrityl)-Wang resin, swollen with $CH_2Cl_2$ followed by DMF. A solution of 20% piperidine in DMF was added to the resin, and argon was bubbled for 5 minutes. The resin was washed with DMF and isopropyl alcohol. Formation of free amine was assessed by the Kaiser test. After swelling the resin in DMF, a solution of Fmoc-Asp-(OtBu)-OH, DAPA-OH, succinic anhydride, oseltamivir-3-pentyloxy-Peg amine, and HBTU, HOBt plus DIPEA in DMF was added. Argon was bubbled for 2 hours, and resin was washed with DMF and i-PrOH. The coupling efficiency was assessed by the Kaiser Test. The above sequence was repeated for the 4 required sequential coupling steps. The final compound was cleaved from the resin using a TFA/$H_2O$/iPr3SiH/ethanedithiol cocktail (37:1:1:1) and concentrated under vacuum. The concentrated product was precipitated in diethyl ether and dried under vacuum. The crude product was purified by preparative RP-HPLC using aqueous $CH_3CN$ and then freeze-dried to yield the desired compound as a white solid.

Scheme 16. Synthesis of oseltamivir-3-pentyloxy-Peg-Succinyl-Diaminopropionyl-Asp-Cys-conjugates.

-continued

Preparation of oseltamivir-3-pentyloxy-PEG-Succinyl-Diaminopropionyl-Asp-Cys-conjugate-Bovine serum albumin(BSA) (Scheme 17)

To a solution of oseltamivir-3-pentyloxy-PEG-Succinyl-Diaminopropionyl-Asp-Cys-conjugate (2.5 mg), BSA (10 mg) was dissolved in 350 microliter PBS (pH 7.4) and EDC (3 mg) was added. The reaction mixture was stirred for 3 hours at room temperature. The oseltamivir-3-pentyloxy-PEG-Succinyl-Diaminopropionyl-Asp-Cys-conjugate-BSA was separated from all low molecular weight materials with a 10-kD molecular weight cutoff spin filter with multiple washes of PBS per the manufacturer's instructions.

Scheme 17. Synthesis of oseltamivir-3-pentyloxy-PEG-Succinyl-Diaminopropionyl-Asp-Cys-conjugate-Bovine serum albumin (BSA).

Synthetic Procedure of
New Oseltamivir Derivatives at 3-pentyloxy position
(Scheme 18)

(1R,2S,3S,6R,7R)-8-benzyloxycarbonyl-2-Bromo-4-oxa-8-azatricyclo [4,3,103,7]decan-5-one (53)

To a stirred solution of pyridine (51) in methanol was added sodium borohydride at about −40° C. To this was added benzyl chloroformate dropwise through the dropping funnel over a period of 30 minutes at such a rate that inner temperature was maintained between −45 and −35° C. After stirring for 40 minutes, the resulting solution was gradually warmed to 0° C. Water was added and the mixture was extracted three times with diethyl ether. The combined organic extracts were washed with 1 N HCl (100 ml), 1 N NaOH, water (50 ml), and brine (50 ml), dried over sodium sulfate, and concentrated under reduced pressure to give the crude dihydropyridine 52 as a pale yellow oil, which was used to the next reaction without purification.

To a stirred solution of 52 and the MacMillan's catalyst in acetonitrile and water was added acrolein at room temperature. After stirring for 16 hours, the reaction mixture was diluted with diethyl ether, and washed with water. The aqueous layer was diluted with water and extracted with diethyl ether. The combined organic extracts were washed with water, brine, dried over sodium sulfate, and concentrated under reduced pressure to give aldehyde 53 as a pale yellow oil, which was used to the next reaction without purification.

To a stirred solution of the aldehyde 53 in tert-butyl alcohol and water were added sodium dihydrogenphosphate dihydrate, and 2-methyl-2-butene. To this was added sodium chlorite portion wise at 0° C. After 10 minutes, the solution was warmed to room temperature and stirring was continued for an additional 1 hour. The reaction was then quenched with sodium sulfite, and the reaction mixture was partitioned between ethyl acetate and 3 N HCl. The aqueous layer was thoroughly extracted with ethyl acetate. The combined organic extracts were washed with water, brine, and concentrated under reduced pressure. The concentrated solution (54) was diluted with ethyl acetate and extracted four times with a saturated aqueous sodium bicarbonate solution. To a vigorously stirred mixture of the combined aqueous extracts and dichloromethane was added bromine until the reddish color of bromine persisted. The reaction was quenched with sodium sulfite, and the reaction mixture was extracted three times with ethyl acetate. The combined organic extracts were washed with water, brine, dried over sodium sulfate, and concentrated under reduced pressure. The residue was left at room temperature overnight, during which time crystallization took place. The crude product was treated with methanol to promote crystallization and then concentrated to a small volume under reduced pressure. The crystals were filtered and washed with cold methanol 3 times to afford bromolactone 55.

(1R,2S,3S,6R,7R)-2-Bromo-8-t-butoxycarbonyl-4-oxa-8-azatricyclo [4,3,1,06,7]decan-5-one (56)

To a stirred solution of 55 and di-t-butyl pyrocarbonate in ethanol and tetrahydrofuran was added 10% Pd/C. The flask was charged with hydrogen gas (1 atm) at room temperature. The resulting suspension was vigorously stirred for 3 hours. The reaction mixture was then filtered through a Celite pad and concentrated under reduced pressure. The crude product was purified by silica gel chromatography (dichloromethane) to give 56 as white crystals.

(1R,2S,3S,6R,7R)-2-Bromo-8-t-butoxycarbonyl-4-oxa-8-azatricyclo [4,3,1,06,7]decan-5,9-dione (57)

To a solution of 56 and ruthenium dioxide n-hydrate in 1,2-dichloroethane were added water and sodium periodate. The resulting solution was stirred at 80° C. for 3 hours. Additional sodium periodate was added to the reaction mixture, which was stirred at 80° C. for another 45 minutes before quenching with isopropyl alcohol. After addition of water, the reaction mixture was filtered through filter paper to recover ruthenium dioxide n-hydrate. The filtrate was then partitioned between water and dichloromethane. The aqueous phase was extracted once with dichloromethane. The combined organic extracts were washed with aqueous sodium sulfite solution, brine, dried over sodium sulfate, filtered, and concentrated under reduced pressure to give 57 as white crystals.

(1S,4R,5S,6S,7S)-5-Bromo-6-hydroxy-24-butoxycarbonyl-2-azabicyclo [2,2,2]octan-3-one-7-carboxamide (58)

Ammonia gas was passed through an ice-cold solution of lactone 57 in tetrahydrofuran and tert-butyl alcohol over a period of 2.5 hours. After concentration of the reaction mixture under reduced pressure, the crude product was purified by silica gel column chromatography (methanol/dichloromethane=1/9) to give 8 as white crystals.

(1S,4R,5S,6S,7S)-5-Bromo-6-methanesulfonyloxy-24-butoxycarbonyl-2-azabicyclo[2,2,2]octan-3-one-7-carboxamide (59)

To a solution of alcohol 58 and triethylamine in dichloromethane was added methanesulfonyl chloride slowly at room temperature. After stirring for 15 minutes, additional methanesulfonyl chloride was added. The reaction mixture was stirred for an additional 25 minutes before quenching with aqueous saturated sodium bicarbonate. After the aqueous phase was saturated with sodium chloride, the organic phase was separated and the aqueous layer was extracted twice with dichloromethane. The combined organic extracts were dried over sodium sulfate and concentrated under reduced pressure. The crude product was purified by silica gel column chromatography (methanol/dichloromethane=1/19 to 1/9) to give 9 as a white solid.

(1S,4R,5S,6S,7S)-5-Bromo-7-allyloxycarbonyl-6-methanesulfonyloxy-2-t-butoxycarbonyl-2-azabicyclo[2,2,2]octan-3-one (60)

To a mixture of 9 allyl alcohol and molecular sieves (4)A° in 1,2-dichloroethane was added diacetoxyiodobenzene. After stirring for 15 minutes at room temperature, the reaction mixture was heated at 60° C. for 11 hours. After quenching with saturated aqueous sodium bicarbonate and saturated aqueous sodium thiosulfate, the resulting mixture was filtered through a Celite pad, and washed with saturated aqueous sodium bicarbonate. The aqueous layer was extracted with ethyl acetate, and the combined organic extracts were washed with brine, dried over sodium sulfate, and concentrated under reduced pressure. The crude product was purified by silica gel column chromatography (ethyl acetate/hexane=1/1) to give 60 as a white amorphous solid.

(1S,5S,6R)-5-allyloxycarbonylamino-7-t-butoxycarbonyl-3-ethoxycarbonyl-7-azabicyclo[4, 1, 0]heptan-2-ene (61)

To a stirred solution of 60 in ethanol was added portion wise a 1.0 M solution of sodium ethoxide in ethanol at 0° C. until TLC (ethyl acetate/hexane=1/2) indicated complete reaction. The resulting solution was diluted with dichloromethane, quenched with acetic acid, and neutralized with aqueous saturated sodium bicarbonate. After the reaction mixture was filtered through a Celite pad, aqueous saturated sodium bicarbonate was added. The aqueous phase was saturated with sodium chloride and extracted with dichloromethane three times. The combined organic extracts were dried over sodium sulfate and concentrated under reduced pressure. The crude product was purified by silica gel column chromatography (ethyl acetate/hexane=1/2) to give 61 as an off-white amorphous solid.

(3S,4S,5S)-5-allyloxycarbonylamino-4-t-butoxycarbonylamino-1-ethoxy carbonyl-3-(1{2-azido-ethyl}-propoxy)-cyclohex-2-ene (62)

Aziridine 61 was dissolved in 1-azido-3-pentanol and then cooled to 0° C. To the stirred suspension was added 10 mol % of copper triflate in dichloro methane at 0° C. over 30 minutes. The reaction mixture was warmed to room temperature. After stirring for an additional 16 hours and quenched with aqueous saturated sodium bicarbonate. The mixture was extracted twice with toluene, and the combined organic extracts were washed with brine, dried over sodium sulfate, filtered, and evaporated under reduced pressure. The crude product was purified by silica gel column chromatography (dichloromethane/hexane=1/3) to give 62 as a white amorphous solid.

(3S,4S,5S)-5-allyloxycarbonylamino-4-t-butoxycarbonylamino-1-ethoxycarbonyl-3-({1-(2{Fmoc-PEG-amide-ethyl}-propoxy)-cyclohex-2-ene (63 and 64)

To a stirred solution of (3S,4S,5S)-5-allyloxycarbonylamino-4-t-butoxy carbonylamino-1-ethoxy carbonyl-3-(1{2-azido-ethyl}-propoxy-cyclohex-2-ene 62 and Lindlar catalyst in ethanol was added. The flask was charged with hydrogen gas (1 atm) at room temperature. The resulting suspension was vigorously stirred for 24 hours. The reaction mixture was diluted with dichloro methane and the combined organic layers were filtered through a Celite pad. The combined organic phases were dried over $Na_2SO_4$ and the combined organic phases were evaporated in a rotary evaporator to yield the (3S,4S,5S)-5-allyloxycarbonylamino-4-t-butoxycarbonylamino-1-ethoxycarbonyl-3-({1-(2-amino-ethyl}-propoxy)-cyclohex-2-ene as a pale yellow liquid (63), which was used without further purification in the next step.

The 3S,4S,5S)-5-allyloxycarbonylamino-44-butoxycarbonylamino-1-ethoxycarbonyl-3-({1-{2-amino-ethyl}-propoxy)-cyclohex-2-ene (13) was coupled with Fmoc-PEG-acid (16 atoms), EDC, HOBt plus DIPEA in DCM were added. The solution was stirred over a period of 18 hours at room temperature. The crude product was purified by a silica column chromatography using a 9:1 mixture of DCM and hexane. The combined fractions were evaporated and dried on a rotary evaporator to obtain as (3S,4S,5S)-5-allyloxycarbonylamino-4-t-butoxycarbonylamino-1-ethoxycarbonyl-3-({1-{2-Fmoc-PEG-amide-ethyl}-propoxy)-cyclohex-2-ene. The crude product was purified by silica gel column chromatography (dichloro methane/hexane=4/1) to give 64.

(3S,4S,5S)-5-allyloxycarbonylamino-4-amino-1-ethoxycarbonyl-3-({1-(2-Fmoc-PEG-amide-ethyl}-propoxy)cyclohex-2-ene (65)

To a stirred solution of 64 in dichloromethane was added trifluoroacetic acid at 0° C., and the resulting solution was allowed to warm to room temperature. After stirring for 3 hours, the reaction mixture was cooled to 0° C., quenched with saturated aqueous sodium bicarbonate, and warmed to room temperature. The aqueous phase was saturated with sodium chloride and extracted with dichloromethane 3 times. The combined organic extracts were dried over sodium sulfate, filtered, and concentrated under reduced pressure to give crude amine 65 as a pale yellow amorphous solid, which was used for the next acetylation without further purification.

(3S,4S,5S)-4-Acetamido-5-allyloxycarbonylamino-1-ethoxycarbonyl-3-(1-{2-Fmoc-PEG-amide-ethyl}-propoxy)cyclohex-2-ene (66)

To a stirred solution of 65 in pyridine was added acetic anhydride (1.3 ml) at room temperature. After stirring for an hour, and the reaction mixture was concentrated under reduced pressure. The crude product was purified by a silica column chromatography using a 9:1 mixture of DCM and hexane. The combined fractions were evaporated and dried on a rotary evaporator to obtain (3S,4S,5S)-4-acetamido-5-allyloxycarbonylamino-1-ethoxycarbonyl-3-(1[2-{Fmoc-PEG-amide}-ethyl]-propoxy)cyclohex-2-ene 66 as a colorless liquid.

(3S,4S,5S)-4-Acetamido-5-allyloxycarbonylamino-1-ethoxycarbonyl-3-(1{2-(Amine-PEG-amide-ethyl}-propoxy)cyclohex-2-ene (66A)

A solution of 20% piperidine in dichloromethane was added to the (3S,4S,5S)-4-acetamido-5-allyloxycarbonylamino-1-ethoxycarbonyl-3-(-(1{2-(Fmoc-PEG-amide-ethyl}-propoxy)cyclohex-2-ene (66) This reaction mixture was stirred for 30 minutes at room temperature. The resulting yellow suspension was treated with aqueous saturated sodium bicarbonate and the reaction mixture was extracted with dichloro methane, dried over $Na_2SO_4$ and evaporated in a rotary evaporator to yield crude product. The crude product was purified by preparative RP-HPLC using aqueous $CH_3CN$, then freeze-dried to yield the desired product (3S, 4S,5S)-4-acetamido-5-allyloxycarbonylamino-1-ethoxycarbonyl-3-(-1{2-(Amine-PEG-amide}-ethyl]-propoxy)cyclohex-2-ene (66A).

Scheme 18. Synthesis of New Oseltamivir Derivatives at 3-pentyloxy position.
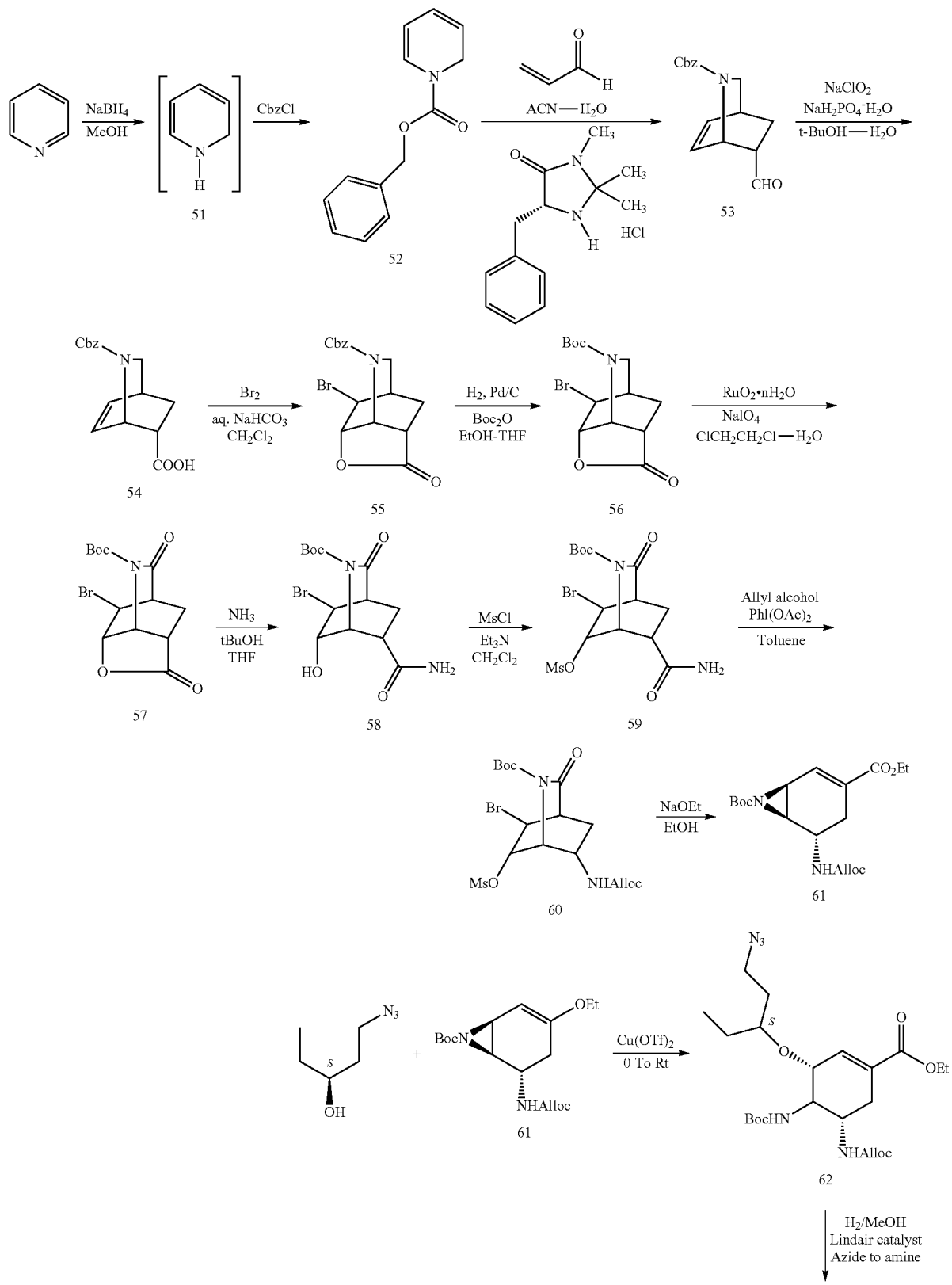

125 126
-continued
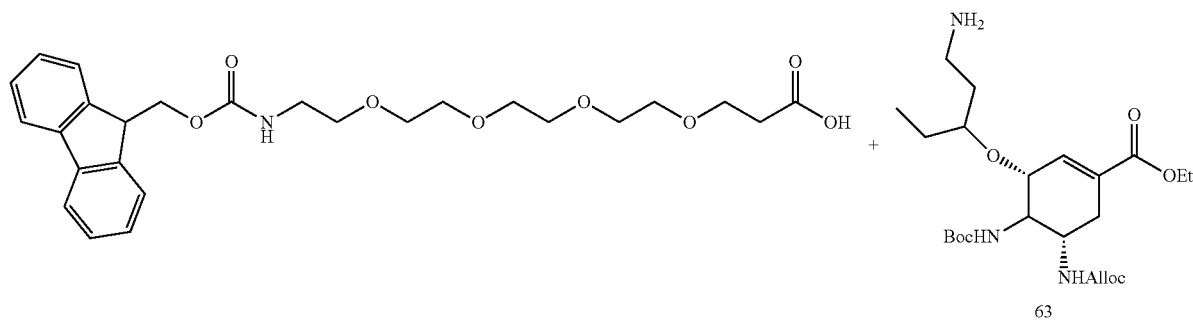
↓ EDCl, HOBT | DIPEA, DCM
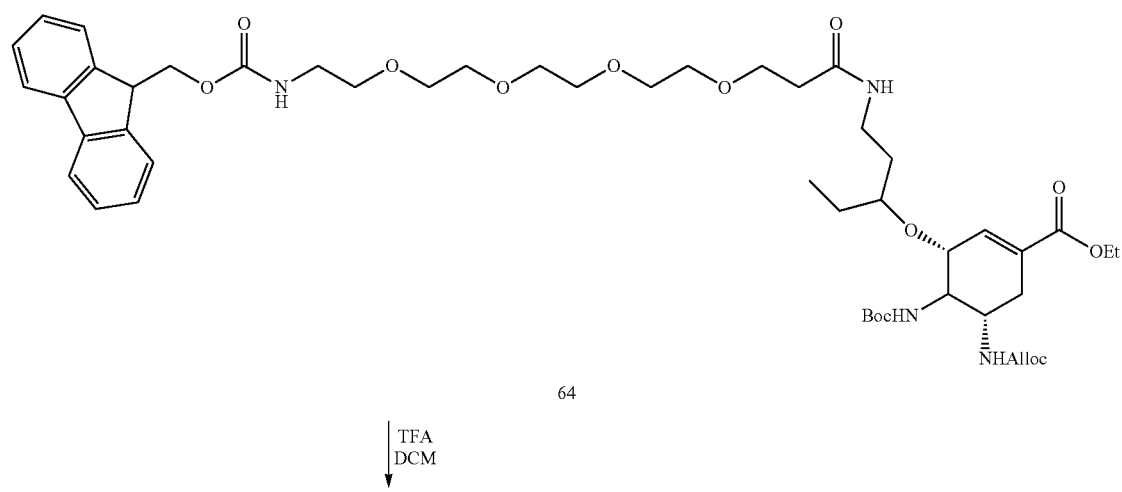
64
↓ TFA
DCM
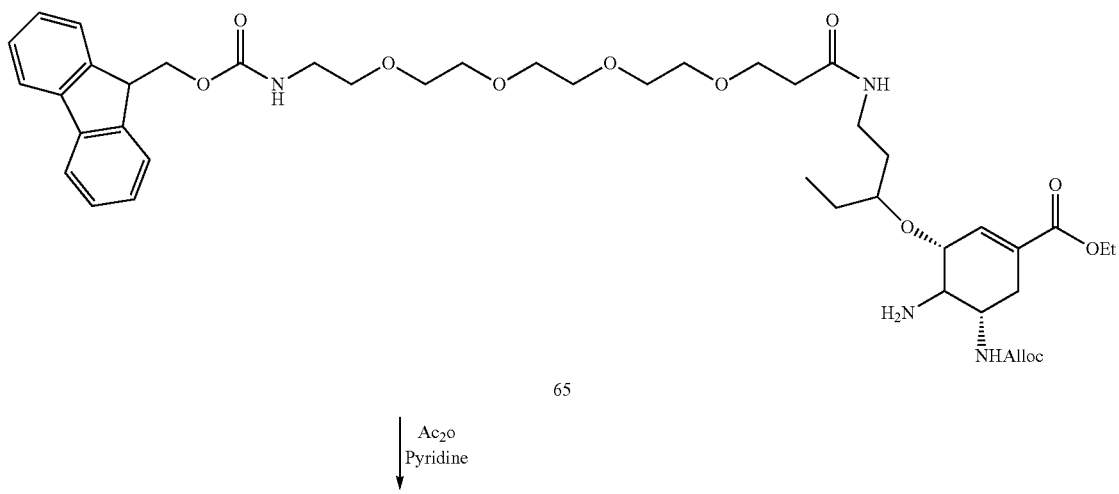
65
↓ Ac₂O
Pyridine -continued
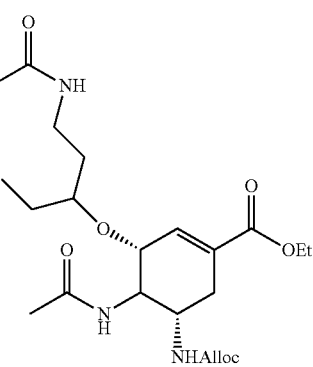
66

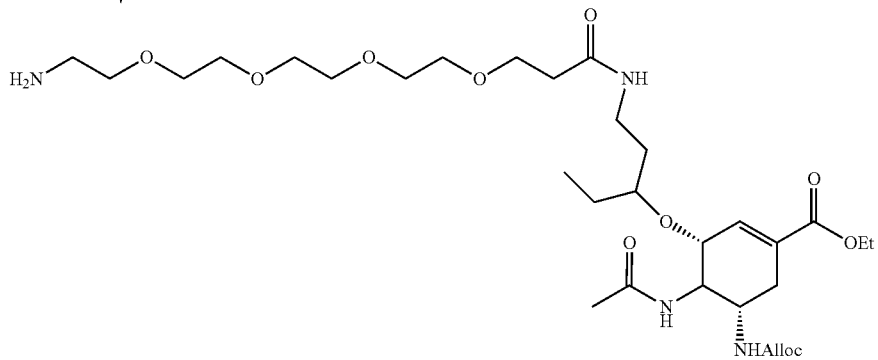
66A
Preparation of Bovine Serum Albumin (BSA)-PEG-3-pentyloxy Oseltamivir (Scheme 19)

To a solution of oseltamivir-3-pentyloxy-PEG-$NH_2$ conjugate (2.5 mg) in 30 microliters DMSO was added BSA (10 mg) dissolved in 350 microliters PBS (pH 7.4) containing EDC (3 mg) and the solution was stirred for 3 hours at room temperature. The Bovine serum albumin (BSA)-PEG-3-pentyloxy oseltamivir conjugate was separated from all low molecular weight materials with a 10-kD molecular weight cutoff spin filter with multiple washes of PBS per the manufacturer's instructions.

Scheme 19. Synthesis of BSA-PEG-3-pentyloxy-oseltamivir conjugate.

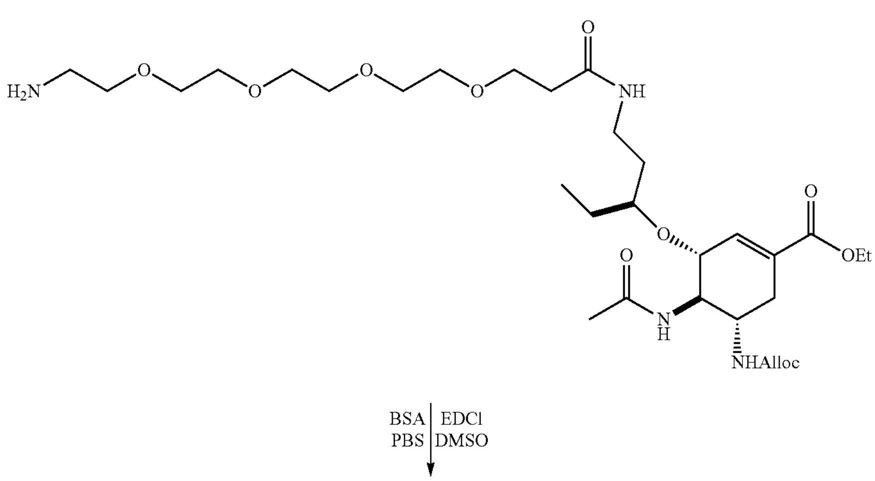

Synthesis of Oseltamivir-Succinyl-Diaminopropionyl-Asp-Cys-conjugates (Scheme 20)

A oseltamivir-PEG-Succinyl-Diaminopropionyl-Asp-Cys-conjugate (a novel water soluble neuraminidase inhibitor for the detection of influenza viruses) has been synthesized for direct attachment to inorganic surfaces. This conjugate was prepared from Fmoc-Cys(4-methoxytrityl)-Wang resin, swollen with $CH_2Cl_2$ followed by DMF. A solution of 20% piperidine in DMF was added to the resin, and argon was bubbled for 5 minutes. The resin was washed with DMF and isopropyl alcohol. Formation of free amine was assessed by the Kaiser test. After swelling the resin in DMF, a solution of Fmoc-Asp-(OtBu)-OH, Diaminopropionic acid, succinic anhydride, oseltamivir-amine, and HBTU, HOBt plus DIPEA in DMF was added. Argon was bubbled for 2 hours, and resin was washed with DMF and i-PrOH. The coupling efficiency was assessed by the Kaiser Test. The above sequence was repeated for the 4 required sequential coupling steps. The final compound was cleaved from the resin using a TFA/$H_2O$/iPr3SiH/ethanedithiol cocktail (37:1:1:1) and concentrated under vacuum. The concentrated product was precipitated in diethyl ether and dried under vacuum. The crude product was purified by preparative RP-HPLC using aqueous $CH_3CN$ and then freeze-dried to yield the desired compound as a white solid.

Scheme 20. Synthesis of oseltamivir-Succinyl-Diaminopropionyl-Asp-Cys-conjugates.

-continued
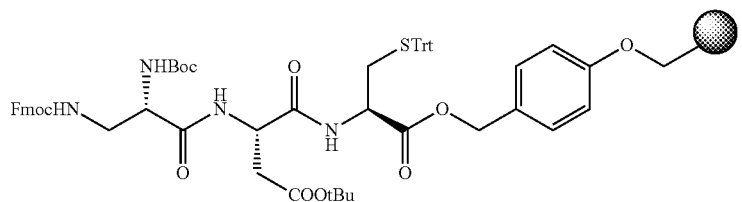
1) 20% Piperdine, DMF
2) Succinic anhydride DIPEA/DMF
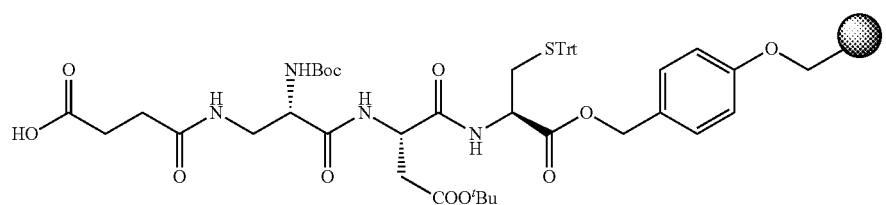
Tami-amine | HBTU, HOBT/DMF
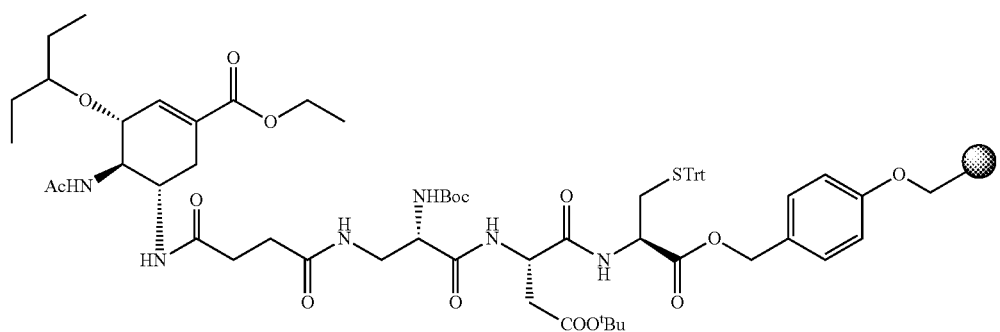
TFA/TIPS/EtSH/H₂O
92.5; 2.5; 2.5; 2.5
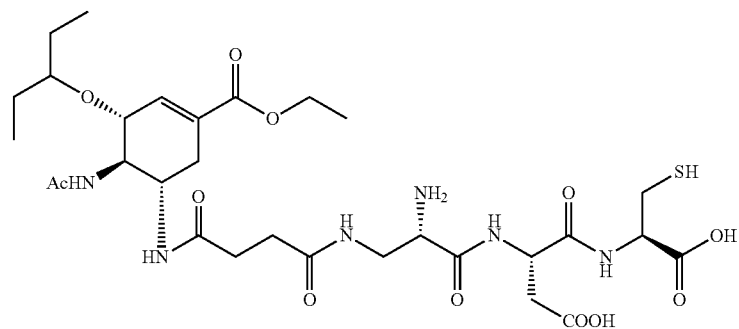

Oseltamivir-Succinyl-Diaminopropionyl-Asp-Cys-Conjugate-Bovine Serum Albumin (BSA) (Scheme 21).

To a solution of oseltamivir-Succinyl-Diaminopropionyl-Asp-Cys-conjugate (2.5 mg), BSA (10 mg) dissolved in 350 microliters PBS (pH 7.4) containing EDC (3 mg) was added and the solution was stirred for 3 hours at room temperature. The Oseltamivir-Succinyl-Diaminopropionyl-Asp-Cys-conjugate-BSA conjugate was separated from all low molecular weight materials with a 10-kD molecular weight cutoff spin filter with multiple washes of PBS per the manufacturer's instructions.

The trypsin-EDTA was distributed over entire cell sheet by gently rocking the flask for 1 minute. The trypsin-EDTA was removed from the flask with a pipette. Another 5 ml of trypsin-EDTA solution was added and the flask was rocked as described above for 1 minute. The trypsin-EDTA was removed from the flask with a pipette. 1 ml of trypsin-EDTA solution was added. The trypsin-EDTA was distributed over entire cell sheet and the flask was incubated at 37° C. until all cells detached from the plastic surface (5 minutes).

Scheme 21. Synthesis of Oseltamivir-Succinyl-Diaminopropionyl-Asp-Cys-conjugate-Bovine serum albumin (BSA).

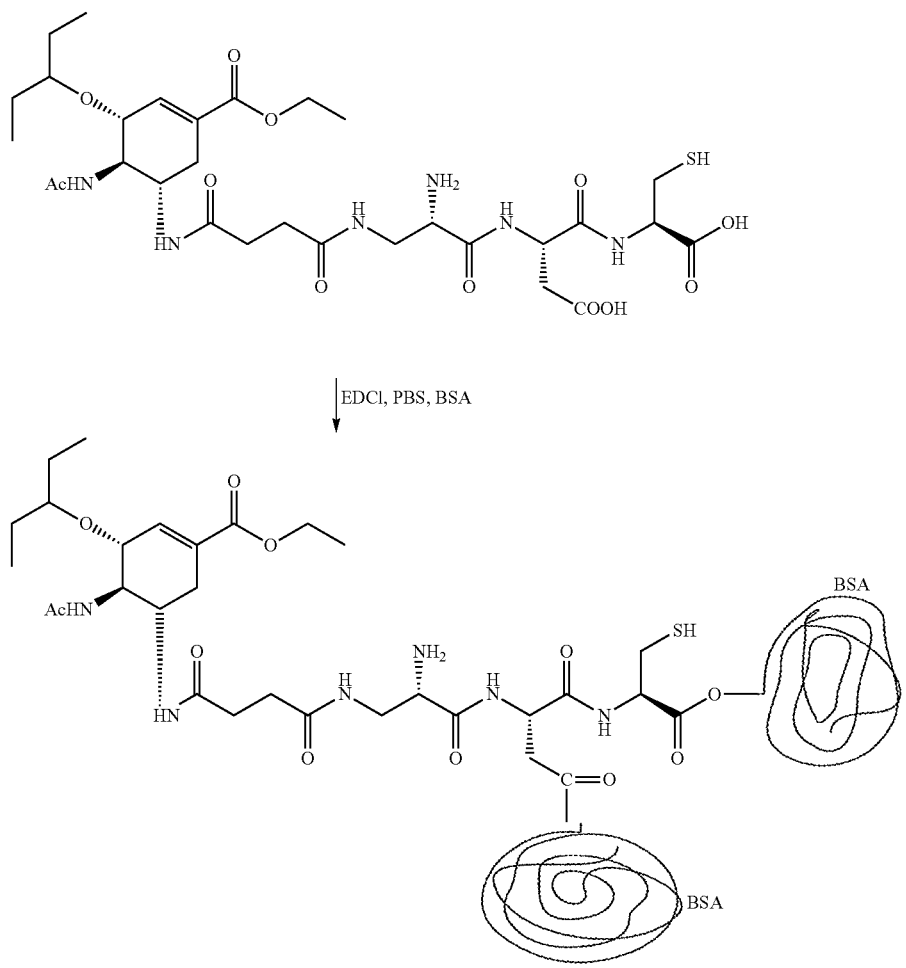

Quantification of Influenza Virus.

The concentration of influenza virus was determined via plaque assay and flow cytometry. The method explored is the counting influenza virus via plating various dilutions and counting the number of viral particle per mL.

Preparation of MDCK Cells in Tissue Culture T75 Flasks.

The procedure for preparing an MDCK cell suspension is described for confluent T-75 flasks. (If cell culture flasks of other sizes are used, the volumes have to be adjusted accordingly). One T-75 flask with a confluent monolayer of MDCK cells contains approximately $10^6$ cells. Medium was removed and 5 ml of trypsin-EDTA pre warmed to 37° C. was added.

MDCK Cell Harvest and Sample Storage.

MDCK Cells from 6-well cell culture plates were harvested for immunostaining of influenza virus ($10^6$ to $10^2$) infected MDCK cells. Supernatants of tissue-culture 6-well cell culture plates were centrifuged (15 g, 5 minutes, 4° C.) to concentrate floating cells in a reduced volume. Adherent cells were washed with PBS and detached by trypsin/EDTA treatment (0.05% w/v trypsin, 0.02% w/v EDTA in PBS) at 37° C. Subsequently, detached cells and cells from supernatant were pooled. Samples from 6-well cell culture plate cultivations were separated into six fractions by sedimentation of the microcarriers. The culture supernatants were centrifuged to concentrate floating cells as described for 6-well cell culture plates supernatants. The settled microcarriers were washed with PBS. In a subsequent step the adherent cells were detached from the microcarriers with Trypsin/EDTA (0.5% w/v trypsin, 0.02% w/v EDTA in PBS).

After MDCK cell detachment, the cells from culture supernatants were added again. Cells were separated from the empty microcarriers by sedimentation of the microcarriers. From these pooled cell suspensions, $1.0 \times 10^6$ cells per aliquot were fixed in methanol (70% v/v, 20° C.) and stored at −20° C.

Direct Immunostaining Against Influenza A Virus Neuraminidase Procedure for Flow Cytometry.

For the detection of influenza A virus infection, The oseltamivir-PEG-FITC fluorescein-conjugate was used against human influenza A virus neuraminidase. Methanol-fixed aliquots of suspended MDCK cells were centrifuged at 50 g for 10 minutes at 4° C. The supernatant was discarded and the pellet was washed with 5 ml PBS. Subsequently, the samples were centrifuged at 50 g for 10 minutes at 4° C. The pellet was resuspended in 2 nil PBS, transferred into 2 ml reaction tubes and centrifuged at 60 g for 15 minutes at 4° C. After removal of the supernatant the pellet was dissolved in 100 µl of the oseltamivir-PEG-FITC solution and incubated for 1 hour in the dark at 37° C. on a tube roller. Following the incubation, unbound oseltamivir-FITC was removed by addition of 1.8 ml PBS and subsequent centrifugation (60 g, 15 minutes, 4° C.). Finally, the pellet was resuspended in 0.5 ml PBS for flow cytometry or in 0.1 ml PBS for immuno-fluorescence microscopy, respectively. The samples were stored in the dark at room temperature until analysis Immunostaining Against Influenza A Virus Hemagglutinin (HA).

For the detection of influenza A virus infection, a mixture of murine monoclonal antibodies was used. The ready-to-use antibody mixture (IMAGEN™ Influenza virus A and B, reagent A, DakoCytomation,) contained fluorescein-conjugated monoclonal antibodies (FITC-MAbs) against human influenza A virus HA at a concentration of 25 µg/ml each. Methanol-fixed aliquots of suspended cells were centrifuged at 100 g for 20 minutes at 4° C. The supernatant was discarded and the pellet was washed with 5 ml PBS containing glycine (2% w/v) and BSA (0.1% w/v). Subsequently, the samples were centrifuged at 100 g for 30 minutes at 4° C. The pellet was resuspended in 2 ml PBS with glycine and BSA, transferred into 2 ml reaction tubes and centrifuged at 60 g for 15 minutes at 4° C. After removal of the supernatant the pellet was dissolved in 25 µl of the FITC-MAb solution and incubated for 1 hour in the dark at 37° C. on a tube roller. Following the incubation, unbound antibody was removed by addition of 1.8 ml PBS and subsequent centrifugation (60 g, 15 minutes, 4° C.). Finally, the pellet was resuspended in 0.5 ml PBS for flow cytometry or in 0.1 ml PBS for immunofluorescence microscopy, respectively. The samples were stored in the dark at room temperature until analysis.

Preparation of Standard Samples.

Uninfected MDCK cells from tissue flasks were harvested and fixed after four days of cultivation (negative control). For positive controls, MDCK cells after 4 days were used. H1N1 influenza A virus infected MDCK cells were harvested 20.0 h post infection, All standard samples were stored in aliquots at −20° C. until further analysis.

Synthesis of oseltamivir-PEG-15-Mercaptopentadecanoamide (Scheme 22)

Synthesis of oseltamivir-PEG-15-mercaptopentadecanoamide from 15-mercapto pentadecanoic acid, protection of mercapto pentadecanoic acid with trityl chloride (1.1 eq) in the presence of triethyl amine in dichloro methane at room temperature for overnight. S-Trityl protected mercapto pentadecanoic acid ((3) was reacted with oseltamivir-PEG-amine in the presence of N-(3-Dimethylaminopropyl)-N'-ethylcarbodiimide (EDCI), 1-Hydroxybenzotriazole hydrate (HOST), N,N-Diisopropylethylamine (DIPEA), in dichloro methane to give oseltamivir-PEG-15-trityl-mercaptopentadecanoamide (β) The deprotection of trityl group with DCM-TFA-Triisopropylsilane (TIS) (5/4/1) mixture for 24 hours at room temperature.

Scheme 22. Synthesis of oseltamivir-PEG-15-Mercaptopentadecanoamide.

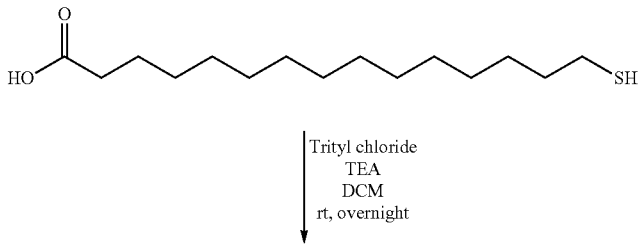

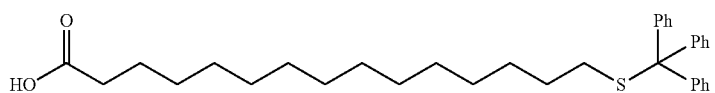
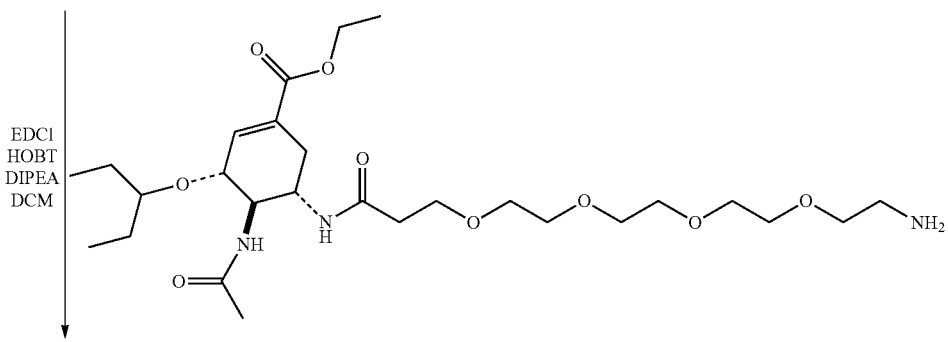
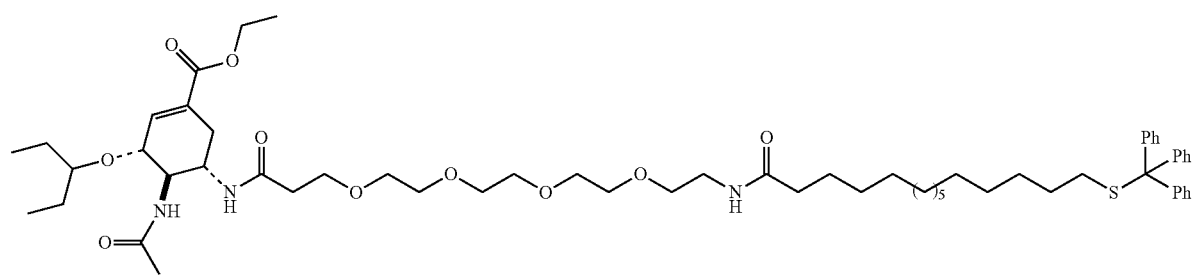
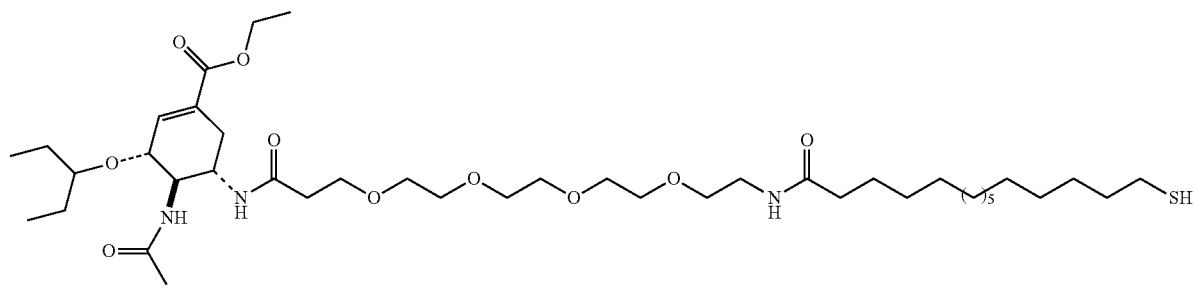

Example 10

Pathogens Detected Using PathoChip Ligands

TABLE 4

Current list of pathogens detected using PathoChip technology (sensitivity in cfu/mL).

| Pathogen species | PT1 (glycan) | 2,3a-Sialy Lactose | heparin | Hemin/ Deuterohemin | Aerobactin | DFO | Pyo-verdine | Other siderophores |
|---|---|---|---|---|---|---|---|---|
| Acinetobacter baumanii | 1E5 | 1E6 | 1E6 | 1E5 | | | | |
| Chlamydia trachomatis | 1E5 | 1E6 | 1E3 | 1E5 | — | | | |
| Klebsiella pneumoniae | 1E4 | | | 1E5 | | | | |
| Mycobacterium smegmatis | — | — | 1E6 | | 1E6+ | 1E6+ | | Mycobactin T (1E3) |
| Pseudomonas aeruginosa* | 1E3 | <1E6 | 1E6 | 1E3/1E4 | 1E6+ | 1E6+ | 1E2 | Mycobactin: 1E6+ Salmochelin: 1E6+ |
| Salmonella enterica | — | <1E6 | | 1E6 | 1E2 | 1E3 | 1E6+ | Salmochelin S (1E3) |
| Shigella spp. | — | — | 1E6+ | 1E6 | 1E3 | | 1E7+ | Salmochelin: 1E6+ |
| Staphylococcus aureus* | 1E3 | 1E6 | 1E6 | 1E3/1E4 | 1E6+ | 1E6+ | 1E7+ | Mycobactin: 1E6+ Sahnochelin: 1E6+ |
| Streptococcus pneumonaie | 1E5 | 1E3 | | 1E5/1E7+ | — | | | |
| Vibrio cholerae | 1E6+ | 1E6 | 1E6+ | 1E6/1E6 | | 1E3 | 1E7 | Vibriobactin (1E4) Mycobactin: 1E6+ |
| Yersinia enterocolita | 1E6 | <1E6 | | 1E6 | 1E6+ | 1E3 | 1E7+ | Salmochelin: 1E6+ |
| Influenza, H1N1 | | (2,6-Sial-lac) | | | | | | Tamiflu (1E3) |
| Influenza, H3N1 | | (2,6-Sial-lac) | | | | | | Tamiflu |
| Influenza, H5N1 | | | | | | | | Tamiflu |

All ligands are conjugated to BSA.
*No antigen test available yet
PT1 glycan is Pulmonary Trisaccharide The following ligands demonstrated low pair-wise cross-reactivity (1000+-fold difference in limit of detection): Heparin: *Chlamydia trachomatis* ($10^3$ cfu/mL); Pyoverdine: *Pseudomonas aeruginosa* ($10^2$ cfu/mL); Mycobactin J: *Mycobacterium smegmatis* ($10^3$ cfu/mL); Salmochelin S: *Salmonella enterica* ($10^3$ cfu/mL); Aerobactin: *Salmonella enterica, Shigella* spp. ($10^2$ cfu/mL, $10^3$ cfu/mL); and DFO: *Salmonella enterica, Vibrio cholerae, Yersinia enterocolita*: ($10^3$ cfu/mL each).

The following are fully orthogonal pathogen-ligand sets: #1: *Pseudomonas aeruginosa*—Pyoverdine; #2: *Chlamydia trachomatis*—Heparin; #3: *Mycobacterium smegmatis*—Mycobactin J; #4: *Salmonella enterica*—Aerobactin or Salmochelin S (*Salmonella* can switch with *Shigella*); and #5: *Vibrio cholerae*—Vibriobactin.

Many other pairings are possible if selection is limited to 3 bacteria.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An article comprising:
   a substrate; and
   one or more mutation-resistant ligands affixed in a predetermined periodic pattern to at least a portion of the substrate, wherein the one or more mutation-resistant ligands is affixed to the substrate via a linker, wherein the one or more mutation-resistant ligands can be bound by pathogens wherein the predetermined periodic pattern is indicative of the pathogen to be selectively bound to the mutation resistant ligand and is recognizable when a pathogen is bound to the ligand, and wherein the mutation-resistant ligands are involved in functions important to or essential to virulence of the pathogens.

2. The article of claim 1 wherein the linker comprises bovine serum albumin or polyethylene glycol.

3. The article of claim 1 wherein the mutation-resistant ligand comprises a siderophore, a glycan, or a neuraminidase inhibitor.

4. The article of claim 3 wherein the glycan comprises a cell surface molecule involved in a pathogen infecting a host cell.

5. The article of claim 3 wherein the neuraminidase inhibitor comprises oseltamivir or a derivative thereof.

6. The article of claim 1 wherein the one or more mutation-resistant ligands comprises a first mutation-resistant ligand and a second mutation-resistant ligand.

7. The article of claim 6 wherein the first mutation-resistant ligand selectively binds a first pathogen and the second mutation-resistant ligand selectively binds to a second pathogen different from said first pathogen.

8. The article of claim 6 wherein the first mutation-resistant ligand is affixed to the substrate in a first predetermined pattern and the second mutation-resistant ligand is affixed to the substrate in a second predetermined pattern.

9. A method comprising:

contacting a biological sample comprising a pathogen with the article of claim 1 for a time sufficient to allow the one or more mutation-resistant ligands to selectively bind to the pathogen; and detecting the pathogen bound to the one or more mutation-resistant ligands.

10. The method of claim 9 wherein the at least one mutation-resistant ligand comprises a first mutation-resistant ligand that selectively binds to a first pathogen and a second mutation-resistant ligand that selectively binds to a second pathogen.

11. The method of claim 9 wherein the at least one mutation-resistant ligand comprises a first mutation-resistant ligand and a second mutation-resistant ligand, each of which selectively binds the same pathogen.

12. The method of claim 9 wherein detecting the pathogen bound to the one or more mutation-resistant ligands comprises labeling the bound pathogen and detecting the label.

13. The method of claim 9 wherein detecting the pathogen bound to the one or more mutation-resistant ligands comprises label-free detection.

14. The method of claim 13 wherein label-free detection comprises optical imaging.

15. The method of claim 14 wherein the label-free detection further comprises recognizing the predetermined pattern produced by the pathogen selectively bound to the one or more mutation-resistant ligands.

16. The method of claim 15 wherein:

the one or more mutation-resistant ligand comprises:

a first mutation-resistant ligand that selectively binds to a first pathogen and is affixed to the substrate in a first predetermined pattern; and a second mutation-resistant ligand that selectively binds to a second pathogen and is affixed to the substrate in a second predetermined pattern; and the label-free detection comprises recognizing the first predetermined pattern and the second predetermined pattern.

17. The method of claim 15 wherein recognizing the predetermined pattern comprises using a two-dimensional fast Fourier transform.

18. The method of claim 9 wherein the pathogen comprises a bacterium, a virus, a parasite, a protozoan, a protist, or a fungus.

19. A device comprising:

an analytical chamber;

a sample reservoir in fluid communication with the analytical chamber;

the article of claim 1; and an image recorder.

20. The device of claim 19 further comprising:

a dielectrophoretic concentrator in fluid communication between the analytical chamber and the sample reservoir; and a wash reservoir in fluid communication with the dielectrophoretic concentrator.

21. The device of claim 20 further comprising:

a pump in functional communication with the sample reservoir and/or a pump in functional communication with the wash reservoir; and a control processing unit in functional communication with at least one of the pumps.

22. The device of claim 19 further comprising at least one of:

a magnifying lens functionally positioned between the article and the image recorder;

an illumination source situated to illuminate the article;

a control processing unit in functional communication with the image recorder; and a user interface display functionally connected to the image recorder.

* * * * *